US011065294B2

(12) United States Patent
Byun et al.

(10) Patent No.: US 11,065,294 B2
(45) Date of Patent: Jul. 20, 2021

(54) COMPOSITION INCLUDING ORIENTAL MEDICINE TO TREAT NEOPLASTIC DISEASE

(71) Applicant: COMPREHENSIVE AND INTEGRATIVE MEDICINE INSTITUTE, Daegu (KR)

(72) Inventors: Joon Seok Byun, Daegu (KR); Sae Kwang Ku, Daegu (KR); Ki Cheul Sohn, Daegu (KR); Seung Mo Kim, Daegu (KR); Chang Hyeong Lee, Daegu (KR); Dae Sung Hyun, Daegu (KR); Jong Dae Kim, Daegu (KR); Sung Hwan Park, Daegu (KR); Min A. Kwak, Daegu (KR)

(73) Assignee: COMPREHENSIVE AND INTEGRATIVE MEDICINE INSTITUTE, Daegu (KR)

( * ) Notice: Subject to any disclaimer, the term of this patent is extended or adjusted under 35 U.S.C. 154(b) by 948 days.

(21) Appl. No.: 14/891,284

(22) PCT Filed: May 15, 2014

(86) PCT No.: PCT/KR2014/004375
§ 371 (c)(1),
(2) Date: Nov. 13, 2015

(87) PCT Pub. No.: WO2014/185733
PCT Pub. Date: Nov. 20, 2014

(65) Prior Publication Data
US 2016/0184382 A1 Jun. 30, 2016

(30) Foreign Application Priority Data

May 15, 2013 (KR) .......... 10-2013-0055364
May 31, 2013 (KR) .......... 10-2013-0063002
Apr. 7, 2014 (KR) .......... 10-2014-0041517
Apr. 7, 2014 (KR) .......... 10-2014-0041519

(51) Int. Cl.
| A61K 36/9068 | (2006.01) |
| A61K 31/138 | (2006.01) |
| A61K 36/232 | (2006.01) |
| A61K 36/484 | (2006.01) |
| A61K 36/725 | (2006.01) |
| A61K 36/00 | (2006.01) |
| A61K 31/44 | (2006.01) |
| A61K 31/4412 | (2006.01) |
| A61K 31/5377 | (2006.01) |
| A61K 36/28 | (2006.01) |
| A61K 36/53 | (2006.01) |
| A61K 36/65 | (2006.01) |
| A61K 36/752 | (2006.01) |
| A61K 36/756 | (2006.01) |
| A61K 36/88 | (2006.01) |

(52) U.S. Cl.
CPC ........ *A61K 36/9068* (2013.01); *A61K 31/138* (2013.01); *A61K 31/44* (2013.01); *A61K 31/4412* (2013.01); *A61K 31/5377* (2013.01); *A61K 36/00* (2013.01); *A61K 36/232* (2013.01); *A61K 36/28* (2013.01); *A61K 36/484* (2013.01); *A61K 36/53* (2013.01); *A61K 36/65* (2013.01); *A61K 36/725* (2013.01); *A61K 36/752* (2013.01); *A61K 36/756* (2013.01); *A61K 36/88* (2013.01)

(58) Field of Classification Search
CPC .................................................. A61K 36/00
See application file for complete search history.

(56) References Cited

U.S. PATENT DOCUMENTS

2010/0150894 A1* 6/2010 Wakabayashi ....... A61K 31/122
424/94.1

OTHER PUBLICATIONS

Shin et al. J Korean Soc Appl Biol Chem (2012) 55, 205-212. (Year: 2012).*
Lazzeroni et al. Breast Cancer Research 2012, 14:214. 11 pages. (Year: 2012).*

* cited by examiner

Primary Examiner — Amy L Clark
(74) Attorney, Agent, or Firm — Lucas & Mercanti, LLP

(57) ABSTRACT

Provided is a composition for enhancing effects of an anticancer agent using an oriental medicine, jaeumganghwa-tang, bojungikgi-tang, or yukmijihwang-tang. More particularly, provided is a composition for treating a neoplastic disease by administering an anticancer agent into an individual, and administering an oriental medicine into the individual within 30 minutes. The composition remarkably reduces side effects occurring when the anticancer agent is administered alone by co-administration of the oriental medicine, reduces cytotoxicity, and has higher anticancer activity than that when the anticancer agent is administered alone.

10 Claims, 95 Drawing Sheets

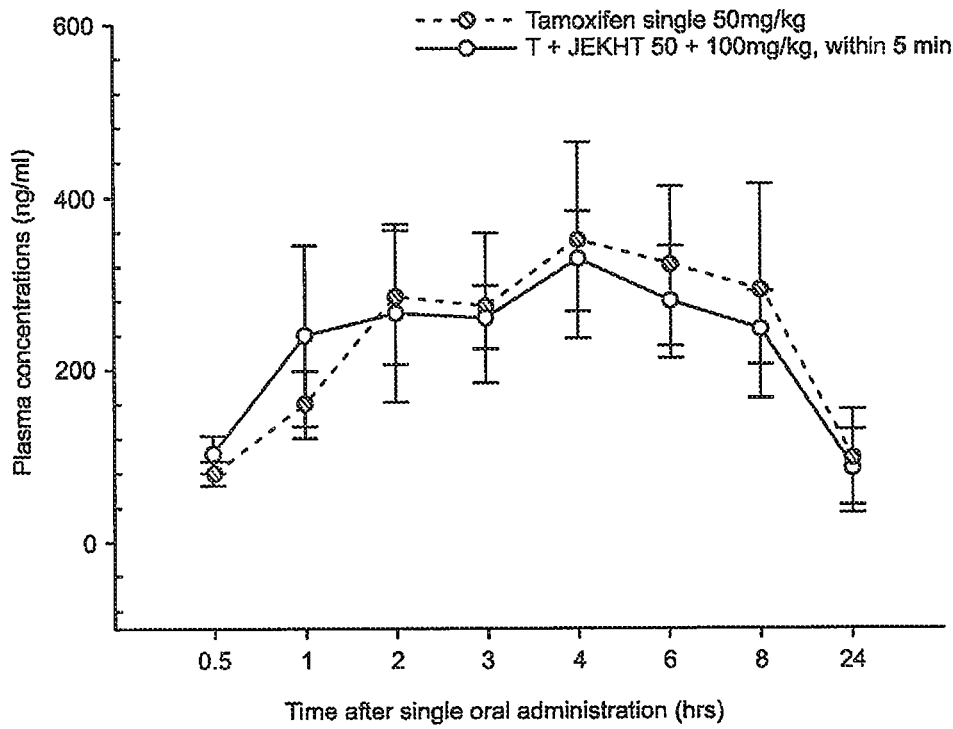

FIG. 2

| | Tamoxifen (50mg/kg) | |
|---|---|---|
| Parameters | Without JEKHT co-administration (Distill water) | With JEKHT co-administration (100mg/kg) |
| Tmax (hrs) | 5.60±2.19 | 4.80±1.10 |
| Cmax (ng/ml) | 364.20±121.77 | 345.00±46.09 |
| AUC$_{0-t}$ (hr*μg/ml) | 5.27±1.79 | 4.73±0.85 |
| AUC$_{0-inf}$ (hr*μg/ml) | 6.86±2.92 | 6.30±2.07 |
| t$_{1/2}$ (hr) | 9.56±4.16 | 10.91±3.99 |
| MRT$_{inf}$ (hr) | 14.87±6.29 | 16.02±5.60 |

Values are expressed as mean ± SD of five rats
JEKHT: Jaeumganghwa-tang aqueous extracts (Hanpoong Pharm Co. Daejeon,Korea)
Cmax: The peak plasma concentration
Tmax: Time to reach Cmax
AUC$_{0-t}$: The total area under the plasma concentration-time from time zero time measured
AUC$_{0-inf}$: The total area under the plasma concentration-time curve time zero to time infinity
t$_{1/2}$: half life
MRT$_{inf}$: mean residence to time infinity

FIG. 3

|  | Tamoxifen (50mg/kg) | |
| --- | --- | --- |
| Parameters | Without JEKHT co-administration (Distill water) | With JEKHT co-administration (100mg/kg) |
| $T_{max}$ (hrs) | 3.60±0.89 | 2.80±1.30 |
| $C_{max}$ (ng/ml) | 0.28±0.16 | 0.32±0.17 |
| $AUC_{0-t}$ (hr*μg/ml) | 3.23±1.79 | 3.70±2.22 |
| $AUC_{0-inf}$ (hr*μg/ml) | 4.86±2.87 | 4.88±4.09 |
| $t_{1/2}$ (hr) | 13.11±5.77 | 12.47±5.01 |
| $MRT_{inf}$ (hr) | 18.12±5.71 | 17.16±8.35 |

FIG. 5A

|  | Tamoxifen (50mg/kg) | |
| --- | --- | --- |
| Parameters | Without JEKHT co-administration (Distill water) | With JEKHT co-administration (100mg/kg) |
| $T_{max}$ (hrs) | 3.40±0.69 | 3.80±0.45 |
| $C_{max}$ (ng/ml) | 0.77±0.22 | 0.70±0.17 |
| $AUC_{0-t}$ (hr*μg/ml) | 12.39±2.66 | 12.11±3.24 |
| $AUC_{0-inf}$ (hr*μg/ml) | 21.50±3.04 | 19.60±2.60 |
| $t_{1/2}$ (hr) | 19.62±5.84 | 18.68±7.30 |
| $MRT_{inf}$ (hr) | 28.48±8.53 | 26.85±10.69 |

Values are expressed as mean ± SD of fiverats
JEKHT: Jaeumganghwa-tang aqueous extracts (Hanpoong Pharm Co. Daejeon,Korea)
$C_{max}$: The peak plasma concentration
$T_{max}$: Time to reach Cmax
$AUC_{0-t}$: The total area under the plasma concentration-time from time zero time measured
$AUC_{0-inf}$: The total area under the plasma concentration-time curve time zero to time infinity
$t_{1/2}$: half life
$MRT_{inf}$: mean residence to time infinity

FIG. 5B

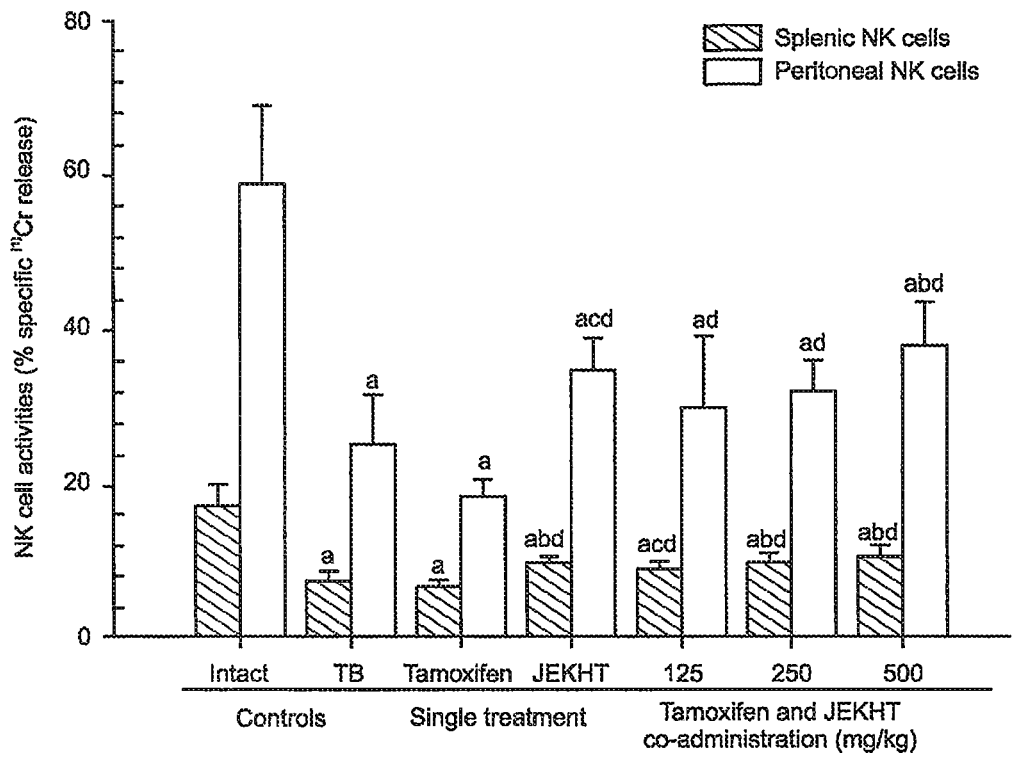

FIG. 11

| Groups | Tumor necrosis factor-α | Interleukin-1β | Interleukin-10 |
|---|---|---|---|
| Controls | | | |
|   Intact | 94.26±26.19 | 31.57±4.72 | 89.40±17.45 |
|   TB | 32.13±11.64[a] | 10.06±10.88[a] | 29.09±10.88[a] |
| Single treated | | | |
|   Tamoxifen | 24.44±7.25a | 8.97±1.36[a] | 19.39±10.43[a] |
|   JEKHT | 50.75±13.68[acd] | 18.58±3.01[abd] | 51.17±10.19[abd] |
| Tamoxifen and JEKHT co-administered | | | |
|   125mg/kg | 38.68±11.37[a] | 12.03±2.76[ac] | 35.60±13.16[ac] |
|   250mg/kg | 48.92±11.02[acd] | 18.38±2.28[abd] | 50.15±14.37[abd] |
|   500mg/kg | 67.76±13.76[abd] | 20.53±2.12[abd] | 58.13±13.87[abd] |

Values are expressed mean ± S.D., pg/ml of seven mice

JEKHT: Jaeumganghwa-tang extracts, which were purchase from Hanpoong Pharm. Co. (Daejeon, Korea)
TB = tumor-bearing Tamoxifen 20mg/kg or JEKHT 500mg/kg were administered in single treated groups

[a]$p<0.01$ as compared with intact control by LSD test
[b]$p<0.01$ and [c]$p<0.05$ as compared with TB control by LSD test
[d]$p<0.01$ and [e]$p<0.05$ as compared with tamoxifen single treated mice by LSD test

FIG. 12

| Groups | Hematological Items. Red Blood Cells | | | | | | | |
|---|---|---|---|---|---|---|---|---|
| | RBC | HGB | HCT | MCV | MCH | MCHC | PLT | RET |
| Vehicle Control | 9.26±0.41 | 17.58±0.93 | 45.89±2.52 | 51.04±3.51 | 19.53±0.47 | 38.36±1.82 | 1177.25±259.69 | 2.83±1.61 |
| Gefitinib single 160mg/kg | 7.89±0.47a | 15.43±0.92a | 42.06±2.83c | 53.45±4.25 | 19.59±1.11 | 36.73±1.90 | 1155.50±266.32 | 2.66±2.64 |
| Gefitinib 160mg/kg and BJIKT co-administration | | | | | | | | |
| 100mg/kg | 7.90±0.93c | 15.45±1.41a | 43.21±4.11 | 54.56±3.28b | 19.63±0.78 | 36.73±1.22 | 1242.88±233.21 | 1.61±0.64 |
| 200mg/kg | 8.61±0.73bd | 18.11±1.30c | 45.25±1.88f | 52.56±2.11 | 19.90±0.98 | 37.91±2.51 | 1264.75±268.35 | 2.46±1.38 |
| 400mg/kg | 9.14±0.33c | 18.53±0.72c | 45.35±2.49f | 52.01±3.63 | 19.41±0.58 | 37.41±1.93 | 1050.63±188.06 | 3.13±2.30 |
| BJIKT single | | | | | | | | |
| 400mg/kg | 9.24±0.68 | 17.89±1.91 | 47.59±6.67 | 53.49±2.28 | 19.59±0.62 | 37.15±2.27 | 1050.75±274.91 | 1.54±0.83 |

| Groups | Hematological Items: White Blood Cells | | | | |
|---|---|---|---|---|---|
| | WBC | NEU(%) | LYM(%) | MONO(%) | EOS(%) | BASO(%) |
| Vehicle Control | 2.95±0.71 | 4.45±1.16 | 87.70±1.35 | 4.86±0.64 | 0.89±0.96 | 0.23±0.14 |
| Gefitinib single 160mg/kg | 3.80±1.04 | 4.86±2.74 | 85.58±3.08 | 6.96±1.59a | 0.91±1.50 | 0.23±0.14 |
| Gefitinib 160mg/kg and BJIKT co-administration | | | | | | |
| 100mg/kg | 4.49±1.77c | 5.51±1.55 | 82.19±4.20ac | 8.18±1.70d | 1.64±2.57 | 0.36±0.18 |
| 200mg/kg | 3.69±1.41 | 3.59±1.31 | 88.09±2.55 | 5.09±1.33d | 0.19±0.38 | 0.31±0.08 |
| 400mg/kg | 3.33±1.22 | 3.45±1.56 | 87.03±2.56 | 4.71±1.33d | 1.33±1.86 | 0.23±0.05 |
| BJIKT single | | | | | | |
| 400mg/kg | 3.17±0.63 | 5.85±2.91 | 86.45±2.95 | 4.18±2.06 | 0.54±0.70 | 0.21±0.16 |

Values are expressed as mean ± S.D. of eight nice
BJIKT= Bojungikgi-tang extracts,which were purchase from Hanpoong Pharm & Foods (Seoul, Korea)

FIG. 24

| Groups | Serum Biochemical Items | | | | | | | |
|---|---|---|---|---|---|---|---|---|
| | AST | ALT | ALP | BUN | CRE | GLU | CHO | |
| Vehicle Controls | 78.63±14.26 | 36.13±17.38 | 105.38±33.53 | 18.33±1.87 | 0.30±0.08 | 64.25±17.53 | 150.25±12.61 | |
| Gefitinib single 160mg/kg | 223.88±47.75[d] | 402.25±165.11[d] | 123.25±49.23 | 17.94±1.95 | 0.46±0.12 | 60.38±19.96 | 161.50±13.97 | |
| Gefitinib and BJIKT co-administered | | | | | | | | |
| 100mg/kg | 214.25±61.23[d] | 321.88±184.54[d] | 127.63±80.45 | 21.28±7.72 | 0.34±0.16 | 78.00±36.94 | 140.88±25.24 | |
| 200mg/kg | 162.38±26.58[d] | 164.25±42.39[d] | 107.63±48.49 | 19.44±1.81 | 0.40±0.15 | 79.63±20.43 | 163.13±24.57 | |
| 400mg/kg | 118.63±23.53[d] | 141.75±43.07[d] | 97.00±36.54 | 19.88±3.83 | 0.40±0.21 | 69.13±27.68 | 168.63±31.47 | |
| BJIKT 400mg/kg | 79.88±15.02 | 39.38±17.19 | 101.00±36.30 | 19.75±4.48 | 0.40±0.16 | 82.75±28.37 | 142.63±25.61 | |

| Groups | FRO | CPK | BIL | ALB | Globlin | AG | TG |
|---|---|---|---|---|---|---|---|
| Vehicle Controls | 4.75±0.21 | 121.88±36.61 | 0.10±0.00 | 3.24±0.18 | 1.51±0.22 | 2.16±0.41 | 168.00±35.46 |
| Gefitinib single 160mg/kg | 4.78±0.20 | 152.25±30.77 | 0.11±0.04 | 2.59±0.49[d] | 1.99±0.18[d] | 1.38±0.14[d] | 178.13±36.26 |
| Gefitinib and BJIKT co-administered | | | | | | | |
| 100mg/kg | 4.88±0.36 | 158.13±37.05 | 0.11±0.04 | 2.68±0.10[d] | 2.19±0.39[d] | 1.25±0.23[d] | 151.88±35.35 |
| 200mg/kg | 4.65±0.31 | 174.25±66.19 | 0.13±0.05 | 3.25±0.46[a] | 1.74±0.24 | 1.88±0.36[g] | 155.50±37.64 |
| 400mg/kg | 4.76±0.66 | 148.88±49.62 | 0.13±0.05 | 3.33±0.49[g] | 1.51±0.43[g] | 2.33±0.56[g] | 150.38±33.07 |
| BJIKT 400mg/kg | 4.85±0.21 | 142.88±51.77 | 0.10±0.00 | 3.20±0.33 | 1.63±0.30 | 2.01±0.43 | 150.25±27.63 |

| Groups | LDH×100 | Ca | P | Na | K | Cl |
|---|---|---|---|---|---|---|
| Vehicle Controls | 9.46±4.24 | 10.60±0.60 | 17.21±0.73 | 147.00±1.41 | 5.30±1.58 | 113.88±1.48 |
| Gefitinib single 160mg/kg | 20.65±11.37[a] | 10.20±0.80 | 16.44±2.01 | 145.13±2.70 | 5.84±1.94 | 113.38±2.00 |
| Gefitinib and BJIKT co-administered | | | | | | |
| 100mg/kg | 18.83±5.12[a] | 10.13±0.73 | 16.03±2.25 | 144.38±3.48 | 5.41±2.49 | 112.50±2.56 |
| 200mg/kg | 10.67±5.10 | 10.35±0.57 | 16.53±1.17 | 144.13±2.36 | 6.74±2.66 | 113.50±1.85 |
| 400mg/kg | 9.92±1.83 | 10.31±0.56 | 16.11±1.64 | 145.00±1.64 | 6.08±2.28 | 116.00±6.99 |
| BJIKT single 400mg/kg | 8.85±1.93 | 10.11±0.82 | 16.68±1.99 | 145.25±3.92 | 5.73±2.86 | 113.75±5.09 |

Values are expressed as mean ± S.D. of eight mice
BJIKT - Bojungikgi-tang extracts, which were purchase from Hanpoong Pharm & Foods (Seoul,Korea)

FIG. 25

| | Spleen | | | | | |
| --- | --- | --- | --- | --- | --- | --- |
| | Submandibular Lymph node | | | | | |

Necropsy Finding at Sacrifice (Day 28)       [Group summary]

| Groups | Vehicle control | Gefitinib single 160mg/kg | Gefitinib 160mg/kg and BJIKT-co administration 100mg/kg | 200mg/kg | 400mg/kg | BJIKT Single 400mg/kg |
| --- | --- | --- | --- | --- | --- | --- |
| Lung | | | | | | |
|   Normal | 7/8 | 6/8 | 7/8 | 7/8 | 7/8 | 7/8 |
|   CG | 1/8 | 2/8 | 1/8 | 1/8 | 1/8 | 1/8 |
|   1+ | 1/8 | 2/8 | 1/8 | 1/8 | 1/8 | 1/8 |
| Thymus | | | | | | |
|   Normal | 6/8 | 5/8 | 8/8 | 6/8 | 8/8 | 8/8 |
|   Atrophy | 2/8 | 3/8 | 0/8 | 2/8 | 0/8 | 0/8 |
|   1+ | 2/8 | 3/8 | 0/8 | 2/8 | 0/8 | 0/8 |
| Spleen | | | | | | |
|   Normal | 5/8 | 0/8 | 0/8 | 4/8 | 5/8 | 7/8 |
|   Atrophy | 1/8 | 0/8 | 0/8 | 0/8 | 0/8 | 0/8 |
|   1+ | 1/8 | 0/8 | 0/8 | 0/8 | 0/8 | 0/8 |
|   Hypertrophy | 1/8 | 8/8 | 8/8 | 4/8 | 3/8 | 1/8 |
|   1+ | 1/8 | 4/8 | 6/8 | 4/8 | 3/8 | 1/8 |
|   2+ | 0/8 | 2/8 | 0/8 | 0/8 | 0/8 | 0/8 |
|   3+ | 0/8 | 2/8 | 2/8 | 0/8 | 0/8 | 0/8 |
| Liver | | | | | | |
|   Normal | 8/8 | 0/8 | 1/8 | 7/8 | 7/8 | 8/8 |
|   DC+ | 0/8 | 8/8 | 7/8 | 1/8 | 1/8 | 0/8 |
|   1+ | 0/8 | 8/8 | 7/8 | 1/8 | 1/8 | 0/8 |
| Lymph node | | | | | | |
|   Normal | 6/8 | 0/8 | 0/8 | 0/8 | 1/8 | 7/8 |
|   Hypertrophy | 2/8 | 8/8 | 8/8 | 8/8 | 7/8 | 1/8 |
|   1+ | 2/8 | 3/8 | 5/8 | 7/8 | 5/8 | 1/8 |
|   2+ | 0/8 | 5/8 | 2/8 | 1/8 | 2/8 | 0/8 |
|   3+ | 0/8 | 0/8 | 1/8 | 0/8 | 0/8 | 0/8 |
| Other | | | | | | |
|   Normal | 8/8 | 8/8 | 8/8 | 8/8 | 8/8 | 8/8 |

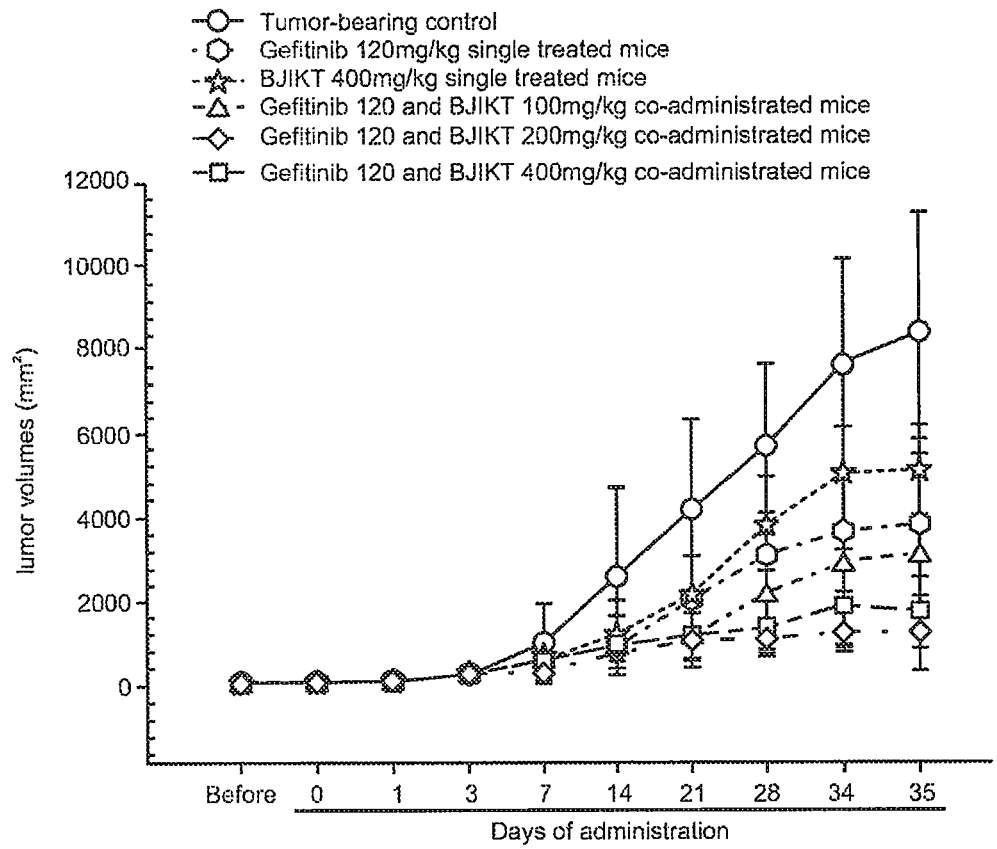

| Groups | Tumor volume (mm³) | | | Changes (mm³) [B-A] |
|---|---|---|---|---|
| | 1 day before first administration | First administration [A] | Sacrifice [B] | |
| Control | | | | |
| TB | 152.34±50.46 | 152.34±50.46 | 8357.98±2884.10 | 8205.64±2818.21 |
| Single treated | | | | |
| Gefitinib | 138.02±29.01 | 137.78±27.18 | 3795.46±1638.24[b] | 3657.68±1625.43[b] |
| BJIKT | 144.73±44.59 | 146.74±47.05 | 5121.38±1085.27 | 4974.64±1056.96 |
| Gefitinib and BJIKT co-administered | | | | |
| 100mg/kg | 148.55±37.52 | 149.89±40.20 | 3116.09±2754.86[b] | 2966.20±2721.73[b] |
| 200mg/kg | 133.94±36.24 | 134.81±38.07 | 1771.93±840.14[ad] | 1637.13±814.03[cd] |
| 400mg/kg | 142.95±36.44 | 153.71±30.85 | 1364.94±483.74[ac] | 1211.23±502.44[cd] |

Values are expressed mean ± S.D. of six mice

BJIKT - Bojungikgi-tang extracts, which were purchase from Hanpoong Pharm & Foods (Seoul, Korea)
TB = tumor-bearing Gefitinib 120mg/kg or BJIKT 400mg/kg were administered in single treated groups

[a]$p<0.01$ and [b]$p<0.05$ as compared with TB control by MW test
[c]$p<0.01$ and [d]$p<0.05$ as compared with gefitinib single treated mice by MW test

FIG. 36

| Groups | Tumor mass | spleen | submandibular lymph node | Periovarian fat pad |
|---|---|---|---|---|
| Controls | | | | |
| Intact | | 0.090±0.043 | 0.012±0.002 | 0.119±0.075 |
| TB | 6.739±1.317 | 0.043±0.006$^f$ | 0.002±0.001$^f$ | 0.016±0.006$^f$ |
| Single treated | | | | |
| Gefitinib | 4.102±0.459$^b$ | 0.049±0.012$^f$ | 0.004±0.002 | 0.016±0.005$^f$ |
| BJIKT | 5.190±1.335$^f$ | 0.067±0.012$^{fg}$ | 0.007±0.003$^{abc}$ | 0.041±0.013$^{abd}$ |
| Gefitinib and BJIKT co-administered | | | | |
| 100mg/kg | 2.913±1.449$^{gh}$ | 0.061±0.006$^{fg}$ | 0.006±0.003$^{ab}$ | 0.019±0.003$^{fgh}$ |
| 200mg/kg | 2.079±1.247$^{gh}$ | 0.067±0.009$^{gh}$ | 0.008±0.003$^{abd}$ | 0.031±0.007$^{fgh}$ |
| 400mg/kg | 1.879±0.752$^{hd}$ | 0.071±0.012$^{gh}$ | 0.010±0.004$^{abd}$ | 0.037±0.007$^{ghi}$ |

Values are expressed mean ± S.D., g of six mice

BJIKT - Bojungikgi-tang extracts, which were purchase from Hanpoong Pharm & Foods (Seoul, Korea)
TB = tumor-bearing Gefitinib 120mg/kg or BJIKT 400mg/kg were administered in single treated groups $^a p<0.01$ as compared with intact control by LSD test
$^b p<0.01$ and $^c p<0.05$ as compared with TB control by LSD test
$^d p<0.01$ and $^e p<0.05$ as compared with gefitinib single treated mice by LSD test
$^f p<0.01$ as compared with intact control by MW test
$^g p<0.01$ as compared with TB control by MW test
$^h p<0.01$ and $^i p<0.05$ as compared with gefitinib single treated mice by MW test

FIG. 37A

| Groups | Tumor mass | spleen | submendibular lymph node | Periovarian fat pad |
|---|---|---|---|---|
| Controls | | | | |
| Intact | | 0.392±0.143 | 0.054±0.008 | 0.516±0.293 |
| TB | 29.786±6.662 | 0.188±0.023$^f$ | 0.010±0.006$^f$ | 0.073±0.029$^f$ |
| Single treated | | | | |
| Gefitinib | 18.743±2.288$^h$ | 0.223±0.051$^f$ | 0.016±0.012 | 0.073±0.023$^f$ |
| BJIKT | 23.256±4.912$^c$ | 0.301±0.044$^{fg}$ | 0.032±0.012$^{abc}$ | 0.186±0.062$^{abd}$ |
| Gefitinib and BJIKT co-administered | | | | |
| 100mg/kg | 12.625±6.561$^{id}$ | 0.267±0.0.48$^{fg}$ | 0.024±0.011$^{ab}$ | 0.081±0.014$^i$ |
| 200mg/kg | 9.355±5.819$^{id}$ | 2.295±0.039$^{gh}$ | 0.035±0.015$^{abd}$ | 0.135±0.031 |
| 400mg/kg | 7.735±2.956$^{id}$ | 0.297±0.062$^{gh}$ | 0.042±0.017$^{abd}$ | 0.155±0.033 |

Values are expressed mean + S.D., % vs body weight of six mice

BJIKT - Bojungikgi-tang extracts, which were purchase from Hanpoong Pharm & Foods (Seoul, Korea)
TB = tumor-bearing Gefitinib 120mg/kg or BJIKT 400mg/kg were administered in single treated groups $^a p<0.01$ as compared with intact control by LSD test
$^b p<0.01$ and $^c p<0.05$ as compared with TB control by LSD test
$^d p<0.01$ and $^e p<0.05$ as compared with gefitinib single treated mice by LSD test
$^f p<0.01$ as compared with intact control by MW test
$^g p<0.01$ as compared with TB control by MW test
$^h p<0.01$ and $^i p<0.05$ as compared with gefitinib single treated mice by MW test

FIG. 37B

| Groups | Tumor necrosis factor - α | Interleukin-1β | Interleukin-10 |
|---|---|---|---|
| Controls | | | |
| Intact | 98.92±20.03 | 32.71±4.45 | 84.93±10.63 |
| TB | 38.92±11.15[d] | 9.19±1.95[a] | 38.32±11.83[a] |
| Single treated | | | |
| Gefitinib | 41.54±5.29[d] | 9.96±2.48[a] | 40.30±6.88[d] |
| BJIKT | 68.83±21.92[abd] | 15.74±3.73[abd] | 56.24±9.51[abc] |
| Gefitinib and BJIKT co-administered | | | |
| 100mg/kg | 44.11±12.61[a] | 11.00±1.84[d] | 43.23±13.10[a] |
| 200mg/kg | 57.38±7.46[acd] | 14.77±4.05[abc] | 55.18±7.81[abd] |
| 400mg/kg | 69.83±12.84[abd] | 16.65±3.52[abd] | 61.45±12.41[abd] |

Values are expressed mean ± S.D. pg/ml of six mice
BJIKT - Bojungikgi-tang extracts, which were purchase from Hanpoong Pharm & Foods (Seoul,Korea)
TB = tumor-bearing Gefitinib 120mg/kg or BJIKT 400mg/kg were administered in single treated groups
[a] $p<0.01$ as compared with intact control by LSD test
[b] $p<0.01$ and [c] $p<0.05$ as compared with TB control by LSD test
[d] $p<0.01$ and [e] $p<0.05$ as compared with gefitinib single treated mice by LSD test

FIG. 39

| Groups | Tumor cell Volume (%/mm²) | Apoptotic cell percentages (%) | immunoreactive cell percentages (%tumor cells) | | | |
|---|---|---|---|---|---|---|
| | | | Caspase-3 | PARP | COX-2 | iNOS | TNF-α |
| Control | | | | | | | |
| TB | 78.61±11.94 | 17.83±4.62 | 13.83±3.49 | 17.67±3.33 | 56.50±12.76 | 22.17±7.73 | 15.83±4.26 |
| Single treated | | | | | | | |
| Gefitinib | 49.70±4.74$^d$ | 41.33±5.24$^a$ | 37.17±3.76$^d$ | 39.83±3.76$^a$ | 32.50±6.63$^a$ | 24.17±5.85 | 17.83±2.32 |
| BJIKT | 74.59±14.74$^f$ | 28.00±10.04$^{bc}$ | 19.67±3.08$^{ef}$ | 26.50±7.34$^{bc}$ | 46.83±10.23$^{bc}$ | 28.33±4.63 | 20.67±1.86$^{ag}$ |
| Gefitinib and BJIKT co-administered | | | | | | | |
| 100mg/kg | 54.12±6.95$^d$ | 50.00±3.74$^a$ | 40.33±4.76$^a$ | 36.50±8.64$^a$ | 39.33±7.09$^a$ | 31.00±8.25$^b$ | 22.33±6.38 |
| 200mg/kg | 39.46±6.77$^{dg}$ | 61.83±9.59$^{ac}$ | 50.33±7.39$^d$ | 52.33±7.61$^{ac}$ | 23.00±5.33$^a$ | 45.83±7.25$^{ac}$ | 42.17±10.32$^{df}$ |
| 400mg/kg | 28.54±5.27$^{df}$ | 75.67±10.50$^{ae}$ | 62.17±8.70$^{df}$ | 67.17±8.01$^{ae}$ | 11.50±2.74$^{ae}$ | 54.33±6.77$^{ae}$ | 64.17±7.68$^{df}$ |

Values are expressed mean ± S.D. pg/ml of six mice

BJIKT - Bojungikgi-tang extracts, which were purchase from Hanpoong Pharm & Foods (Seoul,Korea)
TB = tumor-bearing
PARP = cleaved poly(ADP-ribose) polymerase; COX-2-cyclooxygenase-2;iNOS=inducible nitric oxide synthases;TNF = tumor necrosis factor
Gefitinib 120mg/kg or BJIKT 400mg/kg were administered in single treated groups $^a$p<0.01 and $^b$p<0.05 as compared with TB control by LSD test
$^c$p<0.01 as compared with gefitinib single treated mice by LSD test
$^d$p<0.01 and $^e$p<0.05 as compared with TB control by MW test
$^f$p<0.01 and $^g$p<0.05 as compared with gefitinib single treated mice by MW test

FIG. 41

| Groups | Total thickness (mm/central regions) | White pulp numbers (/mm²) | White pulp diameters (μm/white pulp) |
|---|---|---|---|
| Controls | | | |
| Intact | 1.88±0.17 | 14.83±2.79 | 412.50±26.17 |
| TB | 1.22±0.17$^a$ | 4.50±1.05$^a$ | 210.22±15.81$^a$ |
| Single treated | | | |
| Gefitinib | 1.13±0.16$^a$ | 5.50±1.87$^a$ | 223.90±25.30$^a$ |
| BJIKT | 1.44±0.16$^{acd}$ | 9.17±1.47$^{abd}$ | 319.88±20.45$^{abd}$ |
| Gefitinib and BJIKT co-administered | | | |
| 100mg/kg | 1.30±0.16$^a$ | 7.17±1.17$^{ac}$ | 241.54±28.20$^{ac}$ |
| 200mg/kg | 1.51±0.15$^{abd}$ | 9.33±1.21$^{cbd}$ | 293.02±24.14$^{abd}$ |
| 400mg/kg | 1.63±0.16$^{abd}$ | 10.50±1.87$^{abd}$ | 316.13±13.70$^{abd}$ |

Values are expressed mean ± S.D. of six mice

BJIKT - Bojungikgi-tang extracts, which were purchase from Hanpoong Pharm & Foods (Seoul, Korea)
TB = tumor-bearing Gefitinib 120mg/kg or BJIKT 400mg/kg were administered in single treated groups $^a$p<0.01 as compared with intact control by LSD test
$^b$p<0.01 and $^c$p<0.05 as compared with TB control by LSD test
$^d$p<0.01 as compared with gefitinib single treated mice by LSD test

FIG. 48

| Groups | Total thickness (μm/central regions) | Cortex lymphoid cell follicle numbers (/mm²) | Cortex thickness (μm/lymph node) |
|---|---|---|---|
| Controls | | | |
| Intact | 889.49±108.22 | 11.50±1.87 | 437.12±90.38 |
| TB | 449.68±49.50$^a$ | 3.33±1.03$^a$ | 178.39±35.44$^f$ |
| Single treated | | | |
| Gefitinib | 483.04±70.44$^a$ | 3.83±1.72$^a$ | 207.27±9.27$^f$ |
| BJIKT | 770.82±117.09$^{bcd}$ | 6.17±1.47$^{abc}$ | 342.80±69.01$^{ghf}$ |
| Gefitinib and BJIKT co-administered | | | |
| 100mg/kg | 540.78±78.64$^a$ | 4.83±1.72$^a$ | 226.75±30.66$^h$ |
| 200mg/kg | 688.47±125.46$^{acd}$ | 6.33±1.63$^{ace}$ | 329.65±28.20$^{df}$ |
| 400mg/kg | 869.64±112.88$^{cd}$ | 7.17±2.32$^{acd}$ | 397.04±39.64$^{hf}$ |

Values are expressed mean ± S.D. pg/ml of six mice

BJIKT - Bojungikgi-tang extracts, which were purchase from Hanpoong Pharm & Foods (Seoul,Korea)
TB = tumor-bearing Gefitinib 120mg/kg or BJIKT 400mg/kg were administered in single treated groups $^a$p<0.01 and $^b$p<0.05 as compared with intact control by LSD test
$^c$p<0.01 as compared with TB control by LSD test
$^d$p<0.01 and $^e$p<0.05 as compared with gefitinib single treated mice by LSD test
$^f$p<0.01 and $^g$p<0.05 as compared with intact control by MW test
$^h$p<0.01 and $^i$p<0.05 as compared with TB control by MW test
$^j$p<0.01 as compared with gefitinib single treated mice by MW test

FIG. 50

| Groups | Total thickness (mm/central regions) | White adipocyte diameters (μm) |
|---|---|---|
| Controls | | |
| Intact | 1.78±0.34 | 62.13±7.69 |
| TB | 0.40±0.11[a] | 23.93±3.62[a] |
| Single treated | | |
| Gefitinib | 0.40±0.11[a] | 22.25±3.61[a] |
| BJIKT | 1.03±0.25[a,b] | 48.83±8.06[a,b,d] |
| Gefitinib and BJIKT co-administered | | |
| 100mg/kg | 0.70±0.16[a,g] | 26.54±3.81[b] |
| 200mg/kg | 0.99±0.23[a,g] | 31.78±2.00[a,c,d] |
| 400mg/kg | 1.21±0.18[a,g] | 48.48±5.69[a,b,d] |

Values are expressed mean ± S.D. pg/ml of six mice

BJIKT - Bojungikgi-tang extracts, which were purchase from Hanpoong Pharm & Foods (Seoul,Korea)
TB = tumor-bearing Gefitinib 120mg/kg or BJIKT 400mg/kg were administered in single treated groups

[a] $p<0.01$ as compared with intact control by LSD test
[b] $p<0.01$ and [c] $p<0.05$ as compared with TB control by LSD test
[d] $p<0.01$ as compared with gefitinib single treated mice by LSD test
[e] $p<0.01$ as compared with intact control by MW test
[f] $p<0.01$ as compared with TB control by MW test
[g] $p<0.01$ as compared with gefitinib single treated mice by MW test

FIG. 52

COMPOSITION INCLUDING ORIENTAL MEDICINE TO TREAT NEOPLASTIC DISEASE

CROSS-REFERENCE TO RELATED APPLICATIONS

This application is a 371 of PCT/KR2014/004375, filed May 15, 2014, which claims the benefit of Korean Patent Application Nos. 10-2013-0055364, filed May 15, 2013, 10-2013-0063002, filed May 31, 2013, 10-2014-0041519, filed Apr. 7, 2014 and 10-2014-0041517, filed Apr. 7, 2014, the contents of each of which are incorporated herein by reference.

BACKGROUND

1. Field of the Invention

The present invention relates to a composition for treating a neoplastic disease, which includes an oriental medicine.

2. Discussion of Related Art

Breast cancer is a cancer that occurs in milk ducts and lobules of a breast, and various factors such as administration of female hormone drugs, family history, medical history, childbirth experience, eating habits, etc., have been cited recently as causes, but the cause of breast cancer is still unclear. Today, an occurrence rate of breast cancer in females is rapidly increasing, and is also increasing in females in their twenties and thirties due to factors such as low fertility, a short nursing period, early menarche, late menopause, etc.

Tamoxifen is a representative non-steroidal estrogen agonist-antagonist oral anticancer agent, which is frequently used as a medicine for various diseases including breast cancer, and has also recently been used to treat infertility, gynecomastia, bipolar disorder, Albright's disease, Riedel's struma, angiogenesis, and regulating gene expression. However, tamoxifen has various side effects not intended by clinics, including bone loss, cervical and endometrial adenocarcinoma, thromboembolism, fatty liver, cognitive and memory impairments, hyposexuality, premature closure of the growth plate, immunosuppression, hemolytic anemia and hypersensitivity, and is particularly known to cause damage to reproductive organs through hormone disorders. In addition, an increase in lipid peroxidation and depletion of an antioxidant preventing system are involved in various toxicities of tamoxifen.

Moreover, in some patients, resistance to tamoxifen due to long-term administration thereof and recurrence of breast cancer are caused, which also indicates a risk of endometrial cancer. Accordingly, there have been attempts to solve the toxicity problem of tamoxifen caused by combined administration of various drugs including an antioxidant, and various attempts to overcome resistances due to the combined administration and increase efficacy of tamoxifen.

Meanwhile, jaeumganghwa-tang is a representative yin-strengthening medicine, which is frequently used for gynecological diseases in Oriental medicine, and is a composite formulation composed of a total of twelve natural substances including Glycyrrhizae Rhizoma, Angelicae Gigantis Radix, Zizyphi Ffructus, Liriopis Tuber, Atractylodis Rhizoma Alba, Paeoniae Radix, Anemarrhena Rhizoma, Rehmanniae Radix Crudus, Citri Unshii Pericarpium, Phellodendri Cortex, Zingiberis Rhizoma Crudus, and Asparagi Tuber. Currently, anti-inflammatory and immune activitation effects have been known, and particularly, an effect of jaeumganghwa-tang on reducing the side effects of tamoxifen has been reported recently.

Gefitinib is an oral anticancer agent, which is a representative epidermal growth factor receptor (EGFR) inhibitor having been widely used as a therapeutic agent for treating various malignant tumors including breast cancer and lung cancer, and is generally known to inhibit an EGFR tyrosine kinase domain. Also, gefitinib is known as a target-directed anticancer agent to exhibit very lower toxicity than conventional cytotoxic anticancer agents.

However, gefitinib has a variety of unwanted side effects such as skin rashes, diarrhea, nausea, vomiting, loss of appetite, gastritis, anhydremia, paronychia, hepatotoxicity, lack of energy, conjunctivitis, blepharitis, interstitial pulmonary diseases, corneal erosion, and madarosis, and hypersensitivity reactions to gefitinib itself or gefitinib compositions have been issued. Also, an increase in lipid peroxidation by metabolites produced in the liver and thus hepatotoxicity caused by damage of an antioxidative defense system are problematic. In recent years, problems regarding resistance have been issued due to occurrence of drug-resistant malignant tumor cells by mutation of EGFR.

To solve the above problems, many attempts are currently being made to solve problems regarding toxicity and resistance of gefitinib through co-administration of a natural substance and a drug including various antioxidants.

Meanwhile, bojungikgi-tang is a representative tonic medicine, which has been frequently used for fatigue recovery in Oriental medicine, and is a composite formulation composed of a total of ten natural substances including Astragali Radix, Atractylodis Rhizoma, Ginseng Radix Alba, Angelicae Gigantis Radix, Bupleuri Radix, Zizyphi Fructus, Citri Unshii Pericarpium, Glycyrrhizae Rhizoma, Cimicifugae Rhizoma, and Zingiberis Rhizoma Siccus. Currently, immunoregulatory, antiallergenic, and antioxidant effects of bojungikgi-tang have been relatively well known, and particularly, a fatigue recovery effect of the bojungikgi-tang in cancer patients has been reported.

Recently, due to improvement in living environments, abundant eating living, the spread of westernized eating habits along with high economic growth in Korea, chronic adult diseases such as a cancer, arteriosclerosis, stroke, a neoplastic disease, and hypertension, which may be caused by imbalanced and excessive nutrition intake, have been increasing.

Particularly, the incidence of liver cancer in Korea was known as the highest in the world, and the incidence rate of liver cancer was known as a third place following stomach cancer and lung cancer in Korea. Over the past few decades, methods for treating liver cancer such as surgery, radiation therapy and chemotherapy were performed. At the same time, research, development and commercialization of liver cancer medications, hepatitis medications, hepatitis vaccines and the like were performed. However, the incidence rate and death rate of liver cancer were not significantly reduced. This is because research has been performed on the method of treating liver cancer rather than preventing liver cancer over the past few decades.

Meanwhile, sorafenib is a representative oral anticancer agent that suppresses tyrosine protein kinases and Raf kinases and is frequently used in advanced renal cancer and liver cancer. Recently, it has been known that sorafenib has some effects on inactive thyroid cancer, squamous cell carcinoma of lung, recurrent glioblastoma, and the like. However, frequent immunosuppression characterized in severe lymphopenia, and various unintended side effects such as skin rashes, hand-foot skin reactions, diarrhea, hypertension, reversible posterior leukoencephalopathy syndrome and polycythemia occur in the clinical field. A hypersensitivity reaction to sorafenib has also been reported.

In addition, it has been known that sorafenib influences microsomal enzymes in the liver such as dexamethasone, ketoconazole, rifampin, and doxorubicin, or has a serious interaction with drugs metabolized by liver microsomal enzymes or drugs metabolized by uridine diphosphate-glucuronosyltransferase. Therefore, efforts have been made to solve the toxicity of sorafenib by being co-administered with various drugs, paying attention to drug interaction, and various attempts have also been made to overcome resistance to and increase the drug effects of sorafenib by co-administration with other drugs.

Meanwhile, yukmijihwang-tang is a representative formulation frequently used for various kidney diseases in Oriental medicine, and is a composite formulation composed of a total of six natural substances including Rehmanniae Radix Preparat, Dioscoreae Rhizoma, Corni Fructus, Alismatis Rhizoma, Hoelen, and Moutan Cortex, which is the most frequently used in China and Korea.

SUMMARY OF THE INVENTION

The present invention is directed to providing a composition for treating breast cancer, in which jaeumganghwa-tang is co-administered with an anticancer agent to enhance an anticancer effect and reduce side effects.

The present invention is directed to providing a composition for treating lung cancer, in which bojungikgi-tang is co-administered with an anticancer agent to enhance an anticancer effect and reduce side effects.

The present invention is directed to providing a composition for treating a neoplastic disease using a bojungikgi-tang extract.

The present invention is directed to providing a composition for treating a neoplastic disease using a yukmijihwang-tang extract.

However, technical objects to be accomplished in the present invention are not limited to the above-described object, and other objects which will not be described will be clearly understood to those of ordinary skill in the art from the following descriptions.

One aspect of the present invention provides a composition for treating breast cancer, which includes an anticancer agent and jaeumganghwa-tang.

In one embodiment of the present invention, the anticancer agent may be tamoxifen.

In another embodiment of the present invention, the jaeumganghwa-tang may contain Glycyrrhizae Rhizoma, Angelicae Gigantis Radix, Zizyphi Ffructus, Liriopis Tuber, Atractylodis Rhizoma Alba, Paeoniae Radix, Anemarrhena Rhizoma, Rehmanniae Radix Crudus, Citri Unshii Pericarpium, Phellodendri Cortex, Zingiberis Rhizoma Crudus, and Asparagi Tuber.

In still another embodiment of the present invention, the anticancer agent and the jaeumganghwa-tang may be premixed to be formulated, or separately formulated.

In still another embodiment of the present invention, the anticancer agent and jaeumganghwa-tang may be parenterally, orally, locoregionally, or percutaneously administered.

In yet another embodiment of the present invention, the administration of the jaeumganghwa-tang may start within 30 minutes after the administration of the anticancer agent.

Another aspect of the present invention provides a composition for treating lung cancer, which includes an anticancer agent and bojungikgi-tang.

In one embodiment of the present invention, the anticancer agent may be gefitinib.

In another embodiment of the present invention, the bojungikgi-tang may contain Astragali Radix, Atractylodis Rhizoma, Ginseng Radix Alba, Angelicae Gigantis Radix, Bupleuri Radix, Zizyphi Fructus, Citri Unshii Pericarpium, Glycyrrhizae Rhizoma, Cimicifugae Rhizoma, and Zingiberis Rhizoma Siccus.

In still another embodiment of the present invention, the anticancer agent and the bojungikgi-tang may be premixed to be formulated, or separately formulated.

In yet another embodiment of the present invention, the anticancer agent and bojungikgi-tang may be parenterally, orally, locoregionally, or percutaneously administered.

In yet another embodiment of the present invention, the administration of the bojungikgi-tang may start within 30 minutes after the administration of the anticancer agent.

Still another aspect of the present invention provides a composition for treating a neoplastic disease, which includes an anticancer agent and a bojungikgi-tang extract.

In one embodiment of the present invention, the anticancer agent may be sorafenib.

In another embodiment of the present invention, the neoplastic disease may be liver cancer or a renal cancer.

In still another embodiment of the present invention, the bojungikgi-tang extract may contain Astragali Radix, Atractylodis Rhizoma, Ginseng Radix Alba, Angelicae Gigantis Radix, Bupleuri Radix, Zizyphi Fructus, Citri Unshii Pericarpium, Glycyrrhizae Rhizoma, Cimicifugae Rhizoma, and Zingiberis Rhizoma Siccus.

In yet another embodiment of the present invention, the anticancer agent and the bojungikgi-tang extract may be premixed to be formulated, or separately formulated.

In yet another embodiment of the present invention, the anticancer agent and bojungikgi-tang extract may be parenterally, orally, locoregionally, or percutaneously administered.

In yet another embodiment of the present invention, the administration of the bojungikgi-tang extract may start 30 minutes to 4 hours after the administration of the anticancer agent.

Yet another aspect of the present invention provides a composition for treating a neoplastic disease, which includes an anticancer agent and a yukmijihwang-tang extract.

In one embodiment of the present invention, the anticancer agent may be sorafenib.

In another embodiment of the present invention, the neoplastic disease may be liver cancer or renal cancer.

In another embodiment of the present invention, the yukmijihwang-tang extract may contain Rehmanniae Radix Preparat, Dioscoreae Rhizoma, Corni Fructus, Alismatis Rhizoma, Hoelen, and Moutan Cortex.

In still another embodiment of the present invention, the anticancer agent and the yukmijihwang-tang extract may be premixed to be formulated, or separately formulated.

In yet another embodiment of the present invention, the anticancer agent and the yukmijihwang-tang extract may be parenterally, orally, locoregionally, or percutaneously administered.

In yet another embodiment of the present invention, the administration of the yukmijihwang-tang extract may start 30 minutes to 4 hours after the administration of the anticancer agent.

BRIEF DESCRIPTION OF DRAWINGS

FIG. 2 shows a change in blood tamoxifen concentration when jaeumganghwa-tang is orally co-administered once within 5 minutes;

FIG. 3 shows comparison of Tmax, Cmax, AUC, $t_{1/2}$, and $MRT_{inf}$ values between when the jaeumganghwa-tang is orally co-administered once and when tamoxifen is administered alone;

FIGS. 5A and 5B show comparison of Tmax, Cmax, AUC, $t_{1/2}$, and $MRT_{inf}$ values between when the jaeumganghwa-tang is repeatedly pre-administered for 6 days and repeatedly co-administered for 8 days within 5 minutes, and when tamoxifen is administered alone;

FIG. 11 shows changes in activities of splenic and peritoneal NK cells for each group;

FIG. 12 shows cytokine contents in spleens for each group;

FIG. 24 shows 14 types of hematologic changes;

FIG. 25 shows the results of 20 blood biochemical tests;

FIG. 26 shows the images of a spleen and submandibular lymph nodes after necropsy is performed on a mouse (top), and a diagram showing changes observed in each group based on references shown in the top image (bottom);

FIG. 31 shows the results obtained by combining the results shown in FIGS. 27 to 30;

FIG. 32 shows the results obtained by observing a degree of lipid peroxidation in the liver, a content of an antioxidant substance, or a change in the content;

FIG. 36 shows comparison of changes in tumor volumes ($mm^3$) between groups;

FIG. 37(A) shows the absolute weight change results obtained by observing changes in tumor weight and FIG. 37(B) shows the relative weight change results obtained by observing changes in tumor weight;

FIG. 39 shows the results obtained by estimating contents of TNF-α, IL-1β, and IL-10 based on contents of cytokines in the spleen;

FIG. 41 shows changes in volume of a tumor mass and number of apoptotic cells;

FIG. 48 shows the results obtained by estimating thicknesses of the spleens and diameters and numbers of white pulps based on the histopathological changes in the spleens;

FIG. 50 shows the results obtained by estimating changes in thicknesses of the submandibular lymph nodes, thicknesses of cortices, and numbers of follicles in the cortices based on the histopathological changes in the submandibular lymph nodes;

FIG. 52 shows the results obtained by measuring thicknesses of the periovarian fat pads, and a mean diameter of white adipocytes;

DETAILED DESCRIPTION OF EXEMPLARY EMBODIMENTS

Figure 1:
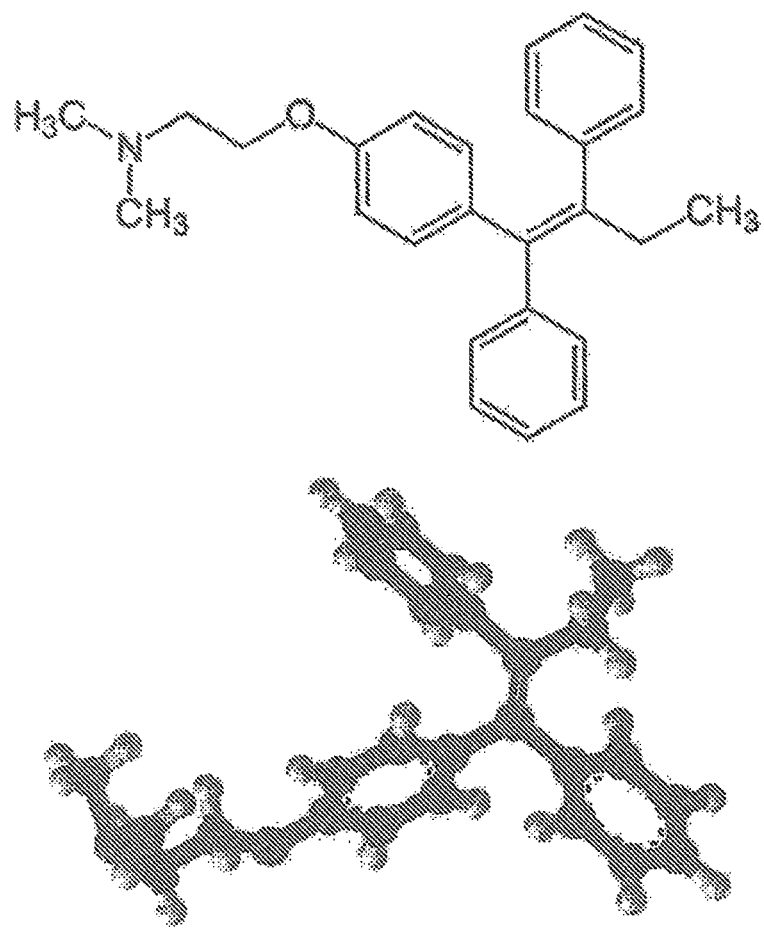
FIG. 1 shows a structural formula of tamoxifen used in the present invention.

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention.

The present inventors focused on an oriental medicine to develop a composition which could reduce various side effects such as cachexia occurring when tamoxifen was administered to treat breast cancer, and further increase an anticancer effect, and confirmed that jaeumganghwa-tang among such oriental medicines has an excellent effect on enhancing anticancer treatment, thereby completing the present invention.

Accordingly, the present invention is directed to providing a composition for treating breast cancer, which includes an anticancer agent and jaeumganghwa-tang.

In one embodiment of the present invention, the anticancer agent may be any one that can be used in a neoplastic disease without limitation, and particularly, tamoxifen may be used as an anticancer agent to treat breast cancer.

In another embodiment of the present invention, the jaeumganghwa-tang contains Glycyrrhizae Rhizoma, Angelicae Gigantis Radix, Zizyphi Ffructus, Liriopis Tuber, Atractylodis Rhizoma Alba, Paeoniae Radix, Anemarrhena Rhizoma, Rehmanniae Radix Crudus, Citri Unshii Pericarpium, Phellodendri Cortex, Zingiberis Rhizoma Crudus, and Asparagi Tuber.

In still another embodiment of the present invention, the anticancer agent and the jaeumganghwa-tang may be premixed to be formulated, or separately formulated.

The jaeumganghwa-tang may be administered within 30 minutes, preferably, 15 minutes, and more preferably 5 minutes, after the anticancer agent has been administered, but the present invention is not limited thereto.

The anticancer agent and the jaeumganghwa-tang may be parenterally, orally, locoregionally or percutaneously administered. It is preferable that the jaeumganghwa-tang be orally administered, but the administration route of the jaeumganghwa-tang may be suitably selected by those skilled in the art according to a patient's condition and body weight, severity of a disease, and duration of administration.

The term "individuals" used herein refer to subjects having a disease to be treated, and more specifically, mammals such as humans, or non-human primates such as mice, rats, dogs, cats, horses, and cattle.

The composition of the present invention may include a pharmaceutically available carrier. The pharmaceutically available carrier may include, but is not limited to, a saline, polyethyleneglycol, ethanol, vegetable oil, and isopropyl myristate.

In one embodiment of the present invention, a preferable dose of the therapeutic composition may vary depending on a patient's condition and body weight, severity of a disease, a dosage form, and administration route and duration, and may be suitably selected by those skilled in the art. However, the composition is preferably administered daily at a dose of 0.001 to 300 mg/kg (body weight), and more preferably 0.01 to 200 mg/kg (body weight).

The composition for treating breast cancer of the present invention may be administered to mammals such as rats, mice, livestock, or humans by various routes. There is no limitation on an administration method, and the composition may be administered by oral, rectal, or intravascular administration, or muscular, subcutaneous, endometrial or intracerebroventricular injection.

The composition for treating breast cancer including the anticancer agent and the jaeumganhwa-tang of the present invention may enhance an anticancer effect, and reduce various side effects occurring when am anticancer agent is conventionally administered alone.

The present inventors focused on an oriental medicine to develop a composition which could reduce various side effects occurring when gefitinib was administered to treat lung cancer, and further increase an anticancer effect, and confirmed that bojungikgi-tang among the oriental medicines has excellent effects on stimulating and differentiating stem cells, thereby completing the present invention.

Therefore, the present invention is directed to providing a composition for treating a lung cancer disease, which includes an anticancer agent and bojungikgi-tang.

According to one exemplary embodiment of the present invention, the anticancer agent may be any one that can be used for a neoplastic disease without limitation, but particularly, gefitinib is used as the anticancer agent to treat lung cancer.

According to another exemplary embodiment of the present invention, the bojungikgi-tang includes Astragali Radix, Atractylodis Rhizoma, Ginseng Radix Alba, Angelicae Gigantis Radix, Bupleuri Radix, Zizyphi Fructus, Citri Unshii Pericarpium, Glycyrrhizae Rhizoma, Cimicifugae Rhizoma, and Zingiberis Rhizoma Siccus.

According to still another exemplary embodiment of the present invention, the anticancer agent and the bojungikgi-tang may be premixed and formulated, or formulated separately.

The administration duration of bojungikgi-tang may be initiated within 30 minutes, preferably 15 minutes, and most preferably 5 minutes after the administration of the anticancer agent, but the present invention is not limited thereto.

The anticancer agent and bojungikgi-tang may be administered parenterally, orally, locoregionally, or percutaneously. The bojungikgi-tang may be orally administered, but may be suitably selected by those skilled in the related art according to a condition and body weight of a patient, the severity of a disease, duration of administration, etc.

The term "individuals" used herein refer to subjects having a disease to be treated, and more specifically, mammals such as humans, or non-human primates such as mice, rats, dogs, cats, horses, and cattle.

The composition according to the present invention may include a pharmaceutically acceptable carrier. The pharmaceutically acceptable carrier may include a physiological saline solution, polyethylene glycol, ethanol, vegetable oil, and isopropyl myristate, but the present invention is not limited thereto.

According to one exemplary embodiment of the present invention, a preferred dose of the composition for treating lung cancer may vary depending on a patient's condition and body weight, severity of a disease, a dosage form, and administration route and duration, but may be suitably selected by those skilled in the related art. However, the composition is preferably administered daily at a dose of 0.001 to 300 mg/kg (body weight), and more preferably 0.01 to 200 mg/kg (body weight).

The composition for treating lung cancer according to the present invention may be administered to a mammal such as a rat, a mouse, livestock, and a human through various routes of administration. Methods of administration are not particularly limited. For example, the composition may be administered orally, or rectally, or by intravenous, intramuscular, subcutaneous, cervical epidural, or intracerebroventricular injection.

The composition including the anticancer agent and bojungikgi-tang to treat lung cancer according to the present invention enhances an anticancer effect and simultaneously reduces various side effects occurring when an anticancer agent was conventionally administered alone.

Moreover, the present inventors focused on an oriental medicine to develop a composition which could reduce various side effects occurring when an anticancer agent was administered to treat a neoplastic disease, and further improve an effect on treating a neoplastic disease, and confirmed that bojungikgi-tang among the oriental medicines has excellent effects on treating a neoplastic disease and reducing side effects, thereby completing the present invention.

Therefore, the present invention provides a composition for treating a neoplastic disease, which includes an anticancer agent and a bojungikgi-tang extract.

The term "bojungikgi-tang extract" used herein refers to an extract that is extracted from ten medical herbs. The ten medical herbs include Astragali Radix, Atractylodis Rhizoma, Ginseng Radix Alba, Angelicae Gigantis Radix, Bupleuri Radix, Zizyphi Fructus, Citri Unshii Pericarpium, Glycyrrhizae Rhizoma, Cimicifugae Rhizoma, and Zingiberis Rhizoma Siccus.

In an embodiment of the present invention, the anticancer agent and the bojungikgi-tang extract may be premixed and formulated, or separately formulated.

The bojungikgi-tang extract may be administered within 2 to 5 hours after the administration of the anticancer agent, preferably 3 to 4 hours, and most preferably 3 hours and 30 minutes, but the present invention is not limited thereto.

The anticancer agent used in the present invention is sorafenib, but the present invention is not limited thereto.

The anticancer agent and the bojungikgi-tang extract may be administered parenterally, orally, locoregionally, or percutaneously. The bojungikgi-tang extract is preferably administrated orally, but the administration route may be suitably selected by those skilled in the art depending on patients' conditions and body weights, severity of a disease, a duration of administration, and the like.

The term "individuals" used herein refer to subjects having a disease to be treated, and more specifically, mammals such as humans, or non-human primates such as mice, rats, dogs, cats, horses, and cattle.

Also, the present invention may provide a composition for treating a neoplastic disease, which includes the bojungikgi-tang extract.

A pharmaceutical composition of the present invention may include a pharmaceutically acceptable carrier. The pharmaceutically acceptable carrier may include a normal saline solution, polyethylene glycol, ethanol, vegetable oils, isopropyl myristate and the like, but the present invention is not limited thereto.

In an exemplary embodiment of the present invention, a preferred dose of the pharmaceutical composition may vary depending on a patient's condition and body weight, severity of a disease, a dosage form, and administration route and duration, but may be suitably selected by those skilled in the related art. However, the composition is preferably administered daily at a dose of 0.001 to 800 mg/kg (body weight), and more preferably 0.01 to 500 mg/kg (body weight).

The pharmaceutical composition according to the present invention may be administered to a mammal such as a rat, a mouse, livestock, and a human through various routes of administration. Methods of administration are not particularly limited. For example, the composition may be administered orally, or rectally, or by intravenous, intramuscular, subcutaneous, cervical epidural, or intracerebroventricular injection.

The composition for treating a neoplastic disease of the present invention, which includes the bojungikgi-tang extract, may enhance a hypoglycemic effect or reduction of blood sugar level, and simultaneously reduce several side effects occurring when the anticancer agent is conventionally administered alone.

Furthermore, the present inventors focused on an oriental medicine to develop a composition which could reduce various side effects occurring when an anticancer agent was administered to treat a neoplastic disease, and further improve an effect on treating a neoplastic disease, and confirmed that yukmijihwang-tang among the oriental medicines has excellent effects on treating a neoplastic disease and reducing side effects, thereby completing the present invention.

Therefore, the present invention is directed to providing a composition for treating a neoplastic disease, which includes an anticancer agent and a yukmijihwang-tang extract.

The term "yukmijihwang-tang extract" used herein refers to an extract that is extracted from six medicinal herbs. The six medicinal herbs include Rehmanniae Radix Preparat, Dioscoreae Rhizoma, Corni Fructus, Hoelen, Alismatis Rhizoma, and Moutan Cortex.

In one exemplary embodiment of the present invention, the anticancer agent and the yukmijihwang-tang extract may be premixed and formulated, or separately formulated.

The yukmijihwang-tang extract may be administered within 2 to 5 hours, preferably 3 to 4 hours, and most preferably 3 hours and 30 minutes, after the administration of the anticancer agent, but the present invention is not limited thereto.

The anticancer agent used in the present invention may be sorafenib, but the present invention is not limited thereto.

The anticancer agent and the yukmijihwang-tang extract may be administered parenterally, orally, locoregionally, or percutaneously. The yukmijihwang-tang extract may be administered orally, but the administration route may be suitably selected by those skilled in the art depending on a patient's condition and body weight, severity of a disease, administration duration and the like.

The term "individuals" used herein refer to subjects having a disease to be treated, and more specifically, mammals such as humans, or non-human primates such as mice, rats, dogs, cats, horses, and cattle.

Also, the present invention may provide a composition for treating a neoplastic disease, which includes the yukmijihwang-tang extract.

The pharmaceutical composition of the present invention may include a pharmaceutically acceptable carrier. The pharmaceutically acceptable carrier may include a physiological saline solution, polyethylene glycol, ethanol, vegetable oil, and isopropyl myristate, but the present invention is not limited thereto.

According to one exemplary embodiment of the present invention, a preferred dose of the pharmaceutical composition may vary depending on a condition and body weight of a patient, the severity of a disease, the dosage form of a drug, and a route and duration of administration, but may be suitably selected by those skilled in the related art. However, the pharmaceutical composition may be preferably administered daily at a dose of 0.001 to 800 mg/body weight (kg), and more preferably 0.01 to 500 mg/kg.

The pharmaceutical composition according to the present invention may be administered to a mammal such as a rat, a mouse, livestock, and a human through various routes of administration. Methods of administration are not particularly limited. For example, the pharmaceutical composition may be administered orally, rectally, or by intravenous, intramuscular, subcutaneous, cervical epidural, or intracerebroventricular injection.

The composition for treating a neoplastic disease of the present invention, which includes the yukmijihwang-tang extract, may improve a hypoglycemic effect or reduction of blood sugar level, and simultaneously reduce several side effects occurring when only the anticancer agent is conventionally administered.

Hereinafter, exemplary embodiments according to the present invention will be provided to help understanding of the present invention. However, the following examples are merely provided such that the present invention can be more easily understood, and the scope of the present invention is not limited to the following examples.

Exemplary Embodiment 1

Example 1. Evaluation of Effects of Jaeumganghwa-Tang on Pharmacokinetics of Tamoxifen—Oral Co-Administration Once within 5 Minutes 1-1. Preparation of Materials Tamoxifen citrate was purchased from Hangzhou Tacon Co., Ltd. (Hangzhou, China), and a structure thereof is shown in FIG. 1.

Jaeumganghwa-tang was purchased from Hanpoong Pharmaceutics (Seoul, Korea), and components and their amounts are shown in Table 1. Jaeumganghwa-tang and tamoxifen used in the following Examples 2 and 3 will be the same as those used in Example 1.

TABLE 1

| Herbs | Scientific Names/Produce Region | Amounts (g) |
| --- | --- | --- |
| Glycyrrhizae Rhizoma | *Glycyrrhiza uralensis* Fisch | 0.50 |
| Angelicae Gigantis Radix | *Angelica gigas* Nakai | 0.83 |
| Zizyphi Fructus | *Zizyphus jujuba* var. *inermis* (Bunge) Rehder | 0.33 |
| Liriopis Tuber | *Liriope platyphylla* Wang et Tang | 0.83 |
| Atractylodis Rhizoma Alba | *Atractylodes ovata* (Thunb.) DC. | 1.00 |
| Paeoniae Radix | *Paeonia lactiflora* Pall. | 0.83 |
| Anemarrhena Rhizoma | *Anemarrhena asphodeloides* Bunge | 0.50 |
| Rehmanniae Radix Crudus | *Rehmannia glutinosa* var. *purpurea* (Makino) Makino & Nemoto | 0.83 |
| Citri Unshii Pericarpium | *Citrus unshiu* S. Marcov. | 0.83 |
| Phellodendri Cortex | *Phellodendron amurense* Ruprecht | 0.50 |
| Zingiberis Rhizoma Crudus | *Zingiber officinale* Roscoe | 0.33 |
| Asparagi Tuber | *Asparagus cochinchinensis* (Lour.) Merr. | 0.83 |
| Total | 12 types | 8.14 |

1-2. Preparation of Laboratory Animals In Example 1, as laboratory animals, male SD rats (SLC, Japan) were used. Ten rats were purchased and divided into two groups of 5 rats each. Tests were performed on a 50 mg/kg tamoxifen single treated group and a tamoxifen 50 mg/kg and jaeumganghwa-tang 100 mg/kg co-administered group.

1-3. Administration Method 50 mg/kg of tamoxifen (Hangzhou Tacon Co., Ltd, Hangzhou, China) was dissolved in sterile distilled water, the diluted tamoxifen was orally treated once at a dose of 5 ml/kg, 100 mg/kg of jaeumganghwa-tang was dissolved in sterile distilled water within 5 minutes after the tamoxifen treatment, and then the diluted jaeumganghwa-tang was orally treated once at a dose of 5 ml/kg. However, only the same dose of sterile distilled water, instead of jaeumganghwa-tang, was orally administered once to the tamoxifen single treated group.

30 minutes before the drug administration, and 30 minutes, 1, 2, 3, 4, 6, 8 and 24 hours after the administration, approximately 0.5 ml of whole blood was taken from a retro-orbital plexus using a tube treated with 50 IU of heparin (Sigma, Mo., USA), and then centrifuged at 13,000 rpm for 10 minutes to separate plasma. The separated plasma was stored at −70° C. before LC-MS/MS analyses.

1-4. Confirmation of Changes in Blood Tamoxifen Concentrations

A concentration of the tamoxifen in the separated plasma was measured by LC-MS/MS methods using Carbamazepine (Sigma, Mo., USA) as an internal standard. Chromatographic analysis was performed using Agilent 1100 Series HPLC (Agilent Technologies, CA, USA), and a column effluent was analyzed using an API 2000 triple-quadruple mass spectrometric detector (Applied Biosystems, Foster City, Calif., USA).

HPLC conditions used herein were as follows:
Column: Waters Xterra MS C18 (2.1×50 mm, 3.5 m) (Waters Corp., MA, USA)
Column oven: 30° C.
Mobile phase: Linear gradient from 5% acetonitrile/95% distilled water (0.1% formic acid) to 95% acetonitrile/5% distilled water (0.1% formic acid)
Flow rate: 0.35 ml/min
Injection volume: 5.0 μl
The LC-MS/MS method was as follows:
Ion source: Turbo Ion Spray (400° C.)
Polarity: Positive
Multiple reaction monitoring (MRM): Carbamazepine (IS)=m/z 237>194 (Retention time: 2.4 min), tamoxifen=372>72 (Retention time: 2.3 min)
Standard Curve: Analyst 1.4.2, Quadratic (1/x, no Iterate)

As a result, in the tamoxifen or tamoxifen+jaeumganghwa-tang co-administered group, tamoxifen was detected in the blood 30 minutes to 24 hours after the administration. In addition, in the tamoxifen single treated group, there were no significant changes in blood tamoxifen concentration, except the insignificant increase in blood tamoxifen concentrations detected in the tamoxifen+jaeumganghwa-tang co-administered group 30 minutes and 1 hour after the administration (FIG. 2).

In the tamoxifen+jaeumganghwa-tang co-administered group, compared to the tamoxifen single treated group, the blood tamoxifen concentrations measured 30 minutes, and 1, 2, 3, 4, 6, 8 and 24 hours after the administration changed by 26.53, 49.94, −6.49, −3.76, −6.59, −13.04, −15.36 and −8.81%, respectively.

1-5. Confirmation of $T_{max}$ Change

Blood $T_{max}$ of tamoxifen was detected at 4.80±1.10 hr in the tamoxifen+jaeumganghwa-tang co-administered group, which showed an insignificantly small decrease of −14.29%, compared to the blood Tmax of 5.60±2.19 hr in the tamoxifen single treated group (FIG. 3).

1-6. Confirmation of $C_{max}$ Change

Blood $C_{max}$ of tamoxifen in the tamoxifen+jaeumganghwa-tang co-administered group was 345.00±46.69 ng/ml, which showed an insignificantly small decrease of −5.27%, compared to the blood Cmax of 364.20±121.77 ng/ml in the tamoxifen single treated group (FIG. 3).

1-7. Confirmation of AUC Change

Blood tamoxifen AUC0-t and AUC0-inf in the tamoxifen+jaeumganghwa-tang co-administered group were 4.73±0.85 and 6.30±2.07 hr·g/ml, respectively, which showed insignificant decreases of −10.37 and −8.16%, compared to the AUC0-t and AUC0-inf of 5.27±1.79 and 6.86±2.92 hr·g/ml in the tamoxifen single treated group, respectively (FIG. 3).

1-8. Confirmation of $T_{1/2}$ Change

Blood $t_{1/2}$ of tamoxifen in the tamoxifen+jaeumganghwa-tang co-administered group was 10.91±3.99 hr, which showed an insignificant decrease of 14.16%, compared to the blood $t_{1/2}$ of 9.56±4.16 hr in the tamoxifen single treated group (FIG. 3).

1-9. Confirmation of $MRT_{inf}$ Change

Blood $MRT_{inf}$ of tamoxifen in the tamoxifen+jaeumganghwa-tang co-administered group was 16.02±5.60 hr, which showed an insignificantly small increase of 7.75%, compared to the blood $MRT_{inf}$ of tamoxifen of 14.87±6.29 hr in the tamoxifen single treated group (FIG. 3).

Summarizing the results of Example 1, it was observed that single-time co-administration of jaeumganghwa-tang within 5 minutes did not have any influence on absorption and excretion of tamoxifen, but to more precisely evaluate an interaction between jaeumganghwa-tang and tamoxifen, it seems that an effect of repeated pre-administration of jaeumganghwa-tang on the pharmacokinetics of tamoxifen should be evaluated after repeated co-administration in a predetermined period.

Example 2. Evaluation of Effects of Jaeumganghwa-Tang on Pharmacokinetics of Tamoxifen—Repeated Oral Pre-Administration of Jaeumganghwa-Tang for 6 Days and Repeated Oral Co-Administration of Jaeumganghwa-Tang for 8 Days within 5 Minutes 2-1. Preparation of Laboratory Animals In Example 2, as laboratory animals, male SD rats (SLC, Japan) were used. Ten rats were purchased and divided into two groups of five rats each. Tests were performed on a tamoxifen 50 mg/kg single treated group and a tamoxifen 50 mg/kg and jaeumganghwa-tang 100 mg/kg co-administered group.

2-2. Administration Method 100 mg/kg of jaeumganghwa-tang was dissolved in sterile distilled water, and the diluted jaeumganghwa-tang was repeatedly treated in an oral route once a day for 14 days in a dose of 5 ml/kg. From the 6th day after the jaeumganghwa-tang administration, 50 mg/kg of tamoxifen (Hangzhou Tacon Co., Ltd, Hangzhou, China) was dissolved in sterile distilled water, and the diluted tamoxifen was orally treated once a day for 8 days in a dose of 5 ml/kg. After the pre-administration of jaeumganghwa-tang, to the co-administered group, 100 mg/kg of jaeumganghwa-tang was orally administered within 5 minutes after the tamoxifen administration, and to the tamoxifen single treated group, during the pre-administration and co-administration of the jaeumganghwa-tang, only the same dose of sterile distilled water was treated instead of the jaeumganghwa-tang.

Approximately 0.5 ml of whole blood was taken from each retro-orbital plexus using a tube treated with 50 IU heparin (Sigma, Mo., USA) at the first administration of tamoxifen, 30 minutes before the final 8th administration, 30 minutes, and 1, 2, 3, 4, 6, 8, and 24 hours after the administration, and then immediately centrifuged at 13,000 rpm for 10 minutes to separate plasma. The separated plasma was stored at −70° C. before LC-MS/MS analyses.

2-3. Confirmation of Changes in Blood Tamoxifen Concentrations

A method, HPLC conditions, and LC-MS/MS conditions used for blood concentration analyses were the same as described in Example 1.

Figure 4A:
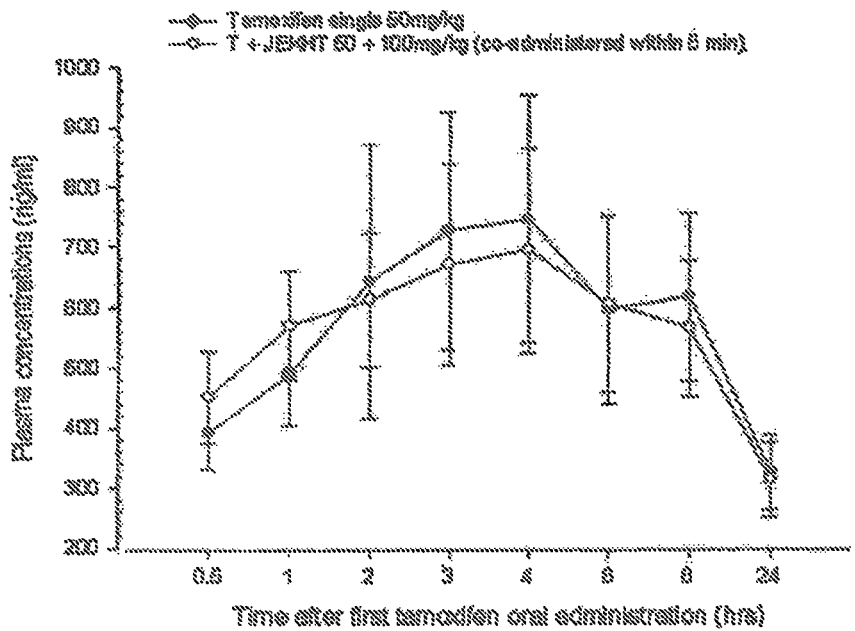
FIGS. 4A and 4B show blood tamoxifen contents, FIG. 4(A) at the first administration of tamoxifen or tamoxifen+jaeumganghwa-tang and FIG. 4(B) at the last $8^{th}$ oral administration of tamoxifen or tamoxifen+jaeumganghwa-tang.
Figure 4B:
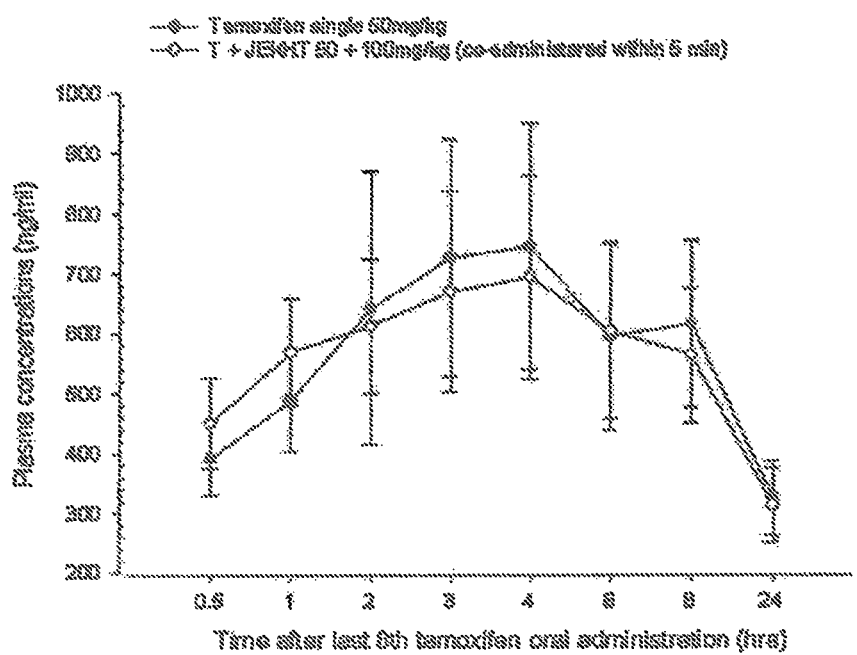

In the tamoxifen or tamoxifen+jaeumganghwa-tang co-administered group to which tamoxifen was orally administered at the first cycle and the last 8th cycle after the pre-administration of jaeumganghwa-tang, tamoxifen was detected from the blood 30 minutes to 24 hours after the administration. In addition, in the tamoxifen+jaeumganghwa-tang co-administered group to which tamoxifen was orally administered at the first cycle and the last 8th cycle after pre-administration of jaeumganghwa-tang, compared to the tamoxifen single treated group, there was no significant change in blood tamoxifen concentration, except an insignificantly small increase in blood tamoxifen content, observed 30 minutes or 1 hour after the administration (FIG. 4).

After the first oral administration of tamoxifen after the pre-administration of jaeumganghwa-tang, in the tamoxifen+jaeumganghwa-tang co-administered group, the blood tamoxifen concentrations detected 30 minutes, and 1, 2, 3, 4, 6, 8 and 24 hours after the administration changed by 9.95, 16.43, 3.22, 9.26, −11.05, −1.26, 0.22 and 0.53%, respectively, compared to the tamoxifen single treated group.

After repeated oral co-administration of tamoxifen 8 times after the jaeumganghwa-tang pre-administration, in the tamoxifen+jaeumganghwa-tang co-administered group, the blood tamoxifen concentrations detected 30 minutes, and 1, 2, 3, 4, 6, 8 and 24 hours after the administration changed by 14.93, 15.95, −4.73, −7.79, −6.95, 1.28, −8.41 and −3.69%, respectively, compared to the tamoxifen single treated group.

2-4. Confirmation of Tmax Change

After the pre-administration of jaeumganghwa-tang and the first oral administration of tamoxifen, in the tamoxifen+jaeumganghwa-tang co-administered group, blood Tmax of tamoxifen was detected at 2.80±1.30 hr, which showed an insignificant decrease of −22.22%, compared to the blood Tmax of 3.60±0.00 hr in the tamoxifen single treated group. However, after the pre-administration of the jaeumganghwa-tang and 8 times-repeated oral co-administrations of tamoxifen, in the tamoxifen+jaeumganghwa-tang co-administered group, blood Tmax of tamoxifen was detected at 3.80±0.45 hr, which showed an insignificantly small increase of 11.76%, compared to the blood Tmax of 3.40±0.89 hr in the tamoxifen single treated group (FIG. 5).

2-5. Confirmation of Cmax Change

After the pre-administration of the jaeumganghwa-tang and the first oral administration of the tamoxifen, in the tamoxifen+jaeumganghwa-tang co-administered group, blood Cmax of the tamoxifen was detected at 0.32±0.17 g/ml, which showed an insignificant increase of 17.39%, compared to the blood Cmax of 0.28±0.16 g/ml in the tamoxifen single treated group. However, after the pre-administration of the jaeumganghwa-tang and the 8 times-repeated oral co-administration of tamoxifen, in the tamoxifen+jaeumganghwa-tang co-administered group, blood Cmax of the tamoxifen was detected at 0.70±0.17 g/ml, which showed an insignificant decrease of −9.54%, compared to the blood Cmax of 0.77±0.22 g/ml in the tamoxifen single treated group (FIG. 5).

2-6. Confirmation of AUC Change

After the pre-administration of the jaeumganghwa-tang and the first oral administration of tamoxifen, in the tamoxifen+jaeumganghwa-tang co-administered group, blood tamoxifen AUC0-t and AUC0-inf were 3.70±2.22 and 4.88±4.09 hr·g/ml, respectively, which showed insignificantly small decreases of 14.32 and 0.40%, compared to blood tamoxifen AUC0-t and AUC0-inf of 3.23±1.79 and 4.86±2.87 hr·g/ml in the tamoxifen single treated group, respectively. Even after the pre-administration of the jaeumganghwa-tang and the 8 times-repeated oral co-administration of tamoxifen, in the tamoxifen+jaeumganghwa-tang co-administered group, blood tamoxifen AUC0-t and AUC0-inf were detected at 12.11±3.24 and 19.60±2.60 hr·g/ml, respectively, which showed insignificantly small decreases of −2.26 and −8.83%, compared to the blood tamoxifen AUC0-t and AUC0-inf of 12.39±2.66 and 21.50±3.04 hr·g/ml in the tamoxifen single treated group, respectively (FIG. 5).

2-7. Confirmation of $T_{1/2}$ Change

After the pre-administration of the jaeumganghwa-tang and the first oral administration of the tamoxifen, in the tamoxifen+jaeumganghwa-tang co-administered group, blood $t_{1/2}$ of the tamoxifen was detected at 12.47±5.01 hr, which showed an insignificantly small increase of −4.86%, compared to the blood $t_{1/2}$ of 13.11±5.77 hr in the tamoxifen single treated group. However, even after the pre-administration of the jaeumganghwa-tang and the 8 times-repeated oral co-administration of tamoxifen, in the tamoxifen+jaeumganghwa-tang co-administered group, blood $t_{1/2}$ of the tamoxifen was measured at 18.86±7.30 hr, which showed an insignificantly small decrease of −4.79%, compared to the blood $t_{1/2}$ of 19.62±5.84 hr in the tamoxifen single treated group (FIG. 5).

2-8. Confirmation of $MRT_{inf}$ Change

After the pre-administration of the jaeumganghwa-tang and the first oral administration of the tamoxifen, in the tamoxifen+jaeumganghwa-tang co-administered group, blood $MRT_{inf}$ of the tamoxifen was detected at 17.16±8.35 hr, which showed an insignificant decrease of −5.30%, compared to the blood $MRT_{inf}$ of 18.12±5.71 hr in the tamoxifen single treated group. However, even after the pre-administration of the jaeumganghwa-tang and the 8 times-repeated oral co-administration of tamoxifen, in the tamoxifen+jaeumganghwa-tang co-administered group, blood $MRT_{inf}$ of the tamoxifen was detected at 26.85±10.69 hr, which showed an insignificant decrease of −5.75%, compared to the blood $MRT_{inf}$ of 28.48±8.53 hr in the tamoxifen single treated group (FIG. 5).

Summarizing the results of Example 2, it was observed that jaeumganghwa-tang pre-administration did not have any influence on pharmacokinetics of tamoxifen, which was similar to the single-time co-administration test within 5 minutes described in Example 1, and the jaeumganghwa-tang co-administration repeated for 8 days did not have any influence on oral bioavailability of tamoxifen either. Therefore, it seems that if the jaeumganghwa-tang has good synergic effects on pharmacodynamics and reduction of toxicity, it can be a new effective method for treating breast cancer in integrative medicine.

Example 3. Test for Co-Administration of Jaeumganghwa-Tang and Tamoxifen: Confirmation of Influence of Jaeumganghwa-Tang on Anticancer Effect of Tamoxifen 3-1. Preparation of Laboratory Animals In Example 3, as laboratory animals, Balb/c Slc nu/nu mice (5-week-old females, SLC, Shizuoka, Japan) were used. Seventy three nude mice were purchased, and sixty seven xenografted mice having a tumor volume of 50 mm³ or more 14 days after MCF-7 cells were xenografted into subcutaneous parts of a right hip of each mouse were selected, and divided into groups of seven mice each. Seven separate mice were also prepared as an vehicle control, and used in the test as shown in Table 2.

The xenografted MCF-7 cells were maintained by sub-culturing the MCF-7 cells (American Type Culture Collection Center, VA, USA) using 10% fetal bovine serum (FBS)-added RPMI 1640 (Gibco, Grand Island, N.Y., USA) media in a 5% $CO_2$ incubator at 37° C., and a solid tumor mass was formed by preparing a tumor cell suspension to have a cell concentration of $1.0 \times 10^8$ cell/ml, and grafting 0.2 ml ($2 \times 10^7$ cell/mouse) of the MCF-7 tumor cell suspension on a subcutaneous part of a right hip of each mouse. In the test, tamoxifen or jaeumganghwa-tang was administered 15 days after the grafting of the MCF-7 breast cancer cell lines (tumor volume; 50 mm³ or more).

TABLE 2

MCa003-PD: Effects on MCF-7 cell xenografted nude mice

| Group | Xenograft | Dose (mg/kg/day) | Animal No. |
|---|---|---|---|
| Control | Saline | Vehicle 10 ml/kg | M01~M07 |
| Control | MCF-7 cells | Vehicle 10 ml/kg | M08~M14 |
| Reference | MCF-7 cells | Tamoxifen single (120 mg/kg) | M15~M21 |
| Reference | MCF-7 cells | BJIK single (400 mg/kg) | M22~M28 |
| Active | MCF-7 cells | Tamoxifen and JEKHT (120 and 100 mg/kg) | M29~M35 |
| Active | MCF-7 cells | Tamoxifen and JEKHT (120 and 200 mg/kg) | M36~M42 |
| Active | MCF-7 cells | Tamoxifen and JEKHT (120 and 400 mg/kg) | M43~M49 |

3-2. Administration Method

From 15 days after the grafting of the MCF-7 breast cancer cells, 500, 250 or 125 mg/kg of jaeumganghwa-tang was co-administered with 20 mg/kg of tamoxifen within 5 minutes once a day for 35 days, and to each single treated group, during the jaeumganghwa-tang or tamoxifen administration, only the same dose of sterile distilled water was treated, and in the vehicle control, only a vehicle, sterile distilled water, was administered twice at intervals of 5 minutes.

3-3. Confirmation of Cytotoxicity (1) Influence of Jaeumganghwa-Tang on MCF-7 Cell Viability Compared to the vehicle control, a significant decrease ($p<0.01$) in MCF-7 cell viability was shown in a jaeumganghwa-tang 5 mg/ml treated group, and $IC_{50}$ was calculated at 38.01 mg/ml (FIG. 6(A)).

In jaeumganghwa-tang 0.5, 1, 5, 10, 50, 100 and 500 mg/ml treated groups, compared to the vehicle control (0 mg/ml treated group), MCF-7 cell viabilities changed by −5.57, −5.97, −15.21, −32.00, −57.58, −65.67 and −83.90%, respectively.

(2) Influence of Tamoxifen on MCF-7 Cell Viability

Figure 6A:
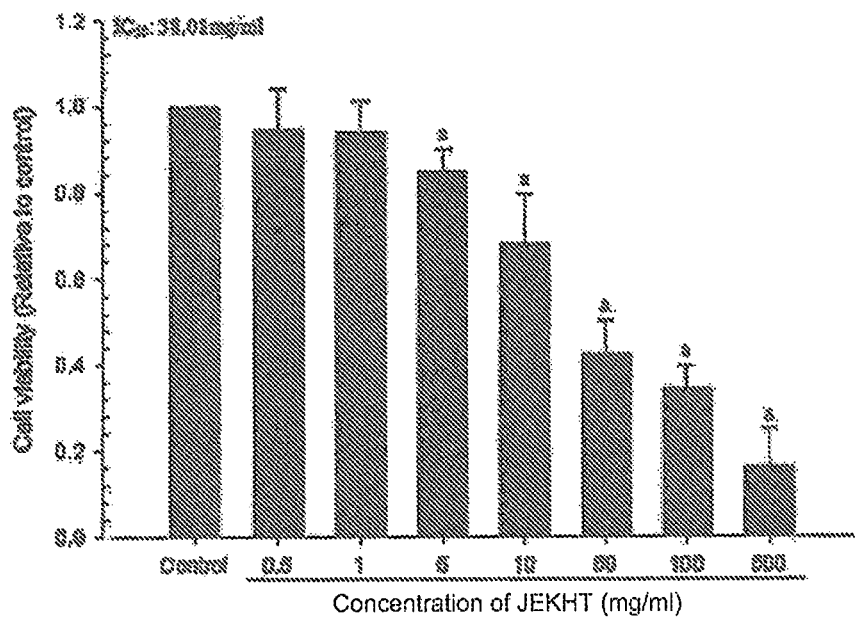
FIGS. 6A and 6B show cell viability estimated when the jaeumganghwa-tang is administered.
Figure 6B:
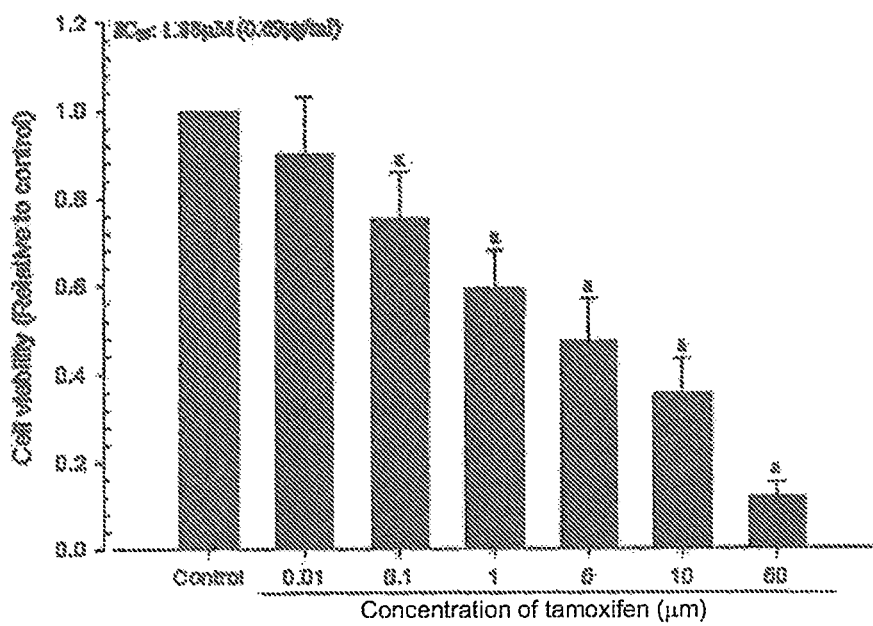

Compared to the vehicle control, a significant decrease ($p<0.01$) in MCF-7 cell viability was shown in a 0.1 μM treated group, and $IC_{50}$ was calculated at 1.88 μM (0.69 g/ml) (FIG. 6(A)).

In 0.01, 0.1, 1, 5, 10 and 50 μM tamoxifen treated groups, compared to the vehicle control (0 mg/ml treated group), MCF-7 cell viabilities changed by −9.94, −24.71, −40.55, −52.69, −64.60 and −87.95%, respectively.

3-4. Confirmation of Changes in Body Weights and Body Weight Gains

Figure 7:
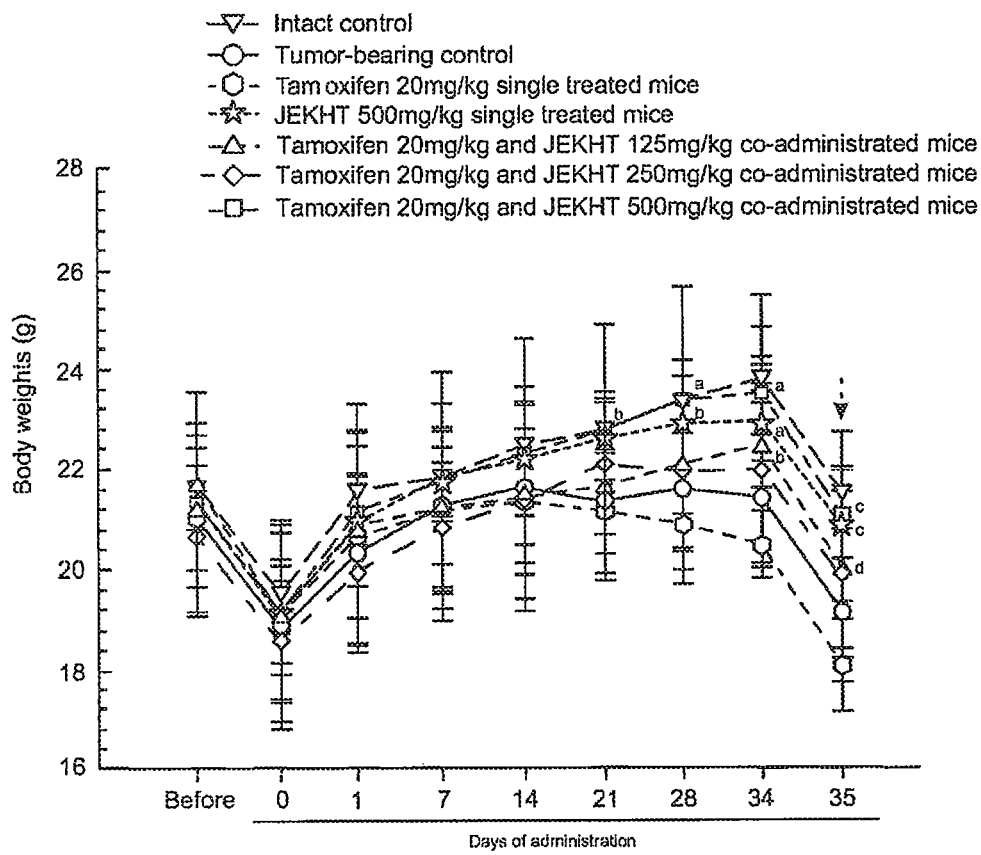
FIG. 7 shows changes in body weights and body weight gains in a tumor-bearing control and a vehicle control.

In a tumor-bearing control, compared to an vehicle control, a significant decrease (p<0.01 or p<0.05) in body weight was shown from 28 days after the administration, and in the final necropsy, compared to the vehicle control, significant decreases (p<0.01) in actual body weight excluding a tumor weight and body weight gain in the duration of administration period based on the actual body weight were shown (actual body weight=body weight at sacrifice—tumor weight at sacrifice; body weight gain=actual body weight −body weight at initial administration). Meanwhile, in the tamoxifen single treated group, compared to the tumor-bearing control, a significant change in body weight was not shown, but in the jaeumganghwa-tang single treated group, compared to the tumor-bearing control, a significant increase (p<0.01 or p<0.05) in body weight was only shown at the final sacrifice day, and significant increases (p<0.01) in actual body weight and body weight gain were shown. In tamoxifen 20 mg/kg and jaeumganghwa-tang 250 and 500 mg/kg co-administered groups, compared to the tamoxifen 20 mg/kg single treated group, significant increases (p<0.01 or p<0.05) in body weights were shown from 34 and 21 days after the administration, significant increases (p<0.01 or p<0.05) in the actual body weights and body weight gains were shown (FIG. 7).

In the tumor-bearing control, the body weight gain (35 days; actual weight-body weight at the first day of the administration) during an administration period based on the actual body weight changed by 99.57%, compared to the vehicle control, and in the tamoxifen 20 mg/kg and jaeumganghwa-tang 500 mg/kg single treated groups, and the jaeumganghwa-tang 125, 250 and 500 mg/kg and tamoxifen 20-mg/kg co-administered groups, compared to the tumor-bearing control, the body weight gains changed by −11162.72, 19162.71, 12132.20, 15800.00 and 22328.81%, respectively.

3-5. Confirmation of Change in Tumor Volume

Tumor volume variations are shown in Table 3. In the tamoxifen single treated group, compared to the tumor-bearing control, 7 days after the administration, a significant decrease (p<0.01) in tumor volume was shown, and variations in tumor volume in the duration of administration period had also significantly decreased (p<0.01). Meanwhile, in a jaeumganghwa-tang 500 mg/kg single treated group, 21 days after the administration, compared to the tumor-bearing control, a significant decrease (p<0.01 or p<0.05) in tumor volume was shown, and in the jaeumganghwa-tang 125, 250 and 500 mg/kg and tamoxifen co-administered groups, 7 days or 1 day after the administration, compared to the tumor-bearing control, a significant decrease (p<0.015) in tumor volume was observed. Particularly, compared to the tamoxifen single treated group, significant decreases (p<0.01 or p<0.05) in tumor volume were shown 34 and 14 days of the administration in the jaeumganghwa-tang 250 and 500 mg/kg single treated groups, respectively (refer to FIGS. 8 and 9).

Variations in tumor volume during the drug administration period (5 weeks; tumor volume at the final sacrifice day—tumor volume at the first day of administration) changed by −66.73, −55.42, −62.60, −84.93 and −93.17% in the tamoxifen 20 mg/kg and jaeumganghwa-tang 500 mg/kg single treated groups, and the jaeumganghwa-tang 125, 250 and 500 mg/kg and tamoxifen 20 mg/kg co-administered groups, respectively, compared to the tumor-bearing control.

TABLE 3

| | Tumor volume (mm$^3$) | | | |
|---|---|---|---|---|
| Groups | 1 day before first administration | First administration [A] | Sacrifice [B] | Changes (mm$^3$) [B − A] |
| | Control | | | |
| TB | 55.23 ± 6.32 | 58.26 ± 5.70 | 436.78 ± 67.11 | 373.53 ± 67.43 |
| | Single treated | | | |
| Tamoxifen | 55.05 ± 6.24 | 58.92 ± 13.22 | 184.85 ± 37.69$^a$ | 125.92 ± 40.49$^a$ |
| JEKHT | 54.58 ± 4.55 | 57.00 ± 8.55 | 225.74 ± 43.71$^a$ | 168.74 ± 47.65$^a$ |
| | Tamoxifen and JEKHT co-administered | | | |
| 125 mg/kg | 54.76 ± 3.44 | 56.86 ± 4.89 | 198.45 ± 51.46$^a$ | 141.58 ± 51.13$^a$ |
| 250 mg/kg | 54.24 ± 3.80 | 59.03 ± 8.17 | 116.08 ± 42.20$^{ab}$ | 57.05 ± 41.33$^{ab}$ |
| 500 mg/kg | 54.58 ± 2.92 | 56.47 ± 4.17 | 82.32 ± 19.34$^{ab}$ | 25.85 ± 17.76$^{ab}$ |

$^a$p < 0.01 and bp < 0.05 as compared with vehicle control by LSD test
c: p < 0.01 as compared with TB control by LSD test
d: p < 0.01 as compared with tamoxifen single treated mice by LSD test
e: p < 0.01 and fp < 0.05 as compared with vehicle control by MW test
g: p < 0.01 and hp < 0.05 as compared with TB control by MW test
i: p < 0.01 and jp < 0.05 as compared with tamoxifen single treated mice by MW test 3-6. Confirmation of Weight Change Changes in weights of a tumor, spleen, submandibular lymph node and periovarian fat pad were measured, and are shown in Table 4.

TABLE 4

| (A) | | | | |
|---|---|---|---|---|
| Groups | Tumor mass | Spleen | Submandibular lymph node | Periovarian fat pad |
| | Controls | | | |
| Intact | | 0.109 ± 0.012 | 0.013 ± 0.004 | 0.072 ± 0.029 |
| TB | 0.092 ± 0.017 | 0.053 ± 0.015 | 0.004 ± 0.002 | 0.017 ± 0.006 |
| | Single treated | | | |
| Tamoxifen | 0.047 ± 0.010 | 0.049 ± 0.009 | 0.002 ± 0.001 | 0.009 ± 0.003 |
| JEKHT | 0.062 ± 0.008 | 0.080 ± 0.019 | 0.007 ± 0.002 | 0.035 ± 0.012 |

TABLE 4-continued

Tamoxifen and JEKHT co-administered

| | | | | |
|---|---|---|---|---|
| 125 mg/kg | 0.040 ± 0.010 | 0.061 ± 0.016 | 0.006 ± 0.004 | 0.019 ± 0.006 |
| 250 mg/kg | 0.031 ± 0.005 | 0.077 ± 0.015 | 0.007 ± 0.004 | 0.032 ± 0.007 |
| 500 mg/kg | 0.024 ± 0.008 | 0.089 ± 0.019 | 0.009 ± 0.005 | 0.047 ± 0.021 |

Values are expressed mean ± S.D., g of seven mice (B)

| Groups | Tumor mass | Spleen | Submandibular lymph node | Periovarian fat pad |
|---|---|---|---|---|
| Controls | | | | |
| Intact | | 0.507 ± 0.056 | 0.061 ± 0.019 | 0.336 ± 0.135 |
| TB | 0.426 ± 0.073 | 0.249 ± 0.071 | 0.017 ± 0.008 | 0.077 ± 0.027 |
| Single treated | | | | |
| Tamoxifen | 0.246 ± 0.065 | 0.257 ± 0.053 | 0.012 ± 0.004 | 0.046 ± 0.014 |
| JEKHT | 0.342 ± 0.052 | 0.441 ± 0.104 | 0.037 ± 0.009 | 0.193 ± 0.066 |
| Tamoxifen and JEKHT co-administered | | | | |
| 125 mg/kg | 0.191 ± 0.045 | 0.293 ± 0.081 | 0.027 ± 0.016 | 0.089 ± 0.028 |
| 250 mg/kg | 0.160 ± 0.042 | 0.389 ± 0.065 | 0.036 ± 0.014 | 0.162 ± 0.034 |
| 500 mg/kg | 0.120 ± 0.040 | 0.451 ± 0.109 | 0.048 ± 0.027 | 0.233 ± 0.106 |

Figure 8:
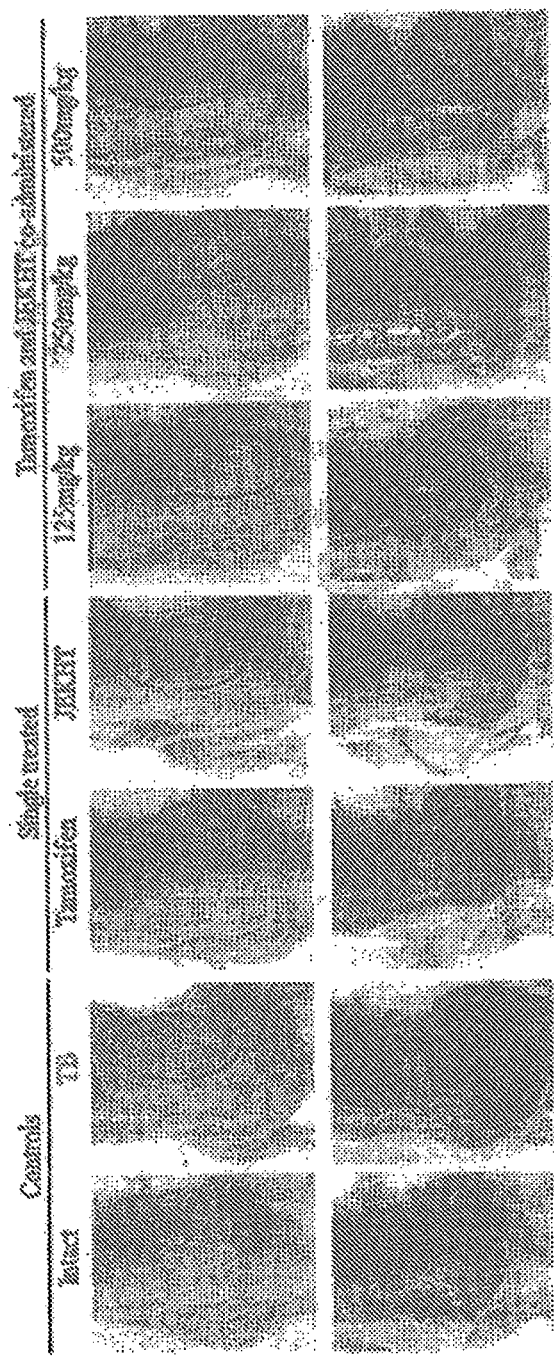
FIGS. 8 and 9 show changes in tumor volumes and weights in a tamoxifen single treated group and a jaeumganghwa-tang co-administered group.
Figure 9:
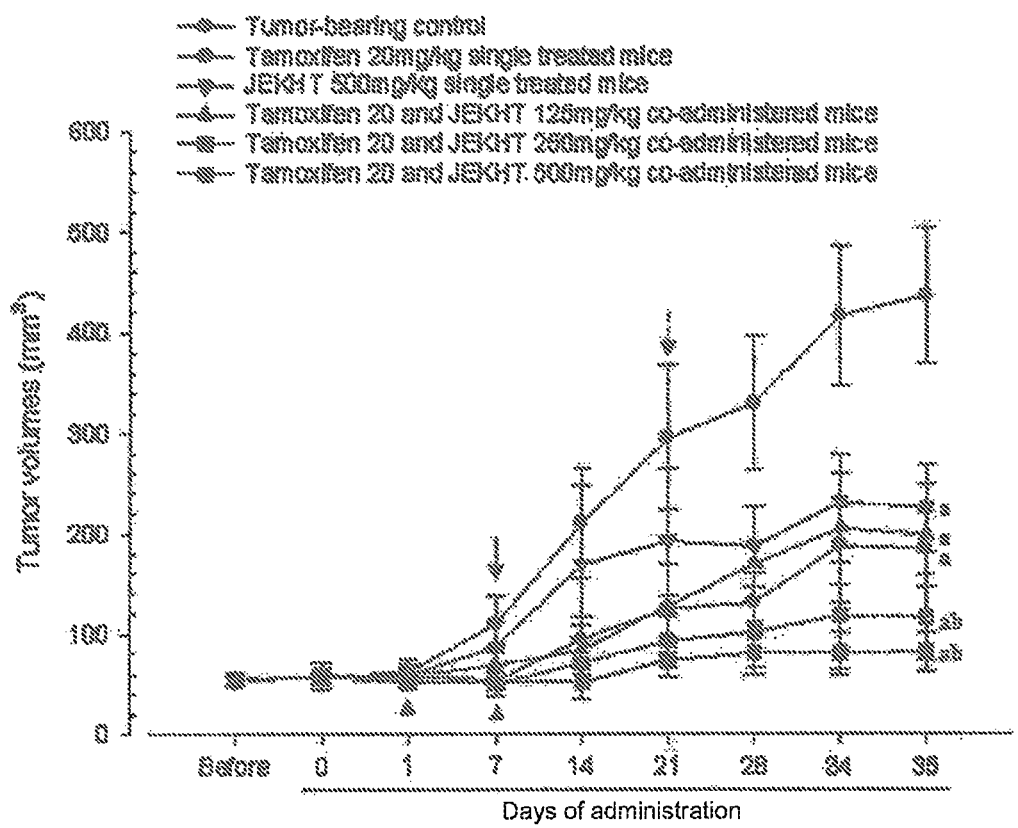

Values are expressed mean ± S.D., % vs body weight of seven mice (1) Changes in Tumor Weight An absolute variation (A) and a relative variation (B) of a tumor weight are shown in Table 4. In all of the drug administered groups including the jaeumganghwa-tang 500 mg/kg single treated group, compared to the tumor-bearing control, significant decreases (p<0.01) in relative and absolute tumor weights were shown. Meanwhile, in each of the jaeumganghwa-tang 250 and 500 mg/kg and tamoxifen co-administered groups, compared to the tamoxifen 20 mg/kg single treated group, significant decreases (p<0.01) in tumor weight were shown, and also in the jaeumganghwa-tang 125 mg/kg and tamoxifen co-administered group, compared to the tamoxifen single treated group, an insignificant decrease in tumor weight was shown (FIG. 8).

The absolute tumor weights changed by −48.99, −32.76, −55.85, −65.83 and −73.95% in the tamoxifen 20 mg/kg and jaeumganghwa-tang 500 mg/kg single treated groups, and jaeumganghwa-tang 125, 250 and 500 mg/kg and tamoxifen 20 mg/kg co-administered groups, respectively, compared to the tumor-bearing control.

The relative tumor weights changed by −42.22, −19.59, −55.15, −62.33 and −71.84% in the tamoxifen 20 mg/kg and jaeumganghwa-tang 500 mg/kg single treated groups, and jaeumganghwa-tang 125, 250 and 500 mg/kg and tamoxifen 20 mg/kg co-administered groups, respectively, compared to the tumor-bearing control.

(2) Confirmation of Changes in Spleen Weight

As shown in Table 4, in the tumor-bearing control, compared to the vehicle control, significant decreases (p<0.01) in absolute and relative spleen weights were shown, but in the jaeumganghwa-tang 500 mg/kg single treated group, and in the jaeumganghwa-tang 250 and 500 mg/kg and tamoxifen 20 mg/kg co-administered groups, compared to the tumor-bearing control, significant increases (p<0.01) in spleen weight were shown. Particularly, in the jaeumganghwa-tang 250 and 500 mg/kg and tamoxifen co-administered groups, compared to the tamoxifen single treated group, significant increases (p<0.01) in absolute and relative spleen weights were shown (FIG. 4).

Compared to the vehicle control, the tumor-bearing control showed a change in the absolute spleen weight of −50.92%, and the tamoxifen 20 mg/kg and jaeumganghwa-tang 500 mg/kg single treated groups, and the jaeumganghwa-tang 125, 250 and 500 mg/kg and tamoxifen 20 mg/kg co-administered groups showed changes in the absolute spleen weight of −8.29, 48.93, 14.97, 44.39 and 67.11%, respectively, compared to the tumor-bearing control.

Compared to the vehicle control, the tumor-bearing control showed a change in the relative spleen weight of −50.94%, and the tamoxifen 20 mg/kg and jaeumganghwa-tang 500 mg/kg single treated groups, and the jaeumganghwa-tang 125, 250 and 500 mg/kg and tamoxifen 20 mg/kg co-administered groups showed changes in the absolute spleen weight of 3.26, 77.01, 17.55, 56.45 and 81.12%, respectively, compared to the tumor-bearing control.

(3) Changes in Weight of Submandibular Lymph Node

Compared to the vehicle control, the tumor-bearing control showed significant decreases (p<0.01) in absolute and relative weights of the submandibular lymph node, but compared to the tumor-bearing control, the jaeumganghwa-tang single treated group, and jaeumganghwa-tang 250 or 500 mg/kg and tamoxifen co-administered groups showed significant increases (p<0.01 or p<0.05) in weight of the submandibular lymph node. Particularly, in the jaeumganghwa-tang 250 and 500 mg/kg and tamoxifen co-administered groups, compared to the tamoxifen single treated group, significant increases (p<0.01) in the absolute and relative weights of the submandibular lymph node were shown (FIG. 4).

The absolute weight of the submandibular lymph node changed by −71.74% in the tumor-bearing control, compared to the vehicle control, and changed by −38.46, 80.77, 57.69, 100.00 and 153.85% in the tamoxifen 20 mg/kg and jaeumganghwa-tang 500 mg/kg single treated groups, and the jaeumganghwa-tang 125, 250 and 500 mg/kg and tamoxifen 20 mg/kg co-administered groups, respectively, compared to the tumor-bearing control.

The relative weight of the submandibular lymph node changed by −71.85% in the tumor-bearing control, compared to the vehicle control, and changed by −30.48, 114.04, 58.19, 110.52 and 175.14% in the tamoxifen 20 mg/kg and jaeumganghwa-tang 500 mg/kg single treated groups, and the jaeumganghwa-tang 125, 250 and 500 mg/kg and tamoxifen 20 mg/kg co-administered groups, respectively, compared to the tumor-bearing control.

(4) Changes in Weight of Periovarian Fat Pad

In the tumor-bearing control, compared to the vehicle control, significant decreases (p<0.01) in absolute and relative weights of a periovarian fat pad were shown, and in the jaeumganghwa-tang single treated group, and the jaeumganghwa-tang 250 or 500 mg/kg and tamoxifen co-administered group, compared to the tumor-bearing control, significant increases (p<0.01) in weight of a periovarian fat pad were shown. Particularly, in all of the jaeumganghwa-tang and tamoxifen co-administered groups, compared to the tamoxifen single treated group, significant increases (p<0.01 or p<0.05) in weight of the periovarian fat pad were shown. Meanwhile, in the tamoxifen 20 mg/kg single treated group, compared to the tumor-bearing control, a significant decrease (p<0.01 or p<0.05) in weight of the periovarian fat pad was shown (refer to Table 4).

The absolute weight of the periovarian fat pad changed by −77.08% in the tumor-bearing control, compared to the vehicle control, and changed by −46.55, 109.48, 13.79, 92.24 and 181.90% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

The relative weight of the periovarian fat pad changed by −76.99% in the tumor-bearing control, compared to the vehicle control, and changed by −40.34, 149.36, 15.66, 108.98 and 200.94% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

3-7. Changes in Blood IL-6 and IFN-γ Contents

Figure 10:
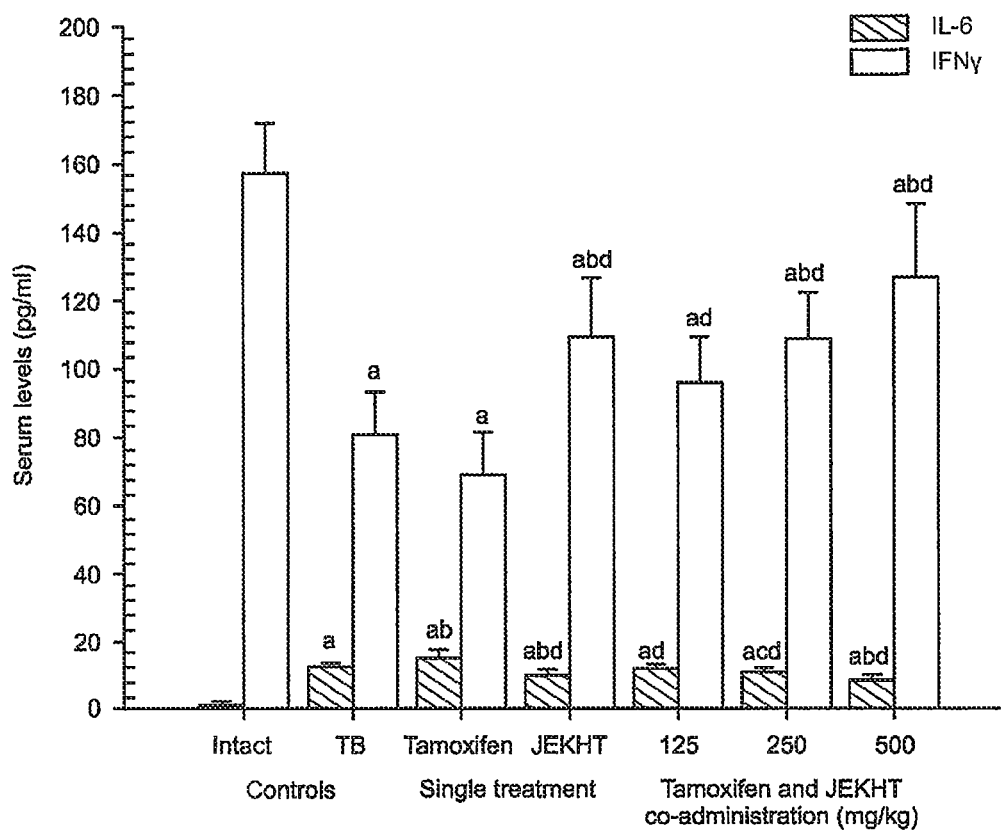
FIG. 10 shows variations in IL-6 and IF-γ contents for each group.

Variations in IL-6 and IFN-γ contents for each group are shown in FIG. 10. In the tumor-bearing control, compared to the vehicle control, a significant increase ($p<0.01$) in blood IL-6 content and a decrease in IFN-γ content were shown, but in the jaeumganghwa-tang single treated group, and in the jaeumganghwa-tang 250 or 500 mg/kg and tamoxifen co-administered group, compared to the tumor-bearing control, significant decreases ($p<0.01$ or $p<0.05$) in blood IL-6 content and increases in IFN-γ content were shown. Particularly, in all of the three doses of jaeumganghwa-tang and tamoxifen co-administered groups, also compared to the tamoxifen single treated group, significant decreases ($p<0.01$) in blood IL-6 content and increases in IFN-γ content were shown. Meanwhile, in the tamoxifen single treated group, also compared to the tumor-bearing control, a significant increase ($p<0.01$) in blood IL-6 content and an insignificant decrease in blood IFN-γ content were shown.

The blood IL-6 content changed by 507.46%, compared to the vehicle control, in the tumor-bearing control, and changed by 21.68, −20.65, −10.07, −16.99 and −38.79% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

The blood IFN-γ content changed by −48.74%, compared to the vehicle control, in the tumor-bearing control, and changed by −14.77, 35.76, 18.11, 34.12 and 56.19% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

3-8. Changes in Activity of NK Cells

Changes in activities of splenic and peritoneal NK cells for each group are shown in FIG. 11. In the tumor-bearing control, compared to the vehicle control, significant decreases ($p<0.01$) in activities of splenic and peritoneal NK cells were shown, but in the jaeumganghwa-tang single treated group and all of the co-administered groups, compared to the tumor-bearing control, considerable increases in activities of splenic and peritoneal NK cells were shown. Particularly, in all of the jaeumganghwa-tang and tamoxifen co-administered groups, compared to the tamoxifen single treated group, significant increases ($p<0.01$) in activities of splenic and peritoneal NK cells were also shown. However, in the tamoxifen single treated group, compared to the tumor-bearing control, significance was not shown, but considerable decreases in activities of splenic and peritoneal NK cells were shown.

The activity of splenic NK cells changed by −57.37% in the tumor-bearing control, compared to the vehicle control, and changed −12.73, 37.32, 20.57, 34.09 and 47.02% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

The activity in peritoneal NK cells changed by −57.69% in the tumor-bearing control, compared to the vehicle control, and changed by −26.39, 38.94, 19.38, 28.98 and 52.09% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

3-9. Confirmation of Changes in Splenic Cytokine Content

A splenic cytokine content for each group is shown in FIG. 12. In the tumor-bearing control, compared to the vehicle control, significant decreases ($p<0.01$) in splenic TNF-α, IL-10 and IL-10 contents were shown, but in the jaeumganghwa-tang single treated group, and the jaeumganghwa-tang 250 and 500 mg/kg and tamoxifen co-administered group, compared to the tumor-bearing control, significant increases ($p<0.01$ or $p<0.05$) in splenic cytokine content were shown. Particularly, in all of the three doses of jaeumganghwa-tang (125, 250 and 500 mg/kg) and tamoxifen co-administered groups, compared to the tamoxifen single treated group, considerable increases in splenic TNF-α, IL-1β and IL-10 contents were shown. However, in the tamoxifen single treated group, compared to the tumor-bearing control, significance was not shown, but considerable decreases in splenic TNF-α, IL-1β and IL-10 contents were shown.

The splenic TNF-α content changed by −65.91% in the tumor-bearing control, compared to the vehicle control, and changed by −23.94, 57.95, 20.38, 52.24 and 110.88% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

The splenic IL-1β content changed by −68.15% in the tumor-bearing control, compared to the vehicle control, and changed by −10.82, 84.73, 19.66, 82.76 and 104.18% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

The splenic IL-10 content changed by −67.46% in the tumor-bearing control, compared to the vehicle control, and changed by −33.33, 75.89, 22.36, 72.39 and 99.81% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

3-10. Confirmation of Histopathological Changes (1) Confirmation of Histopathological Changes in Tumor Mass The tumor cell volume, apoptotic cell percentages, Caspase-3, PARP, and TNF-α immunoreactive cell percentages are shown in Table 5.

TABLE 5

| Groups | Tumor cell volume (%/mm$^2$) | Apoptotic cell percentages (%) | Immunoreactive cell percentages (%/tumor cells) | | |
|---|---|---|---|---|---|
| | | | Caspase-3 | PARP | TNF-α |
| Control | | | | | |
| TB | 83.93 ± 11.78 | 12.36 ± 3.37 | 7.43 ± 1.72 | 8.43 ± 2.82 | 6.86 ± 3.02 |
| Single-treated | | | | | |
| Tamoxifen | 51.00 ± 10.37 | 27.50 ± 6.62 | 21.86 ± 4.22 | 22.14 ± 4.26 | 3.71 ± 1.80 |
| JEKHT | 68.92 ± 8.45 | 22.34 ± 5.47 | 16.71 ± 3.25 | 12.86 ± 1.95 | 14.00 ± 3.37 |
| Tamoxifen and JEKHT co-administered | | | | | |
| 125 mg/kg | 58.11 ± 5.07 | 25.79 ± 7.31 | 20.00 ± 3.37 | 19.43 ± 3.41 | 10.29 ± 3.50 |
| 250 mg/kg | 35.87 ± 4.73 | 48.53 ± 8.23 | 32.00 ± 6.06 | 37.71 ± 5.82 | 20.14 ± 4.60 |
| 500 mg/kg | 26.35 ± 8.57 | 66.09 ± 12.05 | 48.14 ± 12.28 | 53.86 ± 10.21 | 26.00 ± 5.45 |

Values are expressed as mean ± S.D. of seven mice

Figure 13:
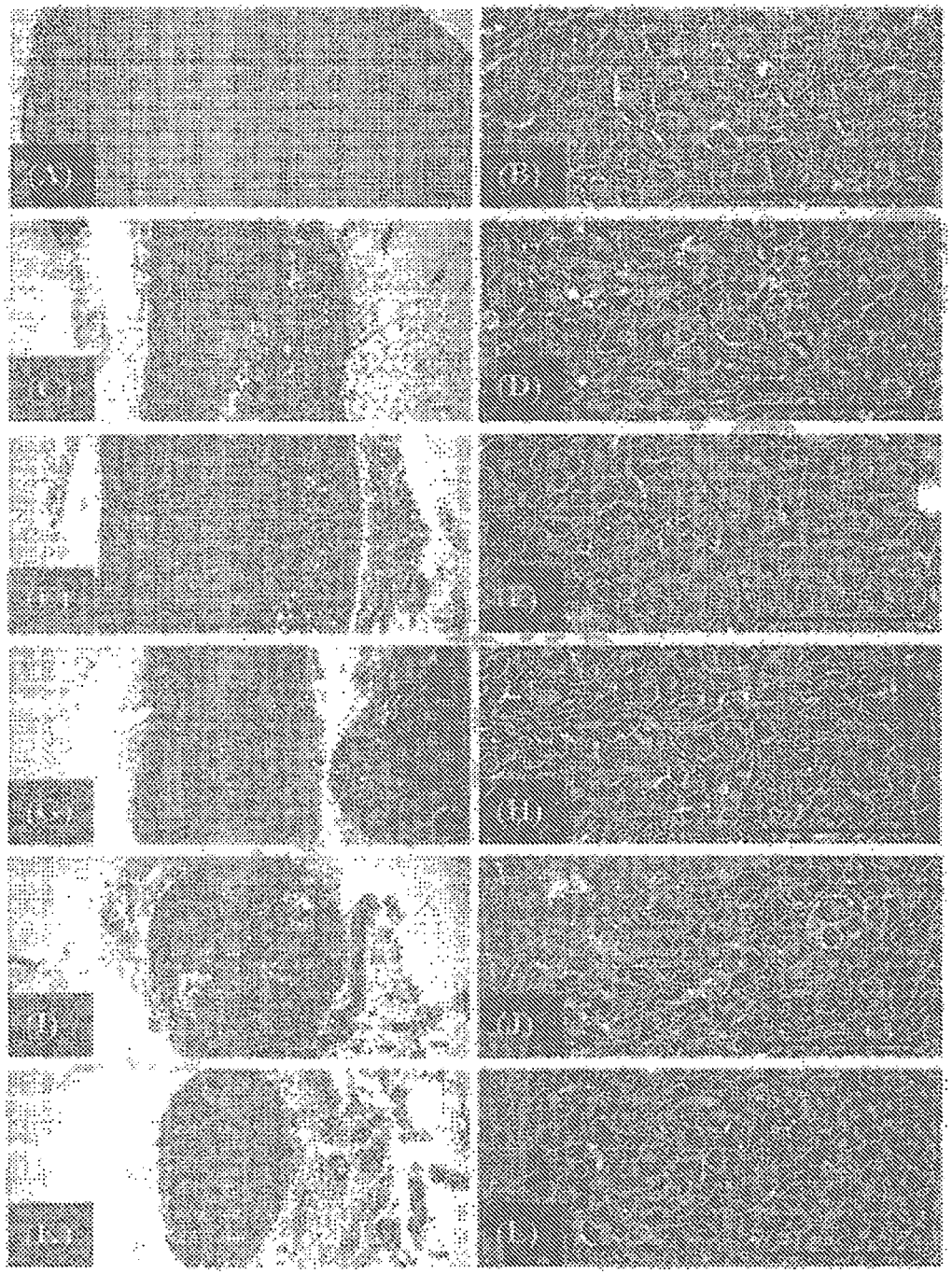
FIG. 13 shows histopathological changes in a tumor mass for each group.
Figure 14:
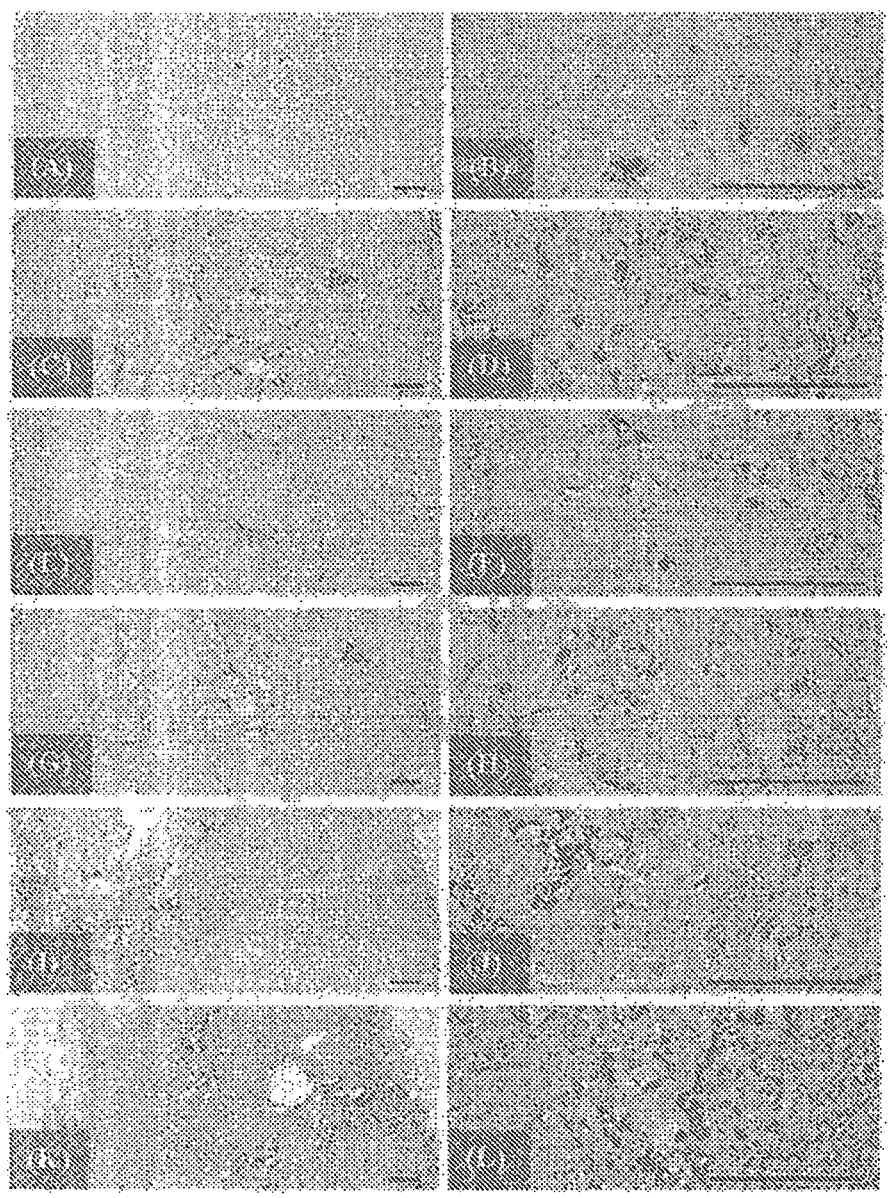
FIG. 14 shows caspase-3 immunoreactive cells in the tumor mass for each group.
Figure 15:
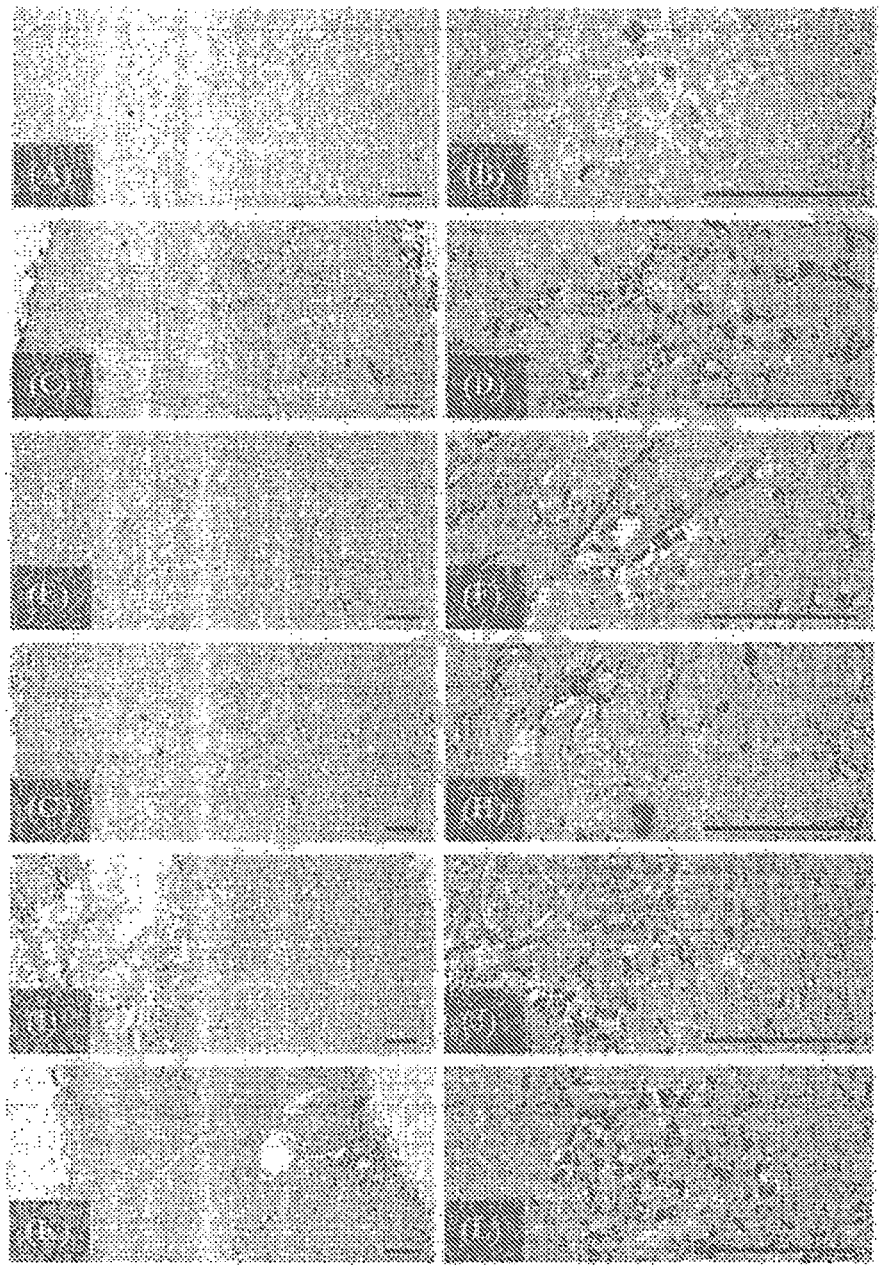
FIG. 15 shows PARP immunoreactive cells in the tumor mass for each group.

In the tumor-bearing control, strongly undifferentiated polymorphic adenocarcinoma was sufficiently composed of MCF-7 cells, and in some cells, an increase in acidophil of a cytoplasm caused by apoptosis and pyknosis were shown. However, in the tamoxifen single treated group and all of the three doses of jaeumganghwa-tang co-administered groups, compared to the tumor-bearing control, considerable increases in apoptotic cells were shown, and thus percentages of the MCF-7 cells also considerably decreased. Particularly, in the jaeumganghwa-tang 250 and 500 mg/kg and tamoxifen 20 mg/kg co-administered groups, compared to the tamoxifen single treated group, significant decreases ($p<0.01$) in volumes of tumor cells and numeric increases in apoptotic cells were also shown (FIG. 13) (in FIGS. 13 to 16, A, B: tumor-bearing controls; C, D: tamoxifen 20 mg/kg single treated mice; E, F: JEKHT 500 mg/kg single treated mice; G, H: tamoxifen 20 mg/kg and JEKHT 125 mg/kg co-administered mice; I, J: tamoxifen 20 mg/kg and JEKHT 250 mg/kg co-administered mice; and K, L: tamoxifen 20 mg/kg and JEKHT 500 mg/kg co-administered mice).

In addition, in all administered groups including a jaeumganghwa-tang 500 mg/kg single treated group, compared to the tumor-bearing control, significant numeric increases ($p<0.01$) in caspase-3 and PARP immunoreactive cells in the tumor mass were shown. Particularly, in the jaeumganghwa-tang 250 and 500 mg/kg and tamoxifen 20 mg/kg co-administered groups, compared to the tamoxifen single treated group, significant numeric increases ($p<0.01$) in caspase-3 and PARP immunoreactive cells were also shown (refer to FIGS. 14 and 15).

Figure 16:
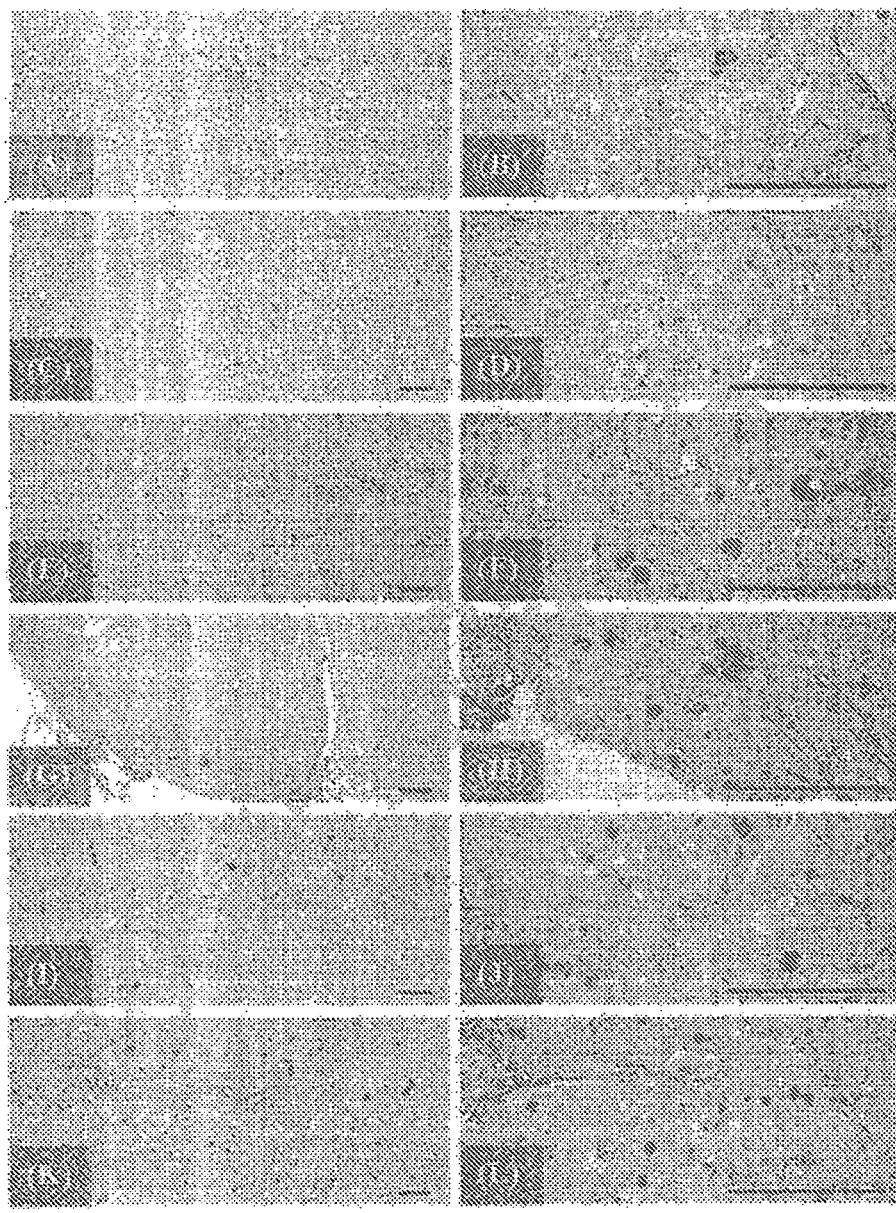
FIG. 16 shows TNF-α immunoreactive cells in the tumor mass for each group.

In addition, in the single treated group and the jaeumganghwa-tang 250 and 500 mg/kg and tamoxifen co-administered groups, compared to the tumor-bearing control, considerable numeric increases in TNF-α immunoreactive cells in the tumor mass were shown. Particularly, in all of the three doses of jaeumganghwa-tang and tamoxifen co-administered groups, compared to the tamoxifen single treated group, significant numeric increases ($p<0.01$) in TNF-α immunoreactive cells were also shown, but in the tamoxifen single treated group, compared to the tumor-bearing control, an insignificant numeric decrease in TNF-α immunoreactive cells in the tumor mass was shown (FIG. 16).

The percentages of tumor cells in a tumor tissue changed by −39.26, −17.92, −30.79, −57.28 and −68.62% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

The percentages of apoptotic cells in the tumor tissue changed by 122.52, 80.74, 108.65, 292.66 and 434.67% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

The percentages of caspase-3 immunoreactive cells in a tumor tissue changed by 194.23, 125.00, 169.23, 330.77 and 548.08% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

The percentages of PARP immunoreactive cells in a tumor tissue changed by 162.71, 52.54, 130.51, 347.46 and 538.98% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

The percentages of TNF-α immunoreactive cells in a tumor tissue changed by −45.83, 104.17, 50.00, 193.75 and 279.17% in the tamoxifen 20 mg/kg and jaeumganghwa-tang 500 mg/kg single treated group, and in the jaeumganghwa-tang 125, 250 and 500 mg/kg and tamoxifen 20 mg/kg co-administered groups, respectively, compared to the tumor-bearing control.

(2) Confirmation of Histopathological Changes of Spleen

The thickness, the number of white pulps, and the diameter of a spleen are shown in Table 6.

TABLE 6

| Groups | Total thickness (mm/central regions) | White pulp numbers (/mm$^2$) | White pulp diameters (μm/white pulp) |
|---|---|---|---|
| Controls | | | |
| Intact | 1.63 ± 0.16 | 16.00 ± 1.41 | 560.61 ± 110.01 |
| TB | 1.18 ± 0.13[a] | 5.14 ± 1.35[a] | 323.60 ± 36.28[a] |
| Single treated | | | |
| Tamoxifen | 1.15 ± 0.13[a] | 4.14 ± 1.07[a] | 298.11 ± 61.88[a] |
| JEKHT | 1.45 ± 0.11[bcd] | 9.86 ± 1.57[acd] | 438.05 ± 67.25[acd] |

TABLE 6-continued

| Groups | Total thickness (mm/central regions) | White pulp numbers (/mm$^2$) | White pulp diameters (μm/white pulp) |
|---|---|---|---|
| Tamoxifen and JEKHT co-administered | | | |
| 125 mg/kg | 1.37 ± 0.15$^{acd}$ | 6.29 ± 1.38$^{ad}$ | 386.88 ± 107.60$^{ae}$ |
| 250 mg/kg | 1.47 ± 0.10$^{bcd}$ | 9.57 ± 1.51$^{acd}$ | 460.53 ± 43.88$^{bcd}$ |
| 500 mg/kg | 1.63 ± 0.11$^{cd}$ | 12.86 ± 1.35$^{acd}$ | 517.32 ± 71.28$^{cd}$ |

Figure 17:
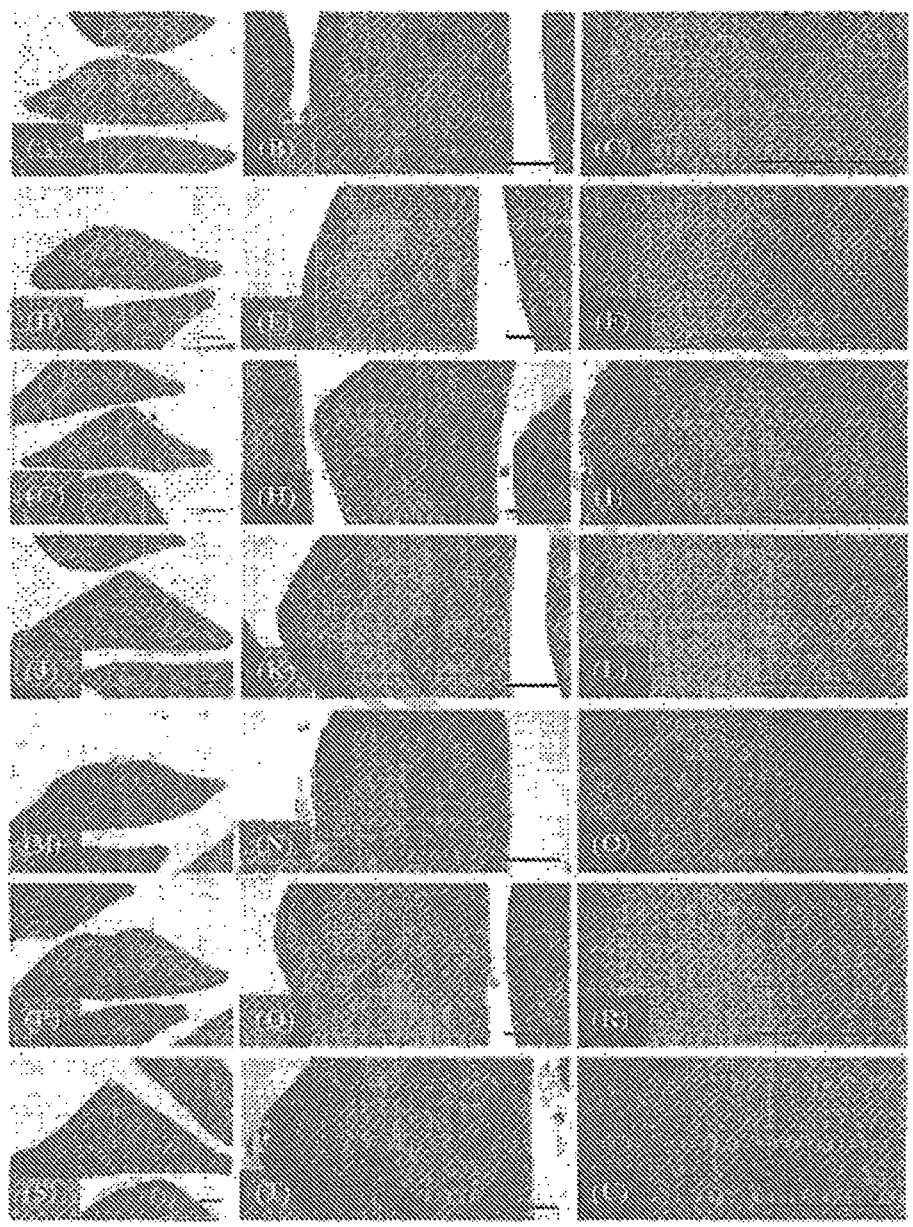
FIG. 17 shows histopathological changes in spleens, which are observed with the naked eye.

As shown in Table 6, in the tumor-bearing control, compared to the vehicle control, atrophy characterized by a considerable decrease in lymphocytes in a splenic white pulp part was shown, and thus a spleen thickness, and the diameter and number of white pulps were significantly decreased (p<0.01). However, in the jaeumganghwa-tang treated group, and all three doses of jaeumganghwa-tang co-administered groups, compared to the tumor-bearing control, considerable numeric increases in spleen thickness, and diameter and number of white pulps were histopathologically identified, and particularly, in all of the jaeumganghwa-tang and tamoxifen 20 mg/kg co-administered groups, compared to the tamoxifen single treated group, significant increases (p<0.01 or p<0.05) in spleen thickness, and diameter and number of white pulps were shown (in FIG. 17, A~C: Vehicle controls; D~F: tumor-bearing controls; G~I: tamoxifen 20 mg/kg single treated mice; J~L: JEKHT 500 mg/kg single treated mice; M~O: tamoxifen 20 mg/kg and JEKHT 125 mg/kg co-administered mice; P~R: tamoxifen 20 mg/kg and JEKHT 250 mg/kg co-administered mice; SU: tamoxifen 20 mg/kg and JEKHT 500 mg/kg co-administered mice).

The total spleen thickness changed by −27.93% in the tumor-bearing control, compared to the vehicle control, and changed by −2.43, 23.57, 16.52, 24.79 and 38.40% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

The number of splenic white pulps changed by −67.68% in the tumor-bearing control, compared to the vehicle control, and changed by −19.44, 91.67, 22.22, 86.11 and 150.00% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively.

The diameter of the splenic white pulp changed by −42.28%, compared to the vehicle control, in the tumor-bearing control, and changed by −7.87, 35.37, 19.56, 42.32 and 59.87% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

(3) Confirmation of Histopathological Changes in a Submandibular Lymph Node

Histopathological changes in a submandibular lymph node were measured, and values thereof are shown in Table 7.

TABLE 7

| Groups | Total thickness (μm/central regions) | Cortex lymphoid cell follicle numbers (/mm$^2$) | Cortex thickness (μm/lymph node) | TNF-positive cells (cells/mm$^2$ of lymph node) |
|---|---|---|---|---|
| Controls | | | | |
| Intact | 1030.73 ± 192.31 | 14.57 ± 2.64 | 531.34 ± 103.85 | 46.43 ± 10.03 |
| TB | 596.37 ± 86.25$^a$ | 6.57 ± 1.51$^g$ | 320.49 ± 53.38$^a$ | 9.86 ± 2.61$^g$ |
| Single treated | | | | |
| Tamoxifen | 487.38 ± 83.96$^a$ | 4.14 ± 1.68$^{gj}$ | 255.43 ± 46.37$^a$ | 6.57 ± 2.51$^{gj}$ |
| JEKHT | 795.63 ± 170.00$^{ace}$ | 11.71 ± 1.60$^{hik}$ | 429.74 ± 88.96$^{bce}$ | 27.14 ± 5.96$^{gik}$ |
| Tamoxifen and JEKHT co-administered | | | | |
| 125 mg/kg | 637.30 ± 101.28$^{af}$ | 7.14 ± 1.07$^{gk}$ | 325.51 ± 44.65$^a$ | 12.00 ± 3.27$^{gk}$ |
| 250 mg/kg | 763.09 ± 79.94$^{ade}$ | 10.71 ± 2.69$^{hik}$ | 392.35 ± 58.56$^{ae}$ | 16.14 ± 3.13$^{gik}$ |
| 500 mg/kg | 869.17 ± 109.94$^{bce}$ | 13.43 ± 1.72$^{ik}$ | 492.20 ± 85.39$^{ce}$ | 25.71 ± 6.05$^{gik}$ |

Figure 18:
FIG. 18 shows histopathological changes in submandibular lymph nodes, which are observed with the naked eye.
Figure 19:
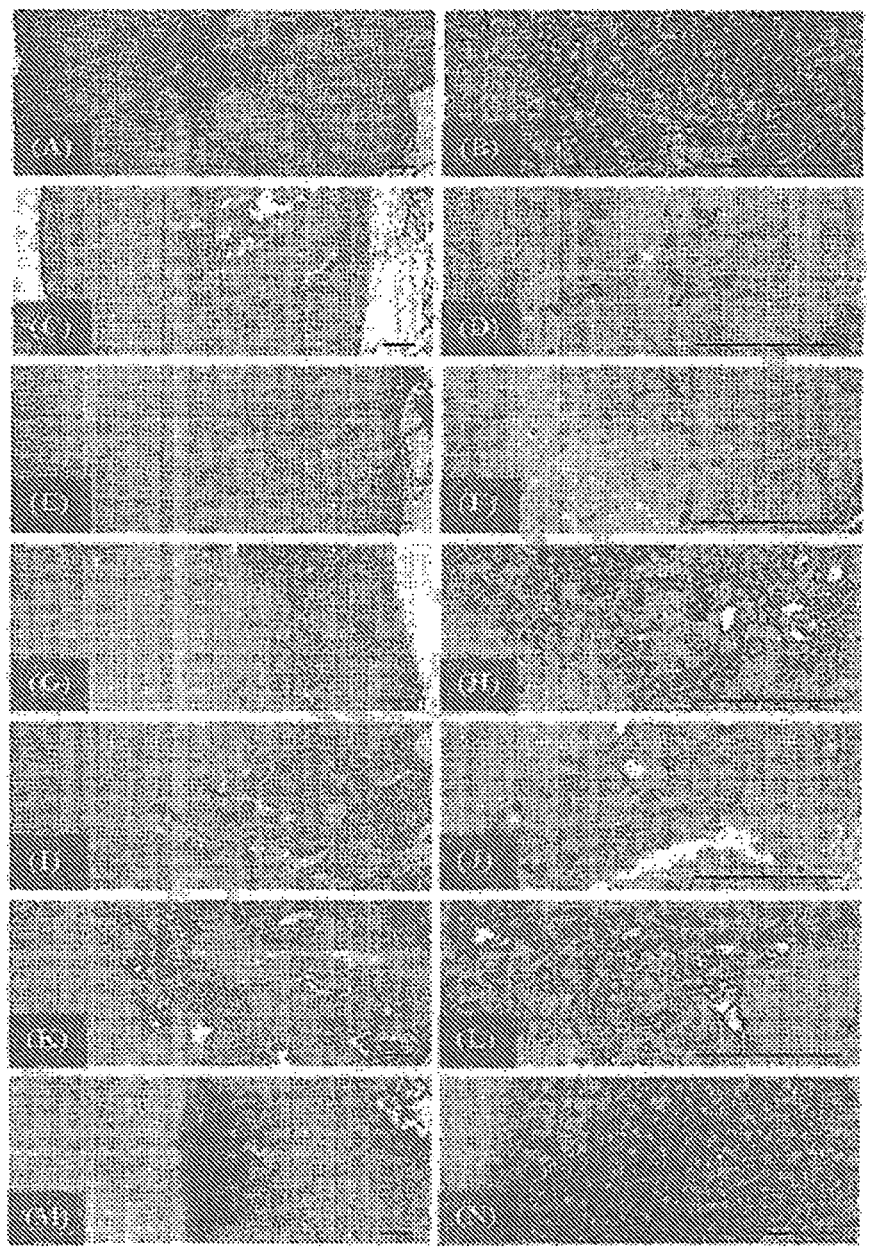
FIG. 19 shows TNF-α immunoreactive cells in the submandibular lymph nodes for each group.

In the tumor-bearing control, compared to the vehicle control, atrophy characterized by a considerable decrease in lymphocytes in a cortex of a lymph node was identified, and thus thicknesses of an entire submandibular lymph node and a cortex, and a number of follicles in the cortex were significantly decreased (p<0.01), and a significant decrease (p<0.01) in TNF-α immunoreactive cells was also shown. However, in the jaeumganghwa-tang single treated group and jaeumganghwa-tang 250 and 500 mg/kg and tamoxifen co-administered groups, compared to the tumor-bearing control, considerable increases in thicknesses of an entire submandibular lymph node and a cortex, and numbers of follicles in the cortex and TNF-α immunoreactive cells were histopathologically identified, and particularly, in the jaeumganghwa-tang 250 and 500 mg/kg and tamoxifen 20 mg/kg co-administered groups, compared to the tamoxifen single treated group, significant increases (p<0.01) in thicknesses of an entire lymph node and a cortex, and numbers of follicles in the cortex and TNF-α immunoreactive cells were shown. However, in the tamoxifen single treated group, even compared to the tumor-bearing control, considerable decreases in thickness of an entire lymph node and a cortex, and in numbers of follicles in the cortex and TNF-α immunoreactive cells were shown (refer to FIGS. 18 and 19).

The thickness of an entire submandibular lymph node changed by −42.14% in the tumor-bearing control, compared to the vehicle control, and changed by −18.28, 33.41, 6.86, 27.96 and 45.74% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

The number of follicles in a cortex of the submandibular lymph node changed by −54.90% in the tumor-bearing control, compared with the vehicle control, and changed by −36.96, 78.26, 8.70, 63.04 and 104.35% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

The thickness of the cortex of the submandibular lymph node changed by −39.68% in the tumor-bearing control, compared with the vehicle control, and changed by −20.30, 34.09, 1.57, 22.42 and 53.58% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

The percentage of TNF-α immunoreactive cells in a tissue of the submandibular lymph node changed by −78.77% in the tumor-bearing control, compared to the vehicle control, and changed by −33.33, 175.38, 21.74, 63.77 and 160.87% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

(4) Confirmation of Histopathological Changes in Periovarian Fat Pad

A thickness of a periovarian fat pad and an mean diameter of a white adipocyte are shown in Table 8.

TABLE 8

| Groups | Total thickness (mm/central regions) | White adipocyte diameters (μm) |
|---|---|---|
| Controls | | |
| Intact | 1.94 ± 0.17 | 53.75 ± 11.29 |
| TB | 0.40 ± 0.15$^a$ | 23.01 ± 6.90$^a$ |
| Single treated | | |
| Tamoxifen | 0.28 ± 0.10$^a$ | 19.89 ± 5.09$^a$ |
| JEKHT | 1.31 ± 0.19$^{abc}$ | 38.72 ± 4.69$^{abc}$ |
| Tamoxifen and JEKHT co-administered | | |
| 125 mg/kg | 0.58 ± 0.20$^{ac}$ | 29.38 ± 6.46$^{ad}$ |
| 250 mg/kg | 1.18 ± 0.22$^{abc}$ | 33.61 ± 4.96$^{abc}$ |
| 500 mg/kg | 1.55 ± 0.13$^{abc}$ | 41.43 ± 4.18$^{abc}$ |

Figure 20:
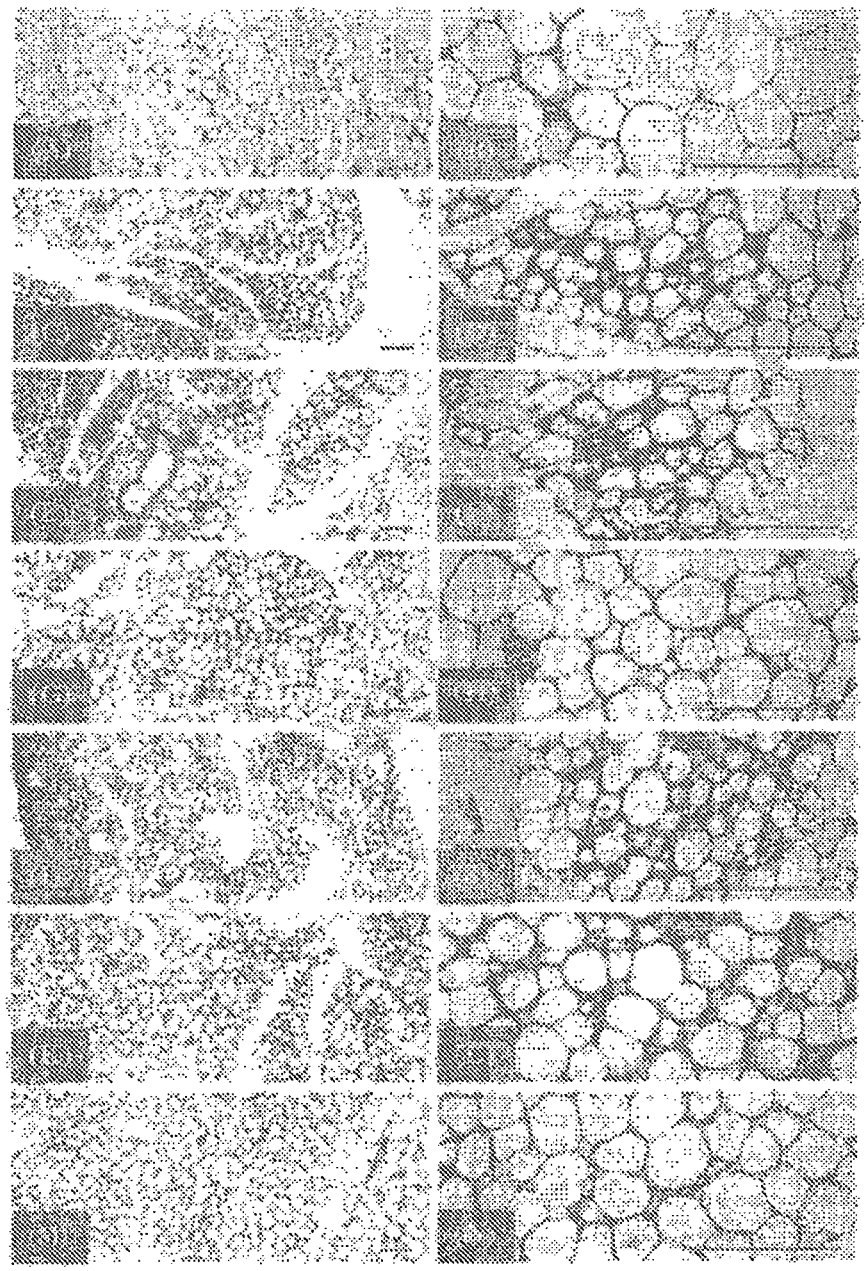
FIG. 20 shows histopathological changes in a periovarian fat pad.

In the tumor-bearing control, compared to the vehicle control, atrophy characterized by a considerable decrease in size of a white adipocyte was identified, and thus a thickness of accumulated fats and an mean diameter of a white adipocyte were significantly decreased ($p<0.01$). However, in the jaeumganghwa-tang single treated group and in the 250 and 500 mg/kg jaeumganghwa-tang and tamoxifen co-administered groups, compared to the tumor-bearing control, significant increases ($p<0.01$) in thickness of accumulated fats and mean diameter of a white adipocyte were histopathologically identified, and particularly, in the all of the jaeumganghwa-tang and tamoxifen co-administered groups, compared to the tamoxifen single treated group, significant increases ($p<0.01$ or $p<0.05$) in thickness of accumulated fats and mean diameter of a white adipocyte were also shown. However, in the tamoxifen single treated group, compared to the tumor-bearing control, insignificant decreases in thickness of a fat pad and mean diameter of a white adipocyte were shown (FIG. 20).

The thickness of a periovarian fat pad changed by −79.46% in the tumor-bearing control, compared to the vehicle control, and changed by −28.67, 229.03, 44.80, 195.34 and 289.25% in the tamoxifen 20 mg/kg and jaeumganghwa-tang 500 mg/kg single treated groups, and in the jaeumganghwa-tang 125, 250 and 500 mg/kg and tamoxifen 20 mg/kg co-administered groups, respectively, compared to the tumor-bearing control.

The mean diameter of a periovarian white adipocyte changed by −57.19% in the tumor-bearing control, compared to the vehicle control, and changed by −13.57, 68.29, 27.66, 46.07 and 80.07% in the tamoxifen 20 mg/kg and jaeumganghwa-tang 500 mg/kg single treated groups, in the jaeumganghwa-tang 125, 250 and 500 mg/kg and tamoxifen 20 mg/kg co-administered groups, respectively, compared to the tumor-bearing control.

Summarizing the results of Example 3, it was observed that the co-administration of 500 or 250 mg/kg of jaeumganghwa-tang significantly increased an anticancer effect of the tamoxifen through immune activity, and a tumor-induced cachexia phenomenon was also significantly inhibited. Accordingly, it is determined that the co-administration of 250 mg/kg or more of jaeumganghwa-tang did not have an influence on bioavailability of tamoxifen, considerably increased an anticancer effect of tamoxifen in the MCF-7 cell-xenografted mice through the immune activity, and decreased a tumor-associated cachexia phenomenon. Therefore, co-administration of tamoxifen and jaeumganghwa-tang to a breast cancer patient is expected to provide a new treating method very useful in integrative medicine and treatment.

Exemplary Embodiment 2

Example 4. Preparation of Materials

Figure 21:
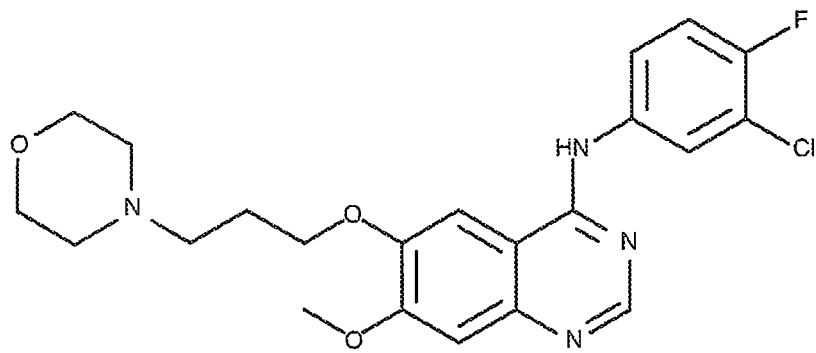
FIG. 21 shows a structural formula of gepitinib used in the present invention.

Gefitinib used in Example 2 of the present invention was purchased from Hangzhou Tacon Co., Ltd. (Hangzhou, China), and a structural formula of gefitinib is shown in FIG. 21.

Bojungikgi-tang was purchased from Hanpoong Pharm & Foods (Seoul, Korea), and the amounts of components of bojungikgi-tang are listed in Table 9.

TABLE 9

| Herbs | Scientific Names/Produce Region | Amounts (g) |
|---|---|---|
| Astragali Radix | Astragalus membranaceus Bunge | 1.33 |
| Atractylodis Rhizoma | Atractylodes lancea D.C | 1.33 |
| Ginseng Radix Alba | Panax ginseng C. A. Meyer | 1.33 |
| Angelicae Gigantis Radix | Angelica gigas N. | 1.00 |
| Bupleuri Radix | Bupleurum falcatum L. | 0.67 |
| Zizyphi Fructus | Zizyphus jujuba var. inermis (Bunge) Rehder | 0.67 |
| Citri Unshii Pericarpium | Citrus unshiu S. Marcov. | 0.67 |
| Glycyrrhizae Rhizoma | Glycyrrhiza uralensis Fisch | 0.50 |
| Cimicifugae Rhizoma | Cimicifuga heracleifolia Kom | 0.33 |
| Zingiberis Rhizoma Siccus | Zingiber officinale Roscoe | 0.17 |
| Total | 10 types | 8.00 |

Example 5: Evaluation of Effect of Bojungikgi-Tang on Pharmacokinetics of Gefitinib: Oral Co-Administration Once within 5 Minutes 5-1. Preparation of Laboratory Animals In this Example, male SD rats (SLC, Japan) were used as laboratory animals. Ten rats were divided into two groups of five rats and used in the experiment as shown in Table 10.

TABLE 10

Gefitinib + BJIKT [within 5 minutes]

| Group | Sex | Dose (mg/kg/day) | Animal No. |
|---|---|---|---|
| Active | Male | Gefitinib (50 mg/kg; orally administered) | A01 to A05 |
| Active | Male | Gefitinib + BJIKT (50 + 100 mg/kg; orally co-administered) | B01 to B05 |

5-2. Administration Method

Fifty mg/kg of gefitinib (Hangzhou Tacon Co., Ltd, Hangzhou, China) was dissolved in sterile distilled water, and orally administered once at a dose of 5 ml/kg. 100 mg/kg of bojungikgi-tang was dissolved in sterile distilled water, and the diluted bojungikgi-tang was orally administered once at the same dose as the gefitinib within 5 minutes after the administration of gefitinib. Meanwhile, in the gefitinib-single treated group, the same dose of sterile distilled water was orally administered once, instead of bojungikgi-tang.

30 minutes before administration of the drug, and 30 minutes, 1, 2, 3, 4, 6, 8, and 24 hours after administration of the drug, approximately 0.5 ml of whole blood was obtained from the ophthalmic venous plexus using tubes treated with 50 IU of heparin (Sigma, Mo., USA). Right after the obtaining of the whole blood, the whole blood was centrifuged at 13,000 rpm for 10 minutes to separate plasma. The separated plasma was stored at −70° C. before LC-MS/MS analyses.

5-3. Experimental Method and Findings

In this Example, changes in blood gefitinib concentrations (ng/ml) were observed 30 minutes before administration, and 30 minutes, 1, 2, 3, 4, 6, 8, and 24 hours after administration, and pharmacokinetic parameters such as $C_{max}$, Tmax, AUC, $t_{1/2}$, and MRT (noncompartmental pharmacokinetics data analyzer program; PK solutions 2.0; Summit, Colo., USA), were analyzed. The results are listed in Table 11.

The blood gefitinib concentration was measured from the separated plasma by an LC-MS/MS method using carbamazepine (Sigma, Mo., USA) as the internal standard. Chromatographic analysis was performed using Agilent 1100 Series HPLC (Agilent Technologies, CA, USA), and a column effluent was analyzed using an API 2000 triple-quadruple mass-spectometric detector (Applied Biosystems, Foster City, Calif., USA).

The HPLC conditions are as follows:

Column: Waters Xterra MS C18 (2.1×50 mm, 3.5 m) (Waters Corp., MA, USA)

Column Oven: 30° C.

Mobile phase: Linear gradient from 2% acetonitrile/98% distilled water (0.1% formic acid) to 98% acetonitrile/2% distilled water (0.1% formic acid)

Flow rate: 0.35 ml/min

Injection Volume: 5.0 µl

The LC-MS/MS conditions are as follows:

Ion source: Turbo Ion Spray (400° C.)

Polarity: Positive

The multiple reaction monitoring (MRM): Carbamazepine (IS)=m/z 237>194 (Retention time: 2.4 min), gefitinib=447>128 (Retention time: 2.3 min)

Standard Curve: Analyst 1.4.2, Quadratic (1/x, no Iterate)

TABLE 11

| | Gefitinib (50 mg/kg) | |
|---|---|---|
| Parameters | Without BJIKT co-administration (Distilled water) | With BJIKT co-administration (100 mg/kg) |
| $T_{max}$ (hrs) | 3.40 ± 1.34 | 3.00 ± 1.41 |
| $C_{max}$ (µg/ml) | 2.16 ± 0.76 | 2.54 ± 1.18 |
| $AUC_{0-t}$ (hr·g/ml) | 14.60 ± 9.45 | 15.16 ± 9.87 |
| $AUC_{0-inf}$ (hr·g/ml) | 16.39 ± 9.31 | 16.46 ± 9.66 |
| $t_{1/2}$ (hr) | 2.59 ± 0.76 | 2.30 ± 0.73 |
| $MRT_{inf}$ (hr) | 5.05 ± 0.90 | 4.35 ± 0.75 |

(1) Confirmation of Changes in Blood Gefitinib Concentrations

Figure 22:
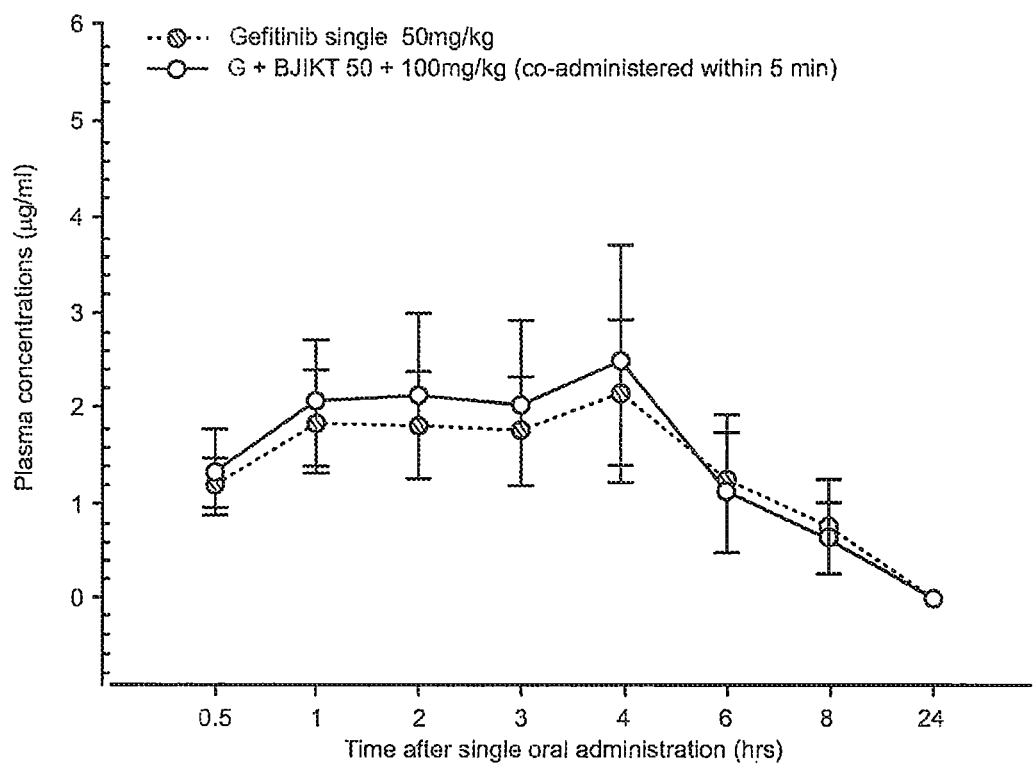
FIG. 22 shows a change in blood gepitinib concentration when bojungikgi-tang is orally co-administered once within 5 minutes.

In the gefitinib treated group or the gefitinib+bojungikgi-tang co-administered group, blood gefitinib started to be detected from 30 minutes after the drug administration, and was detected until 8 hours after the administration. There were no significant changes in blood gefitinib concentrations, except an insignificant increase in the blood gefitinib concentration detected 2 to 4 hours after the administration and an insignificant decrease in the blood gefitinib concentration detected 8 hours after the administration, which were shown in the gefitinib+bojungikgi-tang co-administered group, compared with the gefitinib single treated group (FIG. 22).

In the gefitinib+bojungikgi-tang co-administered group, the blood gefitinib concentrations detected at 30 minutes after the administration, and 1, 2, 3, 4, 6, and 8 hours after the administration changed by 9.68%, 11.42%, 17.47%, 15.32%, 14.94%, −9.04%, and −13.99%, respectively, compared with the gefitinib single treated group.

(2) Confirmation of Changes in Tmax

In the gefitinib+bojungikgi-tang co-administered group, the $T_{max}$ of gefitinib in blood was detected at 3.00±1.41 hr, indicating that the Tmax of gefitinib in blood insignificantly changed by −11.76%, compared with the Tmax, 3.40±1.34 hr, of the gefitinib single treated group (Table 11).

(3) Confirmation of Changes in Cmax

In the gefitinib+bojungikgi-tang co-administered group, the Cmax of gefitinib in blood was 2.54±1.18 µg/ml, indicating that the $C_{max}$ of gefitinib in blood insignificantly changed by 17.38%, compared with the $C_{max}$ of 2.16±0.76 µg/ml in the gefitinib single treated group (Table 11).

(4) Confirmation of Changes in AUC

In the gefitinib+bojungikgi-tang co-administered group, the $AUC_{0-t}$ and $AUC_{0-inf}$ of gefitinib in blood were 15.16±9.87 hr·g/ml and 16.46±9.66 hr·g/ml, respectively, indicating that the $AUC_{0-t}$ and $AUC_{0-inf}$ of gefitinib insignificantly changed by 3.82 and 0.44%, respectively, compared with the $AUC_{0-t}$ and $AUC_{0-inf}$ of 14.60±9.45 hr·g/ml and 16.39±9.31 hr·g/ml in the gefitinib single treated group (Table 11).

(5) Confirmation of Changes in $t_{1/2}$

In the gefitinib+bojungikgi-tang co-administered group, the $t_{1/2}$ of gefitinib in blood was 2.30±0.73 hours, indicating that the $t_{1/2}$ of gefitinib insignificantly changed by −11.14%, compared with the $t_{1/2}$ of 2.59±0.76 hours in the gefitinib single treated group (Table 11).

(6) Confirmation of Change $MRT_{inf}$

In the gefitinib+bojungikgi-tang co-administered group, the $MRT_{inf}$ of gefitinib in blood was 4.53±0.75 hours, indicating that the $MRT_{inf}$ of gefitinib insignificantly changed by −10.15%, compared with the $MRT_{inf}$ of 5.05±0.90 hours in the gefitinib single treated group (Table 11).

As seen from the results of Example 5, it was observed that co-administration of bojungikgi-tang once within 5 minutes had no influence on absorption and excretion of gefitinib. To evaluate interaction of a drug with bojungikgi-tang and gefitinib more clearly, an effect of bojungikgi-tang on the pharmacokinetics of gefitinib after repeated pre-administration of bojungikgi-tang, and an effect of bojungikgi-tang on the pharmacokinetics of gefitinib after repeated co-administration for a predetermined period of time were observed in Example 6.

Example 6: Evaluation of Influence of Bojungikgi-Tang on Pharmacokinetics of Gefitinib: Repeated Oral Pre-Administration of Bojungikgi-Tang for 6 Days and Repeated Oral Co-Administration of Bojungikgi-Tang for 9 Days within 5 Minutes 6-1. Preparation of Laboratory Animals In this Example, male SD rats (SLC, Japan) were used as laboratory animals. Ten rats were divided into two groups of five rats each, and used for this experiment as listed in Table 12.

TABLE 12

Gefitinib + BJIKT [within 5 minutes]

| Group | Sex | Dose (mg/kg/day) | Animal No. |
|---|---|---|---|
| Active | Male | Gefitinib (50 mg/kg; orally administered) | A01 to A05 |
| Active | Male | Gefitinib + BJIKT (50 + 100 mg/kg; orally co-administered) | B01 to B05 |

6-2. Administration Method

One hundred mg/kg of bojungikgi-tang was dissolved in sterile distilled water, and repeatedly orally administered at a dose of 5 ml/kg once a day for 16 days. From 7 days after the first administration of bojungikgi-tang, 50 mg/kg of gefitinib (Hangzhou Tacon Co., Ltd, Hangzhou, China) was dissolved in sterile distilled water, and repeatedly orally administered at a dose of 5 ml/kg once a day for 9 days. After the pre-administration of bojungikgi-tang, 100 mg/kg of bojungikgi-tang was orally administered within 5 minutes after administration of gefitinib in the co-administered group. In the gefitinib single treated group, only sterile distilled water was administered at the same amount, instead of bojungikgi-tang, during pre-administration and co-administration of bojungikgi-tang.

Approximately 0.5 ml of whole blood was obtained from the ophthalmic venous plexus using tubes treated with 50 IU of heparin (Sigma, Mo., USA) 30 minutes before the first administration and the last 9th administration of gefitinib and 30 minutes, 1, 2, 3, 4, 6, 8, and 24 hours after the administration of gefitinib. Right after the obtaining of the whole blood, the whole blood was centrifuged at 13,000 rpm for 10 minutes to separate plasma. The separated plasma was stored at −70° C. before LC-MS/MS analyses.

6-3. Experimental Method and Results

A method of analyzing a blood gefitinib concentration, HPLC conditions, LC-MS/MS conditions were the same as described in Example 5.

Variations in $T_{max}$, $C_{max}$, AUC, $t_{1/2}$, and $MRT_{inf}$ are listed in Tables 13 and 14.

TABLE 13

| Parameters | Gefitinib (50 mg/kg) | |
|---|---|---|
| | Without BJIKT co-administration (Distilled water) | With BJIKT co-administration (100 mg/kg) |
| $T_{max}$ (hrs) | 4.00 ± 0.00 | 4.00 ± 0.00 |
| $C_{max}$ (g/ml) | 3.01 ± 0.48 | 3.41 ± 0.15 |
| $AUC_{0-t}$ (hr · g/ml) | 15.35 ± 2.24 | 15.94 ± 1.22 |
| $AUC_{0-inf}$ (hr · g/ml) | 20.17 ± 4.61 | 19.19 ± 2.00 |
| $t_{1/2}$ (hr) | 2.82 ± 0.92 | 2.25 ± 0.27 |
| $MRT_{inf}$ (hr) | 5.94 ± 1.36 | 5.20 ± 0.29 |

TABLE 14

| Parameters | Gefitinib (50 mg/kg) | |
|---|---|---|
| | Without BJIKT co-administration (Distilled water) | With BJIKT co-administration (100 mg/kg) |
| $T_{max}$ (hrs) | 4.00 ± 0.00 | 3.60 ± 0.89 |
| $C_{max}$ (g/ml) | 3.12 ± 0.77 | 2.98 ± 0.25 |
| $AUC_{0-t}$ (hr · g/ml) | 13.53 ± 2.78 | 14.73 ± 1.98 |
| $AUC_{0-inf}$ (hr · g/ml) | 16.88 ± 4.14 | 17.87 ± 2.77 |
| $t_{1/2}$ (hr) | 2.38 ± 0.88 | 2.34 ± 0.33 |
| $MRT_{inf}$ (hr) | 5.71 ± 1.04 | 5.21 ± 0.44 |

(1) Confirmation of Change in Blood Gefitinib Concentration

Figure 23A:
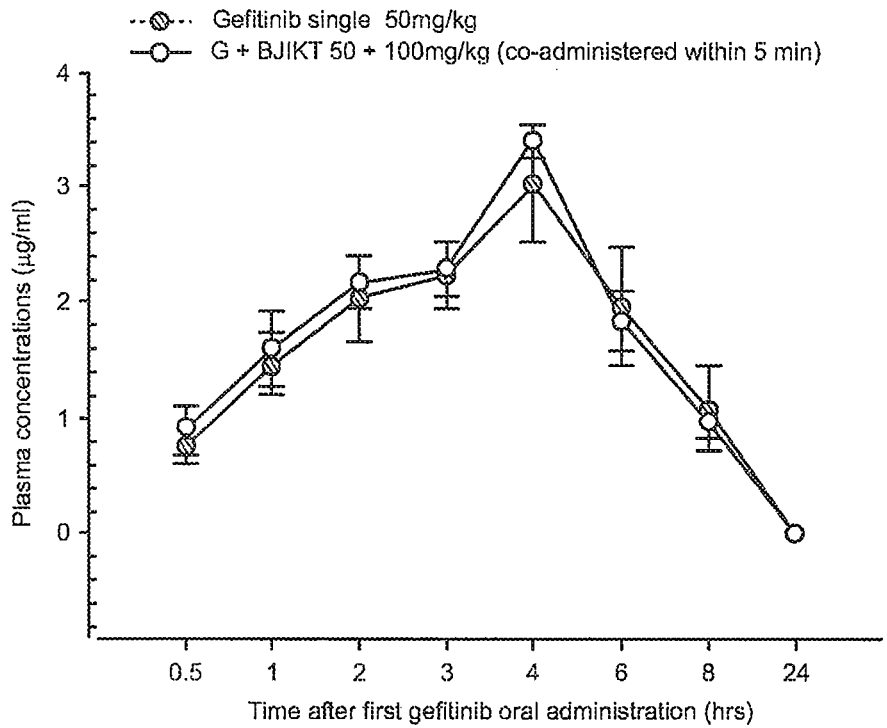
FIGS. 23A and 23B shows changes in blood gefitinib concentrations when bojungikgi-tang is repeatedly administered for 6 days (FIG. 23A), and co-administered within 5 minutes after administration of gefitinib for rest 9 days (FIG. 23B)
Figure 23B:
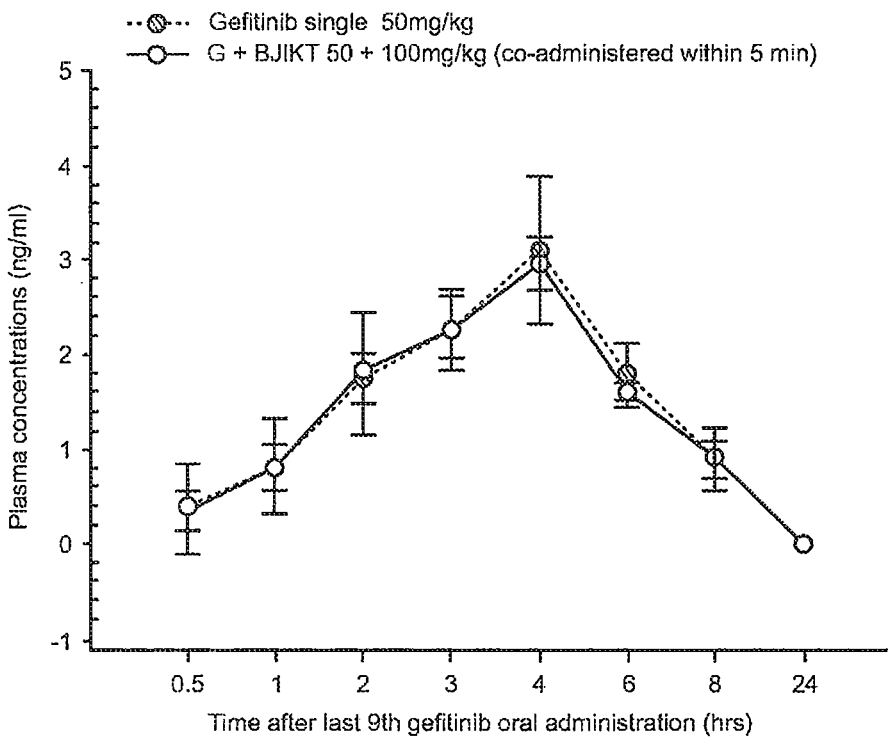

In the gefitinib or gefitinib+bojungikgi-tang co-administered group in which gefitinib was orally administered once and 9 times after pre-administration of bojungikgi-tang, gefitinib started to be detected in blood from 30 minutes after each administration, and was detected at 8 hours after the administration. In the gefitinib+bojungikgi-tang co-administered group in which gefitinib was first orally administered once and 9 times after pre-administration of bojungikgi-tang, compared to the gefitinib single treated group, except that an insignificantly small increase in content of gefitinib in blood 30 minutes after the first co-administration, no significant change in blood gefitinib concentration was not shown (FIG. 23).

After bojungikgi-tang was pre-administered, followed by the first oral gefitinib administration, the blood gefitinib concentrations detected at 30 minutes, 1, 2, 3, 4, 6, and 8 hours after the administration changed by 17.73%, 8.93%, 5.94%, 1.87%, 13.08%, −5.87%, and −9.78% in the gefitinib+bojungikgi-tang co-administered group, respectively, compared with the gefitinib single treated group.

After gefitinib was orally co-administered 9 times after pre-administration of bojungikgi-tang, the blood gefitinib concentrations detected at 30 minutes after the administration and 1, 2, 3, 4, 6, and 8 hours after the administration changed by −9.93%, −1.49%, 4.23%, −0.87%, −4.68%, −10.09%, and 0.13% in the gefitinib+bojungikgi-tang co-administered group, respectively, compared with the gefitinib single treated group.

(2) Confirmation of Changes in $T_{max}$

After gefitinib was first orally administered once after pre-administration of bojungikgi-tang, the $T_{max}$ of gefitinib in blood was detected at 4.00±0.00 hr in the gefitinib+bojungikgi-tang co-administered group, and was also detected at 4.00±0.00 hr in the gefitinib single treated group. After gefitinib was repeatedly orally co-administered 9 times after pre-administration of bojungikgi-tang, the $T_{max}$ of gefitinib in blood was 3.60±0.89 hours in the gefitinib+bojungikgi-tang co-administered group, indicating that the $T_{max}$ of gefitinib in blood insignificantly changed by −10.00%, compared with the $T_{max}$ of 4.00±0.00 hours in the gefitinib single treated group (Tables 13 and 14).

(3) Confirmation of Changes in Cmax

After gefitinib was first orally administered once after pre-administration of bojungikgi-tang, the $C_{max}$ of gefitinib in blood was 3.41±0.15 g/ml in the gefitinib+bojungikgi-tang co-administered group, indicating that the $C_{max}$ of gefitinib in blood insignificantly changed by 13.08%, compared with the $C_{max}$ of 3.01±0.48 g/ml in the gefitinib single treated group. After gefitinib was repeatedly orally co-administered 9 times after pre-administration of bojungikgi-tang, however, the Cmax of gefitinib in blood was 2.98±0.25 g/ml in the gefitinib+bojungikgi-tang co-administered group, indicating that the Cmax of gefitinib in blood insignificantly changed by −4.49%, compared with the Cmax of 3.12±0.77 µg/ml in the gefitinib single treated group (Tables 13 and 14).

(4) Confirmation of Changes in AUC

After the pre-administration of bojungikgi-tang, followed by the first oral gefitinib administration, the $AUC_{0-t}$ and $AUC_{0-inf}$ of gefitinib in blood were 15.94±1.22 hr·g/ml and 19.19±2.00 hr·g/ml, respectively, in the gefitinib+bojungikgi-tang co-administered group, indicating that the $AUC_{0-t}$ and $AUC_{0-inf}$ of gefitinib in blood were insignificantly changed by 3.80% and −4.86%, respectively, compared with the $AUC_{0-t}$ and $AUC_{0-inf}$ of 15.35±2.24 hr·g/ml and 20.17±4.61 hr·g/ml in the gefitinib single treated group. Even after pre-administration of bojungikgi-tang, followed by repeated oral co-administration of gefitinib 9 times, the $AUC_{0-t}$ and $AUC_{0-inf}$ of gefitinib in blood were detected at 14.73±1.98 hr·g/ml and 17.87±2.77 hr·g/ml, respectively, in the gefitinib+bojungikgi-tang co-administered group, indicating that the $AUC_{0-t}$ and $AUC_{0-inf}$ of gefitinib in blood insignificantly changed by 8.93% and 5.85%, respectively, compared with the $AUC_{0-t}$ and $AUC_{0-inf}$ of 13.53±2.78 hr·g/ml and 16.88±4.14 hr·g/ml in the gefitinib single treated group (Tables 13 and 14).

(5) Confirmation of Change in $t_{1/2}$

After the pre-administration of bojungikgi-tang, followed by the first oral administration of gefitinib, the $t_{1/2}$ of gefitinib in blood was 2.25±0.27 hours in the gefitinib+bojungikgi-tang co-administered group, indicating that the $t_{1/2}$ of gefitinib in blood insignificantly changed by −20.32%, compared with the $t_{1/2}$ of 2.82±0.92 hours in the gefitinib single treated group. Even after gefitinib was repeatedly orally co-administered 9 times after pre-administration of bojungikgi-tang, the $t_{1/2}$ of gefitinib in blood was 2.34±0.33 hours in the gefitinib+bojungikgi-tang co-administered group, indicating that the $t_{1/2}$ of gefitinib in blood insignificantly changed by −1.83%, compared with the $t_{1/2}$ of 2.38±0.88 hours in the gefitinib single treated group (Tables 13 and 14).

(6) Confirmation of Change in $MRT_{inf}$

After the pre-administration of bojungikgi-tang, followed by the first oral administration of gefitinib, the $MRT_{inf}$ of gefitinib in blood was 5.20±0.29 hours, indicating that the $MRT_{inf}$ of gefitinib in blood insignificantly changed by −12.46%, compared with the $MRT_{inf}$ of 5.94±1.36 hours in the gefitinib single treated group. Even after the pre-administration of bojungikgi-tang, followed by repeated oral co-administration of gefitinib 9 times, the $MRT_{inf}$ of gefitinib in blood was 5.21±0.44 hours in the gefitinib+bojungikgi-tang co-administered group, indicating that the $MRT_{inf}$ of gefitinib in blood insignificantly changed by −8.84%, compared with the $MRT_{inf}$ of 5.71±1.04 hours in the gefitinib single treated group (Tables 13 and 14).

As seen from the results of Example 6, it was observed that the pre-administration of bojungikgi-tang had no influence on the pharmacokinetics of gefitinib, similarly to Example 5, and that the repeated co-administration for 9 days also had no influence on bioavailability of orally administered gefitinib.

Example 7: Experiment of Co-Administration of Bojungikgi-Tang and Gefitinib: Confirmation of Effect of Bojungikgi-Tang on Reducing Gefitinib Toxicity 7-1. Preparation of Laboratory Animals In this Example, male ICR mice were used as laboratory animals. A total of 48 mice were divided into six groups of eight mice each, and used for this experiment as listed in Table 15.

TABLE 15

PCa004-TX: Toxicity tests after repeated oral administration into mice

| Group | Dose (mg/kg) | Animal No. |
|---|---|---|
| Control | Distilled water 10 ml/kg | M01 to M08 |
| Reference | Gefitinib single (160 mg/kg) | M09 to M16 |
| Active | Gefitinib and BJIKT (160 and 100 mg/kg) | M17 to M24 |
| Active | Gefitinib and BJIKT (160 and 200 mg/kg) | M25 to M32 |
| Active | Gefitinib and BJIKT (160 and 400 mg/kg) | M33 to M40 |
| Reference | BJIKT single (400 mg/kg) | M41 to M48 |

7-2. Administration Method

For administration, sterile distilled water was used as a solvent, and a drug was orally administered at a dose of 10 ml/kg once a day for 28 days. 400, 200, or 100 mg/kg of bojungikgi-tang was co-administered to 160 mg/kg of gefitinib-administered mice within 5 minutes once a day for 28 days. Only the same dose of sterile distilled water was administered to the bojungikgi-tang or gefitinib single treated group, and only sterile distilled water was administered as a vehicle to the vehicle control twice at intervals of 5 minutes.

The dose of gefitinib was set to 160 mg/kg, which was 4 times higher than the minimum dose of 40 mg/kg at which rats were known to exhibit hepatotoxicity when gefitinib was continuously administered for 28 days.

After 28 days, necropsy was finally performed on all of the laboratory animals, thereby analyzing its results.

7-3. Confirmation of Changes in Body Weight and Body Weight Gain

In the gefitinib 160 mg/kg single treated group, significant decreases in body weight (p<0.01 or p<0.05) were observed on $27^{th}$ and $28^{th}$ days after the administration, respectively, resulting in a significantly decrease in body weight gains (p<0.01 or p<0.05) during a period between the first day of the administration and the $14^{th}$ day after the administration and the entire period of experiment, compared with the vehicle control. Also, a significant decrease (p<0.05) in the body weight was detected on the $28^{th}$ day of administration in the bojungikgi-tang 100 mg/kg and gefitinib co-administered group, and a significant decrease (p<0.05) in the body weight gain was detected during the period between the first day of administration and the $14^{th}$ day of administration in the bojungikgi-tang 200 mg/kg and gefitinib co-administered group, compared with the vehicle control. Meanwhile, no significant changes in body weight and body weight gain were not detected in all of the bojungikgi-tang co-administered groups, compared to the gefitinib single treated group, and no significant changes in body weight and body weight gain were not detected during the entire period of experiment in the bojungikgi-tang 400 mg/kg single treated group, compared to the vehicle control.

7-4. Confirmation of Changes in Organ Weight

In the gefitinib 160 mg/kg single treated group, significant decreases in body weight ($p<0.01$ or $p<0.05$) were detected on $27^{th}$ and $28^{th}$ days after the administration, respectively, resulting in significantly decreases in body weight gains ($p<0.01$ or $p<0.05$) during a period between the first day of the administration and the $14^{th}$ day of the administration and the entire period of experiment, compared with the vehicle control. Also, a significant decrease ($p<0.05$) in the body weight was detected on the $28^{th}$ day of administration in the bojungikgi-tang 100 mg/kg and gefitinib co-administered group, and a significant decrease ($p<0.05$) in the body weight gain was detected during the period between the first day of administration and the $14^{th}$ day of administration in the bojungikgi-tang 200 mg/kg and gefitinib co-administered group, compared with the vehicle control. Meanwhile, no significant changes in body weight and body weight gain were detected in all of the bojungikgi-tang and gefitinib co-administered groups, compared with the gefitinib single treated group, and no significant changes in body weight and body weight gain were detected during the entire period of experiment in the bojungikgi-tang 400 mg/kg single co-administered group, compared with the vehicle control.

7-5. Confirmation of Hematological Change

A total of 14 hematological test results are shown in FIG. 24. Significant decreases ($p<0.01$ or $p<0.05$) in the number of red blood cells, HGB, and HCT and a significant increase ($p<0.01$ or $p<0.05$) in the proportion of monocytes were detected in the gefitinib single treated group, compared with the vehicle control, and significant decreases ($p<0.01$ or $p<0.05$) in number of red blood cells, HGB, and proportion of lymphocytes were detected with significant increases in MCV, total number of leukocytes, and proportion of lymphocytes in the bojungikgi-tang 100 mg/kg and gefitinib co-administered group, compared with the vehicle control. Also, a significant decrease ($p<0.05$) in the number of red blood cells was detected in the bojungikgi-tang 200 mg/kg and gefitinib co-administered group, compared with the vehicle control. Meanwhile, significant hematological changes were not detected in the bojungikgi-tang 400 mg/kg single co-administered group and the bojungikgi-tang 400 mg/kg and gefitinib co-administered group, compared with the vehicle control, and significant increases ($p<0.01$ or $p<0.05$) in the number of red blood cells, HGB, and HCT were detected with a decreased proportion of monocytes in the bojungikgi-tang 200 or 400 mg/kg and gefitinib co-administered group, compared with the gefitinib single treated group. Further, a significant decrease ($p<0.05$) in the proportion of lymphocytes was detected in the bojungikgi-tang 100 mg/kg and gefitinib co-administered group, compared with the gefitinib single treated group.

7-6. Confirmation of Blood Biochemical Change

A total of 20 blood biochemical test results are shown in FIG. 25. Significant increases ($p<0.01$ or $p<0.05$) in AST, ALT, globulin, and LDH contents were observed with a decrease in albumin and A/G in the gefitinib single treated group and the bojungikgi-tang 100 mg/kg and gefitinib co-administered group, compared with the vehicle control, and significant increases ($p<0.01$ or $p<0.05$) in AST, ALT, and CPK contents were observed in the bojungikgi-tang 200 mg/kg and gefitinib co-administered group, compared with the vehicle control. Also, significant increases ($p<0.01$) in AST and ALT contents were observed in the bojungikgi-tang 400 mg/kg and gefitinib co-administered group, compared with the vehicle control.

Meanwhile, no significant blood biochemical change was observed in the bojungikgi-tang 400 mg/kg single co-administered group, compared with the vehicle control, and significant decreases in AST, ALT, globulin, and LDH contents and significant increases in albumin and A/G contents were observed in the bojungikgi-tang 200 or 400 mg/kg and gefitinib co-administered group, compared with the gefitinib single treated group.

7-7. Necropsy Findings

Necropsy findings are shown in FIG. 26 (CG: congestion, and DC: discoloration). Significant increases in spleen and submandibular lymph node enlargement and liver discoloration and thus a significant increase in observation frequencies were observed in the gefitinib 160 mg/kg single treated group and all of the three contents of bojungikgi-tang and gefitinib co-administered groups, compared with the vehicle control. However, significant decreases in spleen and submandibular lymph node enlargement and liver discoloration and thus a significant decrease in observation frequencies were observed in the bojungikgi-tang 400 mg/kg and gefitinib co-administered group, compared with the gefitinib single treated group, and significant decreases in spleen enlargement and liver discoloration and thus a significant decrease in observation frequencies were also observed in the bojungikgi-tang 200 mg/kg and gefitinib co-administered group, compared with the gefitinib single treated group. Meanwhile, no significant change in visual necropsy findings was observed in the bojungikgi-tang 400 mg/kg single co-administered group, compared with the vehicle control, and mild [1+] pulmonary congestion, thymus atrophy, and spleen atrophy were sporadically observed in all of the experiment groups including the vehicle control.

7-8. Histopathological Observation

Figure 27:
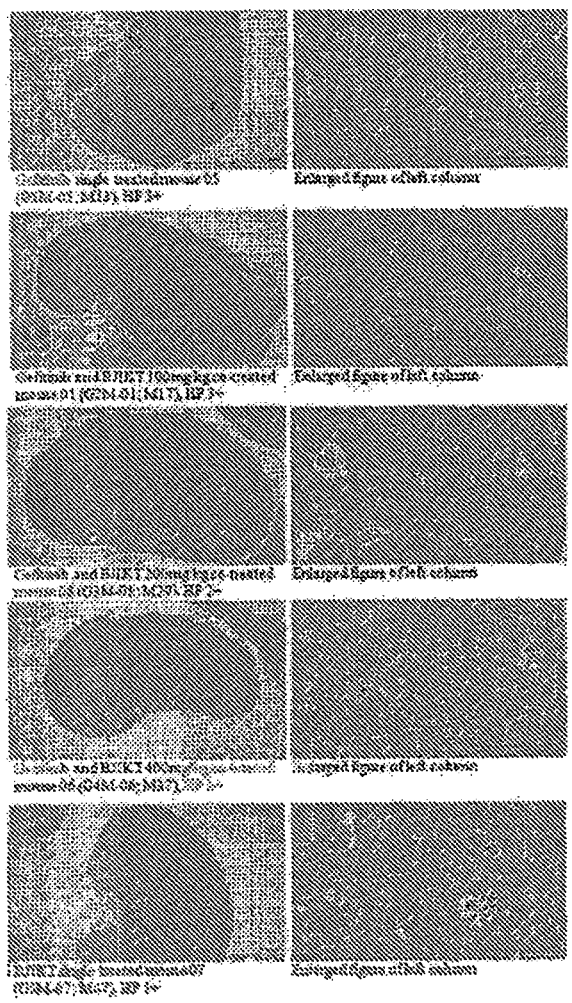
FIG. 27 shows the results of histopathological observation on splenic red pulps.
Figure 28:
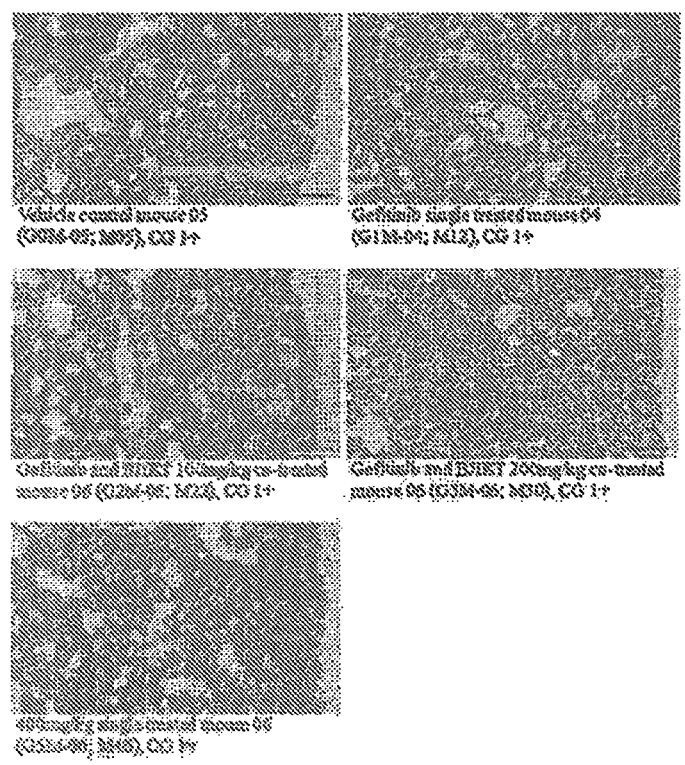
FIG. 28 shows the results of histopathological observation on the submandibular lymph nodes.
Figure 29:
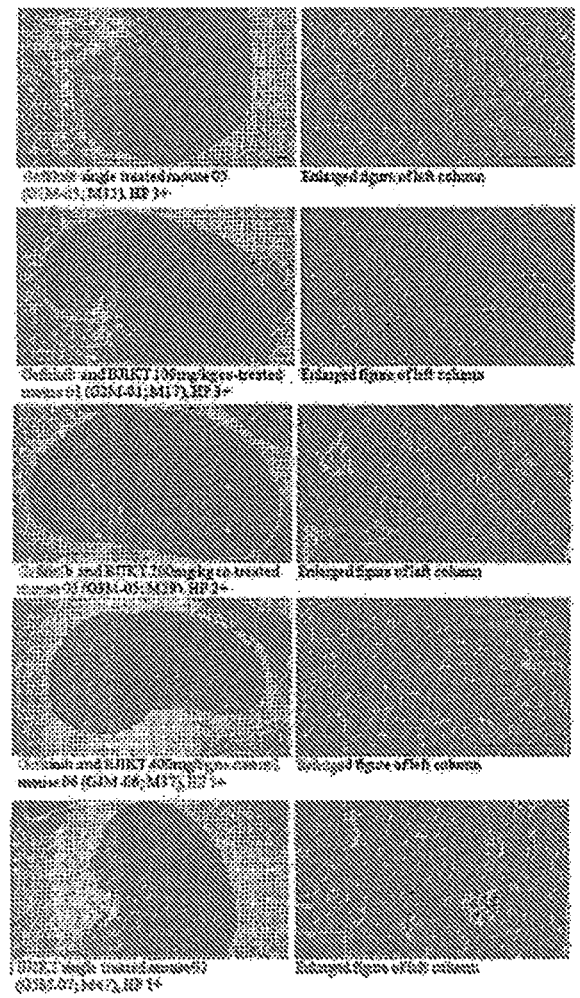
FIG. 29 shows the results obtained by observing lymphoid hyperplasia, local necrosis of the liver, and the infiltration of inflammatory cells.
Figure 30:
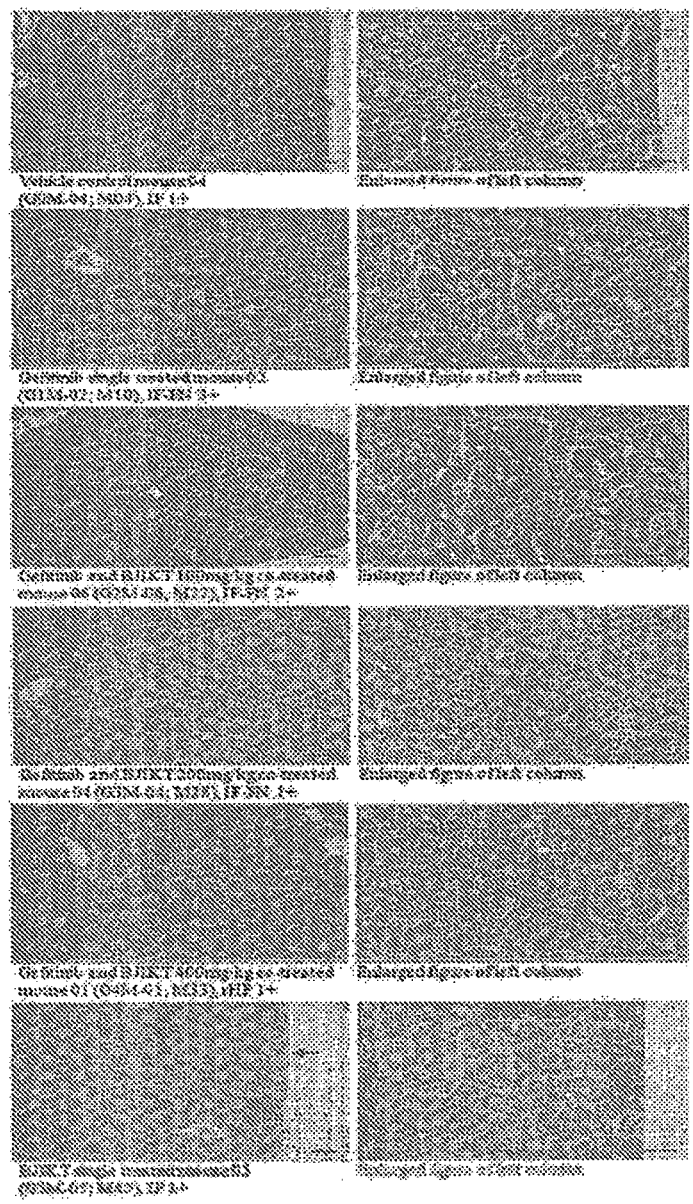
FIG. 30 shows the results obtained by observing the degree of pulmonary congestion.
Figures 31, 32:
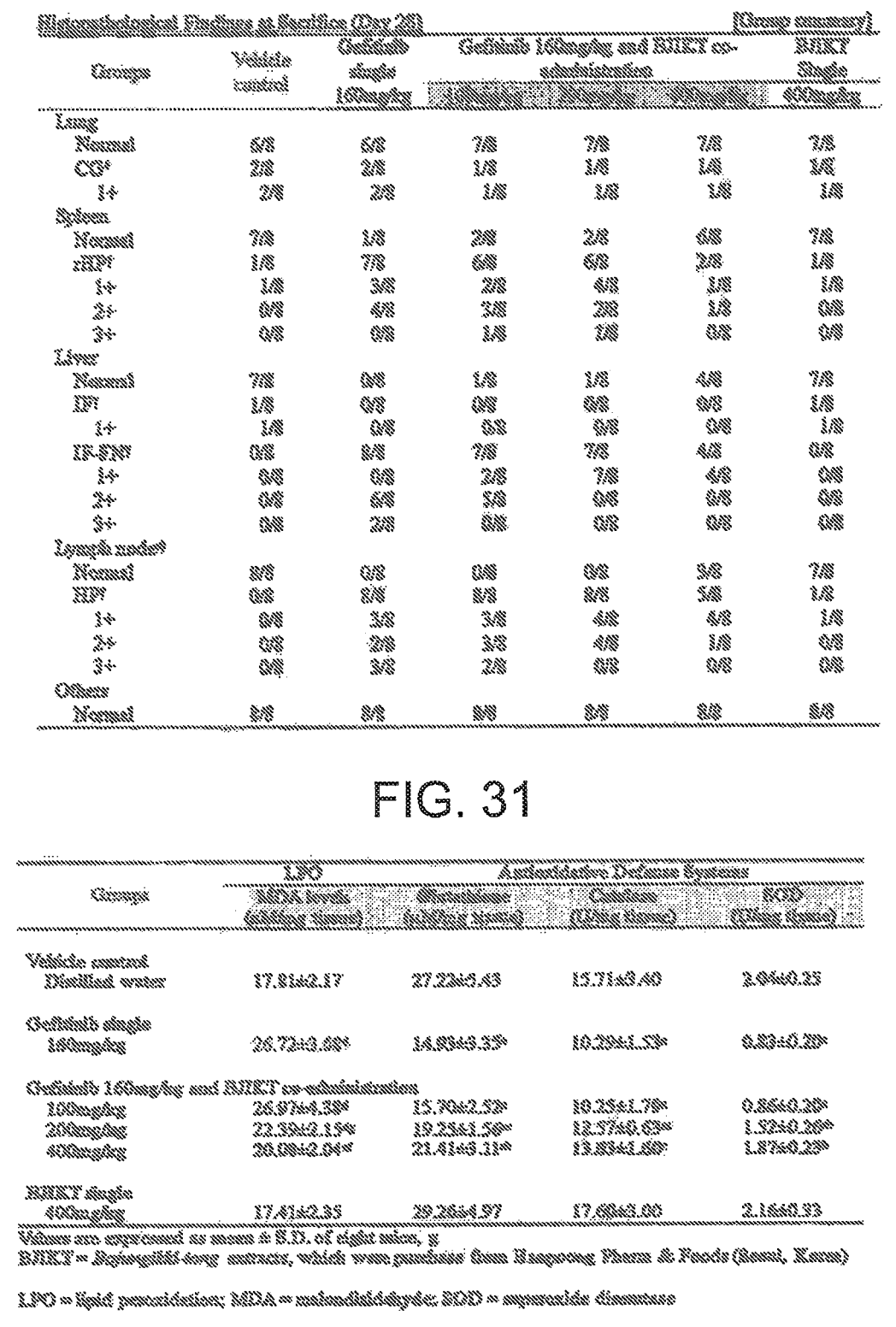

Increases in lymphoid hyperplasia findings in spleen red pulps (FIG. 27) and submandibular lymph nodes (FIG. 28) and local necrosis and inflammatory cell infiltration (FIG. 29) in the liver and thus an increase in observed frequency compared with the vehicle control were observed in the single 160 mg/kg gefitinib administered group and all of the three contents of bojungikgi-tang and gefitinib co-administered groups. However, significant decreases in lymphoid hyperplasia in the spleen and submandibular lymph nodes and liver discoloration and thus a significant decrease in observation frequencies compared with the gefitinib single treated group were observed in the bojungikgi-tang 400 mg/kg and gefitinib co-administered group, and a significant decrease in liver discoloration and thus a significant decrease in observation frequencies compared with the gefitinib single treated group were also observed in the bojungikgi-tang 200 mg/kg and gefitinib co-administered group. Meanwhile, no significant change in visual necropsy findings compared with the vehicle control was observed in the bojungikgi-tang 400 mg/kg single co-administered group, and mild [1+] pulmonary congestion (FIG. 30) and local inflammatory cell infiltration (FIG. 29) in the liver were sporadically observed in all of the experiment groups including the vehicle control (FIG. 31).

7-9. Confirmation of Changes in Hepatic Lipid Peroxidation and Antioxidative Defense System A significant increase in hepatic lipid peroxidation and decreases in antioxidant substances, GSH, SOD, and catalase compared with the vehicle control were observed in the gefitinib 160 mg/kg single treated group and all of the three contents of bojungikgi-tang and gefitinib co-administered groups. However, a significant inhibition (p<0.01) of hepatic lipid peroxidation and a significant increase in contents or activities of the antioxidant substances were observed in the bojungikgi-tang 400 or 200 mg/kg and gefitinib co-administered group, compared with the gefitinib single treated group. Meanwhile, no significant change in an antioxidative defense system in the liver was observed in the bojungikgi-tang 400 mg/kg single treated group, compared with the vehicle control, and changes in hepatic lipid peroxidation and contents or activities of the antioxidant substances, which were similar to those in the gefitinib single treated group, were observed in the bojungikgi-tang 100 mg/kg and gefitinib co-administered group (FIG. 32).

From the results of Example 7, it was observed that the co-administration of 400 or 200 mg/kg bojungikgi-tang resulted in a significant decrease in liver damage by the failure of an anemia and antioxidative defense system caused by gefitinib. Therefore, it is determined that the co-administration of 200 mg/kg or more bojungikgi-tang resulted in significant decreases in anemia and hepatotoxicity caused by administration of gefitinib due to the activities of the antioxidative defense system in the liver without affecting bioavailability of gefitinib. As a result, it was expected that the co-administration of gefitinib and bojungikgi-tang to the lung cancer patients provide a new treating method which was very useful in integrative medicine and treatment.

Example 8: Experiment of Co-Administration of Bojungikgi-Tang and Gefitinib: Influence of Bojungikgi-Tang on Anticancer Effect of Gefitinib in NCI-H520 Lung Cancer Cell Xenografted Nude Mice In Example 8, to evaluate the influence of bojungikgi-tang on an anticancer effect of gefitinib, Balb/c Slc nu/nu mice into which a representative squamous cell carcinoma-type non-small cell lung cancer cell line, NCI-H520, having a resistance to gefitinib, were xenografted were used.

8-1. Preparation of Laboratory Animals

In Example 8, Balb/c Slc nu/nu mice (5-week-old females, SLC, Shizuoka, Japan) were used as laboratory animals. A total of 73 nude mice were purchased, and NCI-H520 cells were xenografted into a subcutaneous region of a right hip each of 67 mice. 14 days after the grafting, the xenografted mice having a tumor volume of 100 mm$^3$ or more were selected, and divided into seven groups of 6 mice each to be used in the experiment as listed in Table 16. Separately, 6 mice were prepared as the vehicle control. Results of the experiments performed on the seven groups are listed in Table 16.

TABLE 16

PCa003-PD: Effects on NCI-H520 cell xenograft nude mice

| Group | Xenograft | Dose (mg/kg/day) | Animal No. |
|---|---|---|---|
| Control | Saline | Vehicle 10 ml/kg | M01 to M06 |
| Control | NCI-H520 cells | Vehicle 10 ml/kg | M07 to M12 |
| Reference | NCI-H520 cells | Gefitinib single (120 mg/kg) | M13 to M18 |
| Reference | NCI-H520 cells | BJIK single (400 mg/kg) | M19 to M24 |
| Active | NCI-H520 cells | Gefitinib and BJIKT (120 and 100 mg/kg) | M25 to M30 |
| Active | NCI-H520 cells | Gefitinib and BJIKT (120 and 200 mg/kg) | M31 to M36 |
| Active | NCI-H520 cells | Gefitinib and BJIKT (120 and 400 mg/kg) | M37 to M42 |

8-2. Methods for Tumor Cell Xenograft and Drug Administration

NCI-H520 (American Type Culture Collection Center, VA, USA) cells were sub-cultured at 37° C. in an RPMI 1640 (Gibco, Grand Island, N.Y., USA) medium supplemented with 10% FBS in a 5% $CO_2$ incubator and maintained. Then, the NCI-H520 cells were cultured to a density of $1.0 \times 10^8$ cells/ml to prepare a tumor cell suspension, and 0.2 mL ($2 \times 10^7$ cells/head) of the NCI-H520 tumor cell suspension was injected into subcutaneous regions of right back buttocks of the mice to form a solid tumor mass. Gefitinib or bojungikgi-tang was administered from the 15$^{th}$ day of the grafting of the NCI-H520 lung cancer cell line (tumor volume; 100 mm$^3$ or more).

From the 15$^{th}$ day of the grafting of the NCI-H520 lung cancer cell line, 400, 200, or 100 mg/kg of bojungikgi-tang and 120 mg/kg of gefitinib were co-administered once a day for 35 days within 5 minutes. In the bojungikgi-tang or gefitinib single treated group, the same dose of sterile distilled water was only administered, and in the vehicle control, only sterile distilled water was administered twice as a vehicle at intervals of 5 minutes.

Figure 33A:
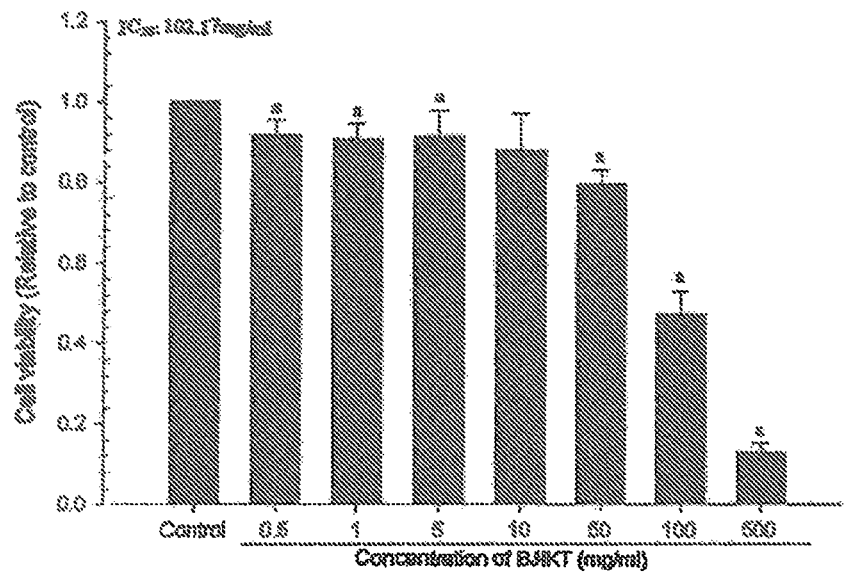
FIGS. 33(A) and 33(B) show viability of NCI-H520 cells in bojungikgi-tang (FIG. 33(A)), and in gefitinib (FIG. 33(B))

8-3. Confirmation of Cytotoxicity (1) Influence of Bojungikgi-Tang on NCI-H520 Cell Viability A significant decrease (p<0.01) in NCI-H520 cell viability started to be observed in the 0.5 mg/ml bojungikgi-tang-treated group, compared with the vehicle control, and an $IC_{50}$ value was then calculated at 102.17 mg/ml (FIG. 33A).

In the bojungikgi-tang 0.5, 1, 5, 10, 50, 100, and 500 mg/ml treated groups, the NCI-H520 cell viabilities changed by −8.35%, −9.21%, −8.64%, −12.11%, −20.39%, −52.43%, and −87.01%, respectively, compared with the non-treated vehicle control (0 mg/ml treated group).

(2) Influence of Gefitinib on NCI-H520 Cell Viability

Figure 33B:
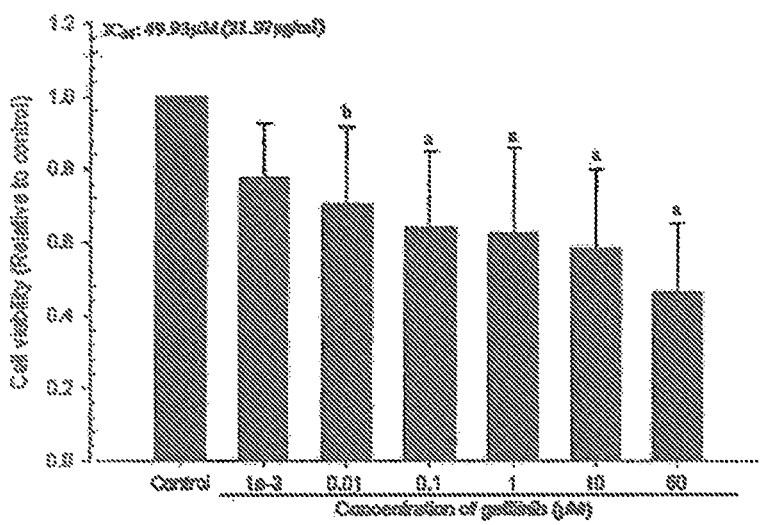

A significant decrease (p<0.01 or p<0.05) in NCI-H520 cell viability started to be observed in the 0.01 m gefitinib-treated group, compared with the vehicle control, and an $IC_{50}$ value was then calculated at 49.93 m (21.97 g/ml) (FIG. 33B).

In the gefitinib 0.001, 0.01, 0.1, 1, 10, and 50 µM treated groups, the NCI-H520 cell viabilities changed by −22.09%, −29.64%, −35.98%, −37.31%, −41.65%, and −53.32%, respectively, compared with the non-treated vehicle control (0 mg/ml treated group).

Therefore, it was shown that bojungikgi-tang did not exhibit any specific cytotoxicity to the NCI-H520 cells.

8-4. Confirmation of Changes in Body Weight and Body Weight Gain

Figure 34:
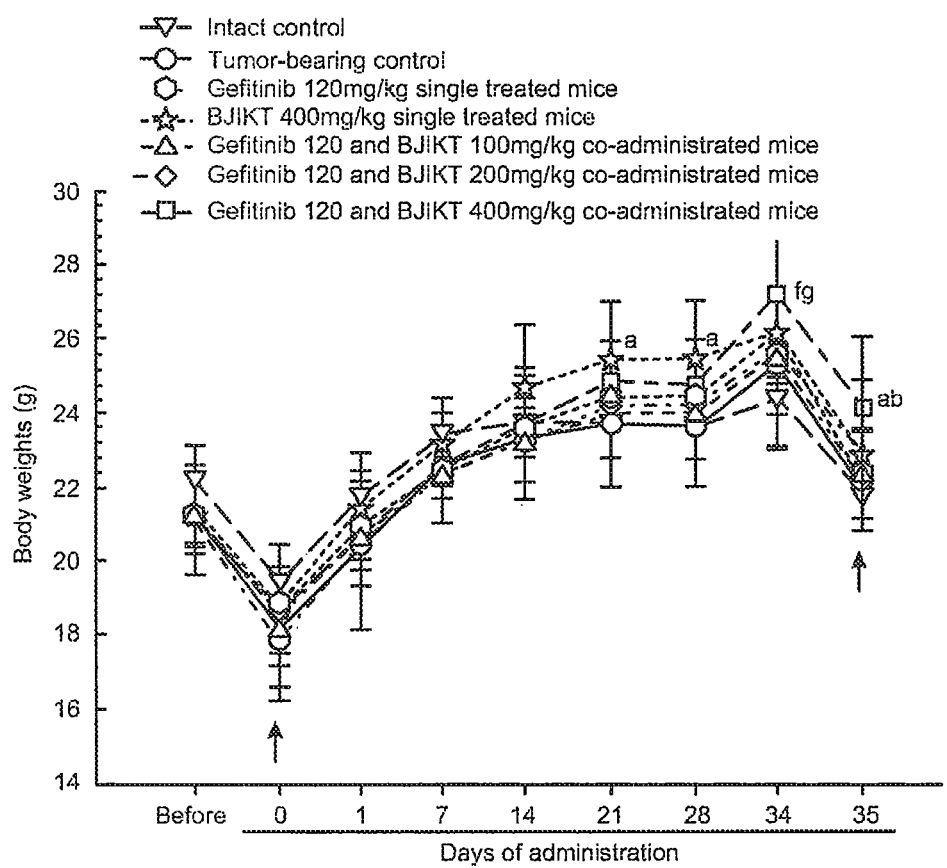
FIG. 34 shows changes in body weight and body weight gains for each group in Example 5.

No significant change in body weight was observed in the tumor-bearing control during the entire period of experiment, compared with the vehicle control. However, a significant decrease (p<0.01) in actual body weight except a tumor weight, and a significant decrease (p<0.01) in body weight gain with respect to the actual body weight during an administration duration were observed, compared with the vehicle control. Meanwhile, no significant change in body weight was observed in the gefitinib and bojungikgi-tang single treated groups, compared with the tumor-bearing control, but significant dose-dependent increases (p<0.01 or p<0.05) in the actual body weight and the body weight gain were observed in the bojungikgi-tang 100, 200, and 400 mg/kg and gefitinib 120 mg/kg co-administered groups, compared with the tumor-bearing control and the gefitinib 120 mg/kg single treated group (FIG. 34).

In the tumor-bearing control, the body weight gain in the duration of administration with respect to the actual body weight (35 days: Actual body weight-body weight on the first day of administration) changed by −184.92%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the body weight gains changed by 68.23%, 8.68%, 163.92%, 212.96%, and 311.84%, respectively, compared with the tumor-bearing control.

8-5. Confirmation of Changes in Tumor Volume

Figure 35:
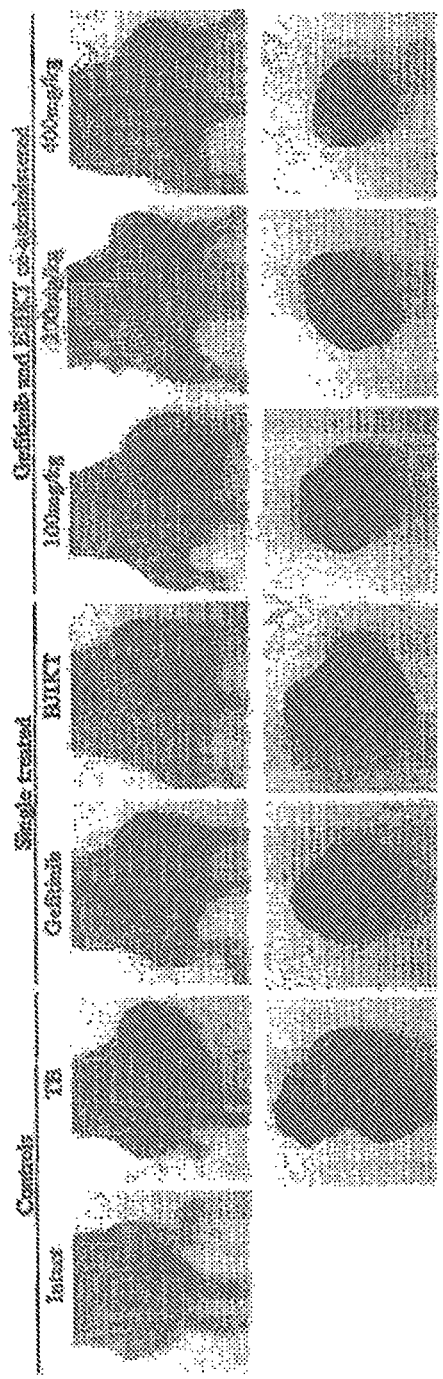
FIG. 35 shows changes in tumor volumes ($mm^3$) for each group, observed with the naked eye.

From the $21^{st}$ day of administration, a significant decrease ($p<0.01$ or $p<0.05$) in a tumor volume was observed in the gefitinib single treated group, compared with the tumor-bearing control, and thus a variation of the tumor volume in the duration of administration significantly decreased ($p<0.05$), compared with the tumor-bearing control. Meanwhile, a significant decrease in the tumor volume was observed from the $21^{st}$ day of administration in the bojungikgi-tang 400 mg/kg single treated group, compared with the tumor-bearing control, and significant decreases ($p<0.01$ or $p<0.05$) in tumor volume were also observed from the $21^{st}$, $7^{th}$, and $3^{rd}$ days of administration in the bojungikgi-tang 100, 200, and 400 mg/kg and gefitinib 120 mg/kg co-administered groups, compared with the tumor-bearing control. In particular, significant decreases ($p<0.01$ or $p<0.05$) in tumor volumes were observed from the $28^{th}$ day of administration in the bojungikgi-tang 200 and 400 mg/kg co-administered groups, compared with the gefitinib single treated group (FIGS. 35 and 36).

In the gefitinib 120 mg/kg and bojungikgi-tang 400 mg/kg single treated groups and the bojungikgi-tang 100, 200, and 400 mg/kg and gefitinib 120 mg/kg co-administered groups, variations in tumor volumes during the duration of drug administration (5 weeks: Volume of tumor on the final sacrifice date-volume of tumor on the first day of administration) changed by −55.42%, −39.38%, −63.85%, −80.05%, and −85.24%, respectively, compared with the tumor-bearing control.

8-6. Confirmation of Changes in Tumor Weight

Significant decreases ($p<0.01$ or $p<0.05$) in relative and absolute tumor weights were observed in all of the drug-administered groups including the bojungikgi-tang 400 mg/kg single treated group, compared with the tumor-bearing control. Meanwhile, significant decreases ($p<0.01$) in tumor weights were observed in the bojungikgi-tang 200 and 400 mg/kg and gefitinib co-administered groups, compared with the gefitinib 120 mg/kg single treated group, and an insignificant decrease ($p<0.05$) in absolute tumor weight was also observed with a significant decrease ($p<0.05$) in relative tumor weight in the bojungikgi-tang 100 mg/kg and gefitinib co-administered group, compared with the gefitinib single treated group (FIGS. 35 and 37).

The absolute tumor weights changed by −39.14%, −22.98%, −56.77%, −69.15%, and −72.12%, respectively, in the gefitinib 120 mg/kg and bojungikgi-tang 400 mg/kg single treated groups and the bojungikgi-tang 100, 200, and 400 mg/kg and gefitinib 120 mg/kg co-administered groups.

The relative tumor weights changed by −37.07%, −21.92%, −57.61%, −68.59, and −74.03%, respectively, in the gefitinib 120 mg/kg and bojungikgi-tang 400 mg/kg single treated groups and the bojungikgi-tang 100, 200, and 400 mg/kg and gefitinib 120 mg/kg co-administered groups.

As seen from the results of Examples 8-5 and 8-6, it was shown that the highly significant decreases in the volume and tumor weight were observed in bojungikgi-tang the 200 and 400 mg/kg co-administered groups, compared with the gefitinib 120 mg/kg single treated group, indicating that the anticancer effect of gefitinib was significantly improved by the co-administration of bojungikgi-tang.

8-7. Confirmation of Changes in Spleen Weight

Significant decreases ($p<0.01$) in absolute and relative weights of a spleen were observed in the tumor-bearing control, compared with the vehicle control. However, significant increases ($p<0.01$) in the weights of the spleen were observed in the bojungikgi-tang co-administered group and all of the co-administered groups, compared with the tumor-bearing control. In particular, the significant increases in the absolute and relative weights of the spleen were observed in the bojungikgi-tang 200 and 400 mg/kg and gefitinib co-administered groups, compared with the gefitinib single treated group (FIG. 37).

In the tumor-bearing control, the absolute weight of the spleen changed by −52.14%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the absolute weights of the spleens changed by 14.01%, 56.42%, 41.63%, 57.20% and 66.15%, respectively, compared with the tumor-bearing control.

In the tumor-bearing control, the relative weight of the spleen changed by −52.13%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the relative weights of the spleens changed by 18.67%, 60.53%, 42.59%, 57.45%, and 58.47%, respectively, compared with the tumor-bearing control.

8-8. Confirmation of Changes in Weight of Submandibular Lymph Node

Significant decreases ($p<0.01$) in absolute and relative weights of a submandibular lymph node were observed in the tumor-bearing control, compared with the vehicle control. However, significant increases ($p<0.01$ or $p<0.05$) in the weights of the submandibular lymph node were observed in the bojungikgi-tang treated group and all of the bojungikgi-tang and gefitinib co-administered groups, compared with the tumor-bearing control. In particular, the significant increases ($p<0.01$ or $p<0.05$) in the absolute and relative weights of the submandibular lymph node were observed in the bojungikgi-tang 200 and 400 mg/kg and gefitinib co-administered groups, compared with the gefitinib single treated group (FIG. 37).

In the tumor-bearing control, the absolute weight of the submandibular lymph node changed by −81.08%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the absolute weights of the submandibular lymph nodes changed by 50.00%, 200.00%, 142.86%, 235.71%, and 328.57%, respectively, compared with the tumor-bearing control.

In the tumor-bearing control, the relative weight of the submandibular lymph node changed by −80.84%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the relative weights of the submandibular lymph nodes changed by 56.54%, 204.65%, 136.35%, 236.78%, and 307.59%, respectively, compared with the tumor-bearing control.

From the results of Examples 8-7 and 8-8, it was shown that significant immunosuppression caused by grafting of the NCI-H520 tumor cells was observed, and the significant atrophy caused by a decrease in the number of lymphocytes in the spleen and lymph node was observed with a decrease in weights of immune organs in a histopathologic aspect. Meanwhile, it was observed that gefitinib had no influence on such immunosuppression associated with the tumor xenograft in the gefitinib single treated group, but the significant immune activation findings were observed in the bojungikgi-tang single treated group and all of the three contents of bojungikgi-tang co-administered groups. In particular, significant immune activation effects were observed in the bojungikgi-tang 400 and 200 mg/kg and gefitinib 120 mg/kg co-administered groups, compared with the gefitinib single treated group, and thus were sufficiently comparable with the immune activation effects of bojungikgi-tang and gefitinib. Therefore, since a decrease in weight and volume of tumor and an increase in apoptosis were observed in the co-administered groups, the improved anticancer effect of gefitinib by the co-administration of bojungikgi-tang was considered to be associated with immune activation.

8-9. Confirmation of Changes in Weight of Periovarian Fat Pad

Significant decreases ($p<0.01$) in absolute and relative weights of a periovarian fat pad were observed in the tumor-bearing control, compared with the vehicle control. However, significant increases ($p<0.01$ or $p<0.05$) in weights of fats around the ovary were observed in the bojungikgi-tang single treated group and the bojungikgi-tang 200 and 400 mg/kg and gefitinib co-administered groups, compared with the tumor-bearing control. In particular, significant increases ($p<0.01$) in weights of the periovarian fat pad were observed in the bojungikgi-tang 200 and 400 mg/kg and gefitinib co-administered groups, compared with the gefitinib single treated group (FIG. 37).

In the tumor-bearing control, the absolute weight of the periovarian fat pad changed by −86.27%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the absolute weights of the periovarian fat pad changed by −3.06%, 151.02%, 13.27%, 88.78%, and 127.55%, respectively, compared with the tumor-bearing control.

In the tumor-bearing control, the relative weight of the periovarian fat pad changed by −85.90%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the relative weights of the periovarian fat pad changed by −0.25%, 155.28%, 11.63%, 85.80%, and 113.11%, respectively, compared with the tumor-bearing control.

8-10. Confirmation of Changes in Blood IL-6 and IFN-γ Contents

Figure 38A:
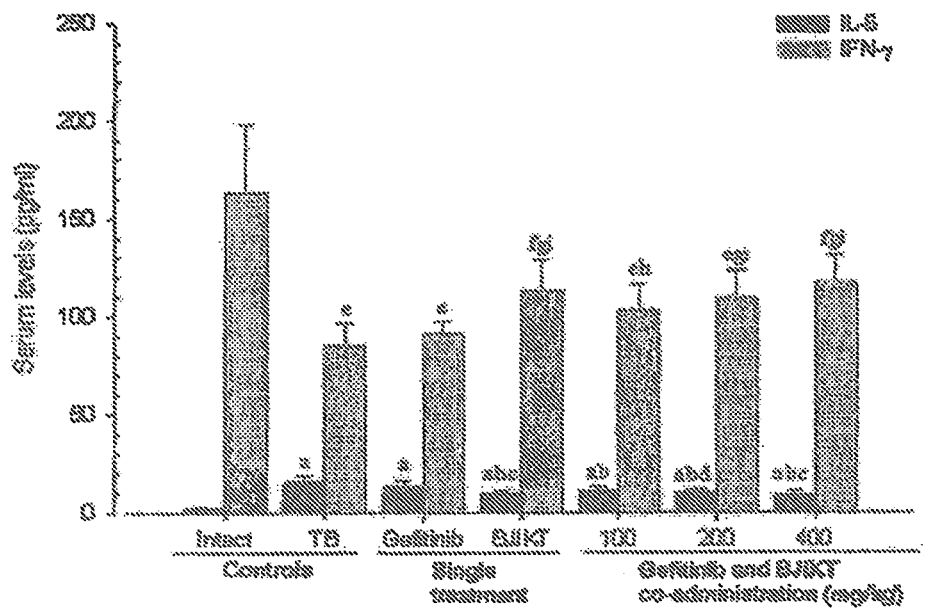
FIG. 38(A) shows changes in blood IL-6 and IFN-γ contents and FIG. 38(B) shows activities of splenic and peritoneal NK cells.

A significant increase ($p<0.01$) in blood IL-6 content and a significant decrease ($p<0.01$) in blood IFN-γ content were observed in the tumor-bearing control, compared with the vehicle control. However, a significant decrease ($p<0.01$) in Blood IL-6 content and a significant increase ($p<0.01$) in blood IFN-γ content compared with the tumor-bearing control were observed in the bojungikgi-tang single treated group and all of the co-administered groups. In particular, significant decreases ($p<0.01$ or $p<0.05$) in blood IL-6 contents and significant increases ($p<0.01$ or $p<0.05$) in blood IFN-γ contents were observed in the bojungikgi-tang 200 and 400 mg/kg and gefitinib co-administered groups, compared with the gefitinib single treated group (FIG. 38A).

In the tumor-bearing control, the blood IL-6 content changed by 583.52%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the blood IL-6 contents changed by −12.33%, −39.83%, −27.25%, −33.96%, and −42.03%, respectively, compared with the tumor-bearing control.

In the tumor-bearing control, the blood IFN-γ content changed by −47.77%, compared with the vehicle control. In the gefitinib 120 mg/kg single treated group and the bojungikgi-tang 400 mg/kg co-administered groups and the bojungikgi-tang 100, 200, and 400 mg/kg and gefitinib 120 mg/kg co-administered groups, the blood IFN-γ contents changed by 6.77%, 32.65%, 20.77%, 28.44%, and 36.89%, respectively, compared with the tumor-bearing control.

8-11. Confirmation of Change in Activities of NK Cells

Figure 38B:
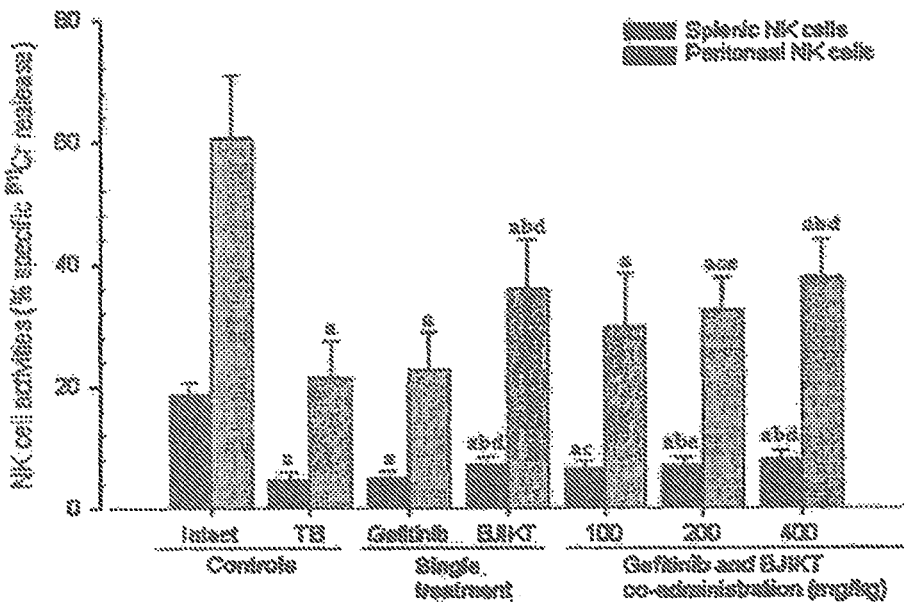

Significant decreases ($p<0.01$) in activities of splenic and peritoneal NK cells were observed in the tumor-bearing control, compared with the vehicle control. However, significant increases in activities of the splenic and peritoneal NK cells were observed in the bojungikgi-tang single treated group and all of the co-administered groups, compared with the tumor-bearing control. In particular, significant increases ($p<0.01$ or $p<0.05$) in activities of the splenic and peritoneal NK cells were also observed in the bojungikgi-tang 200 and 400 mg/kg and gefitinib co-administered groups, compared with the gefitinib single treated group (FIG. 38B).

In the tumor-bearing control, the activities of the splenic NK cells changed by −73.98%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the activities of the splenic NK cells changed by 4.93%, 50.21%, 33.13%, 43.77%, and 66.63%, respectively, compared with the tumor-bearing control.

In the tumor-bearing control, the activities of the peritoneal NK cells changed by −64.48%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the activities of the peritoneal NK cells changed by 5.53%, 66.30%, 37.69%, 50.20%, and 74.46%, respectively, compared with the tumor-bearing control.

From these results, it was shown that the decreases in the activities of macrophagocytes in the spleen and the peritoneal cavity were observed in the tumor-bearing control, and gefitinib had no influence on the activities of the NK cells in the gefitinib single treated group. However, the dose-dependent activities of the peritoneal and splenic NK cells were observed in all of the bojungikgi-tang co-administered groups. In particular, significant increases ($p<0.01$ or $p<0.05$) in the activities of the NK cells were observed in the bojungikgi-tang 400 and 200 mg/kg co-administered groups, compared with the gefitinib single treated group.

8-12. Confirmation of Change in Contents of Splenic Cytokines

Significant decreases ($p<0.01$) in TNF-α, IL-1β, and IL-10 contents in a spleen were observed in the tumor-bearing control, compared with the vehicle control. However, significant increases ($p<0.01$ or $p<0.05$) in the contents of splenic cytokines were observed in the bojungikgi-tang single treated group and the bojungikgi-tang 200 and 400 mg/kg and gefitinib co-administered groups, compared with the tumor-bearing control. In particular, significant increases ($p<0.01$ or $p<0.05$) in the TNF-α, IL-1β, and IL-10 contents in the spleen were observed in the bojungikgi-tang 200 and 400 mg/kg and gefitinib co-administered groups, compared with the gefitinib single treated group (FIG. 39).

In the tumor-bearing control, the TNF-α content in the spleen changed by −60.65%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the TNF-α contents in the spleens changed by 6.73%, 76.83%, 13.33%, 47.43%, and 79.42%, respectively, compared with the tumor-bearing control.

In the vehicle control, the IL-10 content in the spleen changed by −71.90%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the IL-1β contents in the spleens changed by 8.36%, 71.19%, 19.66%, 60.67%, and 81.16%, respectively, compared with the tumor-bearing control.

In the vehicle control, the IL-10 content in the spleen changed by −54.88%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the IL-10 contents in the spleens changed by 5.16%, 46.74%, 12.80%, 43.99%, and 60.33%, respectively, compared with the tumor-bearing control.

From these results, it was shown that a decrease in contents of the immune activating cytokines, TNF-α and IL-1β in the spleen and a decrease in blood IFN-γ content by grafting of human lung cancer cells, NCI-H520, were observed, and that a decrease in T lymphocytes and a decrease in content of the immunosuppressive cytokine, IL-10, by immunosuppression were also observed. Meanwhile, such decreases in the TNF-α, IL-1β, and IL-10 contents in the spleen and the blood IFN-γ content were also significantly suppressed by administration of bojungikgi-tang. In particularly, the significant decreases ($p<0.01$ or $p<0.05$) in the TNF-α, IL-1β, and IL-10 contents in the spleen and the blood IFN-γ content were also be observed in the bojungikgi-tang 400 and 200 mg/kg co-administered groups, compared with the gefitinib single treated group.

Figure 40:
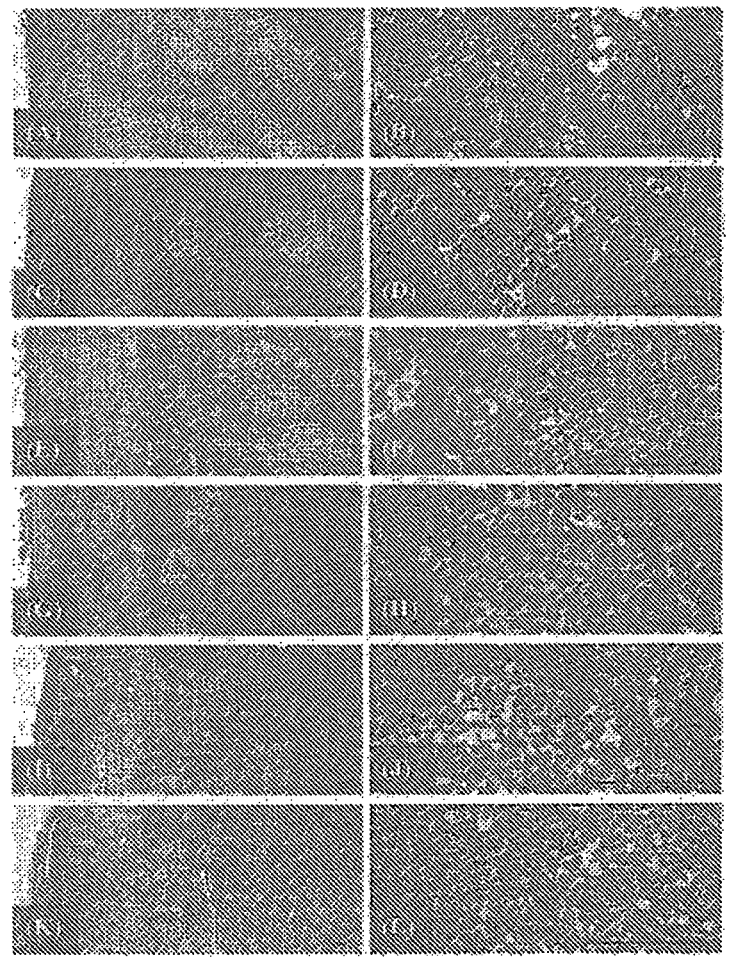
FIG. 40 shows tumor mass cells observed in each group.
Figure 42:
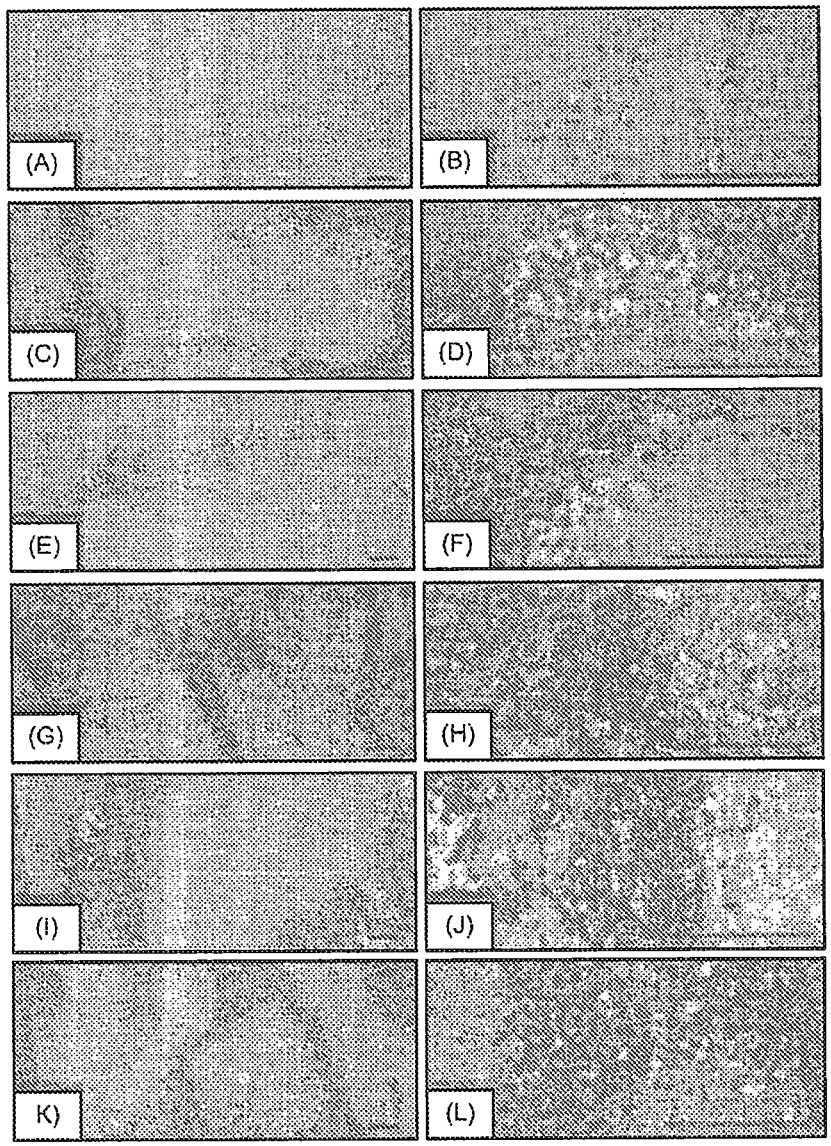
FIG. 42 shows changes in number of caspase-3 immunoreactive cells.
Figure 43:
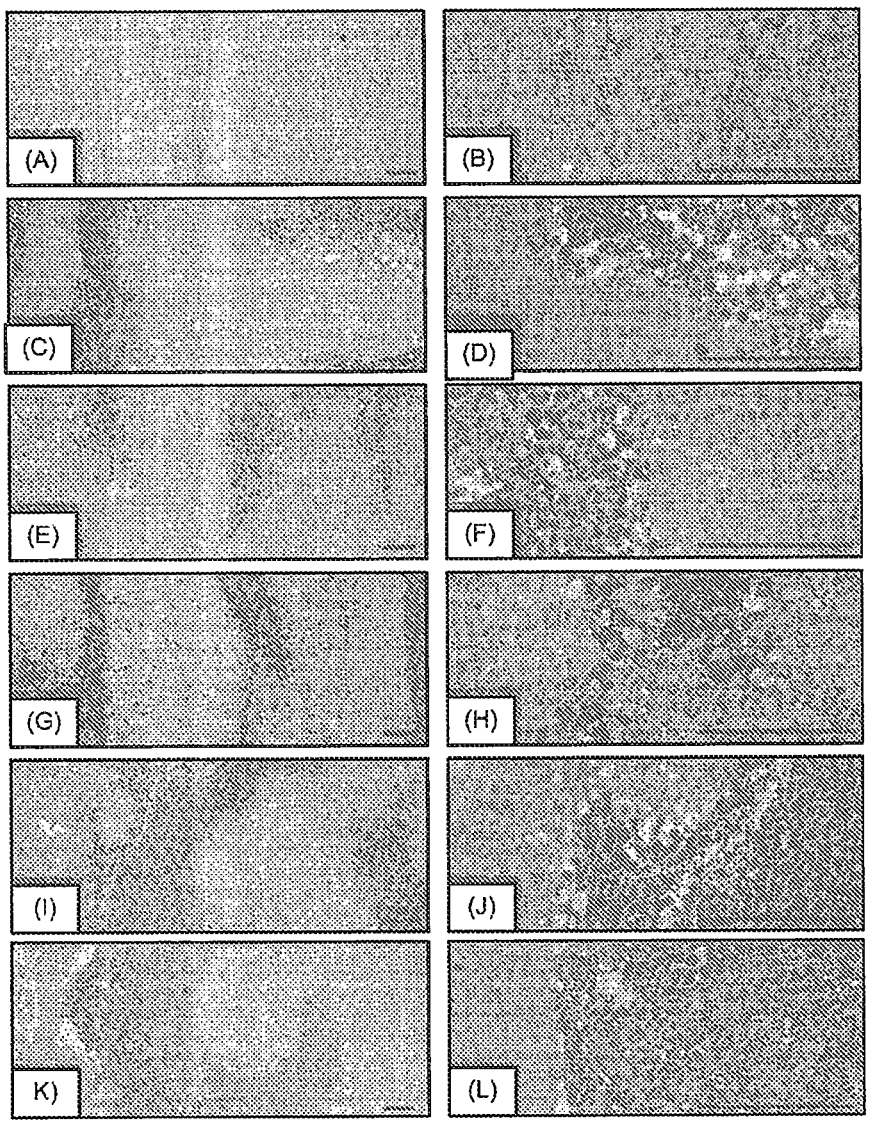
FIG. 43 shows changes in number of PARP immunoreactive cells.
Figure 44:
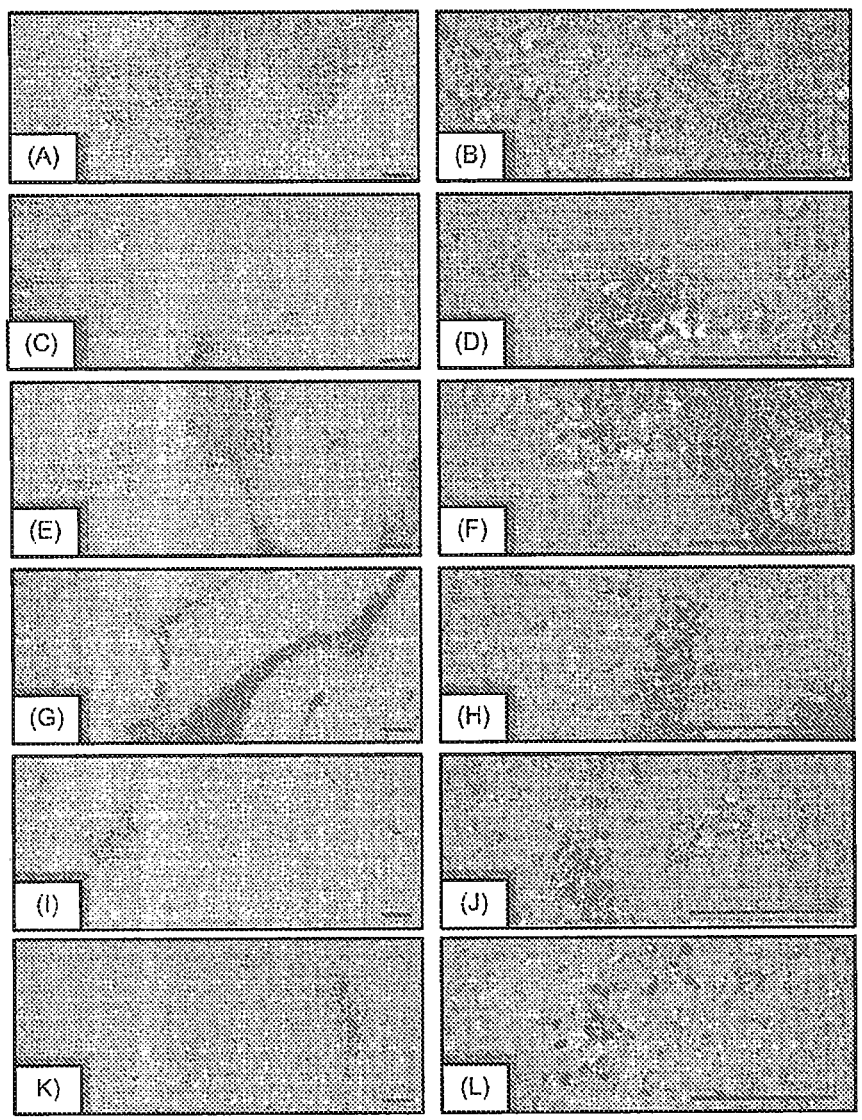
FIG. 44 shows changes in number of COX-2 immunoreactive cells.

8-13. Confirmation of Histological Change (1) Histopathologic Change of Tumor Mass As shown in the image of FIG. 40 (A, B: Tumor-bearing control, C, D: Gefitinib 120 mg/kg single treated mice, E, F: BJIKT 400 mg/kg single treated mice, G, H: Gefitinib 120 mg/kg and BJIKT 100 mg/kg co-administered mice, I, J: Gefitinib 120 mg/kg and BJIKT 200 mg/kg co-administered mice, K, L: Gefitinib 120 mg/kg and BJIKT 400 mg/kg co-administered mice; A to L in FIGS. 42 to 46 denote the same as described above), relatively sufficiently differentiated NCI-H520 lung cancer cells were compactly distributed in the tumor-bearing control, and an eosinophilic increase and pyknosis in the cytoplasm by apoptosis were observed in some cells.

Meanwhile, significant increases in apoptotic cells compared with the tumor-bearing control were observed in the gefitinib single treated group and all of the bojungikgi-tang 100, 200, and 400 mg/kg and gefitinib 120 mg/kg co-administered groups, which resulted in a significant decrease in percentage of the NCI-H520 cells. In particular, a significant decrease ($p<0.01$ or $p<0.05$) in the volume of tumor cells and a significant increase ($p<0.01$ or $p<0.05$) in the number of apoptotic cells were observed in the bojungikgi-tang 200 and 400 mg/kg and gefitinib 120 mg/kg co-administered groups, compared with the gefitinib single treated group (FIG. 41).

Figure 45:
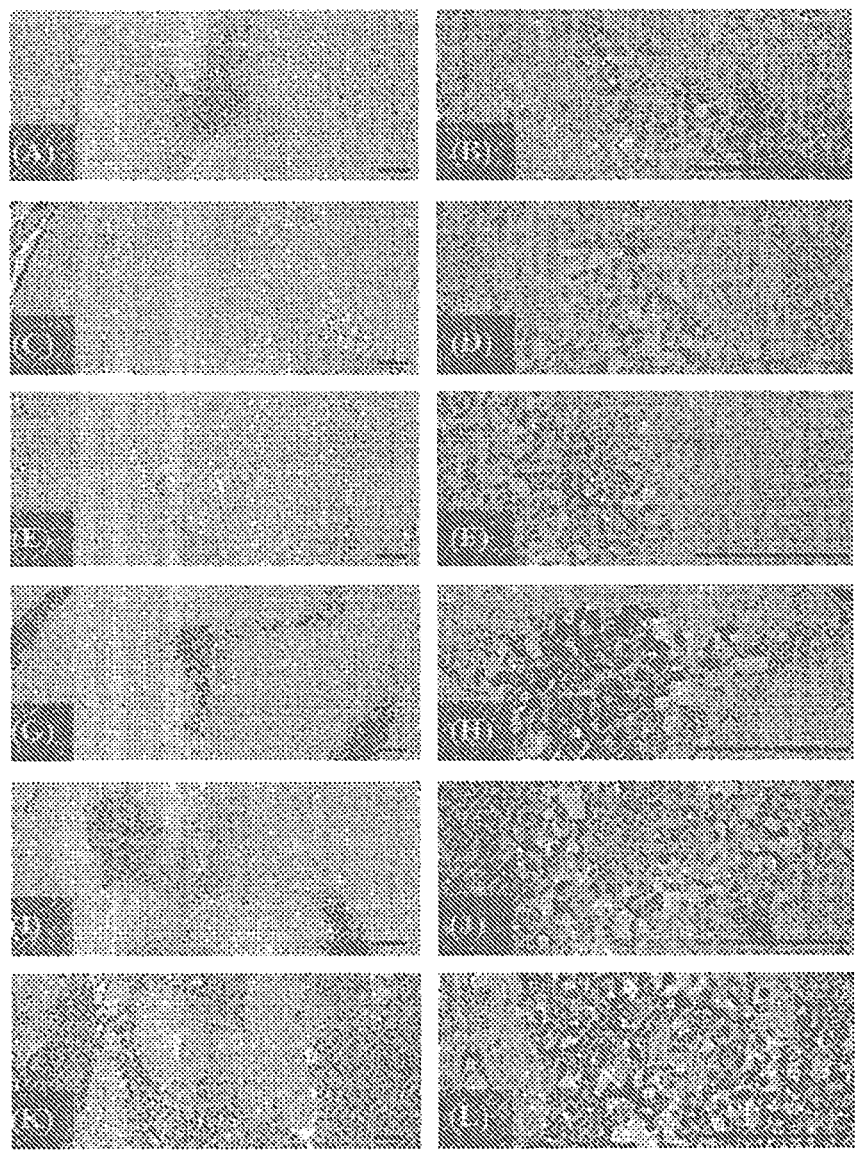
FIG. 45 shows changes in number of iNOS immunoreactive cells.
Figure 46:
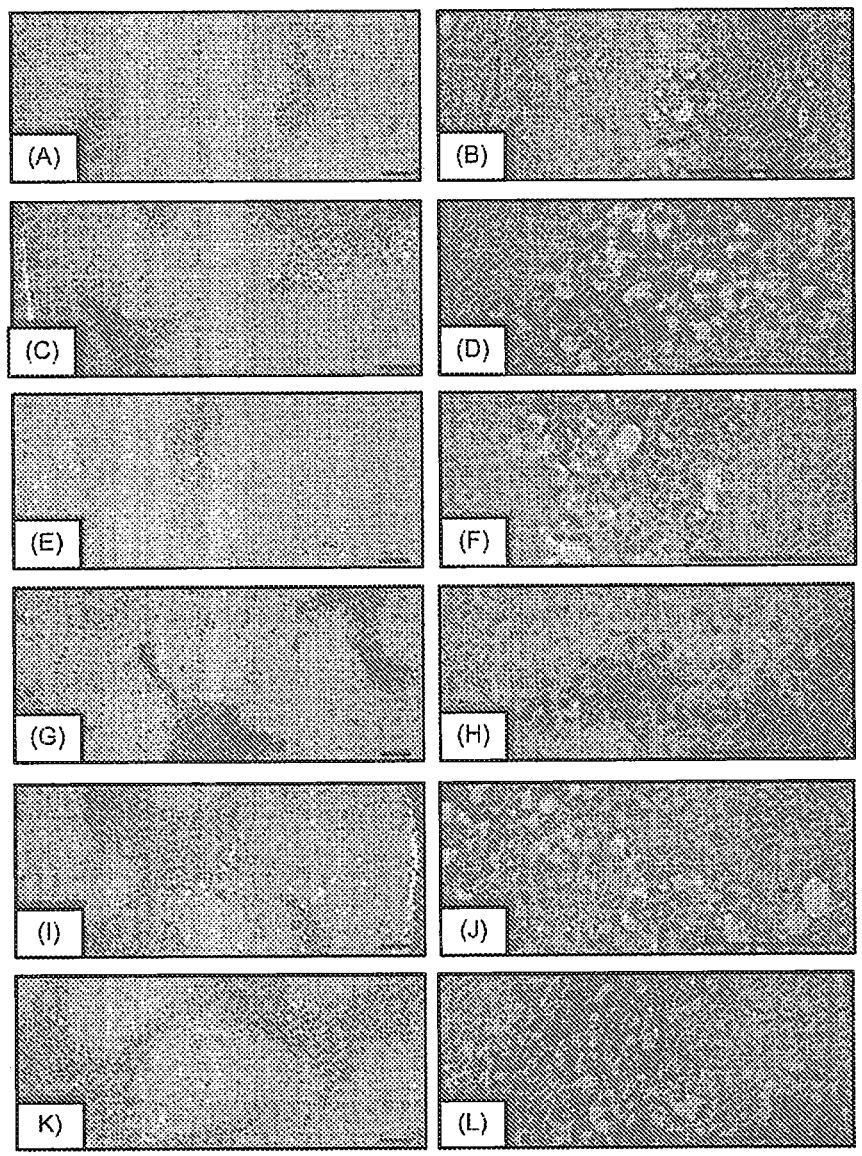
FIG. 46 shows changes in number of TNF-α immunoreactive cells.

Also, a significant decrease ($p<0.01$ or $p<0.05$) in the number of COX-2 immunoreactive cells was observed with significant increases ($p<0.01$ or $p<0.05$) in the number of caspase-3 and PARP immunoreactive cells in all of the administered groups including the bojungikgi-tang 400 mg/kg single treated group, compared with the tumor-bearing control. In particular, significant increases ($p<0.01$) in the number of the caspase-3 and PARP immunoreactive cells were observed with a significant decreases in the number of the COX-2 immunoreactive cells in the bojungikgi-tang 200 and 400 mg/kg and gefitinib 120 mg/kg co-administered groups, compared with the gefitinib single treated group (FIGS. 42 to 44, and FIG. 41). Further, significant increases in the number of iNOS and TNF-α immunoreactive cells in a tumor mass were observed in all of the bojungikgi-tang single treated group or bojungikgi-tang co-administered groups, compared with the tumor-bearing control. In particular, significant increases ($p<0.01$) in the number of the iNOS and TNF-α immunoreactive cells were observed in the bojungikgi-tang 200 and 400 mg/kg and gefitinib 120 mg/kg co-administered groups, compared with the gefitinib single treated group (FIGS. 45 and 46, and FIG. 41).

In the gefitinib 120 mg/kg and bojungikgi-tang 400 mg/kg single treated groups and the bojungikgi-tang 100, 200, and 400 mg/kg and gefitinib 120 mg/kg co-administered groups, the percentages of the tumor cells in tumor tissues changed by −36.78%, −5.12%, −31.15%, −49.80%, and −63.69%, respectively, compared with the tumor-bearing control.

In the gefitinib 120 mg/kg and bojungikgi-tang 400 mg/kg single treated groups and the bojungikgi-tang 100, 200, and 400 mg/kg and gefitinib 120 mg/kg co-administered groups, the percentages of the apoptotic cells in the tumor tissues changed by 131.78%, 57.01%, 180.37%, 246.73%, and 324.30%, respectively, compared with the tumor-bearing control.

In the gefitinib 120 mg/kg and bojungikgi-tang 400 mg/kg single treated groups and the bojungikgi-tang 100, 200, and 400 mg/kg and gefitinib 120 mg/kg co-administered groups, the percentages of the caspase-3 immunoreactive cells in the tumor tissues changed by 168.67%, 42.17%, 191.57%, 263.86%, and 349.40%, respectively, compared with the tumor-bearing control.

In the gefitinib 120 mg/kg and bojungikgi-tang 400 mg/kg single treated groups and the bojungikgi-tang 100, 200, and 400 mg/kg and gefitinib 120 mg/kg co-administered groups, the percentages of the PARP immunoreactive cells in the tumor tissues changed by 125.47%, 50.00%, 106.60%, 196.23%, and 280.19%, respectively, compared with the tumor-bearing control.

In the gefitinib 120 mg/kg and bojungikgi-tang 400 mg/kg single treated groups and the bojungikgi-tang 100, 200, and 400 mg/kg and gefitinib 120 mg/kg co-administered groups, the percentages of the COX-2 immunoreactive cells in the tumor tissues changed by −42.48%, −17.11%, −30.38%, −59.29%, and −79.65%, respectively, compared with the tumor-bearing control.

In the gefitinib 120 mg/kg and bojungikgi-tang 400 mg/kg single treated groups and the bojungikgi-tang 100, 200, and 400 mg/kg and gefitinib 120 mg/kg co-administered groups, the percentages of the iNOS immunoreactive cells in the tumor tissues changed by 9.02%, 27.82%, 39.85%, 106.77%, and 145.11%, respectively, compared with the tumor-bearing control.

In the gefitinib 120 mg/kg and bojungikgi-tang 400 mg/kg single treated groups and the bojungikgi-tang 100, 200, and 400 mg/kg and gefitinib 120 mg/kg co-administered groups, the percentages of the TNF-α immunoreactive cells in the tumor tissues changed by 12.63%, 30.53%, 41.05%, 166.32%, and 305.26%, respectively, compared with the tumor-bearing control.

Caspase-3 and PARP are representative markers for apoptosis, and an increase in caspase-3 and PARP immunoreactivity in a tumor mass means apoptosis of tumor cells. From these facts, an increase in caspase-3 and PARP immunoreactivity associated with administration of gefitinib or bojungikgi-tang was observed. In particular, significant increases ($p<0.01$) in caspase-3 and PARP immunoreactivity in the tumor compared with the gefitinib single treated group were observed in the bojungikgi-tang 400 and 200 mg/kg co-administered groups, indicating that the anticancer effect of gefitinib was significantly improved by co-administration of bojungikgi-tang at contents of 200 and 400 mg/kg.

Also, suppression of immunoreactivity of COX-2 which was known to play an important role in synthesis of prostaglandins which were representative as inflammatory mediators and participate in angiogenesis in a tumor was observed in all of the drug-administered groups including the gefitinib single treated group. Also, significant decreases ($p<0.01$) in the immunoreactivity compared with the gefitinib single treated group were observed in the bojungikgi-tang 400 and 200 mg/kg co-administered groups. It was known that an increase in iNOS activity causes shocks and excessive inflammatory reactions in combination with endotoxins, IL-10, TNF-α, and IFN-γ, and exacerbates a tumor, for example, angiogenesis in the tumor, but that iNOS secreted from immune activating cells such as macrophages induces apoptosis of tumor cells, resulting in inhibition of growth of the tumor.

In this Example, the significant increases in iNOS immunoreactivity in the NCI-H520 cell-transplanted tumor mass were observed in all of the bojungikgi-tang co-administered groups. In particular, the significant increases ($p<0.01$) in iNOS immunoreactivity in a tumor compared with the gefitinib single treated group were also observed in the bojungikgi-tang 400 and 200 mg/kg co-administered groups. Such increases in iNOS immunoreactivity were considered to be induced by immune activation by administration of bojungikgi-tang, and significant increases ($p<0.01$) in immunoreactivity of TNF-α, stimulating tumor necrosis in the tumor mass, were observed in the bojungikgi-tang 400 and 200 mg/kg co-administered groups, compared with the gefitinib single treated group.

(2) Histopathologic Change of Spleen

Figure 47:
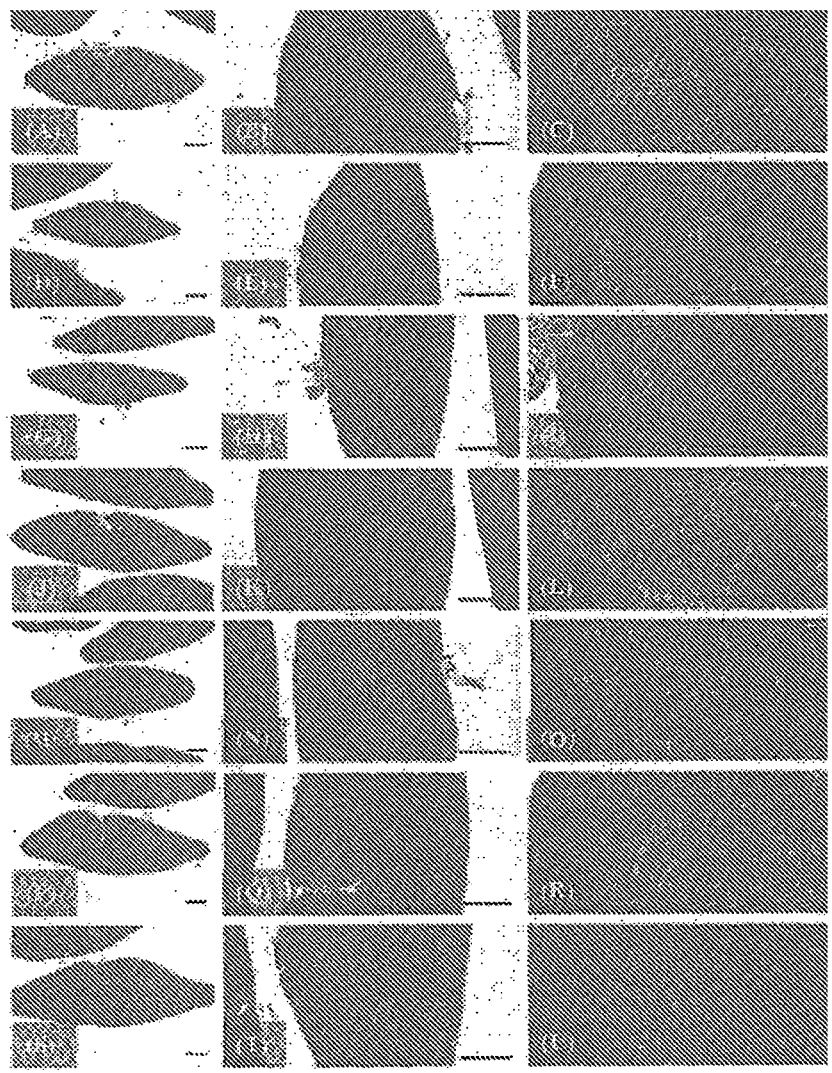
FIG. 47 shows histopathological changes in spleens.

Atrophy featuring a significant decrease in lymphocytes at a splenic white pulp compared with the vehicle control was observed in the tumor-bearing control, and thus significant decreases ($p<0.01$) in thickness of the spleen and diameter and number of white pulps were also observed. Meanwhile, significant increases in thickness of the spleen and diameter and number of the white pulps were observed in a histopathologic aspect in the bojungikgi-tang single treated group and all of the bojungikgi-tang 100, 200, and 400 mg/kg co-administered groups, compared with the tumor-bearing control. In particular, the significant increases ($p<0.01$) in thickness of the spleen and diameter and number of white pulps were also observed in the bojungikgi-tang 200 and 400 mg/kg and gefitinib 120 mg/kg co-administered groups, compared with the gefitinib single treated group (FIGS. 47 and 48, A to C: Vehicle control, D to F: Tumor-bearing control, G to I: Gefitinib 120 mg/kg single treated mice, J to L: BJIKT 400 mg/kg single treated mice, M to O: Gefitinib 120 mg/kg and BJIKT 100 mg/kg co-administered mice, P to R: Gefitinib 120 mg/kg and BJIKT 200 mg/kg co-administered mice, and S to U: Gefitinib 120 mg/kg and BJIKT 400 mg/kg co-administered mice).

In the tumor-bearing control, the total thickness of the spleen changed by −35.23%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the total thicknesses of the spleens changed by −6.99%, 18.08%, 6.44%, 24.25%, and 33.56%, respectively, compared with the tumor-bearing control.

In the tumor-bearing control, the number of white pulps in the spleen changed by −69.66%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the numbers of white pulps in the spleens changed by 22.22%, 103.70%, 59.26%, 107.41%, and 133.33%, respectively, compared with the tumor-bearing control.

In the tumor-bearing control, the diameter of the white pulp in the spleen changed by −49.04%, compared with the vehicle control. In the 120 mg/kg gefitinib- and 400 mg/kg bojungikgi-tang co-administered groups and the bojungikgi-tang 100, 200, and 400 mg/kg and gefitinib 120 mg/kg co-administered groups, the diameters of the white pulps in the spleens changed by 6.51%, 52.16%, 14.90%, 39.38%, and 50.38%, respectively, compared with the tumor-bearing control.

(3) Histopathologic Changes of Submandibular Lymph Nodes

Figure 49:
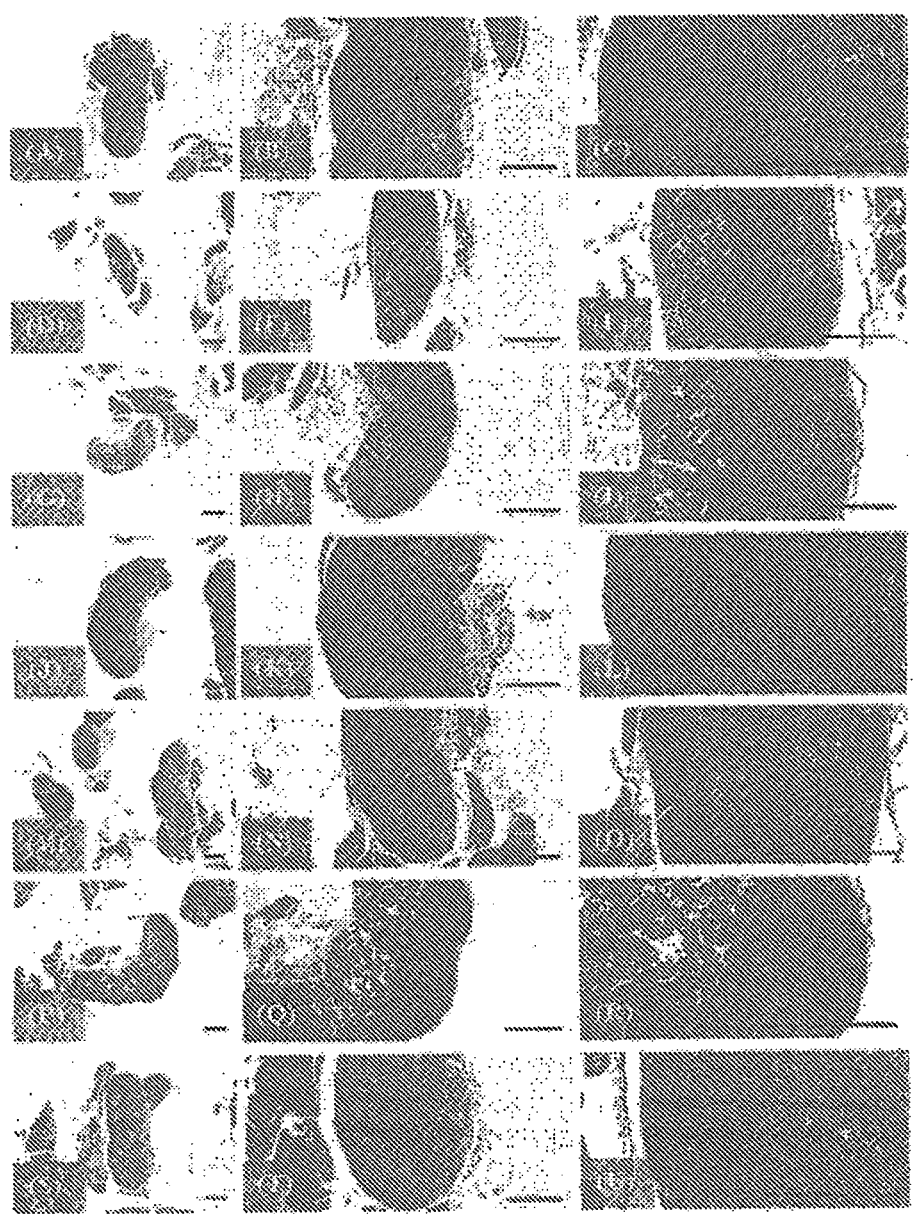
FIG. 49 shows histopathological changes in submandibular lymph nodes.

Atrophy featuring a significant decrease in lymphocytes at a lymph node cortex compared with the vehicle control was observed in the tumor-bearing control, compared with the vehicle control, and thus significant decreases ($p<0.01$) in thicknesses of the submandibular lymph node and the cortex and number of follicles in the cortex were also observed. Meanwhile, significant increases in thicknesses of the lymph node and the cortex and number of follicles in the cortex were observed in a histopathologic aspect in the bojungikgi-tang single treated group and all of the bojungikgi-tang 100, 200, and 400 mg/kg co-administered groups, compared with the tumor-bearing control. In particular, the significant increases ($p<0.01$ or $p<0.05$) in thicknesses of the lymph node and the cortex and number of follicles in the cortex were also observed in the bojungikgi-tang 200 and 400 mg/kg and gefitinib 120 mg/kg co-administered groups, compared with the gefitinib single treated group (FIGS. 49 and 50).

In the tumor-bearing control, the total thickness of the submandibular lymph node changed by −49.45%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the total thicknesses of the submandibular lymph nodes changed by 7.42%, 71.41%, 20.26%, 53.10%, and 93.39%, respectively, compared with the tumor-bearing control.

In the tumor-bearing control, the number of the follicles in the submandibular lymph node cortex changed by −71.01%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the numbers of the follicles in the submandibular lymph node cortices changed by 15.00%, 85.00%, 45.00%, 90.00%, and 115.00%, respectively, compared with the tumor-bearing control.

In the tumor-bearing control, the thickness of the submandibular lymph node cortex changed by −59.19%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the thicknesses of the submandibular lymph node cortices changed by 16.19%, 92.17%, 27.11%, 84.79%, and 122.57%, respectively, compared with the tumor-bearing control.

(4) Histopathologic Change of Periovarian Fat Pad

Figure 51:
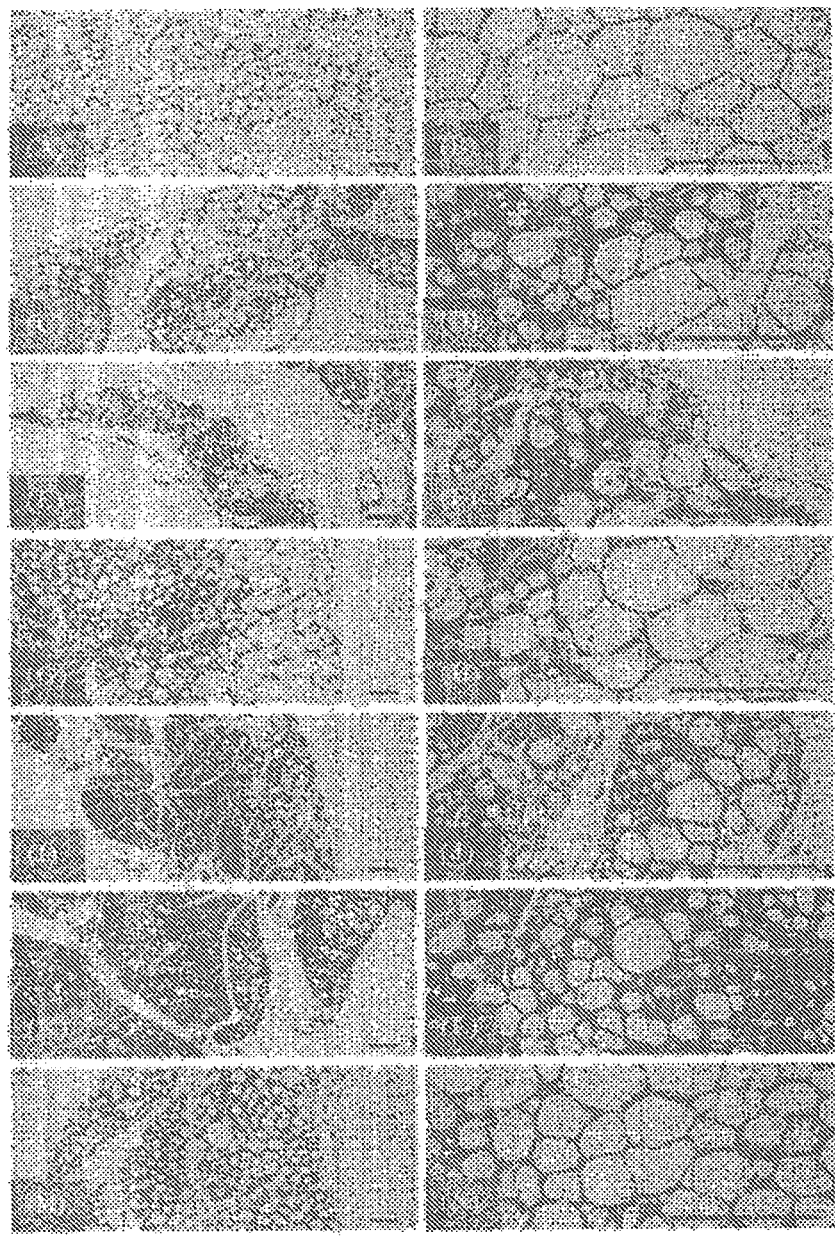
FIG. 51 shows periovarian fat pads.

Atrophy featuring a significant decrease in white adipocytes was observed in the tumor-bearing control, compared with the vehicle control, and thus significant decreases ($p<0.01$) in thicknesses of accumulate fats and mean diameters of the white adipocytes were also observed. Meanwhile, significant increases in thicknesses of the accumulated fats and mean diameters of the white adipocytes compared with the tumor-bearing control were observed in a histopathologic aspect in the bojungikgi-tang single treated group and the bojungikgi-tang 100, 200, and 400 mg/kg co-administered groups. In particular, the significant increases ($p<0.01$) in thickness of the accumulated fats and mean diameters of the white adipocytes were also observed in the bojungikgi-tang 200 and 400 mg/kg and gefitinib 120 mg/kg co-administered groups, compared with the gefitinib single treated group (FIGS. 51 and 52).

In the tumor-bearing control, the thickness of the periovarian fat pads changed by −77.83%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the thicknesses of the periovarian fat pads changed by 2.11%, 160.76%, 77.64%, 150.63%, and 206.33%, respectively, compared with the tumor-bearing control.

In the tumor-bearing control, the mean diameter of the white adipocytes around the ovary changed by −61.49%, compared with the vehicle control. In the gefitinib 120 mg/kg and bojungikgi-tang 400 mg/kg single treated groups and the bojungikgi-tang 100, 200, and 400 mg/kg and gefitinib 120 mg/kg co-administered groups, the mean diameters of the white adipocytes around the ovary changed by −7.01%, 104.05%, 10.90%, 32.80%, and 102.61%, respectively, compared with the tumor-bearing control.

From the results of Example 8, it was observed that the co-administration of 400 or 200 mg/kg bojungikgi-tang resulted in a significant increase in the anticancer effect of gefitinib through immune activation, and that tumor-associated cachexia was significantly inhibited. Therefore, it is determined that the co-administration of 200 mg/kg or more bojungikgi-tang allowed the gefitinib to significantly increase the anticancer effect and reduce the tumor-associated cachexia through the immune activation in the NCI-H520 cell-transplanted mice without affecting bioavailability of the gefitinib. As a result, the co-administration of gefitinib and bojungikgi-tang to the lung cancer patients is expected to provide a new treating method which is very useful in integrative medicine and treatment.

Exemplary Embodiment 3

Figure 53:
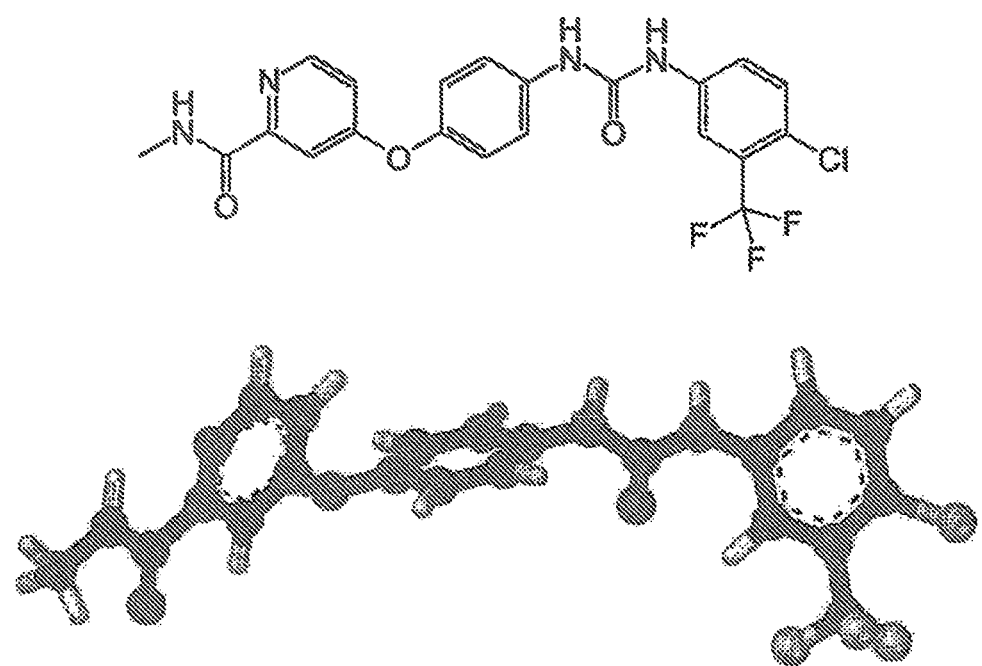
FIG. 53 shows a structure of sorafenib, which is an anticancer agent used in the present invention.

According to exemplary embodiment 3, changes of effects and an effect of reducing side effects, which are caused by co-administration of bojungikgi-tang and an anticancer agent, will be examined. As an anticancer agent according to Exemplary embodiment 3, sorafenib (Jeil Pharmaceutical Co., Ltd, Yongin, Korea, FIG. 53) was used, and bojungikgi-tang (hereinafter referred to as BJIKT) was purchased from Hanpoong Pharm & Foods Co., Ltd (Seoul, Korea), and a composition thereof is shown in Table 17.

TABLE 17

| Herbs | Scientific Names/Produce Region | Amounts (g) |
|---|---|---|
| Astragali Radix | *Astragalus membranaceus* Bunge | 1.33 |
| Atractylodis Rhizoma | *Atractylodes lancea* D.C | 1.33 |
| Ginseng Radix Alba | *Panax ginseng* C. A. Meyer. | 1.33 |
| Angelicae Gigantis Radix | *Angelica gigas* N. | 1.00 |
| Bupleuri Radix | *Bupleurum falcatum* L. | 0.67 |
| Zizyphi Fructus | *Zizyphus jujuba* var. *inermis* (bunge) Render | 0.67 |
| Citri Unshii Pericarpium | *Citrus unshiu* S. Marcov. | 0.67 |
| Glycyrrhizae Rhizoma | *Glycyrrhiza uralensis* Fisch | 0.50 |
| Cimicifugae Rhizoma | *Cimicifuga heracleifolia* Kom. | 0.33 |
| Zingiberis Rhizoma Siccus | *Zingiber officinale* Roscoe | 0.17 |
| Total | 10 types | 8.00 |

As a result of the study on a method of administering BJIKT, the inventors found that single-time oral co-administration of BJIKT within 5 minutes significantly suppressed bioavailability of sorafenib, single-time oral co-administration of BJIKT within 3.5 hours did not show a significant difference in a treating effect, and repeated oral co-administration of BJIKT within 5 minutes for 7 days also did not have a significant influence on absorption and excretion of sorafenib, that is, bioavailability in oral administration.

Therefore, in Exemplary embodiment of the present invention, the bioavailabilities of sorafenib according to single-time and repeated oral co-administration at intervals of 3.5 hours were observed.

Example 9. Check of an Influence on an Anticancer Effect of Sorafenib According to Co-Administration of Sorafenib and BJIKT 9.1. Preparation of Laboratory Animals In Example 9, Balb/c Slc nu/nu mice (6-week-old female, Charles River, Shiga, Japan) were used as laboratory animals. A total of 113 nude mice were purchased and acclimatized for 8 days. Among the mice, 93 mice having uniform body weights were selected, and HepG2 cells were xenografted into subcutaneous regions of right hips of the selected mice. After 27 days, among the mice, those having a tumor volume of 112.10±13.37 mm$^3$ (95.51 to 142.82 mm$^3$) or more were selected again, and divided into groups of 7 mice each to be used in the experiment. Separately, a vehicle control of 7 mice was also prepared (body weight: normal group −23.20±1.72 g, 21.50 to 25.60 g; tumor-bearing group −21.02±0.80 g, 19.40 to 22.70 g).

A concentration of the BJIKT (0, 0.5, 1, 5, 10, 50, 100, and 500 mg/ml) and sorafenib (0, 0.1, 1, 2, 4, 6, 8, and 10 µM) at which viability of HepG2 cells (1×10$^4$ cell) is inhibited by half, which is IC50, was evaluated using a general MTT method with respect to the mice. A total of 49 mice were divided into 7 groups (vehicle control: vehicle control, TB control: a sterile distilled water-administered group after tumor cell xenograft, SF20: sorafenib 20 mg/kg single treated group after tumor cell xenograft, BJIKT400: BJIKT 400 mg/kg single treated group after tumor cell xenograft, SF+BJIKT100: sorafenib 20 mg/kg and BJIKT 100 mg/kg co-administered group after tumor cell xenograft, SF+BJIKT200: sorafenib 20 mg/kg and BJIKT 200 mg/kg co-administered group after tumor cell xenograft, and SF+BJIKT400: sorafenib 20 mg/kg and BJIKT 400 mg/kg co-administered group after tumor cell xenograft) and used for experiments.

9.2. Tumor Cell Xenograft and Drug Administration Method

HepG2 (American Type Culture Collection Center, Manassas, Va., USA) cells were sub-cultured and maintained in a 5% $CO_2$ incubator at 37° C. using an RPMI 1640 (Gibco, Grand Island, N.Y., USA) medium supplemented with 10% fetal bovine serum (FBS) to a density of $1.0 \times 10^8$ cell/ml to prepare a tumor cell suspension, 0.2 mL ($2 \times 10^7$ cell/mouse) of the HepG2 tumor cell suspension was xenografted into subcutaneous regions of right hips of the mice, thereby forming solid tumor mass. In the experiment, from 28 days after the grafting of HepG2 lung cancer cell lines (tumor volume; $104.08 \pm 10.22$ mm$^3$, 87.94 to 131.77 mm$^3$), sorafenib or BJIKT was orally administered.

From 28 days after the grafting of the HepG2 lung cancer cells, 400, 200, or 100 mg/kg of BJIKT was co-administered to the sorafenib 20 mg/kg orally administered mice orally once a day at intervals of 3.5 hours for 35 days. The same dose of sterile distilled water was only administered to the BJIKT or sorafenib single treated group, and only sterile distilled water was administered as a vehicle to the vehicle control twice at intervals of 3.5 hours.

9.3. Observation Items

A concentration of BJIKT and sorafenib that inhibits viability of HepG2 cells by half, that is, IC50 (cytotoxicity) was evaluated using a general MTT method. Anticancer and immune enhancing effect and an influence on tumor-associated cachexia in HepG2 liver cancer cell line xenograft mice were evaluated (Tables 18 and 19).

(1) Anticancer effect: a tumor volume, a tumor weight, changes in tumor cell volumes and apoptotic cell percentages in formed tumor mass, and changes in caspase-3, PARP, COX-2, iNOS, and TNF-α immunoreactivities in the tumor mass (2) Immune enhancing effect: changes in immune organ (thymus and submandibular lymph node) weights, blood IFN-γ contents, NK cell activities, changes in TNF-α, IL-1β, and IL-10 contents in the spleen, histological changes in immune organs, and changes in TNF-α immunoreactivities in the tumor mass and submandibular lymph node (3) Inhibitory effect on tumor-associated cachexia: a change in body weight, weight in periovarian fat pad, blood IL-6 content, and a histological change in the periovarian fat pad

TABLE 18

Effects on HepG2 cell xenograft nude mice

| Group | Xenograft | Dose (mg/kg/day) |
|---|---|---|
| Control | Saline | Vehicle 10 ml/kg |
| Control | HepG2 cells | Vehicle 10 ml/kg |
| Reference | HepG2 cells | Sorafenib single (20 mg/kg) |
| Reference | HepG2 cells | BJIKT single (400 mg/kg) |
| Active | HepG2 cells | Sorafenib and BJIKT (20 and 100 mg/kg) |
| Active | HepG2 cells | Sorafenib and BJIKT (20 and 200 mg/kg) |
| Active | HepG2 cells | Sorafenib and BJIKT (20 and 400 mg/kg) |

TABLE 19

| Antisera or detection kits | Code | Source | Dilution |
|---|---|---|---|
| Primary antisera* | | | |
| Anti-cleaved caspase-3 (Asp175) polyclonal antibody | 9661 | Cell Signaling Technology Inc, Beverly, MA, USA | 1:400 |
| Anti-cleaved PARP (Asp214) rat specific antibody | 9545 | Cell Signaling Technology Inc, Beverly, MA, USA | 1:100 |
| Anti-tumor necrosis factor-α (4E1) antibody | sc-130349 | Santa Cruz Biotechnology, Santa Cruz, CA, USA | 1:200 |

TABLE 19-continued

| Antisera or detection kits | Code | Source | Dilution |
|---|---|---|---|
| Anti-cyclooxygenase (murine) polyclonal antibody | 160126 | Cayman Chemical., Ann Arbor, MI, USA | 1:200 |
| Anti-nitric oxide synthase2 (N-20) polyclonal antibody | sc-651 | Santa Cruz Biotechnology, Santa Cruz, CA, USA | 1:100 |
| Detection kits | | | |
| Vectastain Elite ABC Kit | PK-6200 | Vector Lab. Inc., Burlingame, CA, USA | 1:50 |
| Peroxidae substrate kit | SK-4100 | Vector Lab. Inc., Burlingame, CA, USA | 1:50 |

Figure 54:
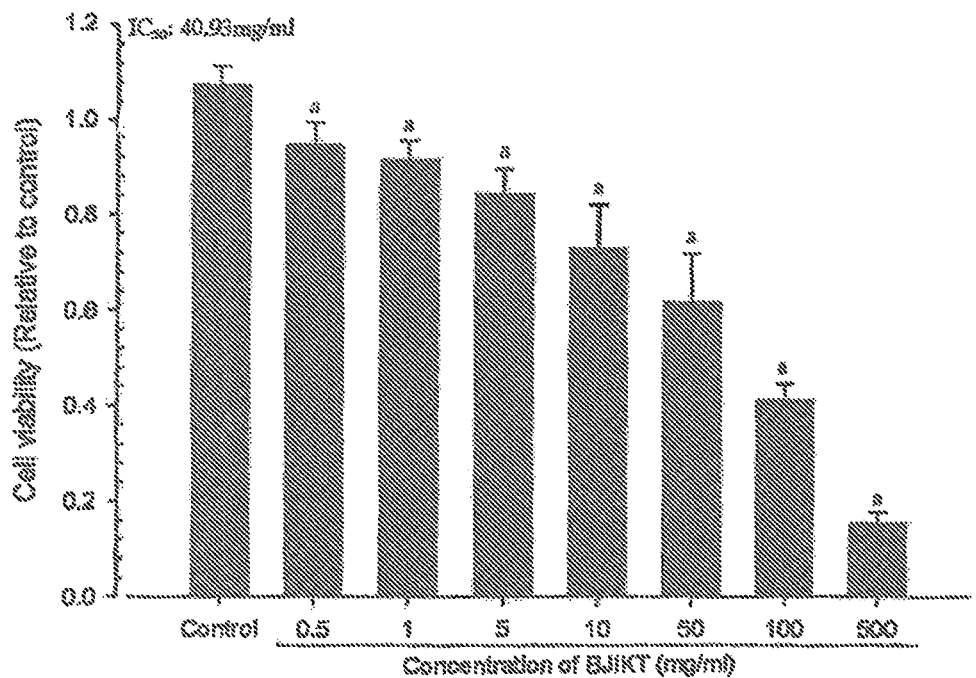
FIG. 54 shows HepG2 cell viability determined by administering bojungikgi-tang.

9.4. Confirmation of Cytotoxicity (1) Influence of BJIKT on HepG2 Cell Viability A significant decrease (p<0.01) in HepG2 cell viability was observed in a BJIKT 0.5 mg/ml treated group, compared to the vehicle control, and IC50 was calculated as 40.93 mg/ml (FIG. 54).

HepG2 cell viability changed by −11.67, −14.69, −21.43, −31.90, −42.40, −61.57, and −85.66% in the BJIKT 0.5, 1, 5, 10, 50, 100, and 500 mg/ml treated groups, compared to the vehicle control (0 mg/ml treated group).

(2) Influence of Sorafenib on HepG2 Cell Viability

Figure 55:
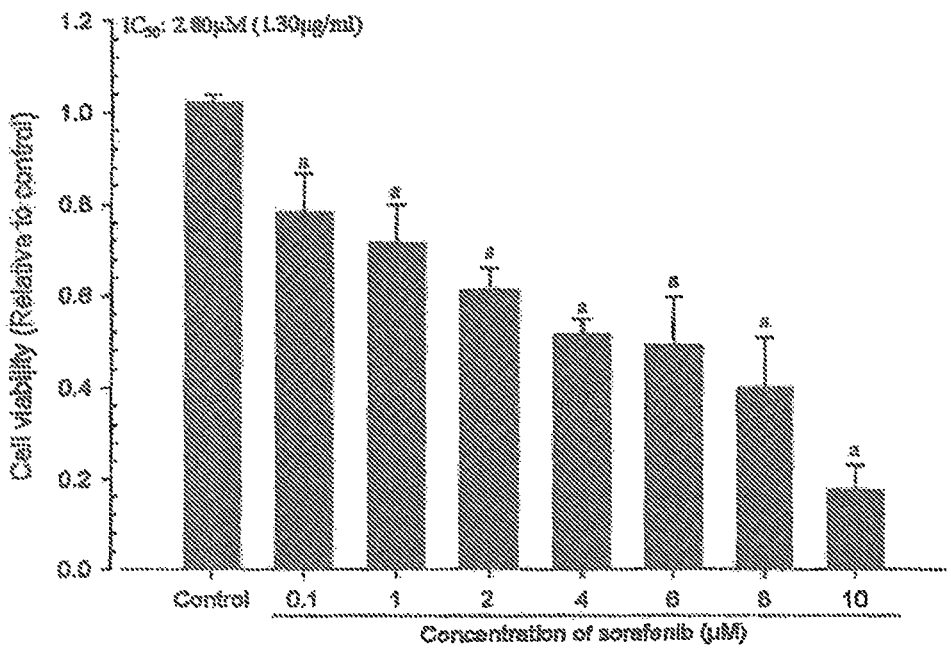
FIG. 55 shows HepG2 cell viability determined by administering sorafenib.

A significant decrease (p<0.01) in HepG2 cell viability was observed in a sorafenib 0.1 μM treated group, compared to the vehicle control, and IC50 was calculated as 2.80 μM (1.30 μg/ml) (FIG. 55).

HepG2 cell viability changed by −23.47, −30.09, −40.03, −49.73, −52.03, −61.01, and −82.88% in the sorafenib 0.1, 1, 2, 4, 6, 8, and 10 μM treated groups, compared to the vehicle control (0 mg/ml treated group).

9.5. Confirmation of Changes in Body Weight and Body Weight Gain

Figure 56:
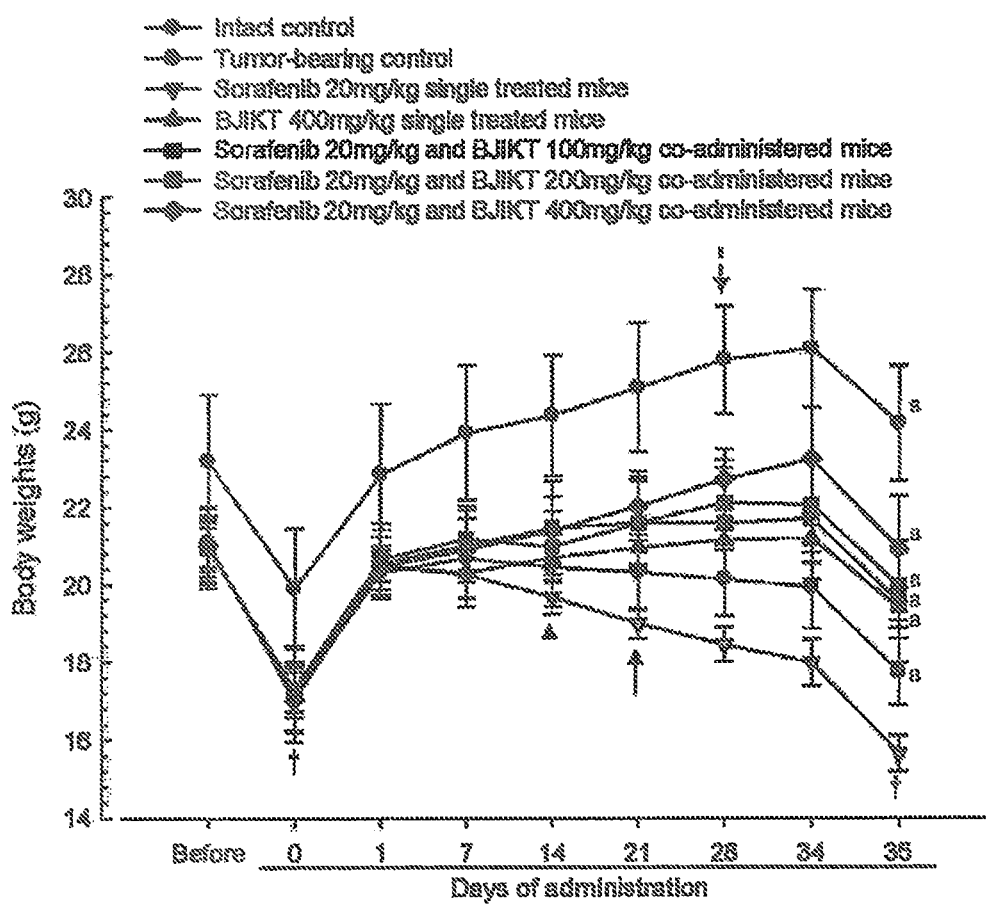
FIG. 56 shows changes in body weight in a bojungikgi-tang single treated group, a sorafenib single treated group, and a bojungikgi-tang and sorafenib co-administered group.

Since only laboratory animals showing a uniform decrease in body weight after 28 days of the HepG2 cell xenograft, compared to the vehicle control, were used, a significant decrease (p<0.01) in body weight had started to be observed before administration in the tumor-bearing control, compared to the vehicle control, and a significant decrease (p<0.01) in body weight gain was also observed in the duration of administration. In the sorafenib single treated group, 21 days after first administration, a significant decrease (p<0.01 or p<0.05) in the weight was observed compared to the tumor-bearing control, and a significant decrease (p<0.01) in the body weight gain was also observed in the duration of administration, compared to the tumor-bearing control. On the other hand, a significant increase (p<0.01) in the weight was observed 28 days after the first administration and a significant increase (p<0.05) in the body weight gain was observed in the BJIKT single treated group, compared to the tumor-bearing control. A significant increase (p<0.01 or p<0.05) in body weight was observed 14 days after the first administration, and significant increases (p<0.01) in body weight gain were observed in the duration of administration in the sorafenib 20 mg/kg and BJIKT 100, 200, and 400 mg/kg co-administered groups, compared to the sorafenib 20 mg/kg single treated group (Table 20 and FIG. 56).

The body weight gain in the duration of administration (day 35; body weight at sacrifice-body weight at first administration) changed by −84.90% in the tumor-bearing control, compared to the vehicle control, and changed by −322.22, 235.56, 266.67, 311.11, and 504.44% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

TABLE 20

| Groups | Body weights | | | Body weight gains [B − A] |
|---|---|---|---|---|
| | Before | At first administration [A] | At sacrifice [B] | |
| Controls | | | | |
| Intact | 23.20 ± 1.72 | 19.90 ± 1.57 | 24.16 ± 1.47 | 4.26 ± 1.05 |
| TB | 21.09 ± 0.61$^f$ | 17.11 ± 0.36$^f$ | 17.76 ± 0.85$^f$ | 0.64 ± 0.96$^a$ |
| Single treated | | | | |
| Sorafenib | 21.00 ± 0.99$^g$ | 17.10 ± 0.84$^f$ | 15.67 ± 0.46$^{fh}$ | −1.43 ± 0.80$^{ac}$ |
| BJIKT | 21.01 ± 0.79$^g$ | 17.24 ± 0.54$^f$ | 19.40 ± 0.51$^{fhj}$ | 2.16 ± 0.76$^{ade}$ |
| Sorafenib and BJIKT co-administered | | | | |
| 100 mg/kg | 20.97 ± 1.06$^g$ | 17.20 ± 1.24$^f$ | 19.56 ± 1.57$^{fij}$ | 2.36 ± 0.87$^{ace}$ |
| 200 mg/kg | 20.99 ± 0.63$^f$ | 17.31 ± 0.72$^f$ | 19.96 ± 0.88$^{fhj}$ | 2.64 ± 0.97$^{bce}$ |
| 400 mg/kg | 21.04 ± 0.93$^g$ | 17.04 ± 0.85$^f$ | 20.93 ± 1.37$^{fhj}$ | 3.89 ± 1.95$^{ce}$ |

9.6. Confirmation of Change in Tumor Volume

Figure 57:
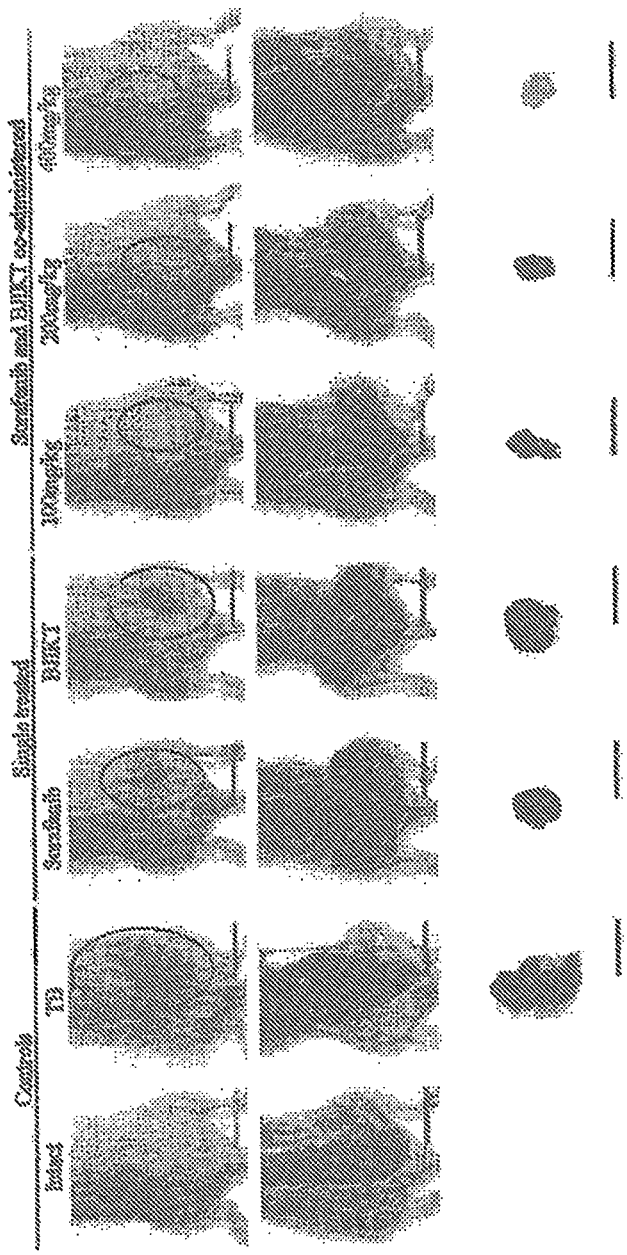
FIG. 57 shows differences in tumor size between groups.
Figure 58:
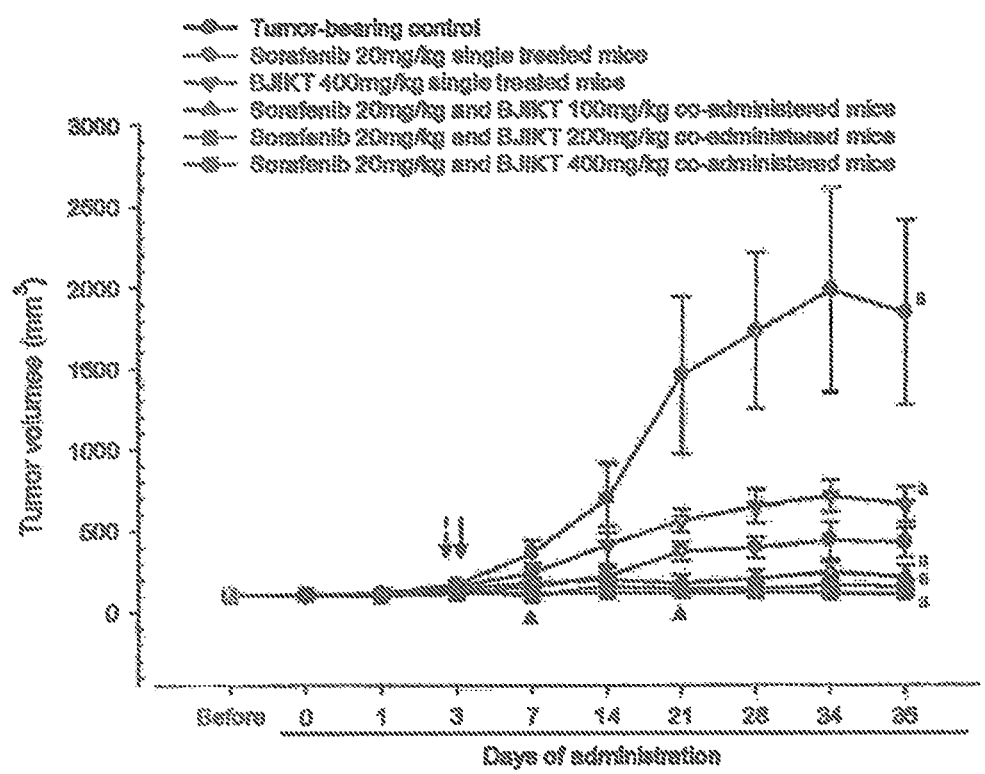
FIG. 58 shows changes in tumor volume for each group.

In the sorafenib single treated group, 3 days after the first administration, a significant decrease ($p<0.01$) in the tumor volume was observed compared to the tumor-bearing control, and a significant decrease ($p<0.01$) in a variation of the tumor volume was also observed for the administration duration compared to the tumor-bearing control. Also, after 7 days from first administration, a significant decrease ($p<0.01$) in the tumor volume was observed in the BJIKT 400 mg/kg single treated group, compared to the tumor-bearing control. In particular, in the BJIKT 200 and 400 mg/kg and sorafenib 20 mg/kg co-administered groups, 7 days after the first administration, a significant decrease ($p<0.01$) in the tumor volume was observed compared to the sorafenib single treated group, and a significant decrease ($p<0.01$) in variation of the tumor volume was observed for the administration duration compared to the sorafenib single treated group. In addition, a significant decrease ($p<0.01$) in the tumor volume was also observed from 21 days after the first administration, and a significant decrease ($p<0.01$) in variation of the tumor volume was also observed during the duration of the administration in the BJIKT 100 mg/kg and sorafenib 20 mg/kg co-administered group, compared to the sorafenib single treated group (Table 21 and FIGS. 57 and 58).

The variations in tumor volumes week 5; tumor volume at final sacrifice day-tumor volume at first administration day) in the duration of drug administration changed by −81.78, −68.16, −93.73, −97.27, and −99.78% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

9.7. ☐Confirmation of Change in Tumor Weight

Significant decreases ($p<0.01$ in relative and absolute tumor weights were observed in all of the drug administered groups including the BJIKT 400 mg/kg single treated group, compared to the tumor-bearing control. Meanwhile, significant decreases ($p<0.01$ or $p<0.05$) in tumor weight were also observed in all of the BJIKT 100, 200, and 400 mg/kg and sorafenib 20 mg/kg co-administered groups, compared to the sorafenib 20 mg/kg single treated group (Tables 22 and 23, and FIG. 57).

TABLE 21

| Groups | Tumor volume (mm³) | | | Changes (mm³) [B − A] |
|---|---|---|---|---|
| | 1 day before first administration | First administration [A] | Sacrifice [B] | |
| Control | | | | |
| TB | 111.95 ± 18.11 | 114.18 ± 16.78 | 1845.61 ± 564.60 | 1731.43 ± 580.08 |
| Single treated | | | | |
| Sorafenib | 111.20 ± 16.86 | 112.84 ± 13.70 | 428.32 ± 90.63$^a$ | 315.48 ± 84.36$^a$ |
| BJIKT | 112.21 ± 12.76 | 112.34 ± 11.93 | 663.58 ± 106.31$^{ab}$ | 551.24 ± 97.52$^{ab}$ |
| Sorafenib and BJIKT co-administered | | | | |
| 100 mg/kg | 112.92 ± 14.05 | 111.19 ± 10.69 | 219.68 ± 70.83$^{ab}$ | 108.49 ± 64.33$^{ab}$ |
| 200 mg/kg | 111.42 ± 11.53 | 112.30 ± 12.23 | 159.55 ± 15.98$^{ab}$ | 47.25 ± 13.61$^{ab}$ |
| 400 mg/kg | 112.92 ± 10.61 | 111.94 ± 9.12 | 115.83 ± 11.72$^{ab}$ | 3.89 ± 6.65$^{ab}$ |

TABLE 22

| Groups | Tumor mass | Spleen | Submandibular lymph node | Periovarian fat pad |
|---|---|---|---|---|
| Controls | | | | |
| Intact |  | 0.165 ± 0.018 | 0.021 ± 0.006 | 0.065 ± 0.018 |
| TB | 0.697 ± 0.133 | 0.093 ± 0.013$^a$ | 0.006 ± 0.002$^d$ | 0.024 ± 0.007$^d$ |
| Single treated | | | | |
| Sorafenib | 0.202 ± 0.029$^f$ | 0.067 ± 0.009$^{ab}$ | 0.003 ± 0.001$^{df}$ | 0.015 ± 0.003$^{dg}$ |
| BJIKT | 0.275 ± 0.070$^f$ | 0.114 ± 0.008$^{abc}$ | 0.011 ± 0.002$^{dfh}$ | 0.032 ± 0.004$^{dgh}$ |
| Sorafenib and BJIKT co-administered | | | | |
| 100 mg/kg | 0.151 ± 0.036$^{fi}$ | 0.123 ± 0.006$^{abc}$ | 0.013 ± 0.001$^{dfh}$ | 0.033 ± 0.004$^{dfh}$ |
| 200 mg/kg | 0.120 ± 0.042$^{fh}$ | 0.130 ± 0.007$^{abc}$ | 0.014 ± 0.002$^{dfh}$ | 0.039 ± 0.008$^{dfh}$ |
| 400 mg/kg | 0.084 ± 0.028$^{fh}$ | 0.142 ± 0.009$^{abc}$ | 0.015 ± 0.003$^{efh}$ | 0.041 ± 0.007$^{dfh}$ |

TABLE 23

| Groups | Tumor mass | Spleen | Submandibular lymph node | Periovarian fat pad |
|---|---|---|---|---|
| Controls | | | | |
| Intact |  | 0.681 ± 0.063 | 0.088 ± 0.017 | 0.267 ± 0.060 |
| TB | 3.939 ± 0.816 | 0.525 ± 0.080$^a$ | 0.037 ± 0.015$^a$ | 0.135 ± 0.038$^f$ |
| Single treated | | | | |
| Sorafenib | 1.289 ± 0.200$^h$ | 0.426 ± 0.057$^{ac}$ | 0.020 ± 0.008$^{ad}$ | 0.096 ± 0.022$^f$ |
| BJIKT | 1.414 ± 0.335$^h$ | 0.589 ± 0.043$^{ade}$ | 0.055 ± 0.013$^{ace}$ | 0.167 ± 0.024$^{fi}$ |
| Sorafenib and BJIKT co-administered | | | | |
| 100 mg/kg | 0.766 ± 0.152$^{hi}$ | 0.636 ± 0.078$^{ce}$ | 0.067 ± 0.011$^{ace}$ | 0.171 ± 0.028$^{fi}$ |
| 200 mg/kg | 0.597 ± 0.196$^{hi}$ | 0.652 ± 0.042$^{ce}$ | 0.069 ± 0.010$^{ace}$ | 0.195 ± 0.038$^{ghi}$ |
| 400 mg/kg | 0.403 ± 0.144$^{hi}$ | 0.679 ± 0.040$^{ce}$ | 0.072 ± 0.013$^{bce}$ | 0.195 ± 0.025$^{ghi}$ |

As shown in Tables 22 and 23, the absolute tumor weight changed by −71.05, −60.50, −78.35, −82.76, and −87.97% and the relative tumor weight changed by −67.28, −64.10, −80.54, −84.84, and −89.76% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

That is, it can be seen that the BJIKT and sorafenib co-administered group showed the most excellent effect of reducing a tumor weight.

9.8. Confirmation of Change in Weight of Spleen

Significant decreases (p<0.01) in relative and absolute weights of the spleen were observed in the tumor-bearing control, compared to the vehicle control. However, significant increases (p<0.01 or p<0.05) in weight were observed in the BJIKT 400 mg/kg single treated group and the BJIKT 100, 200, and 400 mg/kg and sorafenib 20 mg/kg co-administered groups, compared to the tumor-bearing control. In particular, significant increases (p<0.01) in relative and absolute weights of the spleen were observed in all of the BJIKT and sorafenib co-administered groups, compared to the sorafenib single treated group. On the other hand, significant decreases (p<0.01) in relative and absolute weights of the spleen were observed in the sorafenib single treated group, compared to the tumor-bearing control (Tables 22 and 23).

The absolute weight of the spleen changed by −43.58% in the tumor-bearing control, compared to the vehicle control, and changed by −28.15, 23.08, 32.92, 38.85, and 52.77% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

The relative weight of the spleen changed by −23.01% in the tumor-bearing control compared to the vehicle control, and changed by −18.76, 12.36, 21.26, 24.21, and 29.43% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

9.9. Confirmation of Change in Weight of Submandibular Lymph Node

A significant decrease (p<0.01) in absolute and relative weights of submandibular lymph nodes was observed in the tumor-bearing control, compared to the vehicle control. However, significant increases (p<0.01) in weights of the submandibular lymph node were observed in the BJIKT single treated group and the BJIKT 100, 200, and 400 mg/kg and sorafenib co-administered groups, compared to the tumor-bearing control. In particular, significant increases (p<0.01) in absolute and relative weights of the submandibular lymph nodes were observed in the BJIKT 100, 200, and 400 mg/kg and sorafenib co-administered groups, compared to the sorafenib single treated group. On the other hand, significant decreases (p<0.01 or p<0.05) in absolute and relative weights of the submandibular lymph nodes were observed in the sorafenib 20 mg/kg single treated group, compared to the tumor-bearing control (Tables 22 and 23).

The absolute weight of the submandibular lymph nodes changed by −70.00% in the tumor-bearing control, compared to the vehicle control, and changed by −51.11, 66.67, 102.22, 113.33, and 135.56% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

The relative weight of the submandibular lymph node changed by −58.39% in the tumor-bearing control, compared to the vehicle control, and changed by −44.91, 51.52, 83.58, 88.60, and 97.45% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

9.10. Confirmation of Change in Weight of Periovarian Fat Pad

Significant decreases ($p<0.01$) in absolute and relative weights of the periovarian fat pad were observed in the tumor-bearing control, compared to the vehicle control. However, a significant increase ($p<0.01$ or $p<0.05$) was observed in the BJIKT single treated group and all three doses of BJIKT and sorafenib co-administered groups except the BJIKT single treated group and the BJIKT 100 mg/kg and sorafenib co-administered group which show an insignificant increase in the relative weight of periovarian fat pad, compared to the tumor-bearing control. In particular, a significant increase ($p<0.01$) in the weight of the periovarian fat pad was observed in the BJIKT 100, 200, and 400 mg/kg and sorafenib 20 mg/kg co-administered groups, compared to the sorafenib single treated group. On the other hand, a significant decrease ($p<0.05$) in the absolute weight of the periovarian fat pad and an insignificant decrease in the relative weight of the periovarian fat pad were observed in the sorafenib 20 mg/kg single treated group, compared to the tumor-bearing control (Tables 22 and 23).

The absolute weight of the periovarian fat pad changed by −63.22% in the tumor-bearing control, compared to the vehicle control, and changed by −37.13, 35.33, 38.92, 62.87, and 71.86% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

The relative weight of the periovarian fat pad changed by −49.53% in the tumor-bearing control, compared to the vehicle control, and changed by −28.79, 23.88, 27.09, 44.83, and 45.02% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

9.11. Confirmation of Change in Blood IL-6 and IFN-γ Contents

Figure 59:
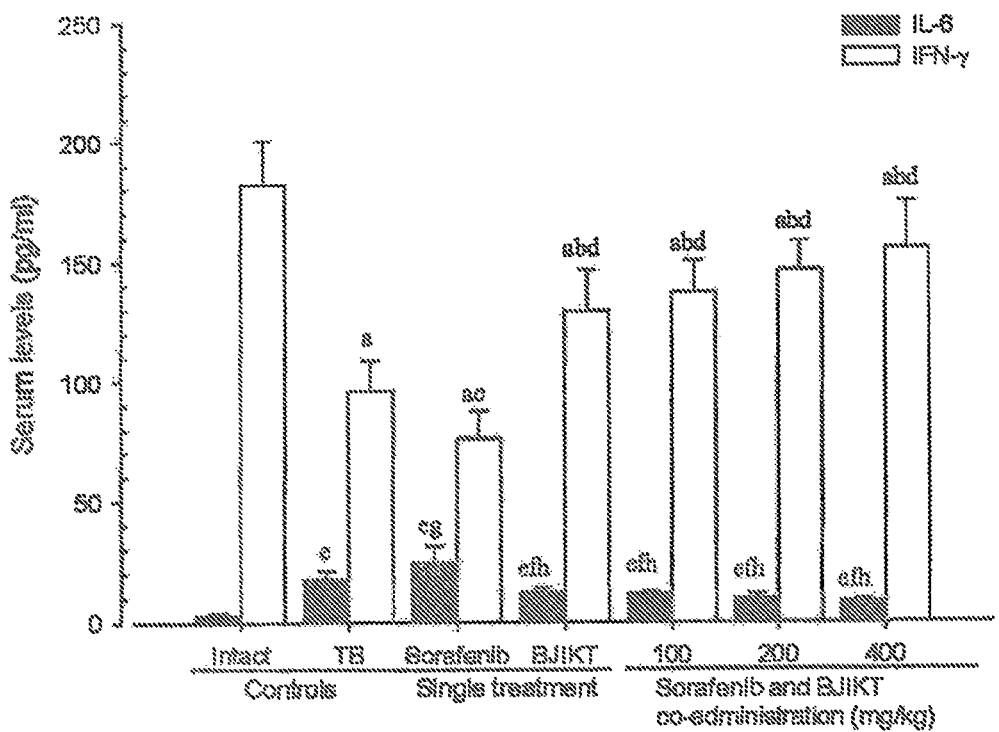
FIG. 59 shows changes in blood IL-6 contents and IFN-γ contents for each group.

A significant increase ($p<0.01$) in blood IL-6 contents and a significant decrease in blood IFN-γ contents were observed in the tumor-bearing control, compared to the vehicle control. However, a significant decrease ($p<0.01$) in the blood IL-6 contents and a significant increase in the blood IFN-γ contents were observed in the BJIKT single treated group and the BJIKT 100, 200, and 400 mg/kg and sorafenib co-administered groups, compared to the tumor-bearing control. In particular, a significant decrease ($p<0.01$) in the blood IL-6 contents and a significant increase in the blood IFN-γ contents were observed in all three doses of BJIKT and sorafenib co-administered groups, compared to the sorafenib single treated group. On the other hand, a significant increase ($p<0.05$) in the blood IL-6 contents and an insignificant decrease in blood IFN-γ contents were observed in the sorafenib single treated group, compared to the tumor-bearing control (FIG. 59).

The blood IL-6 level changed by 533.93% in the tumor-bearing control, compared to the vehicle control, and changed by 41.48, −30.19, −35.69, −46.11, and −53.00% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

The blood IFN-γ level changed by −47.27% in the tumor-bearing control, compared to the vehicle control, and changed by −20.68, 34.51, 42.60, 52.40, and 62.00% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

9.12. Confirmation of Changes in NK Cell Activities

Figure 60:
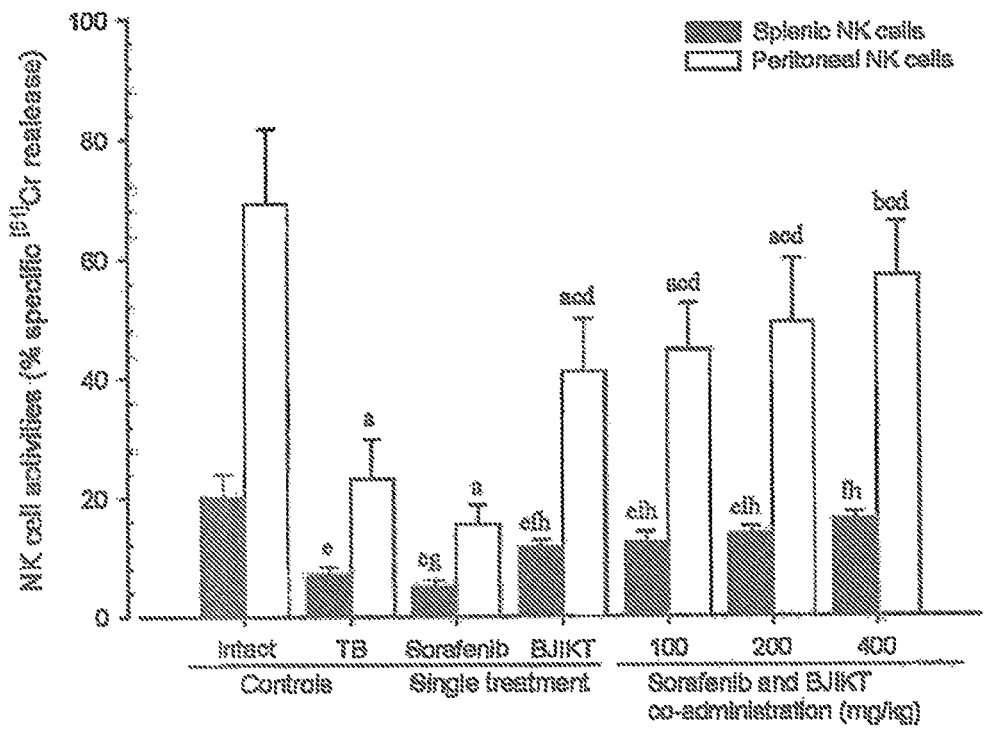
FIG. 60 shows changes in splenic and peritoneal NK cell activities for each group.

Significant decreases ($p<0.01$) in splenic and peritoneal NK cell activities were observed in the tumor-bearing control, compared to the vehicle control. However, significant increases ($p<0.01$) in splenic and peritoneal NK cell activities were observed in the BJIKT single treated group and all of the co-administered groups, compared to the tumor-bearing control. In particular, significant increases ($p<0.01$) in splenic and peritoneal NK cell activities were observed in all of the BJIKT and sorafenib co-administered groups, compared to the sorafenib single treated group. On the other hand, a significant decrease ($p<0.05$) in splenic NK cell activity and an insignificant decrease in peritoneal NK cell activity were observed in the sorafenib single treated group, compared to the tumor-bearing control (FIG. 60).

The splenic NK cell activity changed by −65.80% in the tumor-bearing control compared to the vehicle control, and changed by −30.00, 69.00, 78.00, 97.48, and 133.66% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

The peritoneal NK cell activity changed by −66.34% in the tumor-bearing control compared to the vehicle control, and changed by −33.21, 76.43, 91.85, 111.68, and 145.08% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

9.13. Confirmation of Change in Cytokine Contents in Spleen

Significant decreases ($p<0.01$) in TNF-α, IL-1β, and IL-10 contents in the spleen were observed in the tumor-bearing control, compared to the vehicle control. However, a significant increase ($p<0.01$ or $p<0.05$) in cytokine content in the spleen was observed in the BJIKT single treated group, and the BJIKT 100, 200 and 400 mg/kg and sorafenib co-administered groups, compared to the tumor-bearing control. In particular, significant increases ($p<0.01$) in TNF-α, IL-1β, and IL-10 contents in the spleen were observed in all three doses of BJIKT (100, 200, and 400 mg/kg) and sorafenib co-administered groups, compared to the sorafenib single treated group. On the other hand, significant decreases ($p<0.01$ or $p<0.05$) in TNF-α, IL-1β, and IL-10 contents in the spleen were observed in the sorafenib single treated group, compared to the tumor-bearing control (Table 24).

TABLE 24

| Groups | Tumor necrosis factor-α | Interleukin-1β | Interleukin-10 |
|---|---|---|---|
| Controls | | | |
| Intact | 98.14 ± 24.32 | 44.10 ± 11.73 | 87.27 ± 16.85 |
| TB | 44.45 ± 10.86$^e$ | 13.91 ± 3.04$^e$ | 40.27 ± 10.11$^a$ |
| Single treated | | | |
| Sorafenib | 29.48 ± 12.10$^{eh}$ | 9.44 ± 2.29$^{eg}$ | 21.42 ± 6.84$^{ab}$ |
| BJIKT | 66.58 ± 11.80$^{fgi}$ | 22.82 ± 6.23$^{egi}$ | 56.20 ± 11.17$^{acd}$ |
| Sorafenib and BJIKT co-administered | | | |
| 100 mg/kg | 68.69 ± 12.61$^{gi}$ | 24.15 ± 4.95$^{egi}$ | 62.34 ± 10.48$^{abd}$ |
| 200 mg/kg | 73.61 ± 10.20$^{gi}$ | 27.54 ± 5.52$^{egi}$ | 68.71 ± 10.25$^{abd}$ |
| 400 mg/kg | 82.25 ± 11.15$^{gi}$ | 31.51 ± 7.67$^{fgi}$ | 80.42 ± 11.10$^{bd}$ |

The TNF-α content in the spleen changed by −54.71% in the tumor-bearing control compared to the vehicle control, and changed by −33.67, 49.79, 54.55, 65.61, and 85.05% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

The IL-1β content in the spleen changed by −68.46% in the tumor-bearing control compared to the vehicle control, and changed by −32.15, 64.03, 73.59, 97.96, and 126.56% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

The IL-10 content in the spleen changed by −53.86% in the tumor-bearing control compared to the vehicle control, and changed by −46.81, 39.55, 54.80, 70.63, and 99.69% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

Figure 61:
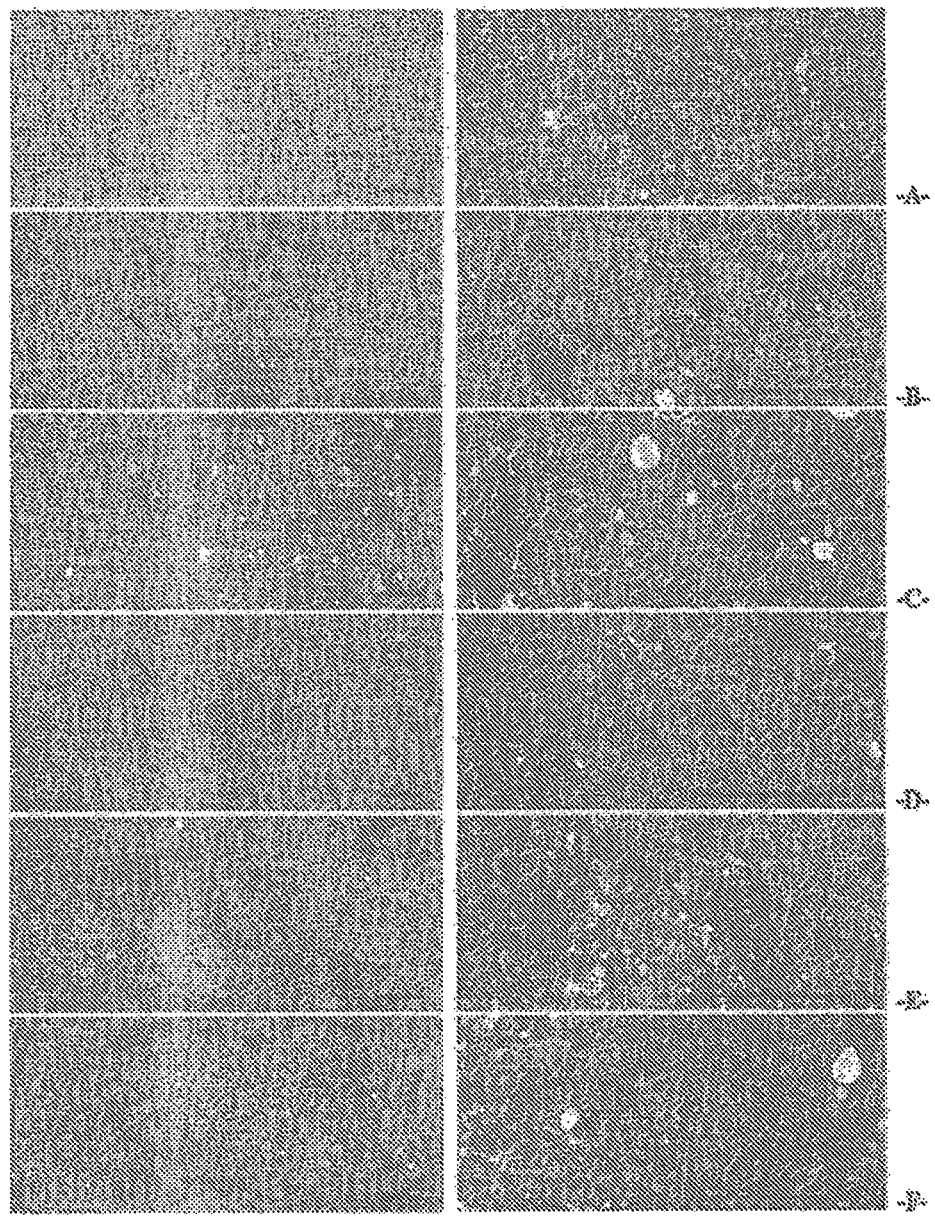
FIG. 61 shows histopathological changes in a tumor mass for each group.
Figure 62:
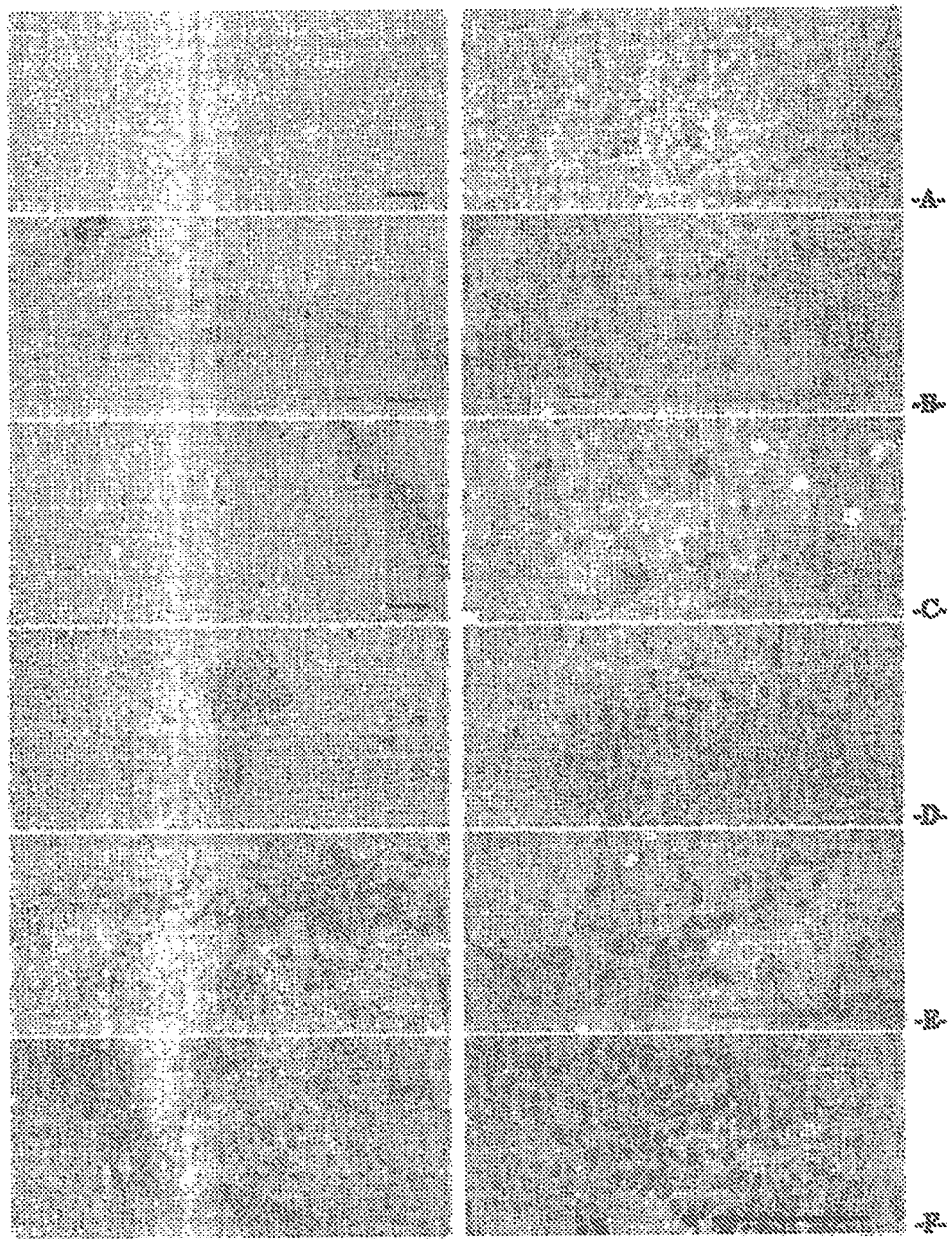
FIG. 62 shows changes in number of caspase-3 immunoreactive cells in tumor mass in group.
Figure 63:
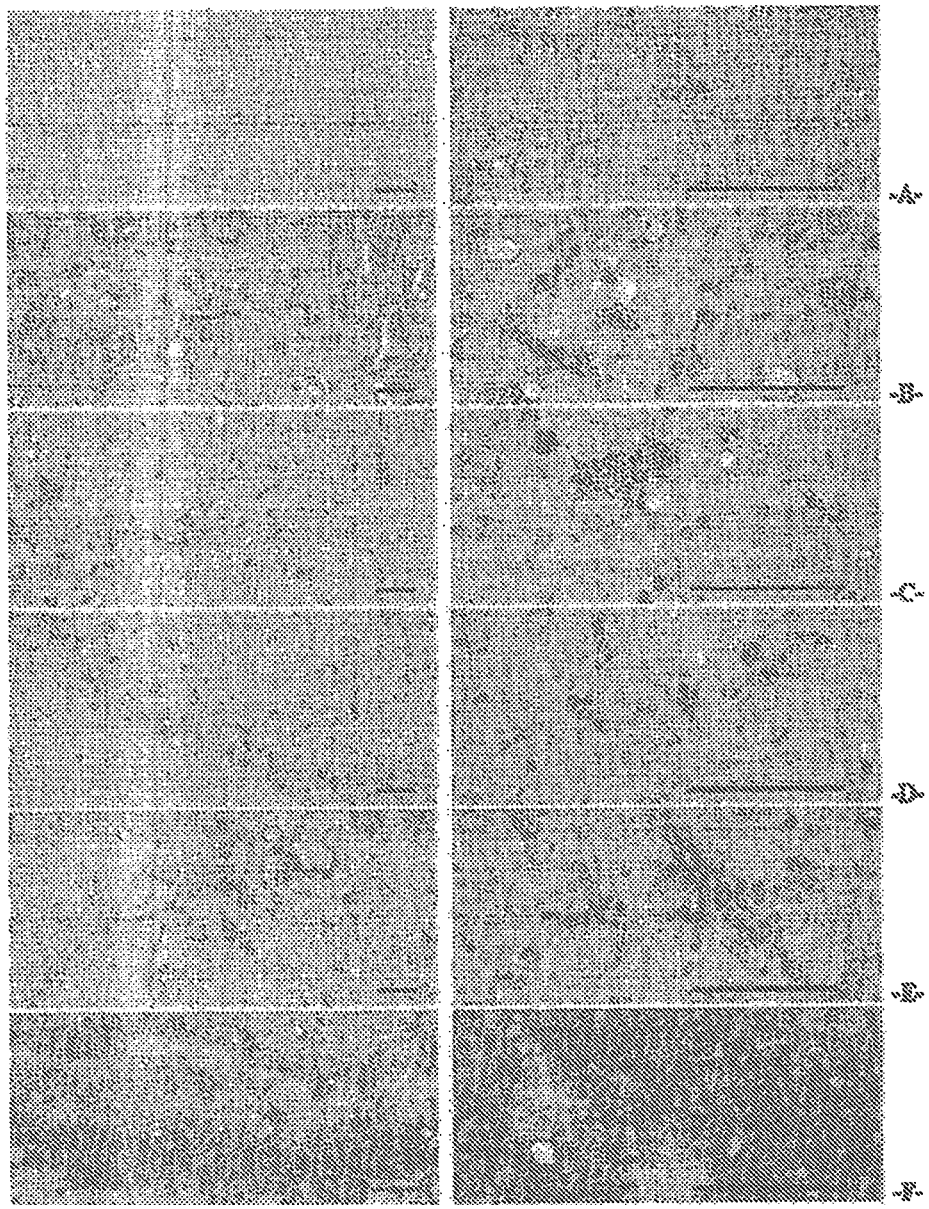
FIG. 63 shows changes in number of PARP immunoreactive cells in tumor mass in group.
Figure 64:
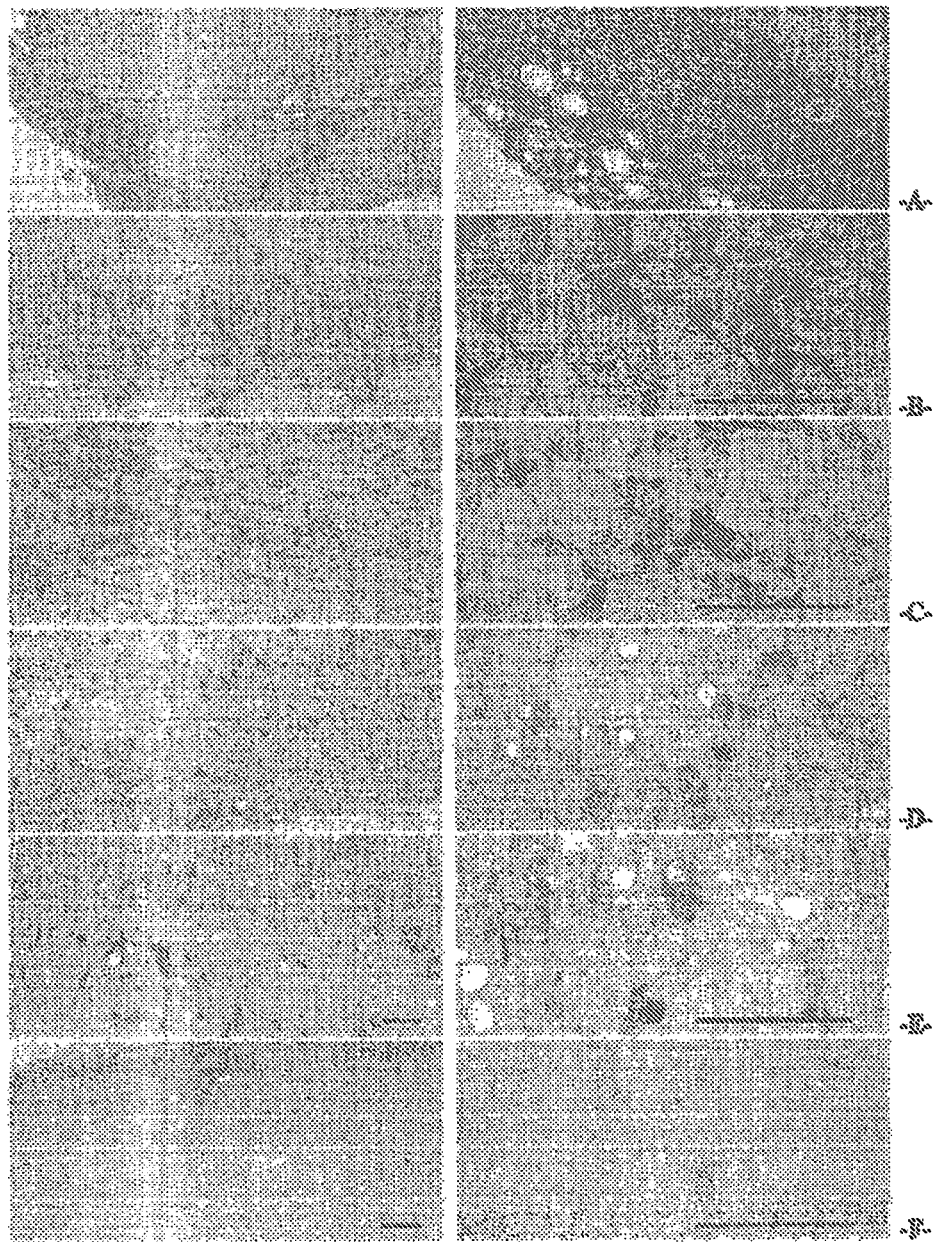
FIG. 64 shows changes in number of COX-2 immunoreactive cells in tumor mass in group.
Figure 65:
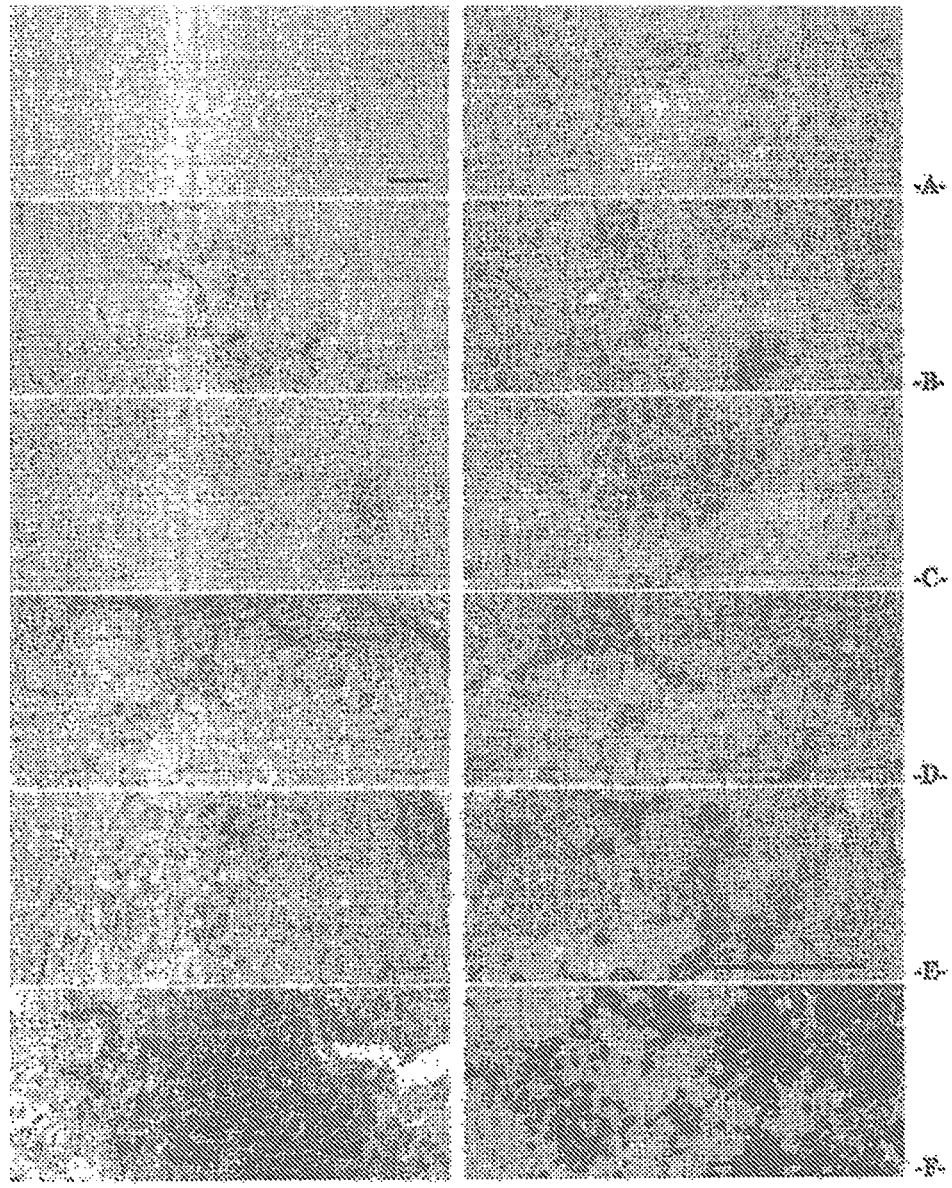
FIG. 65 shows changes in iNOS immunoreactive cells in a tumor mass for each group.
Figure 66:
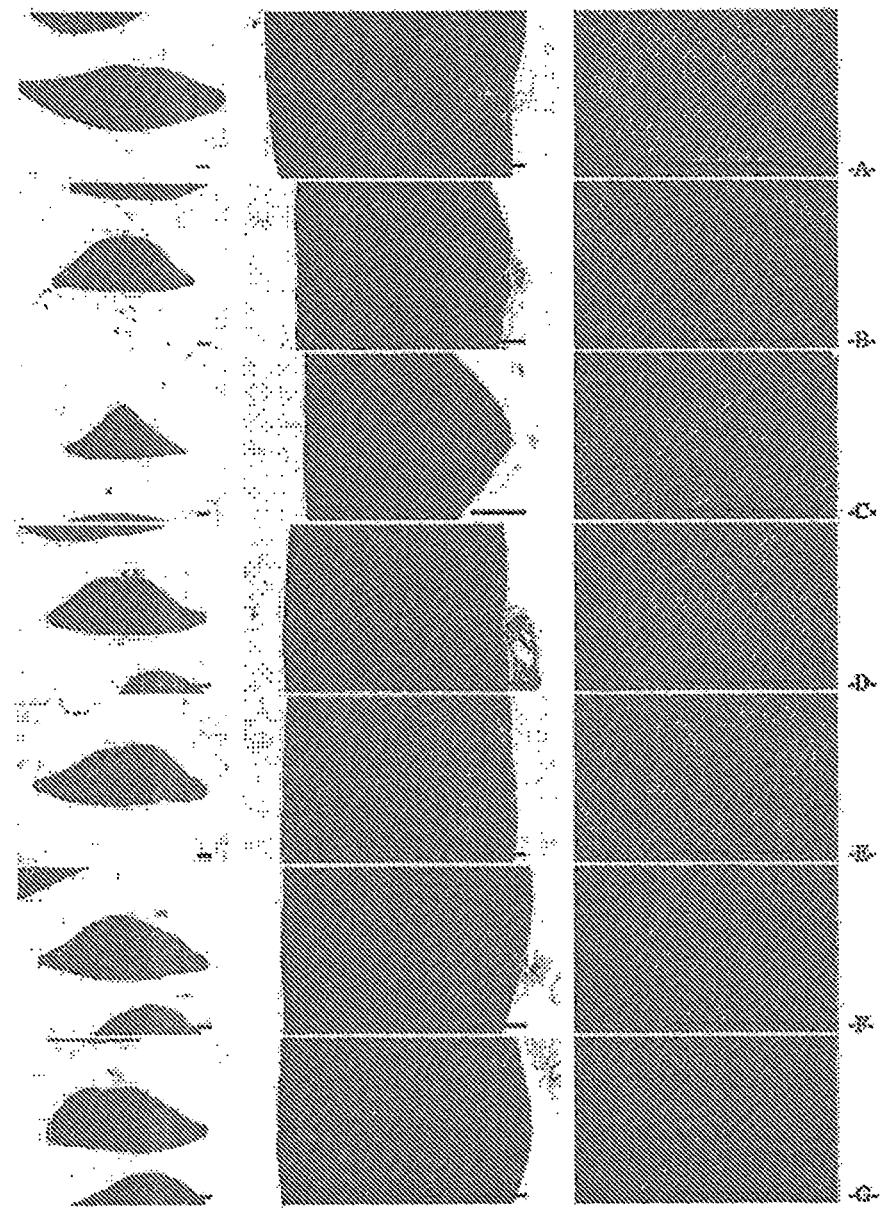
FIG. 66 shows changes in TNF-α immunoreactive cells in a tumor mass for each group.
Figure 68:
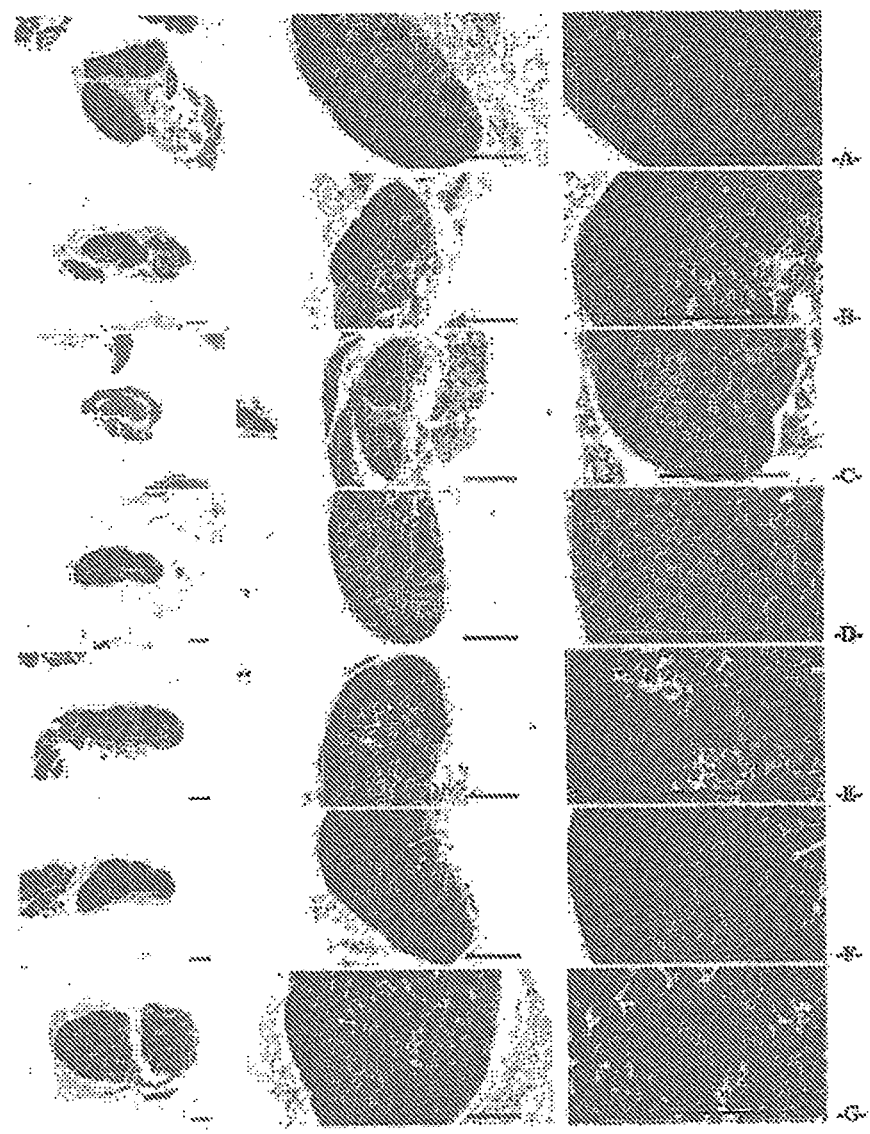
FIG. 68 shows histopathological changes in submandibular lymph nodes.

9.14. Confirmation of histological change
9.14.1. Confirmation of histopathological change in tumor mass In the tumor-bearing control, undifferentiated polymorphic hepatocellular carcinoma HepG2 cells were compactly present, increased cytoplasmic eosinophilia and pyknosis due to apoptosis were observed in some cells, and mitosis was also frequently observed. On the other hand, a significant increase ($p<0.01$ or $p<0.05$) of apoptotic cells was observed in the sorafenib single treated group, the BJIKT single treated group, and all of the three doses of BJIKT and sorafenib co-administered groups, compared to the tumor-bearing control. As a result, a percentage of HepG2 cells was also significantly decreased ($p<0.01$). In particular, a significant decrease ($p<0.01$ or $p<0.05$) in the tumor cell volume and an increase in the number of apoptotic cells were observed in the BJIKT 100, 200, and 400 mg/kg and sorafenib 20 mg/kg co-administered groups, compared to the sorafenib single treated group (Table 25 and FIG. 61).

administered groups, compared to the sorafenib single treated group (Table 25, and FIGS. 62 to 64). A significant increase ($p<0.01$) in the number of iNOS and TNF-α immunoreactive cells in the tumor mass was identified in all of the sorafenib single treated group, the BJIKT single treated group, and the sorafenib and BJIKT co-administered groups, compared to the tumor-bearing control. In particular, a significant increase ($p<0.01$) in the number of iNOS and TNF-α immunoreactive cells was identified in the BJIKT 100, 200, and 400 mg/kg and sorafenib 20 mg/kg co-administered groups, compared to the sorafenib single treated group (Table 25, and FIGS. 65 and 68).

The percentage of tumor cells in tumor tissues changed by −26.52, −16.68, −47.24, −51.46, and −61.58% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

The percentage of apoptotic cells in tumor tissues changed by 238.56, 96.46, 383.00, 540.82, and 720.76% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

The percentage of caspase-3 immunoreactive cells in tumor tissues changed by 142.55, 67.75, 348.04, 459.34, and 700.54% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

The percentage of PARP immunoreactive cells in tumor tissues changed by 252.35, 82.42, 440.63, 491.78, and 821.29% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

The percentage of COX-2 immunoreactive cells in tumor tissues changed by −49.51, −41.81, −62.49, −70.41, and

TABLE 25

| Groups | Tumor cell volume (%/mm$^2$) | Apoptotic cell percentages (%) | Immunoreactive cell percentages (%/tumor cells) | | | | |
|---|---|---|---|---|---|---|---|
| | | | Caspase-3 | PARP | COX-2 | iNOS | TNF-α |
| Control | | | | | | | |
| TB | 85.30 ± 11.39 | 7.03 ± 1.98 | 7.18 ± 2.09 | 5.27 ± 1.42 | 58.58 ± 10.40 | 7.92 ± 2.60 | 5.53 ± 2.51 |
| Single treated | | | | | | | |
| Sorafenib | 62.68 ± 10.98$^a$ | 23.79 ± 6.17$^a$ | 17.42 ± 2.11$^a$ | 18.56 ± 5.85$^a$ | 29.57 ± 2.09$^a$ | 11.83 ± 2.8$^b$ | 10.61 ± 1.88$^a$ |
| BJIKT | 71.07 ± 6.25$^b$ | 13.81 ± 2.36$^{ac}$ | 12.05 ± 1.57$^{ac}$ | 9.61 ± 1.99$^{ac}$ | 34.00 ± 4.20$^{ad}$ | 28.18 ± 3.69$^{ac}$ | 27.39 ± 4.02$^{ac}$ |
| Sorafenib and BJIKT co-administered | | | | | | | |
| 100 mg/kg | 45.01 ± 6.03$^{ac}$ | 33.94 ± 6.02$^{ac}$ | 32.18 ± 3.51$^{ac}$ | 28.48 ± 5.11$^{ad}$ | 21.98 ± 4.68$^{ad}$ | 38.34 ± 10.50$^{ac}$ | 35.84 ± 6.28$^{ac}$ |
| 200 mg/kg | 41.41 ± 3.19$^{ac}$ | 45.03 ± 7.71$^{ac}$ | 40.17 ± 5.63$^{ac}$ | 31.17 ± 4.14$^{ac}$ | 17.34 ± 3.17$^{ac}$ | 51.03 ± 2.45$^{ac}$ | 39.97 ± 5.60$^{ac}$ |
| 400 mg/kg | 32.78 ± 4.78$^{ac}$ | 57.68 ± 14.25$^{ac}$ | 57.49 ± 9.07$^{ac}$ | 48.58 ± 9.00$^{ac}$ | 15.61 ± 2.33$^{ac}$ | 62.28 ± 7.99$^{ac}$ | 65.67 ± 7.68$^{ac}$ |

In addition, a significant increase ($p<0.01$) in the number of caspase-3 and PARP immunoreactive cells in the tumor mass and a decrease in the number of COX-2 immunoreactive cells were observed in all administered groups including the BJIKT 400 mg/kg single treated group, compared to the tumor-bearing control. In particular, a significant increase ($p<0.01$ or $p<0.05$) in the number of caspase-3 and PARP immunoreactive cells and a decrease in the number of COX-2 immunoreactive cells were observed in the BJIKT 100, 200, and 400 mg/kg and sorafenib 20 mg/kg co- −73.35% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

The percentage of iNOS immunoreactive cells in tumor tissues changed by 49.35, 255.75, 384.11, 544.34, and 686.36% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

The percentage of TNF-α immunoreactive cells in tumor tissues changed by 91.86, 395.32, 548.10, 622.84, and 1087.55% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

9.14.2. Confirmation of histopathological change in spleen

Figure 67:
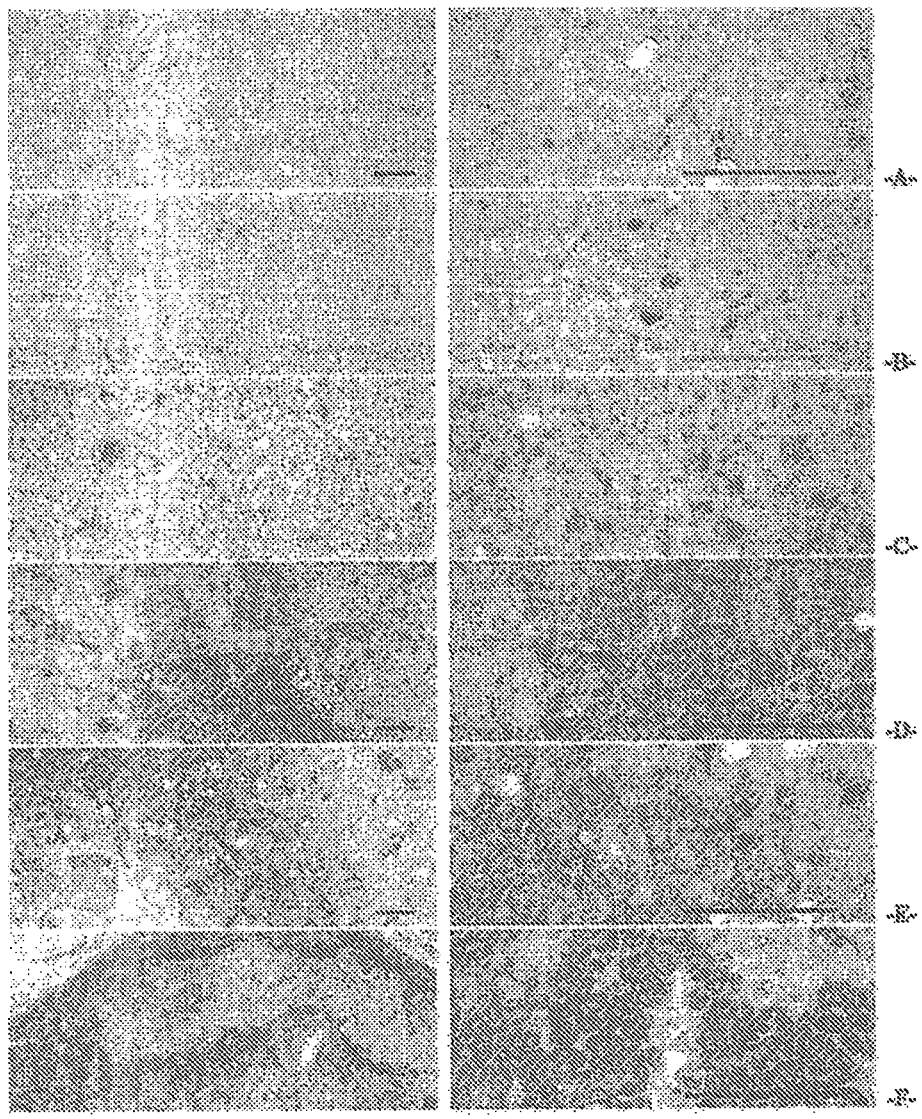
FIG. 67 shows histopathological changes in spleens.

Atrophy characterized in a significant decrease of lymphocytes in splenic white pulp parts was observed in the tumor-bearing control, compared to the vehicle control. Therefore, significant decreases ($p<0.01$) in thickness of the spleen, and diameter and number of white pulps were observed. On the other hand, significant increases ($p<0.01$ or $p<0.05$) in thickness of the spleen, and diameter and number of white pulps were histopathologically observed in the BJIKT single treated group and all of the three doses of BJIKT and sorafenib co-administered groups, compared to the tumor-bearing control. In particular, significant increases ($p<0.01$) in thickness of the spleen, and diameter and number of white pulps were observed in all of the BJIKT and sorafenib 20 mg/kg co-administered groups, compared to the sorafenib single treated group. On the other hand, significant decreases ($p<0.01$) in thickness of the spleen, and diameter and number of white pulps were observed in the sorafenib single treated group, compared to the tumor-bearing control (Table 26 and FIG. 67).

TABLE 26

| Groups | Total thickness (mm/central regions) | White pulp numbers (/mm$^2$) | White pulp diameters (μm/white pulp) |
|---|---|---|---|
| Controls | | | |
| Intact | 2104.66 ± 247.78 | 17.86 ± 2.27 | 815.60 ± 130.63 |
| TB | 1384.02 ± 167.66$^a$ | 8.57 ± 1.27$^e$ | 468.48 ± 76.46$^a$ |
| Single treated | | | |
| Sorafenib | 1074.51 ± 133.98$^{ab}$ | 5.86 ± 0.90$^{eg}$ | 345.22 ± 38.50$^{ab}$ |
| BJIKT | 1614.92 ± 105.91$^{abd}$ | 11.29 ± 1.60$^{egh}$ | 587.60 ± 49.71$^{acd}$ |
| Sorafenib and BJIKT co-administered | | | |
| 100 mg/kg | 1714.41 ± 144.26$^{abd}$ | 11.71 ± 1.11$^{egh}$ | 629.14 ± 107.26$^{abd}$ |
| 200 mg/kg | 1825.23 ± 123.09$^{abd}$ | 14.43 ± 2.76$^{gh}$ | 645.83 ± 72.72$^{abd}$ |
| 400 mg/kg | 1833.30 ± 133.31$^{abd}$ | 15.00 ± 2.16$^{gh}$ | 663.66 ± 65.21$^{abd}$ |

TABLE 26-continued

| Groups | Total thickness (mm/central regions) | White pulp numbers (/mm$^2$) | White pulp diameters (μm/white pulp) |
|---|---|---|---|

A total thickness of the spleen changed by −34.24% in the tumor-bearing control, compared to the vehicle control, and changed by −22.36, 16.68, 23.87, 31.88, and 32.46% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

The number of splenic white pulps changed by −52.00% in the tumor-bearing control compared to the vehicle control, and changed by −31.67, 31.67, 36.67, 68.33, and 75.00% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

The diameter of the splenic white pulp changed by −42.56% in the tumor-bearing control compared to the vehicle control, and changed by −26.31, 25.43, 34.29, 37.86, and 41.66% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

9.14.3. Confirmation of Histopathological Change in Submandibular Lymph Node

Atrophy due to a significant lymphocyte decrease in a lymph node cortex were observed in the tumor-bearing control, compared to the vehicle control. Therefore, significant decreases ($p<0.01$) in a total thickness of the submandibular lymph node, a cortex thickness, and the number of follicles in the cortex were observed. On the other hand, significant increases ($p<0.01$ or $p<0.05$) in total thickness of the lymph node, cortex thickness, and number of follicles in the cortex were histopathologically observed in the BJIKT single treated group and all co-administered groups, compared to the tumor-bearing control. In particular, significant increases ($p<0.01$) in total thickness of the lymph node, cortex thickness, and number of follicles in the cortex were observed in the BJIKT 100, 200, and 400 mg/kg and sorafenib 20 mg/kg co-administered groups, compared to the sorafenib single treated group. On the other hand, significant decreases ($p<0.05$) in total thickness of the lymph node, cortex thickness, and number of follicles in the cortex were observed in the sorafenib single treated group, compared to the tumor-bearing control (Table 27 and FIG. 68).

TABLE 27

| Groups | Total thickness (μm/central regions) | Cortex lymphoid cell follicle numbers (/mm$^2$) | Cortex thickness (μm/lymph node) |
|---|---|---|---|
| Controls | | | |
| Intact | 1476.81 ± 264.31 | 21.43 ± 2.15 | 773.12 ± 85.51 |
| TB | 652.05 ± 93.71$^e$ | 8.57 ± 1.27$^a$ | 348.35 ± 47.79$^e$ |
| Single treated | | | |
| Sorafenib | 490.30 ± 95.50$^{eh}$ | 5.57 ± 2.30$^{ac}$ | 272.62 ± 44.22$^{eh}$ |
| BJIKT | 910.27 ± 100.39$^{egi}$ | 13.43 ± 2.64$^{abd}$ | 464.07 ± 53.27$^{egi}$ |
| Sorafenib and BJIKT co-administered | | | |
| 100 mg/kg | 890.39 ± 70.41$^{egi}$ | 13.43 ± 1.90$^{abd}$ | 418.02 ± 50.18$^{ehi}$ |
| 200 mg/kg | 962.20 ± 122.77$^{egi}$ | 17.71 ± 2.14$^{abd}$ | 652.95 ± 58.19$^{gi}$ |
| 400 mg/kg | 1122.57 ± 233.62$^{gi}$ | 19.43 ± 3.10$^{bd}$ | 784.90 ± 124.77$^{gi}$ |

The total thickness of the submandibular lymph node changed by −55.85% in the tumor-bearing control compared to the vehicle control, and changed by −24.81, 39.60, 36.55, 47.57, and 72.16% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

The number of follicles in the cortex of the submandibular lymph node changed by −60.00% in the tumor-bearing control, compared to the vehicle control, and changed by −35.00, 56.67, 56.67, 106.67, and 126.67% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

The cortex thickness of the submandibular lymph nodes changed by −54.94% in the tumor-bearing control compared to the vehicle control, and changed by −21.74, 33.22, 20.00, 87.44, and 125.32% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

9.14.4. Confirmation of Histopathological Change in Periovarian Fat Pad

Figure 69:
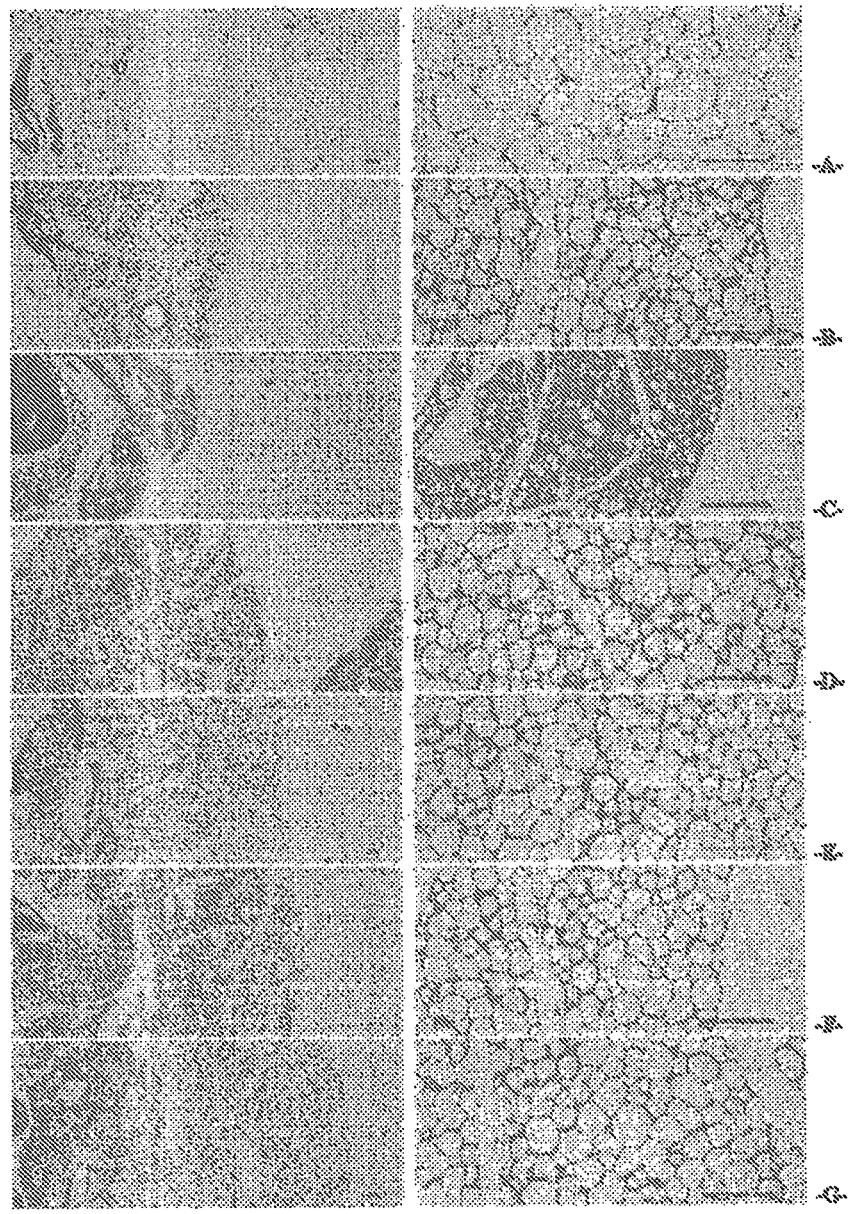
FIG. 69 shows histopathological changes in periovarian fat pads.

Atrophy characterized in a significant decrease in size of a white adipocyte was observed in the tumor-bearing control, compared to the vehicle control. Therefore, significant decreases (p<0.01) in thickness of accumulated fats and mean diameter of the white adipocyte were observed. On the other hand, significant increases (p<0.01) in thickness of accumulated fats and mean diameter of the white adipocyte were histopathologically observed in the BJIKT single treated group, and the BJIKT 100, 200, and 400 mg/kg and sorafenib co-administered groups, compared to the tumor-bearing control. In particular, significant increases (p<0.01) in thickness of accumulated fats and mean diameter of the white adipocyte were observed in all of the three doses of BJIKT and sorafenib co-administered groups, compared to the sorafenib single treated group. On the other hand, significant decreases (p<0.01 or p<0.05) in thickness of periovarian fat pad tissue and mean diameter of the white adipocyte were observed in the sorafenib single treated group, compared to the tumor-bearing control (FIG. 69 and Table 28).

TABLE 28

| Groups | Total thickness (mm/central regions) | White adipocyte diameters (μm) |
|---|---|---|
| Controls | | |
| Intact | 1772.90 ± 168.72 | 57.44 ± 5.70 |
| TB | 799.04 ± 114.98$^a$ | 25.19 ± 4.23$^a$ |
| Single treated | | |
| Sorafenib | 544.43 ± 114.62$^{ab}$ | 18.15 ± 3.38$^{ac}$ |
| BJIKT | 1232.67 ± 144.67$^{abd}$ | 39.35 ± 4.20$^{abd}$ |

TABLE 28-continued

| Groups | Total thickness (mm/central regions) | White adipocyte diameters (μm) |
|---|---|---|
| Sorafenib and BJIKT co-administered | | |
| 100 mg/kg | 1316.88 ± 150.41$^{abd}$ | 39.91 ± 3.79$^{abd}$ |
| 200 mg/kg | 1463.53 ± 118.43$^{abd}$ | 42.98 ± 5.63$^{abd}$ |
| 400 mg/kg | 1644.78 ± 171.78$^{bd}$ | 46.54 ± 6.38$^{bd}$ |

The thickness of the periovarian fat pad changed by −54.93% in the tumor-bearing control, compared to the vehicle control, and changed by −31.86, 54.27, 64.81, 83.16, and 105.84% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

The mean diameter of the periovarian white adipocyte changed by −56.15% in the tumor-bearing control compared to the vehicle control, and changed by −27.95, 56.22, 58.47, 70.63, and 84.77% in the sorafenib 20 mg/kg single treated group, the BJIKT 400 mg/kg single treated group, and the BJIKT 100, 200, and 400 mg/kg and sorafenib 20 mg/kg co-administered groups, respectively, compared to the tumor-bearing control.

According to Example 9, an effect thereof was observed. As a result, IC50s of BJIKT and sorafenib to HepG2 cells were estimated at 40.93 mg/ml and 2.80 μM (1.30 g/ml), respectively. Due to HepG2 cell xenograft, significant decreases in weights of the spleen and the popliteal lymph node, blood IFN-γ content, splenic TNF-α, IL-1β, and IL-10 contents, and activities of spleen cells and peritoneal macrophages were observed with histopathological atrophy caused by lymphocyte decreases in the spleen and popliteal lymph node. Also, decreases in body weight and body weight gain were observed. An increase in blood IL-6 content, a decrease in weight of the periovarian fat pad, and a histopathological atrophy symptom was observed in periovarian accumulated fat tissues. Accordingly, it is determined that typical tumor-associated immunosuppression and cachexia symptoms were induced after tumor xenograft. On the other hand, according to single administration of sorafenib 20 mg/kg, decreases in volume and weight of a tumor mass were observed in a histopathological test with a decrease in percentage of tumor cells due to an increase in apoptotic cells in the tumor mass. A decrease in number of COX-2 immunoreactive cells was observed with increases in caspase-3, PARP, iNOS, and TNF-α immunoreactivities in the tumor mass. However, it was observed that tumor-associated cachexia (changes in body weight, periovarian fat pad and blood IL-6 contents) and immunosuppression (changes in weights of the spleen and submandibular lymph node, blood IFN-γ contents, NK cell activities, and splenic TNF-α, IL-1β, and IL-10 contents, and histological change in immune organs) became significantly worse. Significant immune activity and the tumor-associated cachexia decrease were observed in the BJIKT single treated group, compared to the tumor-bearing control. However, it was observed that an anticancer effect on the tumor mass itself is significantly smaller than that of the sorafenib administered group.

On the other hand, significant decreases in anticancer effect, immune activity, and tumor-associated cachexia were observed in all of the three doses of BJIKT and sorafenib co-administered groups, compared to the tumor-bearing control. In particular, a significant increase (p<0.01 or p<0.05) in anticancer effect was observed in all of the three doses of BJIKT 400, 200, and 100 mg/kg and sorafenib co-administered groups, compared to the sorafenib single treated group. Also, significant increases in effects of reducing immune activity and cachexia were observed in all of the three doses of BJIKT 400, 200, and 100 mg/kg and sorafenib co-administered groups, compared to the sorafenib single treated group.

Accordingly, it is determined that BJIKT and sorafenib co-administration at intervals of 3.5 hours does not influence on bioavailability of sorafenib, and due to the immune activity, significantly enhances an anticancer effect of sorafenib and significantly suppresses the tumor-associated cachexia. Therefore, the sorafenib and BJIKT co-administration to liver cancer patients is expected to provide a new treating method, which is very useful in integrative medicine and treatment.

In addition, a significant tumor-associated cachexia suppression effect and a significant increase in anticancer activities due to immune enhancing were observed in the BJIKT 100 mg/kg and sorafenib co-administered group, compared to the sorafenib single treated group. When 100 mg/kg or more of BJIKT was co-administered, it is determined that, due to immune activity, the anticancer effect of sorafenib is clearly enhanced and the tumor-associated cachexia can be controlled. As a result, an effect of decreasing side effects of the anticancer agent was confirmed.

Exemplary Embodiment 3

Example 10. Sorafenib and BJIKT Co-Administration Experiment: Confirmation of Effect of BJIKT Effect on Reducing Sorafenib Toxicity 10.1. Preparation of Laboratory Animals In Example 10, male ICR mice were used as laboratory animals. A total of 42 mice were divided into six groups [(G0M) vehicle control, (G1M) sorafenib 100 mg/kg single treated group, (G2M) BJIKT 400 mg/kg single treated group, (G3M) sorafenib 100 mg/kg and BJIKT 100 mg/kg co-administered group, (G4M) sorafenib 100 mg/kg and BJIKT 200 mg/kg co-administered group, and (G5M) sorafenib 100 mg/kg and BJIKT 400 mg/kg co-administered group] to be used in the experiment.

10.2. Method of Drug Administration

As shown in Table 29, 400, 200, or 100 mg/kg of BJIKT was co-administered to the mice to which sorafenib 100 mg/kg was administered once a day at intervals of 3.5 hours for 28 days. To each single treated group, when BJIKT or sorafenib was administered, the same dose of sterile distilled water was administered alone. In the vehicle control, only sterile distilled water was administered as a vehicle twice at intervals of 3.5 hours.

TABLE 29

| Group | Sex | Dose (mg/kg) |
|---|---|---|
| BJIKT: Mouse repeated oral dose toxicity test | | |
| Control | Male | Distilled water 10 ml/kg |
| Reference | Male | Sorafenib single (100 mg/kg) |
| Reference | Male | BJIKT single (400 mg/kg) |
| Active | Male | Sorafenib and BJIKT (100 and 100 mg/kg) |
| Active | Male | Sorafenib and BJIKT (100 and 200 mg/kg) |
| Active | Male | Sorafenib and BJIKT (100 and 400 mg/kg) |

10.3. Observation Items

In Example 10, a death rate, clinical symptoms, a change in body weight, necropsy findings, an organ weight, hematologic changes (14 items; Table 30) and hematochemical changes (20 items; Table 31), histopathological changes (23 organs: the brain—cerebrum, cerebellum and medulla oblongata, the heart, the thymus, the lung, the testis, the epididymis, the kidney, the adrenal gland, the spleen, the liver, the pancreas, the gastrointestinal tract—esophagus, stomach fundus, pylorus, duodenum, jejunum, ileum, cecum, colon and rectum, and the submandibular lymph node), and activities of splenic and peritoneal NK cells were observed for 28 days.

TABLE 30

| Hematology Items Abbreviations | Full name | Units | Methods |
|---|---|---|---|
| 1. RBC | Red blood cell count | M/µL | Laser optical (Flow cytometry) |
| 2. HGB | Hemoglobin concentration | g/dl | Cyanmethemoglobin method |
| 3. HCT | Hematocrit | % | Calculated from Item 1 and 4 |
| 4. MCV | Mean corpuscular volume | fL | Laser optical (Flow cytometry) |
| 5. MCH | Mean corpuscular hemoglobin | pg | Calculated from Item 1 and 2 |
| 6. MCHC | Mean corpuscular hemoglobin concentration | g/dL | Calculated from Item 2 and 3 |
| 7. PLT | Platelet count | K/µL | Laser optical (Flow cytometry) |
| 8. RET | Reticulocyte count | ea/1000 | Laser optical with cytochemical reaction |
| 9. WBC | White blood cell count | K/µL | Laser optical with cytochemical reaction |
| Differential counts of white blood cells | | | |
| 10. NEU % | Percentages of neutrophils | % | Perox optical with chemical reaction |
| 11. LYM % | Percentages of lymphocytes | % | Perox optical with chemical reaction |
| 12. MON % | Percentages of monocytes | % | Perox optical with chemical reaction |
| 13. EOS % | Percentages of eosinophils | % | Perox optical with chemical reaction |
| 14. BAS % | Percentages of basophils | % | Perox optical with chemical reaction |

TABLE 31

Hematology Items

| Abbreviations | Full name | Units | Methods |
|---|---|---|---|
| 1. AST | Aspartate aminotransferase | IU/L | UV-Rate method |
| 2. ALT | Alanine aminotransferase | IU/L | UV-Rate method |
| 3. ALP | Alkaline phosphatase | IU/L | P-NPP method |
| 4. BUN | Blood urea nitrogen | mg/dL | Urease-UV method |
| 5. CRE | Creatinine | mg/dL | Jaffe method |
| 6. GLU | Glucose | mg/dL | Enzyme method |
| 7. CHO | Total cholesterol | mg/dL | Enzyme method |
| 8. PRO | Total protein | g/dL | Biuret method |
| 9. CPK | Creatine phosphokinase | IU/L | UV-Rate method |
| 10. ALB | Albumin | g/dL | BCG method |
| 11. BIL | Total bilirubin | mg/dL | Jendrassik-cleghorn method |
| 12. Globulin | Globulin | g/dL | BCG method |
| 13. A/G | Albumin/globulin ratio | Ratio | Calculated from Item 10 and 12 |
| 14. IP | Inorganic phosphorus | mg/dL | UV method |
| 15. Ca | Calcium | mg/dL | OCPC method |
| 16. TG | Triglyceride | mg/dL | Enzyme method |
| 17. LDH | Lactate dehydrogenase | IU/L | UV-Rate method |
| 18. Na | Sodium | mmol/L | Electrode method |
| 19. K | Potassium | mmol/L | Electrode method |
| 20. Cl | Chloride | mmol/L | Electrode method |

10.4. Confirmation of Death Rate and Clinical Symptoms

As a result of the experiment, death caused by the administration of an experiment material was not observed during the experiment for 28 days, and necropsy was performed on all laboratory animals in all experiment groups (7/7; 100%; Table 32). Also, as a result of the present experiment, no clinical symptoms caused by the administration of the experiment material were observed during the experiment for 28 days (Table 33).

TABLE 32

| Groups | Days of treatment Periods (Day 0a~27) | At termination (at end of 28 days of administration) | Total* |
|---|---|---|---|
| Vehicle control | | | |
| Distilled water | 0 | 0 | 0/7 (0%) |
| Sorafenib single | | | |
| 100 mg/kg | 0 | 0 | 0/7 (0%) |
| BJIKT single | | | |
| 400 mg/kg | 0 | 0 | 0/7 (0%) |
| Sorafenib 100 mg/kg and BJIKT co-treated | | | |
| 100 mg/kg | 0 | 0 | 0/7 (0%) |
| 200 mg/kg | 0 | 0 | 0/7 (0%) |
| 400 mg/kg | 0 | 0 | 0/7 (0%) |

TABLE 33

| Groups | Normal appearance | Clinical signs Any abnormal signs |
|---|---|---|
| Vehicle control | | |
| Distilled water | 7/7 (100%) | 0/7 (0%) |
| Sorafenib single | | |
| 100 mg/kg | 7/7 (100%) | 0/7 (0%) |
| BJIKT single | | |
| 400 mg/kg | 7/7 (100%) | 0/7 (0%) |

TABLE 33-continued

| Groups | Normal appearance | Clinical signs Any abnormal signs |
|---|---|---|
| Sorafenib 100 mg/kg and BJIKT co-treated | | |
| 100 mg/kg | 7/7 (100%) | 0/7 (0%) |
| 200 mg/kg | 7/7 (100%) | 0/7 (0%) |
| 400 mg/kg | 7/7 (100%) | 0/7 (0%) |

10.5. Confirmation of Changes in Body Weight and Body Weight Gain

Figure 70:
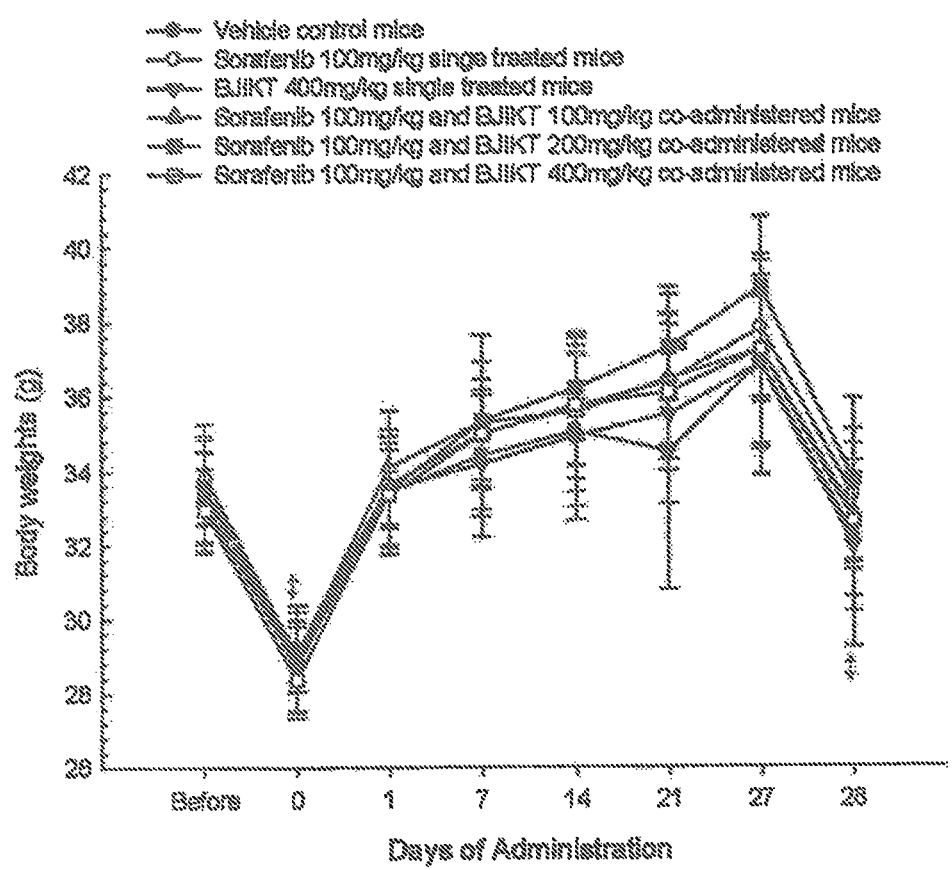
FIG. 70 shows variations in body weight of male ICR mice for each group in Example 10.

Except that a significant increase ($p<0.05$) in body weight was observed only in the BJIKT 200 mg/kg and sorafenib co-administered group 21 days after the administration, compared to the vehicle control, significant changes in body weight and body weight gain were not observed in all of the experiment material administered groups, compared to the vehicle control. The significant changes in body weight and body weight gain were not observed in all of the BJIKT administered groups for an entire period of the experiment, compared to the sorafenib 100 mg/kg single treated group (Table 34, FIG. 70).

TABLE 34

| Groups | Intervals Day 0*~Day 14 | Day 14~Day 27 | Day 0~Day 28** |
|---|---|---|---|
| Vehicle control | | | |
| Distilled water | 6.34 ± 0.97 | 1.84 ± 1.22 | 3.50 ± 1.13 |
| Sorafenib single | | | |
| 100 mg/kg | 6.63 ± 1.62 | 2.11 ± 1.51 | 4.23 ± 1.51 |
| BJIKT single | | | |
| 400 mg/kg | 6.17 ± 1.15 | 1.91 ± 1.34 | 3.21 ± 1.52 |
| Sorafenib 100 mg/kg and BJIKT co-treated | | | |
| 100 mg/kg | 6.57 ± 1.77 | 1.67 ± 1.08 | 3.83 ± 1.89 |
| 200 mg/kg | 7.24 ± 1.39 | 2.70 ± 1.44 | 4.79 ± 2.19 |
| 400 mg/kg | 7.40 ± 0.74 | 1.49 ± 0.59 | 4.26 ± 0.65 |

10.6. Confirmation of Change in Organ Weight

Significant decreases ($p<0.01$) in absolute and relative weights of the thymus, the spleen, the testis, the epididymis, and the submandibular lymph node were observed in the sorafenib 100 mg/kg single treated group, compared to the vehicle control. However, significant increases ($p<0.01$ or $p<0.05$) in absolute and relative weights of the thymus, the spleen, the testis, the epididymis, and the submandibular lymph node were observed in all of the three doses of BJIKT and sorafenib co-administered groups, compared to the sorafenib 100 mg/kg single treated group. On the other hand, a significant decrease ($p<0.05$) in absolute weight of the thymus was observed in the BJIKT 400 mg/kg single treated group, compared to the vehicle control. A significant increase ($p<0.05$) in relative weight of the adrenal gland was observed only in the BJIKT 400 mg/kg and the sorafenib co-administered group, compared to the vehicle control (Tables 35 and 36).

TABLE 35

| Groups | Principal organs | | | | | |
|---|---|---|---|---|---|---|
| | Lung | Heart | Thymus | Kidney L | Adrenal G L | Spleen |
| Vehicle control | 0.174 ± 0.007 | 0.158 ± 0.006 | 0.054 ± 0.011 | 0.302 ± 0.036 | 0.003 ± 0.001 | 0.091 ± 0.006 |
| Sorafenib single | | | | | | |
| 100 mg/kg | 0.172 ± 0.010 | 0.155 ± 0.011 | 0.027 ± 0.004$^a$ | 0.285 ± 0.042 | 0.003 ± 0.002 | 0.063 ± 0.007$^e$ |
| BJIKT single | | | | | | |
| 400 mg/kg | 0.174 ± 0.013 | 0.151 ± 0.014 | 0.044 ± 0.011$^{bc}$ | 0.278 ± 0.042 | 0.004 ± 0.003 | 0.091 ± 0.014$^f$ |
| Sorafenib 100 mg/kg and BJIKT co-treated | | | | | | |
| 100 mg/kg | 0.172 ± 0.010 | 0.161 ± 0.007 | 0.040 ± 0.009$^{ac}$ | 0.273 ± 0.026 | 0.005 ± 0.003 | 0.081 ± 0.014$^f$ |
| 200 mg/kg | 0.172 ± 0.008 | 0.161 ± 0.006 | 0.044 ± 0.055$^{bc}$ | 0.276 ± 0.037 | 0.004 ± 0.002 | 0.092 ± 0.014$^f$ |
| 400 mg/kg | 0.177 ± 0.008 | 0.165 ± 0.015 | 0.045 ± 0.002$^{bc}$ | 0.278 ± 0.024 | 0.005 ± 0.002 | 0.094 ± 0.007$^f$ |

| Groups | Testis L | Liver | Pancreas S | Brain | Epididymis L | LN L |
|---|---|---|---|---|---|---|
| Vehicle control | 0.116 ± 0.009 | 1.256 ± 0.117 | 0.156 ± 0.007 | 0.475 ± 0.019 | 0.046 ± 0.003 | 0.007 ± 0.003 |
| Sorafenib single | | | | | | |
| 100 mg/kg | 0.097 ± 0.006$^a$ | 1.234 ± 0.149 | 0.156 ± 0.022 | 0.471 ± 0.022 | 0.036 ± 0.004$^a$ | 0.002 ± 0.001$^a$ |
| BJIKT single | | | | | | |
| 400 mg/kg | 0.114 ± 0.013$^d$ | 1.225 ± 0.126 | 0.144 ± 0.020 | 0.477 ± 0.016 | 0.044 ± 0.005$^c$ | 0.009 ± 0.003$^c$ |
| Sorafenib 100 mg/kg and BJIKT co-treated | | | | | | |
| 100 mg/kg | 0.112 ± 0.012$^d$ | 1.251 ± 0.095 | 0.162 ± 0.018 | 0.479 ± 0.016 | 0.046 ± 0.004$^c$ | 0.008 ± 0.004$^c$ |
| 200 mg/kg | 0.118 ± 0.016$^c$ | 1.277 ± 0.154 | 0.156 ± 0.012 | 0.470 ± 0.013 | 0.047 ± 0.004$^c$ | 0.008 ± 0.004$^c$ |
| 400 mg/kg | 0.126 ± 0.014$^c$ | 1.274 ± 0.085 | 0.160 ± 0.022 | 0.474 ± 0.012 | 0.047 ± 0.004$^c$ | 0.008 ± 0.002$^c$ |

TABLE 36

| Groups | Principal organs | | | | | |
|---|---|---|---|---|---|---|
| | Lung | Heart | Thymus | Kidney L | Adrenal G L | Spleen |
| Vehicle control | 0.541 ± 0.030 | 0.492 ± 0.021 | 0.168 ± 0.030 | 0.943 ± 0.140 | 0.008 ± 0.004 | 0.283 ± 0.020 |
| Sorafenib single | | | | | | |
| 100 mg/kg | 0.518 ± 0.043 | 0.467 ± 0.036 | 0.080 ± 0.011$^d$ | 0.855 ± 0.107 | 0.010 ± 0.006 | 0.188 ± 0.022$^d$ |
| BJIKT single | | | | | | |
| 400 mg/kg | 0.548 ± 0.062 | 0.474 ± 0.021 | 0.138 ± 0.037$^f$ | 0.875 ± 0.161 | 0.013 ± 0.008 | 0.286 ± 0.051$^d$ |
| Sorafenib 100 mg/kg and BJIKT co-treated | | | | | | |
| 100 mg/kg | 0.526 ± 0.048 | 0.492 ± 0.045 | 0.123 ± 0.025$^{ef}$ | 0.832 ± 0.065 | 0.015 ± 0.011 | 0.247 ± 0.050$^g$ |
| 200 mg/kg | 0.511 ± 0.036 | 0.479 ± 0.033 | 0.132 ± 0.017$^{ef}$ | 0.826 ± 0.161 | 0.012 ± 0.006 | 0.274 ± 0.046$^f$ |
| 400 mg/kg | 0.543 ± 0.025 | 0.506 ± 0.048 | 0.138 ± 0.010$^f$ | 0.855 ± 0.100 | 0.015 ± 0.005$^e$ | 0.289 ± 0.028$^f$ |

| Groups | Testis L | Liver | Pancreas S | Brain | Epididymis L | LN L |
|---|---|---|---|---|---|---|
| Vehicle control | 0.362 ± 0.029 | 3.895 ± 0.192 | 0.486 ± 0.031 | 1.478 ± 0.093 | 0.143 ± 0.012 | 0.022 ± 0.010 |
| Sorafenib single | | | | | | |
| 100 mg/kg | 0.292 ± 0.018$^a$ | 3.729 ± 0.355 | 0.468 ± 0.057 | 1.421 ± 0.120 | 0.108 ± 0.013$^a$ | 0.006 ± 0.003$^a$ |
| BJIKT single | | | | | | |
| 400 mg/kg | 0.358 ± 0.039$^b$ | 3.835 ± 0.256 | 0.451 ± 0.050 | 1.498 ± 0.106 | 0.139 ± 0.029$^b$ | 0.028 ± 0.010$^b$ |
| Sorafenib 100 mg/kg and BJIKT co-treated | | | | | | |
| 100 mg/kg | 0.342 ± 0.038$^c$ | 3.821 ± 0.308 | 0.498 ± 0.077 | 1.465 ± 0.094 | 0.142 ± 0.018$^c$ | 0.023 ± 0.011$^c$ |
| 200 mg/kg | 0.351 ± 0.048$^b$ | 3.777 ± 0.328 | 0.463 ± 0.039 | 1.399 ± 0.104 | 0.139 ± 0.015$^b$ | 0.022 ± 0.010$^b$ |
| 400 mg/kg | 0.387 ± 0.046$^b$ | 3.911 ± 0.290 | 0.490 ± 0.061 | 1.456 ± 0.078 | 0.144 ± 0.012$^b$ | 0.023 ± 0.006$^b$ |

10.7. Confirmation of Hematologic Change

As a result of 14 hematologic tests, a significant decrease ($p<0.01$) in WBC was observed with a decrease of a lymphocyte percentage, and a resulting increase of a neutrophilic leukocyte percentage in the sorafenib single treated group compared to the vehicle control. However, significant increases ($p<0.01$ or $p<0.05$) in WBC were observed with increases in lymphocyte percentages and resultant decreases in neutrophilic leukocyte percentages in the BJIKT 100, 200, and 400 mg/kg and sorafenib co-administered groups, compared to the sorafenib 100 mg/kg single treated group. On the other hand, a significant hematologic change was not observed in the BJIKT 400 mg/kg single treated group, compared to the vehicle control. Significant changes in RBC, HGB, HCT, MCV, MCH, MCHC, PLT, RET, MON %, EOS %, and BAS % were not observed in the sorafenib single treated group and all of the BJIKT and sorafenib co-administered groups, compared to the vehicle control (Table 37).

TABLE 37

| Hematological Items: Red Blood Cells | | | | | | | | |
|---|---|---|---|---|---|---|---|---|
| Groups | RBC | HGB | HCT | MCV | MCH | MCHC | PLT | RET |
| Vehicle control | 8.80 ± 0.50 | 18.76 ± 1.17 | 40.59 ± 3.15 | 46.11 ± 1.72 | 21.31 ± 0.57 | 44.99 ± 1.18 | 795.14 ± 84.35 | 0.30 ± 0.19 |
| Sorafenib single | | | | | | | | |
| 100 mg/kg | 8.89 ± 0.39 | 18.54 ± 0.88 | 41.89 ± 2.13 | 47.13 ± 2.47 | 20.89 ± 0.88 | 44.33 ± 1.04 | 804.86 ± 99.24 | 0.51 ± 0.33 |
| BJIKT single | | | | | | | | |
| 400 mg/kg | 9.17 ± 0.67 | 18.83 ± 1.46 | 43.84 ± 4.24 | 47.80 ± 2.23 | 20.96 ± 1.32 | 44.37 ± 2.21 | 796.00 ± 88.52 | 0.47 ± 0.26 |
| Sorafenib 100 mg/kg and BJIKT co-treated | | | | | | | | |
| 100 mg/kg | 8.68 ± 1.26 | 17.34 ± 2.75 | 41.47 ± 6.24 | 47.46 ± 1.16 | 20.66 ± 1.21 | 44.01 ± 2.43 | 791.86 ± 114.50 | 0.44 ± 0.21 |
| 200 mg/kg | 9.05 ± 0.52 | 18.97 ± 0.72 | 42.74 ± 1.70 | 47.77 ± 2.85 | 21.20 ± 1.22 | 43.43 ± 2.20 | 787.57 ± 119.29 | 0.41 ± 0.28 |
| 400 mg/kg | 8.90 ± 0.76 | 18.27 ± 1.52 | 41.86 ± 3.62 | 47.09 ± 2.16 | 20.86 ± 0.94 | 43.71 ± 1.84 | 824.86 ± 94.75 | 0.43 ± 0.17 |

| Hematological Items: White Blood Cells | | | | | |
|---|---|---|---|---|---|
| Groups | WBC | NEU (%) | LYM (%) | MONO (%) | EOS (%) | BASO (%) |
| Vehicle control | 4.48 ± 0.34 | 8.41 ± 1.07 | 82.77 ± 2.53 | 3.71 ± 1.40 | 0.87 ± 0.87 | 0.31 ± 0.17 |
| Sorafenib single | | | | | | |
| 100 mg/kg | 1.81 ± 0.53[a] | 17.36 ± 5.16[c] | 70.74 ± 6.08[c] | 5.26 ± 1.55 | 1.87 ± 2.05 | 0.30 ± 0.20 |
| BJIKT single | | | | | | |
| 400 mg/kg | 4.36 ± 0.84[b] | 10.84 ± 4.51[e] | 79.70 ± 6.26[e] | 5.59 ± 2.27 | 0.86 ± 1.21 | 0.34 ± 0.24 |
| Sorafenib 100 mg/kg and BJIKT co-treated | | | | | | |
| 100 mg/kg | 3.39 ± 0.40[ab] | 9.67 ± 1.79[d] | 77.31 ± 2.27[ce] | 4.30 ± 2.82 | 1.87 ± 1.77 | 0.31 ± 0.32 |
| 200 mg/kg | 4.30 ± 0.56[b] | 9.23 ± 1.45[d] | 81.89 ± 2.54[d] | 5.16 ± 1.92 | 0.47 ± 0.57 | 0.46 ± 0.32 |
| 400 mg/kg | 4.54 ± 0.87[b] | 9.21 ± 1.46[d] | 81.87 ± 2.77[d] | 3.73 ± 1.76 | 0.50 ± 0.71 | 0.27 ± 0.20 |

10.8. Necropsy Findings

Significant increases in observation frequencies of atrophy of the thymus, spleen and submandibular lymph node were observed in the sorafenib 100 mg/kg single treated group, compared to the vehicle control. However, significant decreases in observation frequencies of atrophy of the thymus, spleen and submandibular lymph node were observed in the BJIKT 100, 200, and 400 mg/kg and sorafenib co-administered groups, compared to the sorafenib single treated group. On the other hand, an increase in observation frequencies of the swollen spleen and submandibular lymph node was observed in the BJIKT 400 mg/kg single treated group, compared to the vehicle control, and mild [1+] pulmonary congestion were sporadically observed in all of the experiment groups including the vehicle control (Table 38).

TABLE 38

| Groups | Vehicle control | Sorafenib single 100 mg/kg | BJIKT single 400 mg/kg | Sorafenib 100 mg/kg and BJIKT co-administration | | |
|---|---|---|---|---|---|---|
| | | | | 100 mg/kg | 200 mg/kg | 400 mg/kg |
| Lung | | | | | | |
| Normal | 5/7 | 6/7 | 5/7 | 6/7 | 6/7 | 6/7 |
| Congestion | 2/7 | 1/7 | 2/7 | 1/7 | 1/7 | 1/7 |
| 1+ | 2/7 | 1/7 | 2/7 | 1/7 | 1/7 | 1/7 |
| Thymus | | | | | | |
| Normal | 6/7 | 1/7 | 7/7 | 7/7 | 7/7 | 6/7 |
| Atrophy | 1/7 | 6/7 | 0/7 | 0/7 | 0/7 | 1/7 |
| 1+ | 1/7 | 6/7 | 0/7 | 0/7 | 0/7 | 1/7 |
| Spleen | | | | | | |
| Normal | 5/7 | 0/7 | 2/7 | 5/7 | 5/7 | 4/7 |
| Atrophy | 2/7 | 7/7 | 0/7 | 2/7 | 0/7 | 0/7 |
| 1+ | 2/7 | 7/7 | 0/7 | 2/7 | 0/7 | 0/7 |
| Hypertrophy | 0/7 | 0/7 | 5/7 | 0/7 | 2/7 | 3/7 |
| 1+ | 0/7 | 0/7 | 5/7 | 0/7 | 2/7 | 3/7 |
| Lymph node a) | | | | | | |
| Normal | 7/7 | 0/7 | 5/7 | 7/7 | 4/7 | 3/7 |
| Atrophy | 0/7 | 7/7 | 0/7 | 0/7 | 0/7 | 0/7 |
| 1+ | 0/7 | 7/7 | 0/7 | 0/7 | 0/7 | 0/7 |
| Hypertrophy | 0/7 | 0/7 | 2/7 | 0/7 | 3/7 | 4/7 |
| 1+ | 0/7 | 0/7 | 2/7 | 0/7 | 3/7 | 4/7 |
| Others | | | | | | |
| Normal | 7/7 | 7/7 | 7/7 | 7/7 | 7/7 | 7/7 |

10.9. Change in NK Cell Activity

Figure 71:
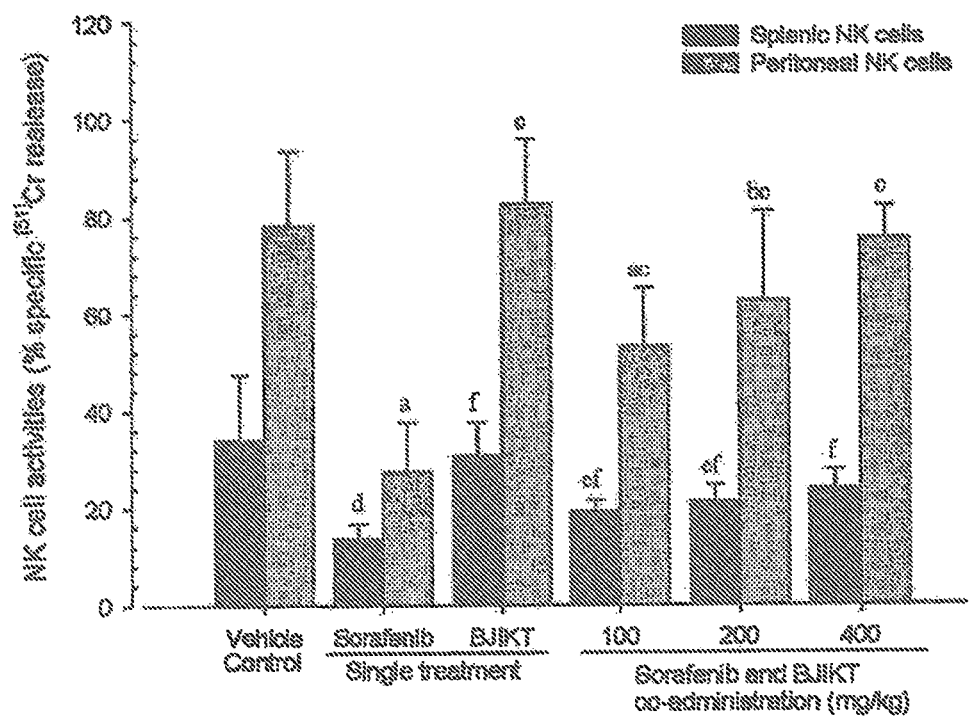
FIG. 71 shows variations in NK cell activities of male ICR mice for each group according to Example 10.

A significant decrease (p<0.01) in activities of splenic and peritoneal NK cells was observed in the sorafenib 100 mg/kg single treated group, compared to the vehicle control. However, significant increases (p<0.01) in activities of the splenic and peritoneal NK cells were observed in all of the BJIKT co-administered groups, compared to the sorafenib single treated group. On the other hand, no significant change in activities of the splenic and peritoneal NK cells was observed in the BJIKT 400 mg/kg single treated group, compared to the vehicle control (FIG. 71).

The activity of the splenic NK cells changed by −59.70% in the sorafenib 100 mg/kg single treated group, compared to the vehicle control, and changed by 123.82, 39.82, 54.92, and 73.73% in the BJIKT 400 mg/kg single treated group, and the BJIKT 100, 200, and 400 mg/kg and sorafenib co-administered groups, respectively, compared to the sorafenib 100 mg/kg single treated group.

The activity of the peritoneal NK cells changed by −64.97% in the sorafenib 100 mg/kg single treated group, compared to the vehicle control, and changed by 200.80, 93.96, 128.15, and 175.28% in the BJIKT 400 mg/kg single treated group, and the BJIKT 100, 200, and 400 mg/kg and sorafenib co-administered groups, respectively, compared to the sorafenib 100 mg/kg single treated group.

10.10. Histopathological Observation

Figure 72:
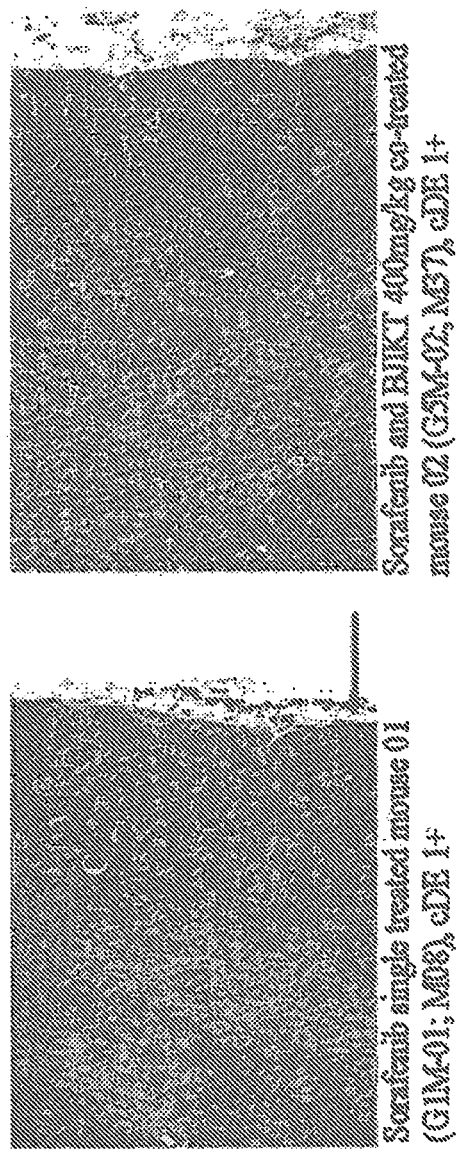
FIG. 72 shows histopathological changes in the thymic cortex in a sorafenib single treated group and a sorafenib and bojungikgi-tang 400 mg/kg co-administered group.
Figure 73:
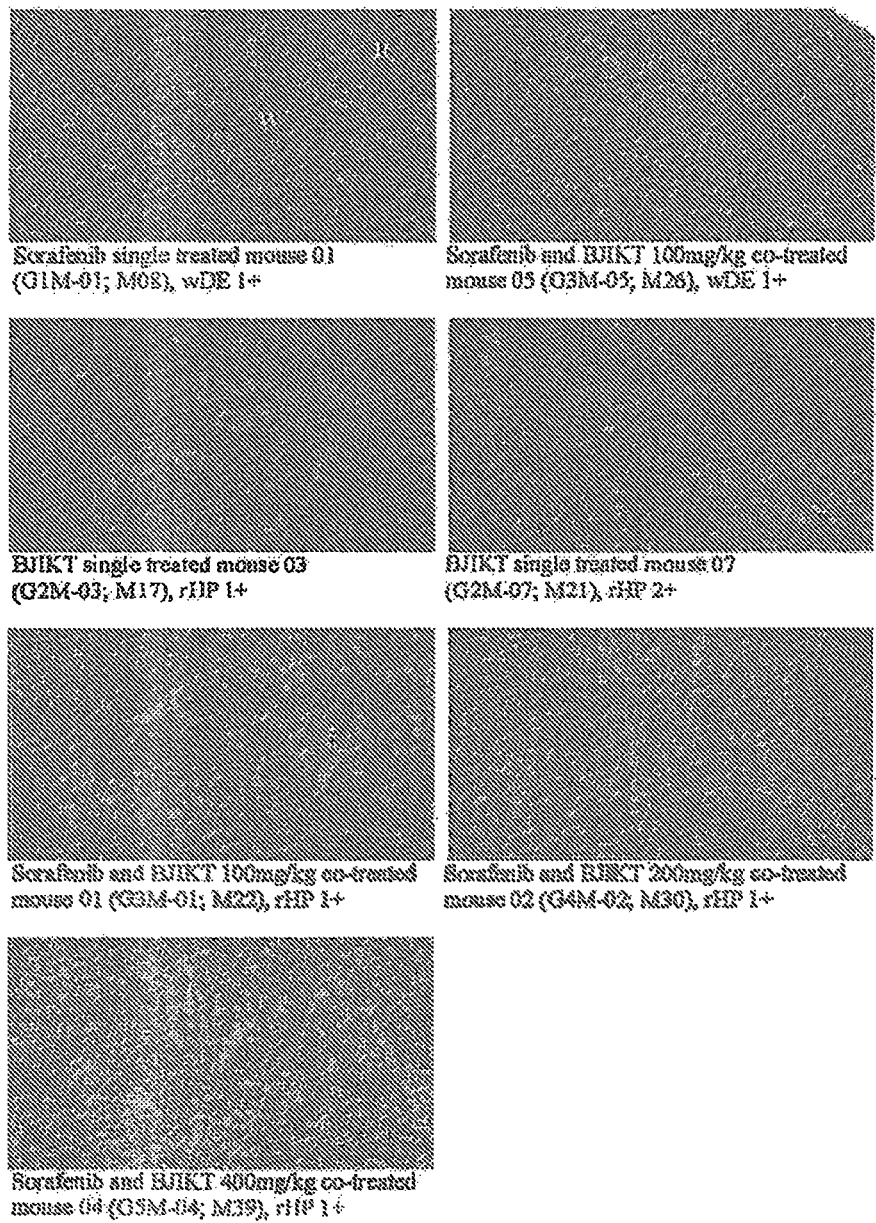
FIG. 73 shows histopathological changes in splenic white pulps for each group.
Figure 74:
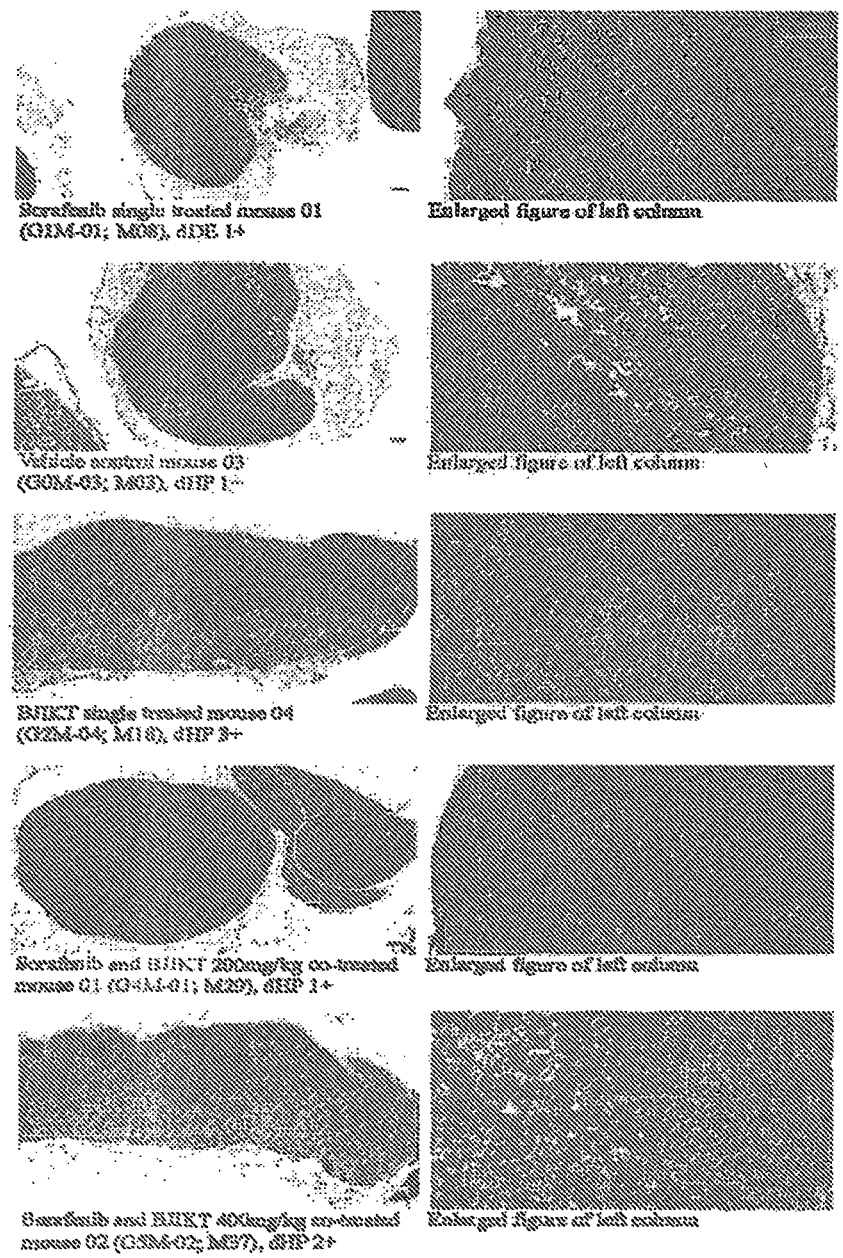
FIG. 74 shows histopathological changes in submandibular lymph nodes in a sorafenib single treated group, a bojungikgi-tang single treated groups, and soratinib and bojungikgi-tang 200 mg/kg and 400 mg/kg co-administered groups.
Figure 75:
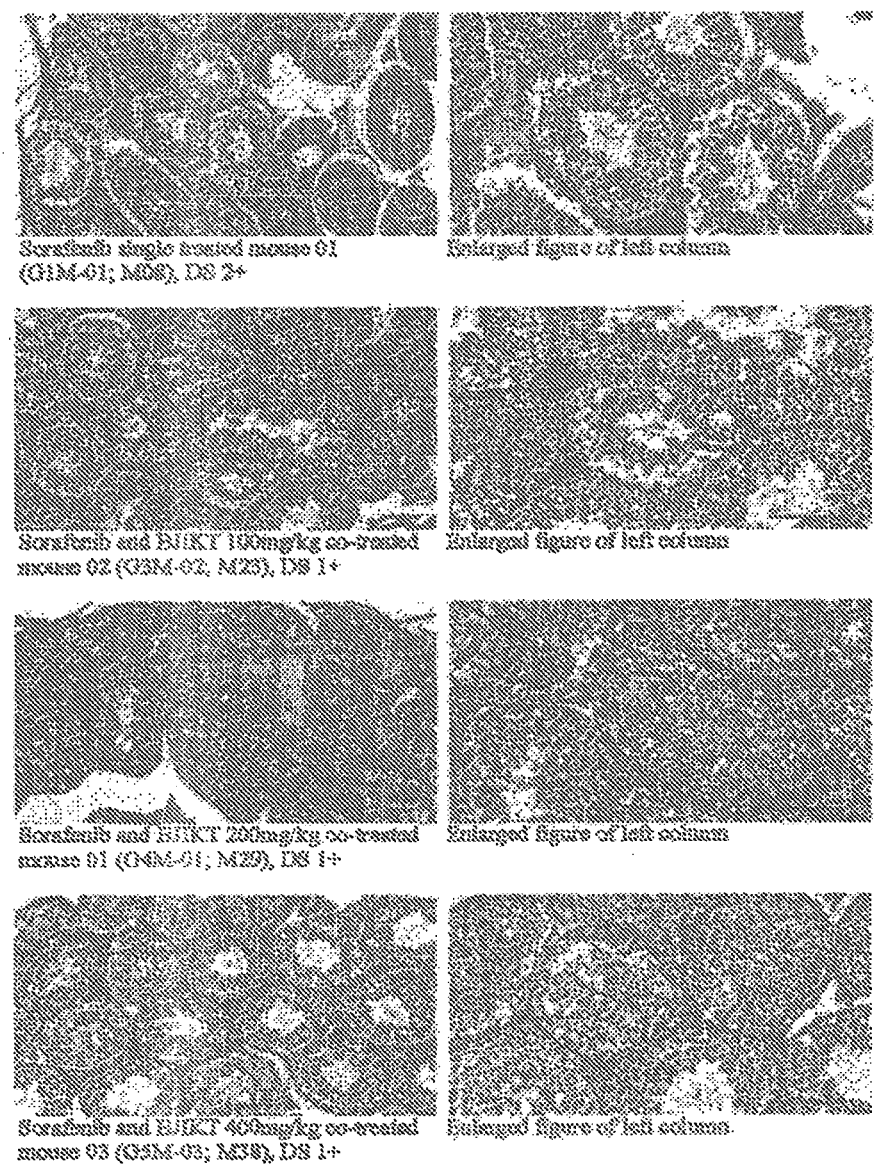
FIG. 75 shows histopathological changes in testis-seminiferous tubules in a sorafenib single treated group, and sorafenib and bojungikgi-tang 100 mg/kg, 200 mg/kg, and 400 mg/kg co-administered groups.
Figure 76:
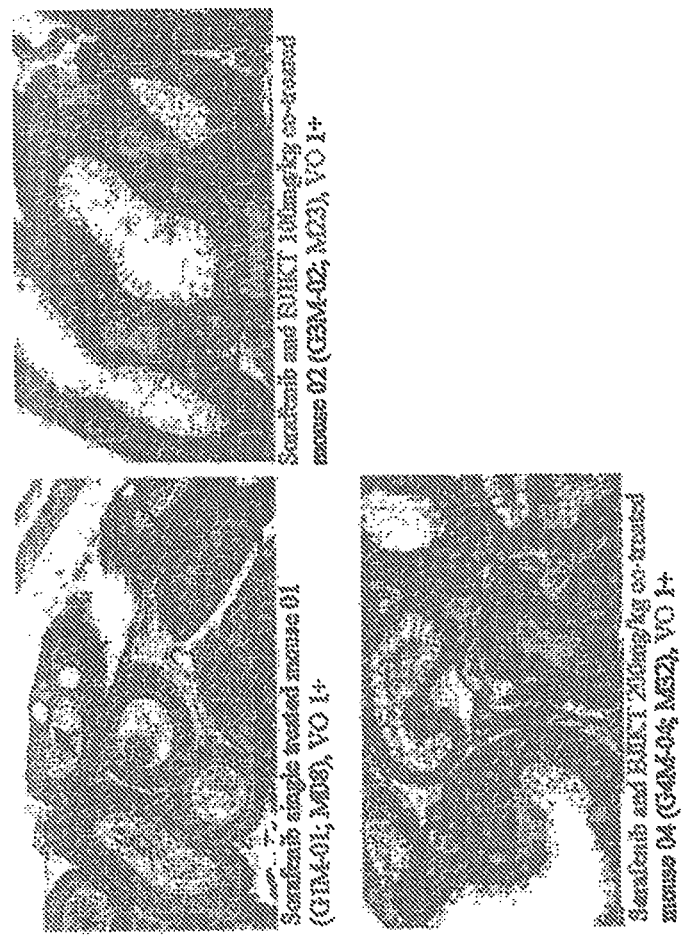
FIG. 76 shows severities of epididymal duct epithelium vacuolation and changes in observation frequencies in the sorafenib single treated group and the sorafenib and bojungikgi-tang 100 mg/kg and 200 mg/kg co-administered groups.
Figure 77:
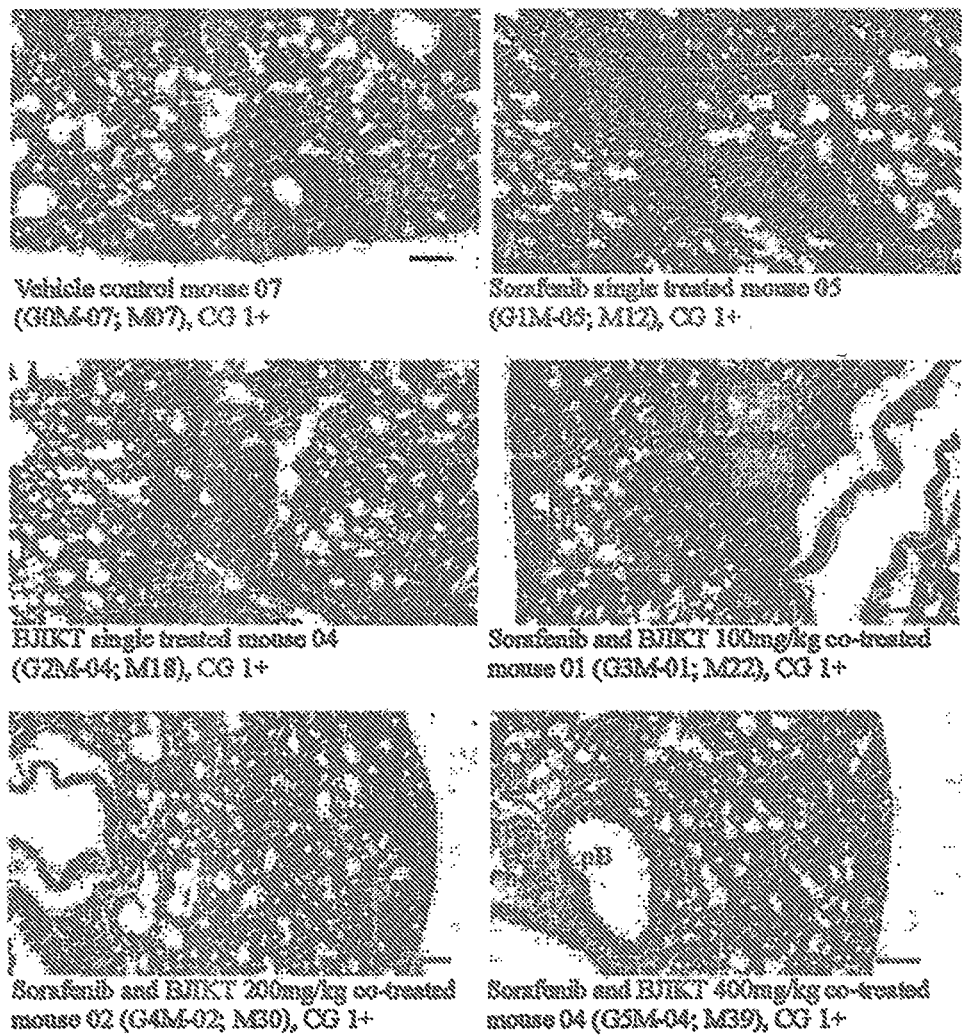
FIG. 77 shows the results obtained by observing pulmonary congestion in a control group, the sorafenib single treated group, and the sorafenib and bojungikgi-tang 100 mg/kg, 200 mg/kg and 400 mg/kg co-administered groups.
Figure 78:
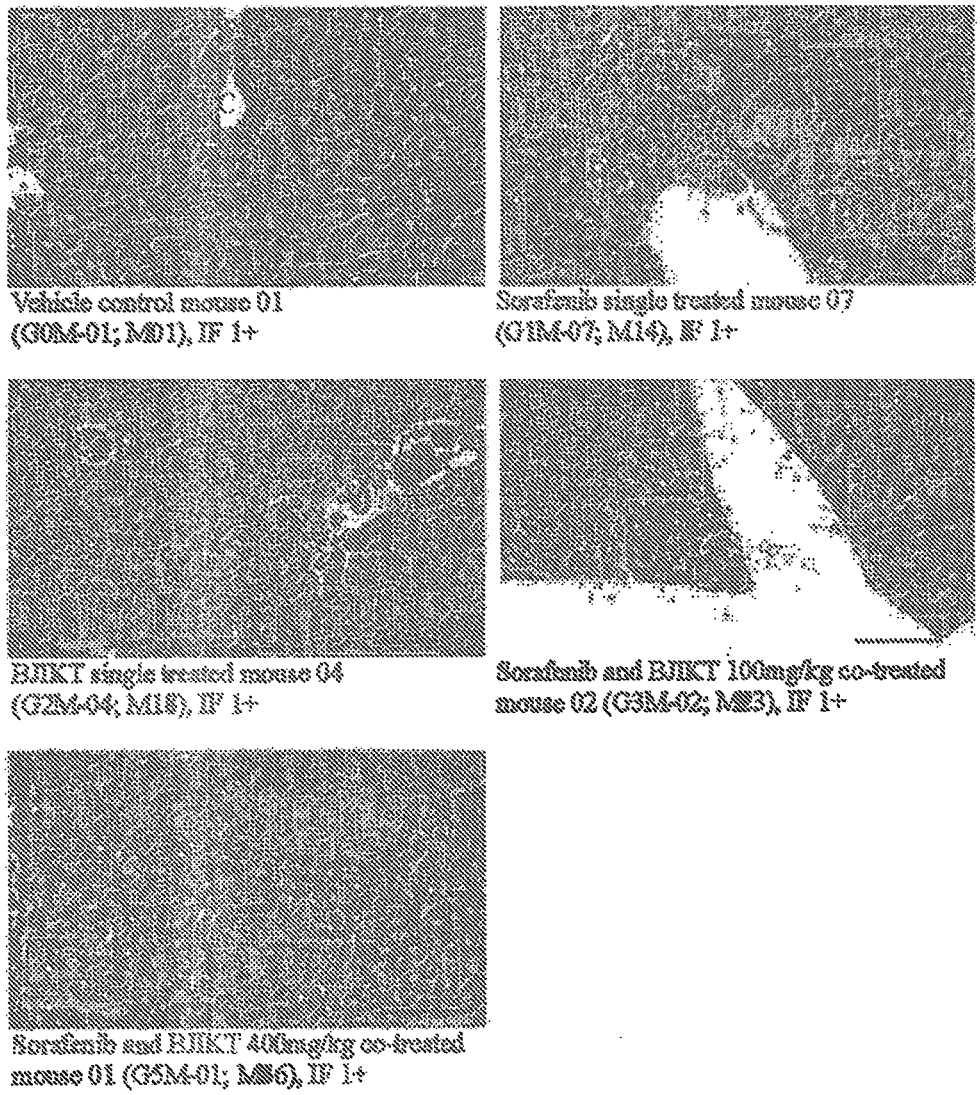
FIG. 78 shows the results obtained by observing local inflammatory cell infiltration in the liver in the control group, the sorafenib single treated group, the bojungikgi-tang single treated group, and the sorafenib and bojungikgi-tang 100 mg/kg and 400 mg/kg co-administered groups.
Figure 79:
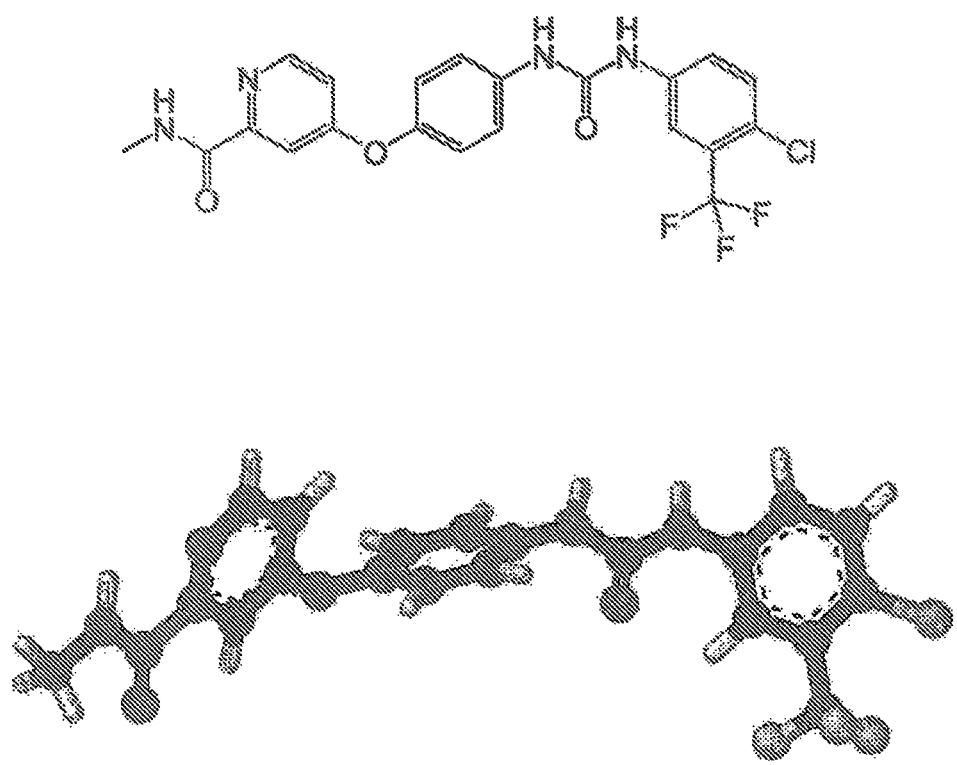
FIG. 79 shows a structural formula of sorafenib, which is an anticancer agent used in the present invention.

A mild [1+] or moderate [2+] decrease in the thymus cortex (FIG. 72), the splenic white pulp (FIG. 73), and the lymphocyte in the submandibular lymph node (FIG. 74), a decrease in spermatogenic cells of the testis-seminiferous tubules (FIG. 75), and severity and observation frequency of epididymal duct epithelium vacuolation (FIG. 76) were observed in the sorafenib 100 mg/kg single treated group, compared to the vehicle control. However, a decrease in lymphocytes in the lymphoid organ, and a histopathological change in and occurring frequency of reproductive organs were significantly decreased in the BJIKT 400, 200, and 100 mg/kg and sorafenib co-administered groups, compared to the sorafenib single treated group. On the other hand, increase in severity of diffused lymphocyte hyperplasia of the splenic red pulps (FIG. 73) and submandibular lymph nodes (FIG. 74) and observation frequency thereof were observed in the BJIKT 400 mg/kg administered group, compared to the vehicle control. Mild pulmonary congestion (FIG. 77) and local inflammatory cell infiltration in the liver (FIG. 78) were sporadically observed in all of the experiment groups including the vehicle control (Table 39).

TABLE 39

| Groups | Vehicle control | Sorafenib single 100 mg/kg | BJIKT single 400 mg/kg | Sorafenib 100 mg/kg and BJIKT co-administration | | |
|---|---|---|---|---|---|---|
| | | | | 100 mg/kg | 200 mg/kg | 400 mg/kg |
| Lung | | | | | | |
| Normal | 4/7 | 6/7 | 5/7 | 6/7 | 6/7 | 6/7 |
| CG 1+ | 3/7 | 1/7 | 2/7 | 1/7 | 1/7 | 1/7 |

TABLE 39-continued

| Groups | Vehicle control | Sorafenib single 100 mg/kg | BJIKT single 400 mg/kg | Sorafenib 100 mg/kg and BJIKT co-administration | | |
|---|---|---|---|---|---|---|
| | | | | 100 mg/kg | 200 mg/kg | 400 mg/kg |
| Thymus | | | | | | |
| Normal | 7/7 | 0/7 | 7/7 | 7/7 | 7/7 | 6/7 |
| cDE 1+ | 0/7 | 7/7 | 0/7 | 0/7 | 0/7 | 1/7 |
| Spleen | | | | | | |
| Normal | 7/7 | 0/7 | 2/7 | 3/7 | 5/7 | 5/7 |
| wDE1+ | 0/7 | 7/7 | 0/7 | 3/7 | 0/7 | 0/7 |
| rHP | 0/7 | 0/7 | 5/7 | 1/7 | 2/7 | 2/7 |
| 1+ | 0/7 | 0/7 | 4/7 | 1/7 | 2/7 | 2/7 |
| 2+ | 0/7 | 0/7 | 1/7 | 0/7 | 0/7 | 0/7 |
| Testis | | | | | | |
| Normal | 0/7 | 0/7 | 7/7 | 4/7 | 4/7 | 6/7 |
| DS | 0/7 | 7/7 | 0/7 | 3/7 | 3/7 | 1/7 |
| 1+ | 0/7 | 3/7 | 0/7 | 3/7 | 3/7 | 1/7 |
| 2+ | 0/7 | 4/7 | 0/7 | 0/7 | 0/7 | 0/7 |
| Liver | | | | | | |
| Normal | 5/7 | 6/7 | 5/7 | 6/7 | 7/7 | 6/7 |
| IF1+ | 2/7 | 1/7 | 2/7 | 1/7 | 0/7 | 1/7 |
| Epididymis | | | | | | |
| Normal | 7/7 | 0/7 | 7/7 | 6/7 | 6/7 | 7/7 |
| VO | 0/7 | 7/7 | 0/7 | 1/7 | 1/7 | 0/7 |
| 1+ | 0/7 | 5/7 | 0/7 | 1/7 | 1/7 | 0/7 |
| 2+ | 0/7 | 2/7 | 0/7 | 0/7 | 0/7 | 0/7 |
| Lymph node a) | | | | | | |
| Normal | 5/7 | 0/7 | 5/7 | 7/7 | 4/7 | 3/7 |
| dHP | 2/7 | 0/7 | 2/7 | 0/7 | 3/7 | 4/7 |
| 1+ | 2/7 | 0/7 | 0/7 | 0/7 | 3/7 | 3/7 |
| 2+ | 0/7 | 0/7 | 1/7 | 0/7 | 0/7 | 1/7 |
| 3+ | 0/7 | 0/7 | 1/7 | 0/7 | 0/7 | 0/7 |
| dDE 1+ | 0/7 | 7/7 | 0/7 | 0/7 | 0/7 | 0/7 |
| Others | | | | | | |
| Normal | 7/7 | 7/7 | 7/7 | 7/7 | 7/7 | 7/7 |

As a result of Example 10, in the BJIKT 400, 200, and 100 mg/kg co-administration at intervals of 3.5 hours, it was observed that a lymphocyte decrease, immunosuppression resulting from NK cell activity suppression, and testis and epididymis organ damages due to sorafenib were significantly suppressed through immune enhancing of the BJIKT itself. Accordingly, it is determined that 100 mg/kg or more of BJIKT co-administration at intervals of 3.5 hours does not influence on bioavailability of sorafenib, immunosuppression and damages to the reproductive organ according to the sorafenib administration were significantly reduced due to immune activity. Therefore, sorafenib and BJIKT co-administration to liver cancer patients is expected to provide a new treating method, which is very useful in integrative medicine.

Exemplary Embodiment 4

In the present embodiment, changes in effects and reduction in side effects according to co-administration of yuk-mijihwang-tang and an anticancer agent were observed. As the anticancer agent used herein, sorafenib (Jeil Pharm. Co., Ltd, Yongin, Korea: FIG. 889) was used, and yukmijihwang-tang (hereinafter referred to as "YMJHT") was purchased from Korea InsPharm Co., Ltd. (Hwasun, Korea), and the composition of the YMJHT is shown in Table 40.

TABLE 40

| Herbs | Scientific Names | Amount (g) |
|---|---|---|
| Rehmanniae Radix Preparat | Rehmannia glutinosa Liboschitz var. purpurea Makino | 2 |
| Dioscoreae Rhizoma | Dioscorea batatas Decaisne | 1 |
| Corni Fructus | Cornus Officinalis Siebold et Zuccarini | 1 |
| Hoelen | Poria cocos Wolf | 1 |
| Moutan Cortex | Paeonia suffruticosa Andrews | 1 |
| Alismatis Rhizoma | Alisma orientale Juzepczuk | 1 |
| Total | 6 types | 7 |

The present researchers have conducted studies on methods of administering YMJHT, and found that YMJHT remarkably inhibits bioavailability of sorafenib when the YMJHT is orally co-administered once within 5 minutes after administration of sorafenib. From these experimental results, the present researchers have found that YMJHT has no significant difference in therapeutic effect when the YMJHT is orally co-administered once within 3.5 hours, and also has no influence on absorption and excretion of sorafenib, that is, bioavailability of orally administered sorafenib, when the YMJHT is repeatedly orally co-administered within 5 minutes for 7 days.

Therefore, the bioavailability of sorafenib according to repeated oral co-administration at intervals of 3.5 hours was observed in Examples of the present invention.

Example 11: Confirmation of Enhancement of Anticancer Effect of Sorafenib According to Sorafenib and YMJHT Co-Administration 11.1. Preparation of Laboratory Animals In Example 11, Balb/c Slc nu/nu mice (5-week-old females, Charles River, Shiga, Japan) were used as laboratory animals. A total of 113 nude mice were purchased, and acclimated for 8 days. Thereafter, 93 nude mice having uniform body weights were selected, and HepG2 cells were xenografted into a subcutaneous region of the right hip of each mouse, and the xenografted mice having a tumor volume of 140.08±10.22 mm$^3$ or more (87.94 to 131.77 mm$^3$) were selected again 27 days after the xenograft. Then, the selected nude mice were divided into six groups of 7 mice each to be used in the experiment, and 7 mice were separately prepared as the vehicle control (body weight: intact group −22.99±1.40 g; tumor xenograft group −21.39±0.79 g).

Grouping (total of 7 groups of 7 mice)

(1) Vehicle control: a intact vehicle control (2) TB control: A group in which sterile distilled water is administered after grafting of tumor cells (3) SF20: A group in which sorafenib 20 mg/kg is administered alone after grafting of tumor cells (4) YMJHT400: A group in which YMJHT 400 mg/kg was administered alone after grafting of tumor cells (5) SF+YMJHT100: A group in which sorafenib 20 mg/kg and YMJHT 100 mg/kg were co-administered after grafting of tumor cells (6) SF+YMJHT200: A group in which sorafenib 20 mg/kg and YMJHT 200 mg/kg were co-administered after grafting of tumor cells (7) SF+YMJHT400: A group in which sorafenib 20 mg/kg and YMJHT 400 mg/kg were co-administered after grafting of tumor cells Concentrations, that is, IC$_{50}$, of YMJHT (0, 0.5, 1, 5, 10, 50, 100 and 500 mg/ml) and sorafenib (0, 0.1, 1, 2, 4, 6, 8 and 10 μM) for inhibiting viability of HepG2 cells (1×10$^4$ cells) a half were evaluated using a general MTT method.

11.2. Methods for Tumor Cell Xenograft and Drug Administration

HepG2 (American Type Culture Collection Center, Manassas, Va., USA) cells were sub-cultured using 37° C. in an RPMI 1640 (Gibco, Grand Island, N.Y., USA) medium supplemented with 10% fetal bovine serum (FBS) and maintained in a 5% CO$_2$ incubator. Thereafter, the HepG2 cells were cultured to a cell density of 1.0×10$^8$ cells/ml to prepare a tumor cell suspension, and 0.2 mL (2×10$^7$ cells/head) of the HepG2 tumor cell suspension was grafted into a subcutaneous region of the right hip of each mouse to form solid tumor mass. In this experiment, sorafenib or YMJHT was orally administered 28 days after the grafting of a HepG2 lung cancer cell line (tumor volume; 104.08±10.22 mm$^3$, 87.94~131.77 mm$^3$).

From 28 days after the grafting of the HepG2 lung cancer cell line, 400, 200, or 100 mg/kg of YMJHT was orally co-administered into sorafenib 20 mg/kg orally administered mice at intervals of 3.5 hours daily for 35 days. In the YMJHT or sorafenib single treated group, only the same dose of sterile distilled water was administered. In the vehicle control, Only sterile distilled water was administered as a vehicle twice at intervals of 3.5 hours.

11.3. Observation Items

The concentrations of YMJHT and sorafenib, IC$_{50}$s (cytotoxicity), at which viability of HepG2 cells were inhibited a half, were evaluated using a general MTT method, and the influences on the anticancer and immune-activating effects and tumor-associated cachexia were evaluated, respectively (Tables 41 and 42).

(1) Anticancer effect: Changes in tumor volume, tumor weight, changes in tumor cell volume and apoptotic cell percentage in a tumor mass, and changes in caspase-3, PARP, COX-2, OS and TNF-α immunoreactivities in the tumor mass (2) Immune-activating effect: Changes in weights of immune organs (the thymus and the submandibular lymph node), blood IFN-γ content, NK cell activity, and splenic TNF-α, IL-1β and IL-10 contents, histological changes in the immune organs, and changes in TNF-α immunoreactivity in tumor mass and submandibular lymph nodes (3) Tumor-associated cachexia inhibitory effect: Changes in body weight, weight of a periovarian fat pad and blood IL-6 content, and histological change of periovarian fat pad

TABLE 41

| Group | Xenograft | Dose (mg/kg/day) |
|---|---|---|
| Effects on HepG2 cell xenograft nude mice | | |
| Control | Saline | Vehicle 10 ml/kg |
| Control | HepG2 cells | Vehicle 10 ml/kg |
| Reference | HepG2 cells | Sorafenib single (20 mg/kg) |
| Reference | HepG2 cells | YMJHT single (400 mg/kg) |
| Active | HepG2 cells | Sorafenib and YMJHT (20 and 100 mg/kg) |
| Active | HepG2 cells | Sorafenib and YMJHT (20 and 200 mg/kg) |
| Active | HepG2 cells | Sorafenib and YMJHT (20 and 400 mg/kg) |

TABLE 42

| Antisera or detection kits | Code | Source | Dilution |
|---|---|---|---|
| Primary antisera* | | | |
| Anti-cleaved caspase-3 (Asp175) polyclonal antibody | 9661 | Cell Signaling Technology Inc, Beverly, MA, USA | 0.319444 |
| Anti-cleaved PARP (Asp214) rat specific antibody | 9545 | Cell Signaling Technology Inc, Beverly, MA, USA | 0.111111 |
| Anti-tumor necrosis factor-α (4E1) antibody | sc-130349 | Santa Cruz Biotechnology, Santa Cruz, CA, USA | 0.180556 |
| Anti-cyclooxygenase (murine) polyclonal antibody | 160126 | Cayman Chemical., Ann Arbor, MI, USA | 0.180556 |
| Anti-nitric oxide synthase 2 (N-20) polyclonal antibody | sc-651 | Santa Cruz Biotechnology, Santa Cruz, CA, USA | 0.111111 |
| Detection kits | | | |
| Vectastain Elite ABC Kit | PK-6200 | Vector Lab. Inc., Burlingame, CA, USA | 1:50 |
| Peroxidae substrate kit | SK-4100 | Vector Lab. Inc., Burlingame, CA, USA | 1:50 |

Figure 80:
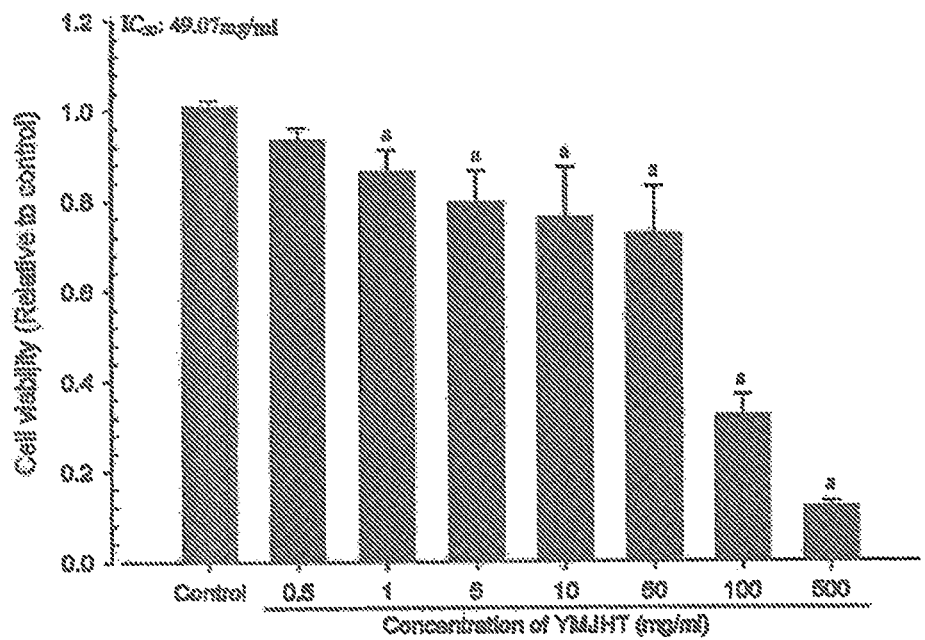
FIG. 80 shows HepG2 cell viability determined by administering yukmijihwang-tang.

11.4. Confirmation of Cytotoxicity (1) Influence of YMJHT on HepG2 Cell Viability A significant decrease (p<0.01) in HepG2 cell viability started to be observed in the 1 mg/ml YMJHT-treated group, compared with the vehicle control, and IC$_{50}$ was calculated at 49.07 mg/ml (FIG. 80).

In the YMJHT 0.5, 1, 5, 10, 50, 100 and 500 mg/ml treated groups, the HepG2 cell viabilities changed by −7.35%, −14.28%, −21.04%, −24.39%, −28.08%, −67.91%, and −88.19%, respectively, compared with the non-treated vehicle control (0 mg/ml treated group).

(2) Influence of Sorafenib on HepG2 Cell Viability

Figure 81:
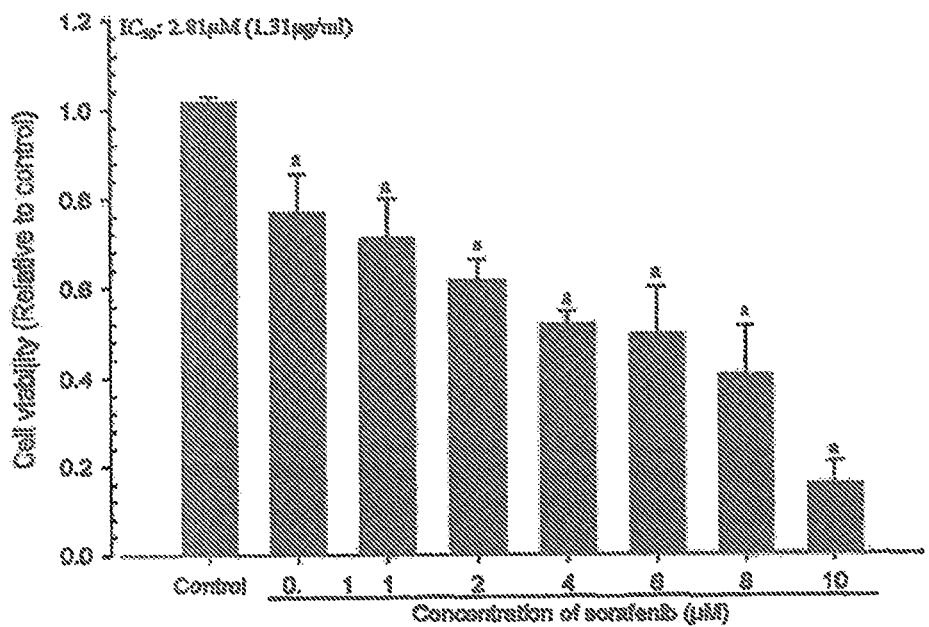
FIG. 81 shows HepG2 cell viability determined by administering sorafenib.

A significant decrease (p<0.01) in HepG2 cell viability started to be observed in the 0.1 μM sorafenib-treated group, compared with the vehicle control, and $IC_{50}$ was calculated at 2.81 μM (1.31 μg/ml) (FIG. 81).

In the sorafenib 0.1, 1, 2, 4, 6, 8 and 10 μM treated groups, the HepG2 cell viabilities changed by −24.41%, −30.06%, −39.56%, −48.89%, −51.31%, −60.23% and −84.55%, respectively, compared with the non-treated vehicle control (0 mg/ml treated group).

Figure 82:
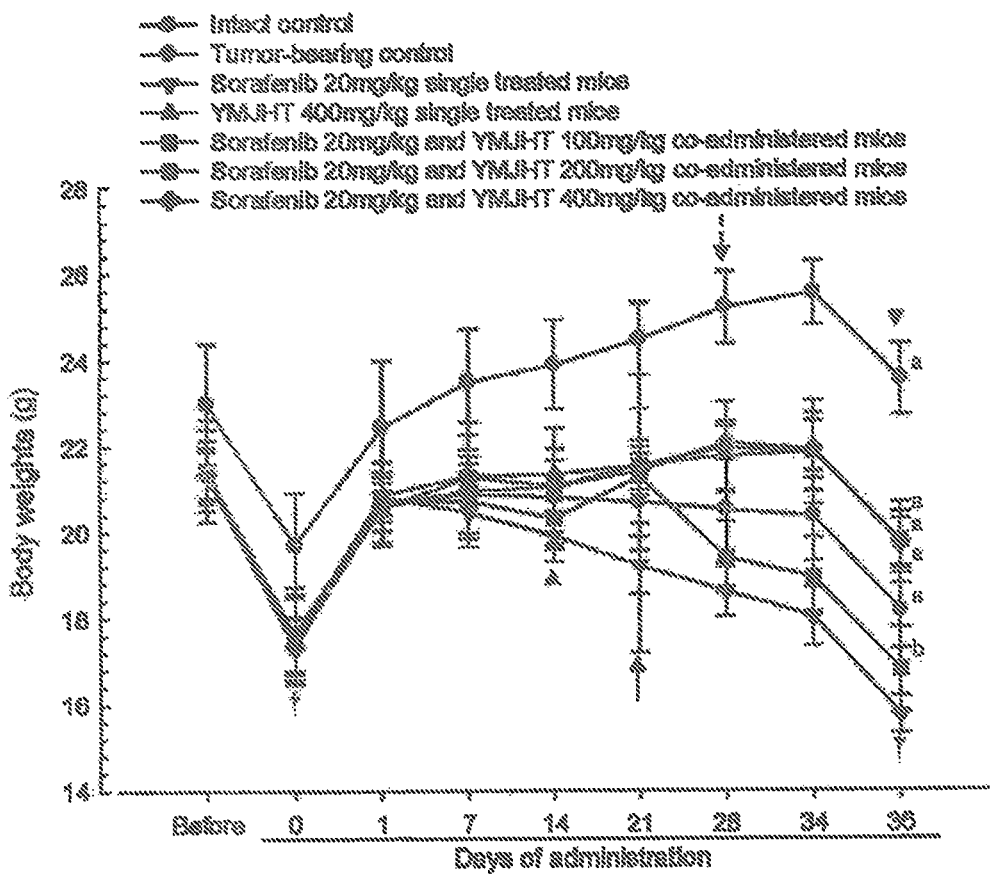
FIG. 82 shows changes in body weights in yukmijihwang-tang and sorafenib single treated groups and a yukmijihwang-tang and sorafenib co-administered group.

35 days was observed, even though the significance was not even observed (Table 43, and FIG. 82).

Compared to the intact vehicle control, in the tumor-bearing control, the body weight gain (35 days: a body weight on the final sacrifice date—a body weight on the first day of the administration) during the administration changed by −79.93%. In the sorafenib 20 mg/kg and YMJHT 400 mg/kg single treated groups and the YMJHT 100, 200 and 400 mg/kg and sorafenib 20 mg/kg co-administered groups, the body weight gains during the administration changed by −301.85%, 187.04%, −209.26%, 179.63%, and 209.26%, respectively, compared with the tumor-bearing control.

TABLE 43

| Group | Body weights | | | Body weight gains |
| --- | --- | --- | --- | --- |
| | Before administration | First administration [A] | Sacrifice date [B] | [B − A] |
| Control | | | | |
| Intact | 22.99 ± 1.40 | 19.70 ± 1.21 | 23.54 ± 0.82 | 3.84 ± 1.04 |
| TB | 21.40 ± 0.75$^a$ | 17.39 ± 0.61$^a$ | 18.16 ± 0.88$^a$ | 0.77 ± 0.88$^a$ |
| Single treated | | | | |
| Sorafenib | 21.33 ± 0.82$^a$ | 17.31 ± 0.73$^a$ | 15.76 ± 0.43$^a$ | −1.56 ± 0.65$^{ab}$ |
| YMJHT | 21.34 ± 0.55$^a$ | 17.51 ± 1.02$^a$ | 19.73 ± 0.94$^{abc}$ | 2.21 ± 0.30$^{abc}$ |
| Sorafenib and YMJHT co-administered | | | | |
| 100 mg/kg | 21.44 ± 0.96$^a$ | 17.64 ± 1.08$^a$ | 16.80 ± 0.98$^{abd}$ | −0.84 ± 0.83$^{ab}$ |
| 200 mg/kg | 21.44 ± 1.18 | 17.64 ± 0.93$^a$ | 19.80 ± 0.66$^{abc}$ | 2.16 ± 0.70$^{abc}$ |
| 400 mg/kg | 21.36 ± 0.60 | 17.36 ± 0.65$^a$ | 19.74 ± 0.55$^{abc}$ | 2.39 ± 0.95$^{abc}$ |

11.5. Confirmation of Changes in Body Weight and Body Weight Gain

Figure 83:
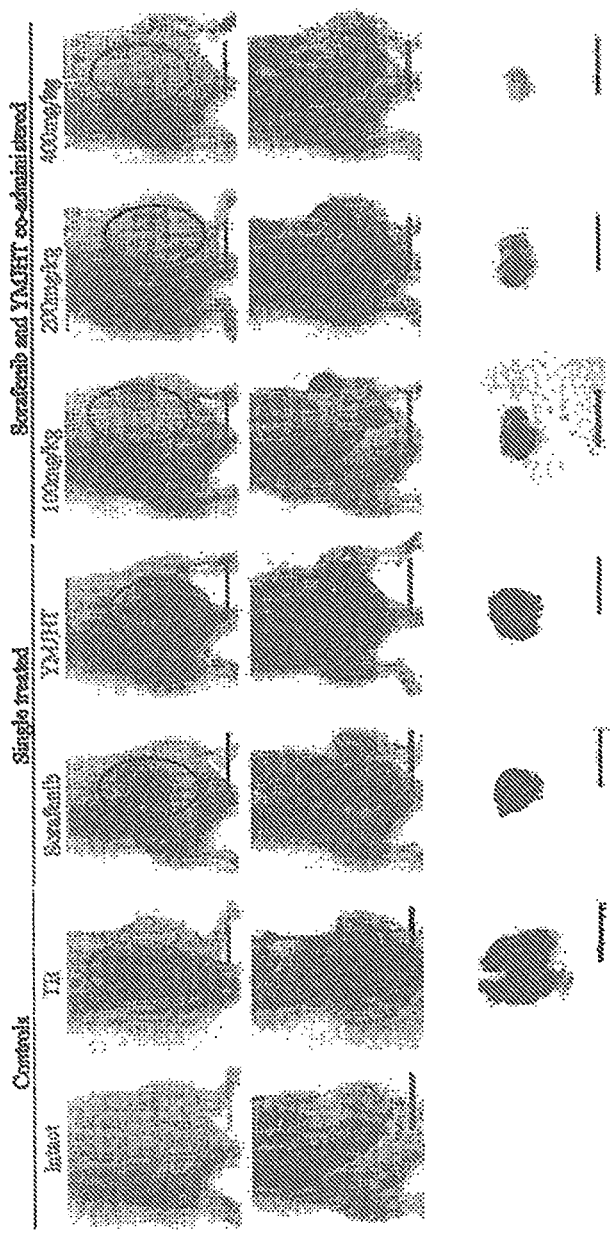
FIG. 83 shows differences in volumes of tumors between groups.
Figure 84:
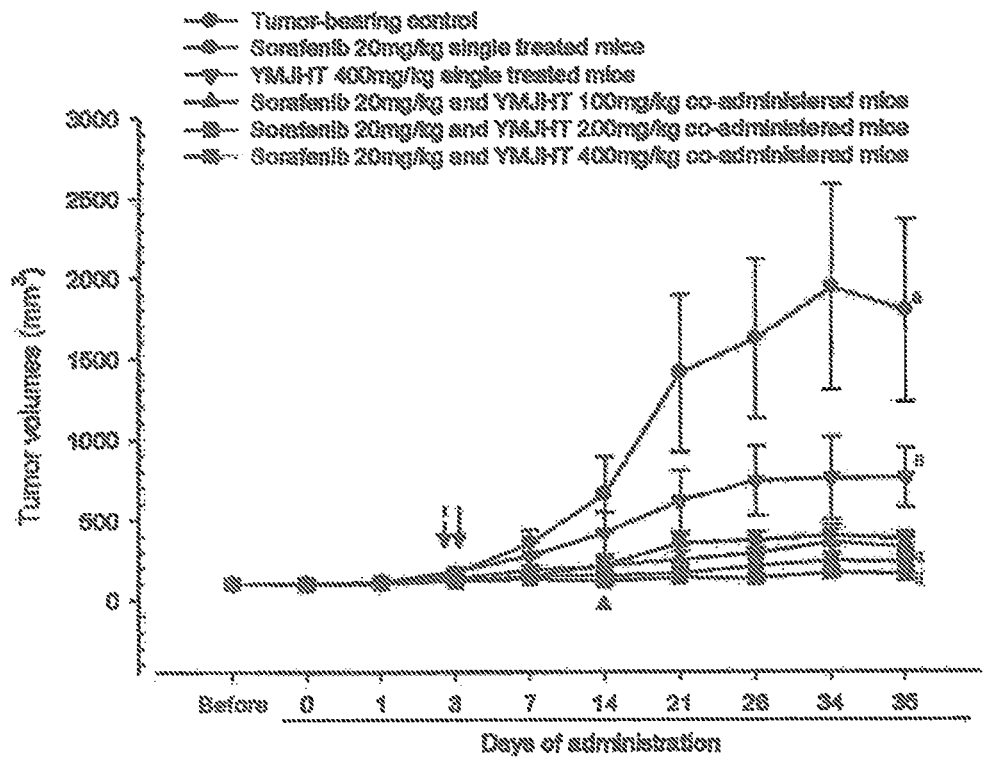
FIG. 84 shows changes in volume of a tumor for each group.

From 28 days after grafting of the HepG2 cells, only the laboratory animals whose body weights decreased at a constant rate were selected, compared with the intact vehicle control. As a result, compared with the vehicle control, in the tumor-bearing control, a significant decrease (p<0.01 or p<0.05) in body weight started to be observed before administration, and a significant decrease (p<0.01) in body weight gain during the administration were also observed. In the sorafenib single treated group, compared with the tumor-bearing control, a significant decrease (p<0.01) in body weight was observed from 21 days after the administration, and compared with the tumor-bearing control, a significant decrease (p<0.01) in body weight gain during the administration was also observed. Meanwhile, in the YMJHT single treated group, compared with the tumor-bearing control, a significant increase (p<0.01) in body weight started to be observed from 28 days after the administration, and a significant increase (p<0.01) in body weight gain was observed. In the sorafenib 20 mg/kg and YMJHT 200 and 400 mg/kg co-administered groups, compared with the single sorafenib 20 mg/kg-administered group, significant increases (p<0.01 or p<0.05) in body weights started to be observed from 14 days after the administration, and significant increases (p<0.01) in body weight gains during the administration were also observed. Also, compared with the single sorafenib 20 mg/kg-administered group, in the sorafenib 20 mg/kg and YMJHT 100 mg/kg co-administered group, a significant increase (p<0.05) in body weight was observed only on the final sacrifice date, and a remarkable increase in body weight gain during the administration for 11.6. Confirmation of Changes in Tumor Volume In the sorafenib single treated group, compared with the tumor-bearing control, a significant decrease (p<0.01) in tumor volume was observed from 3 days after the administration, and a significant decrease (p<0.01) in variation of a tumor volume during the administration was also observed. In the YMJHT 400 mg/kg single treated group, compared with the tumor-bearing control, a significant decrease (p<0.01 or p<0.05) in tumor volume was also observed from 7 days after the administration. In particular, compared with the sorafenib single treated group, a significant decrease (p<0.01) in tumor volume was observed from 14 days after the administration, and compared with the sorafenib single treated group, significant decreases (p<0.01) in variations in the tumor volumes during the administration were also observed in the YMJHT 200 and 400 mg/kg and sorafenib 20 mg/kg co-administered groups. Meanwhile, in the YMJHT 100 mg/kg and sorafenib 20 mg/kg co-administered group, compared with the sorafenib single treated group, a significant increase (p<0.05) in tumor volume were observed only 18 days after the administration, and significant decreases (p<0.05) in the tumor volumes were observed only on the $21^{st}$ and $28^{th}$ days of the administration, but no significant variations in the tumor volumes during the administration were observed (Table 44, and FIGS. 83 and 84).

TABLE 44

| Group | Tumor volume (mm³) | | | Changes (mm³) [B − A] |
|---|---|---|---|---|
| | First day before first administration | First administration [A] | Sacrifice [B] | |
| Control | | | | |
| TB | 107.40 ± 11.88 | 111.65 ± 16.82 | 1796.87 ± 568.89 | 1685.22 ± 574.49 |
| Single treated | | | | |
| Sorafenib | 107.57 ± 12.11 | 110.95 ± 12.86 | 384.88 ± 36.35$^a$ | 273.93 ± 38.27$^a$ |
| YMJHT | 107.84 ± 11.29 | 11.44 ± 10.91 | 761.35 ± 182.21$^{ab}$ | 649.91 ± 174.97$^{ab}$ |
| Sorafenib and YMJHT co-administered | | | | |
| 100 mg/kg | 107.65 ± 8.67 | 104.62 ± 9.23 | 336.29 ± 65.61$^a$ | 231.67 ± 60.62$^a$ |
| 200 mg/kg | 107.34 ± 8.84 | 106.49 ± 11.80 | 241.91 ± 57.55$^{ab}$ | 135.42 ± 58.44$^{ab}$ |
| 400 mg/kg | 107.35 ± 7.13 | 101.69 ± 5.61 | 168.95 ± 41.10$^{ab}$ | 67.26 ± 42.38$^{ab}$ |

In the sorafenib 20 mg/kg and YMJHT 400 mg/kg single treated groups and the YMJHT 100, 200 and 400 mg/kg and sorafenib 20 mg/kg co-administered groups, variations in the tumor volumes during the drug administration (5 weeks: a tumor volume on the final sacrifice date—a tumor volume on the first day of the administration) changed by −83.75%, −61.43%, −86.25%, −91.96%, and −96.01%, respectively, compared with the tumor-bearing control.

11.7. Confirmation of Change in Tumor Weight

Significant decreases (p<0.01) in relative and absolute tumor weights were observed in all of the drug-administered groups including the YMJHT 400 mg/kg single treated group, compared with the tumor-bearing control. Meanwhile, significant decreases (p<0.01) in tumor weights were observed in the YMJHT 200 and 400 mg/kg and sorafenib 20 mg/kg co-administered groups, compared with the sorafenib 20 mg/kg single treated group, but no significant changes in the tumor weights were observed in the YMJHT 100 mg/kg and sorafenib 20 mg/kg orally co-administered group, compared with the sorafenib single treated group (Tables 45 and 46 and FIG. 83).

TABLE 45

| Group | Tumor mass | Spleen | Submandibular lymph node | Periovarian fat pad |
|---|---|---|---|---|
| Control | | | | |
| Intact | | 0.155 ± 0.017 | 0.019 ± 0.003 | 0.063 ± 0.014 |
| TB | 0.679 ± 0.115 | 0.091 ± 0.011$^a$ | 0.006 ± 0.002$^e$ | 0.022 ± 0.005$^e$ |
| Single treated | | | | |
| Sorafenib | 0.195 ± 0.024$^g$ | 0.064 ± 0.009$^{ac}$ | 0.003 ± 0.001$^{eg}$ | 0.013 ± 0.003$^{eg}$ |
| YMJHT | 0.276 ± 0.051$^{gi}$ | 0.113 ± 0.008$^{acd}$ | 0.010 ± 0.003$^{ehi}$ | 0.032 ± 0.004$^{egi}$ |
| Sorafenib and YMJHT co-administered | | | | |
| 100 mg/kg | 0.179 ± 0.043$^g$ | 0.077 ± 0.016$^a$ | 0.009 ± 0.003$^{ehi}$ | 0.030 ± 0.006$^{ehi}$ |
| 200 mg/kg | 0.118 ± 0.033$^{gi}$ | 0.126 ± 0.022$^{acd}$ | 0.012 ± 0.004$^{ehi}$ | 0.038 ± 0.006$^{egi}$ |
| 400 mg/kg | 0.080 ± 0.021$^{gi}$ | 0.137 ± 0.011$^{bcd}$ | 0.015 ± 0.003$^{fgi}$ | 0.040 ± 0.007$^{egi}$ |

TABLE 46

| Group | Tumor mass | Spleen | Submandibular lymph node | Periovarian fat pad |
|---|---|---|---|---|
| Control | | | | |
| Intact | | 0.659 ± 0.063 | 0.081 ± 0.010 | 0.266 ± 0.059 |
| TB | 3.728 ± 0.504 | 0.499 ± 0.054$^a$ | 0.032 ± 0.009$^f$ | 0.120 ± 0.029$^f$ |
| Single treated | | | | |
| Sorafenib | 1.238 ± 0.154$^h$ | 0.406 ± 0.058$^{ad}$ | 0.018 ± 0.009$^{fi}$ | 0.084 ± 0.022$^{fi}$ |
| YMJHT | 1.405 ± 0.288$^h$ | 0.576 ± 0.044$^{bde}$ | 0.051 ± 0.018$^{fj}$ | 0.162 ± 0.025$^{fj}$ |
| Sorafenib and YMJHT co-administered | | | | |
| 100 mg/kg | 1.072 ± 0.267$^h$ | 0.459 ± 0.082$^a$ | 0.054 ± 0.019$^{fj}$ | 0.181 ± 0.034$^{ghj}$ |
| 200 mg/kg | 0.598 ± 0.170$^{hj}$ | 0.635 ± 0.104$^{ce}$ | 0.063 ± 0.023$^{ij}$ | 0.192 ± 0.037$^{ghj}$ |
| 400 mg/kg | 0.408 ± 0.110$^{hj}$ | 0.692 ± 0.055$^{ce}$ | 0.078 ± 0.014$^{hj}$ | 0.204 ± 0.035$^{hj}$ |

In the sorafenib 20 mg/kg and YMJHT 400 mg/kg single treated groups and the YMJHT 100, 200 and 400 mg/kg and sorafenib 20 mg/kg co-administered groups, the absolute tumor weights changed by −71.27%, −59.27%, −73.56%, −82.61%, and −88.15%, and the relative tumor weights changed by −66.80%, −62.30%, −71.24%, −83.96%, and −89.05%, respectively, compared with the tumor-bearing control.

That is, it can be seen that the YMJHT and sorafenib co-administered groups exhibited the most excellent effect on reducing the tumor weight.

11.8. Confirmation of Change in Weight of Spleen

Significant decreases (p<0.01) in absolute and relative weights of the spleen were observed in the tumor-bearing control, compared with the vehicle control. However, significant increases (p<0.01) in the spleen weights were observed in the YMJHT 400 mg/kg single treated group and the YMJHT 200 and 400 mg/kg and sorafenib 20 mg/kg co-administered groups, compared with the tumor-bearing control. In particular, significant increases (p<0.01) in the absolute and relative spleen weights were observed in the YMJHT 200 and 400 mg/kg and sorafenib co-administered, compared with the sorafenib single treated group. Meanwhile, significant decreases (p<0.01 or p<0.05) in the absolute and relative spleen weights were observed in the sorafenib single treated group, compared with the tumor-bearing control, and no significant changes in the spleen weights were observed in the YMJHT 100 mg/kg and sorafenib 20 mg/kg co-administered group, compared with the sorafenib single treated group (Tables 45 and 46).

In the tumor-bearing control, the absolute weight of the spleen changed by −41.67%, compared with the vehicle control. In the sorafenib YMJHT 20 mg/kg- and 400 mg/kg single treated groups and the YMJHT 100, 200 and 400 mg/kg and sorafenib 20 mg/kg co-administered groups, the absolute spleen weights changed by −29.34%, 25.24%, −14.67%, 38.96%, and 50.79%, respectively, compared with the tumor-bearing control.

In the tumor-bearing control, the relative spleen weight changed by −24.36%, compared with the vehicle control. In the sorafenib 20 mg/kg and YMJHT 400 mg/kg single treated groups and the YMJHT 100, 200 and 400 mg/kg and sorafenib 20 mg/kg co-administered groups, the relative spleen weights changed by −18.50%, 15.47%, −7.98%, 27.25%, and 38.74%, respectively, compared with the tumor-bearing control.

11.9. Confirmation of Change in Weight of Submandibular Lymph Node

Significant decreases (p<0.01) in absolute and relative weights of submandibular lymph nodes were observed in the tumor-bearing control, compared with the vehicle control. However, significant increases (p<0.01 or p<0.05) in weights of the submandibular lymph nodes were observed in the YMJHT single treated group and the YMJHT 100, 200 or 400 mg/kg and sorafenib co-administered groups, compared with the tumor-bearing control. In particular, significant increases (p<0.01) in absolute and relative weights of the submandibular lymph nodes were observed in the YMJHT 100, 200 and 400 mg/kg and sorafenib co-administered groups, compared with the sorafenib single treated group. Meanwhile, significant decreases (p<0.01 or p<0.05) in absolute and relative weights of the submandibular lymph nodes were observed in the sorafenib 20 mg/kg single treated group, compared with the tumor-bearing control (Tables 45 and 46).

In the tumor-bearing control, compared with the tumor-bearing control, the absolute weight of the submandibular lymph node changed by −70.15%. In the sorafenib 20 mg/kg and 400 mg/kg single YMJHT-administered groups and the YMJHT 100, 200 and 400 mg/kg and sorafenib 20 mg/kg co-administered groups, the absolute weights of the submandibular lymph nodes changed by −50.00%, 72.50%, 60.00%, 117.50%, and 167.50%, respectively, compared with the tumor-bearing control.

In the tumor-bearing control, compared with the tumor-bearing control, the relative weight of the submandibular lymph node changed by −61.01%. In the sorafenib 20 mg/kg and YMJHT 400 mg/kg single treated groups and the YMJHT 100, 200 and 400 mg/kg and sorafenib 20 mg/kg co-administered groups, the relative weights of the submandibular lymph nodes changed by −42.33%, 59.85%, 72.07%, 99.43%, and 145.20%, respectively, compared with the tumor-bearing control.

11.10. Confirmation of Change in Weight of Periovarian Fat Pad

Significant decreases (p<0.01) in absolute and relative weights of periovarian fat pads were observed in the tumor-bearing control, compared with the vehicle control. However, significant increases (p<0.01 or p<0.05) in weights of the periovarian fat pads were observed in the YMJHT single treated group and all of the YMJHT 100, 200 and 400 mg/kg and sorafenib co-administered groups, compared with the tumor-bearing control. In particular, significant increases (p<0.01) in weights of the periovarian fat pad were observed in the YMJHT 100, 200 and 400 mg/kg and sorafenib 20 mg/kg co-administered groups, compared with the sorafenib single treated group. Meanwhile, a significant decrease (p<0.01 or p<0.05) in weight of the periovarian fat pad was observed in the sorafenib 20 mg/kg-single treated group, compared with the tumor-bearing control (Tables 45 and 46).

In the tumor-bearing control, the absolute weight of the periovarian fat pad changed by −65.30%, compared with the vehicle control. In the sorafenib 20 mg/kg and YMJHT 400 mg/kg single treated groups and the YMJHT 100, 200 and 400 mg/kg and sorafenib 20 mg/kg co-administered groups, the absolute weights of the periovarian fat pads changed by −39.47%, 46.71%, 40.13%, 74.34%, and 85.53%, respectively, compared with the tumor-bearing control.

In the tumor-bearing control, compared with the vehicle control, the relative weight of the periovarian fat pad changed by −54.96%. In the sorafenib 20 mg/kg- and 400 mg/kg YMJHT single treated groups and the YMJHT 100, 200 and 400 mg/kg and sorafenib 20 mg/kg co-administered groups, the relative weights of the periovarian fat pads changed by −30.16%, 35.31%, 50.97%, 60.62%, and 70.67%, respectively, compared with the tumor-bearing control.

11.11. Confirmation of Changes in Blood IL-6 and IFN-γ Contents

Figure 85:
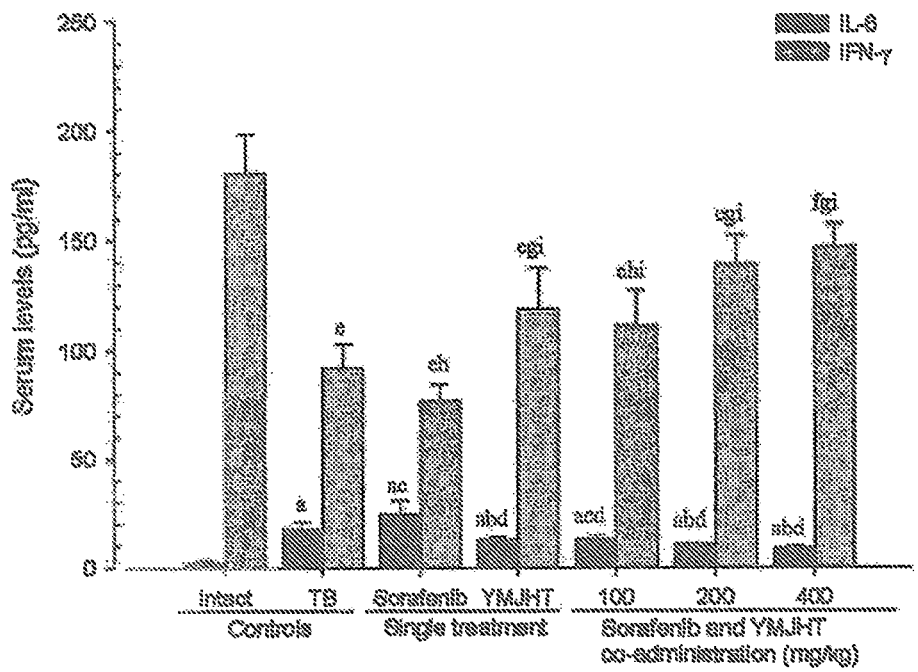
FIG. 85 shows changes in blood IL-6 and IFN-γ contents for each group.

A significant increase (p<0.01) in blood IL-6 content and a significant decrease (p<0.01) in blood IFN-γ content were observed in the tumor-bearing control, compared with the vehicle control. However, significant decreases (p<0.01 or p<0.05) in the blood IL-6 contents and significant increases (p<0.01) in the blood IFN-γ contents were observed in the YMJHT single treated group and the YMJHT 100, 200 or 400 mg/kg and sorafenib co-administered groups, compared with the tumor-bearing control. In particular, significant decreases (p<0.01) in the blood IL-6 contents and significant increases (p<0.01) in the blood IFN-γ contents were observed in all of the YMJHT 100, 200 and 400 mg/kg and sorafenib co-administered groups, compared with the sorafenib single treated group. Meanwhile, a significant increase (p<0.05) in the blood IL-6 content and an insignificant decrease in the blood IFN-γ content were observed in the sorafenib single treated group, compared with the tumor-bearing control (FIG. 85).

In the tumor-bearing control, compared with the vehicle control, the blood IL-6 content changed by 574.74%. In the sorafenib 20 mg/kg and YMJHT 400 mg/kg single treated groups and the YMJHT 100, 200 and 400 mg/kg and sorafenib 20 mg/kg co-administered groups, the blood IL-6 contents changed by 40.40%, −27.71%, −24.45%, −40.71%, and −51.00%, respectively, compared with the tumor-bearing control.

In the tumor-bearing control, compared with the vehicle control, the blood IFN-γ content changed by −48.91%. In the sorafenib 20 mg/kg and YMJHT 400 mg/kg single treated groups and the YMJHT 100, 200 and 400 mg/kg and sorafenib 20 mg/kg co-administered groups, the blood IFN-γ contents changed by −17.14%, 28.92%, 20.62%, 50.54%, and 59.28%, respectively, compared with the tumor-bearing control.

11.12. Confirmation of Change in Activity of NK Cells

Figure 86:
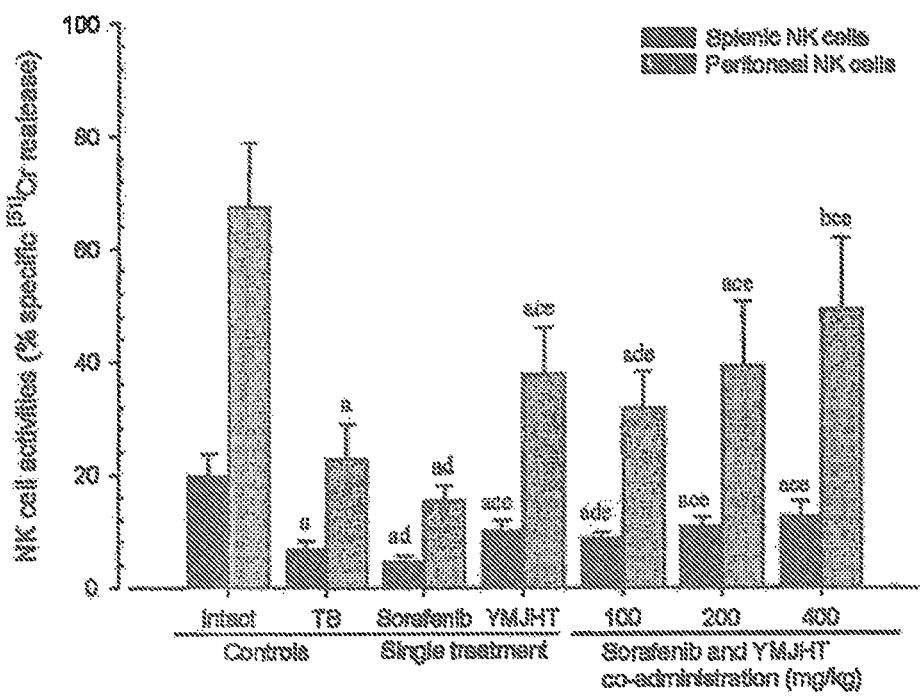
FIG. 86 shows changes in splenic and peritoneal NK cell activities for each group.

Significant decreases (p<0.01) in activities of splenic and peritoneal NK cells were observed in the tumor-bearing control, compared with the vehicle control. However, significant increases in the activities of the splenic and peritoneal NK cells were observed in the YMJHT single treated group and all of the co-administered groups, compared with the tumor-bearing control. In particular, significant increases (p<0.01) in the activities of the splenic and peritoneal NK cells were also observed in all of the YMJHT 100, 200 and 400 mg/kg and sorafenib co-administered groups, compared with the tumor-bearing control. Meanwhile, significant decreases (p<0.05) in the activities of the splenic and peritoneal NK cells were observed in the sorafenib single treated group, compared with the tumor-bearing control (FIG. 86).

In the tumor-bearing control, the activity of the splenic NK cells changed by −66.04%, compared with the vehicle control. In the sorafenib 20 mg/kg and YMJHT 400 mg/kg single treated groups and the YMJHT 100, 200 and 400 mg/kg and sorafenib 20 mg/kg co-administered groups, the activities of the splenic NK cells changed by −30.89%, 48.34%, 27.71%, 59.24%, and 85.33%, respectively, compared with the tumor-bearing control.

In the tumor-bearing control, compared with the vehicle control, the activities of the peritoneal NK cells changed by −66.46%. In the sorafenib 20 mg/kg and YMJHT 400 mg/kg single treated groups and the YMJHT 100, 200 and 400 mg/kg and sorafenib 20 mg/kg co-administered groups, the activities of the peritoneal NK cells changed by −32.16%, 66.68%, 40.37%, 72.95%, and 117.39%, respectively, compared with the tumor-bearing control.

11.13. Confirmation of Change in Splenic Cytokine Content

Significant decreases (p<0.01) in splenic TNF-α, IL-1β, and IL-10 contents were observed in the tumor-bearing control, compared with the vehicle control. However, significant increases (p<0.01 or p<0.05) in splenic cytokine contents were observed in the YMJHT single treated group and the YMJHT 100, 200 and 400 mg/kg and sorafenib co-administered groups, compared with the tumor-bearing control. In particular, significant increases (p<0.01) in the splenic TNF-α, IL-1β, and IL-10 contents were observed in all of the YMJHT 100, 200 and 400 mg/kg and sorafenib co-administered groups, compared with the sorafenib single treated group. Meanwhile, significant decreases (p<0.01 or p<0.05) in the splenic TNF-α, IL-1β, and IL-10 contents were observed in the sorafenib single treated group, compared with the tumor-bearing control (Table 47).

TABLE 47

| Group | Tumor necrosis factor-α | Interleukin-1β | Interleukin-10 |
|---|---|---|---|
| Control | | | |
| Intact | 95.12 ± 23.14 | 41.94 ± 13.13 | 84.28 ± 15.16 |
| TB | 44.56 ± 7.96$^d$ | 13.40 ± 3.23$^d$ | 41.09 ± 12.23$^a$ |
| Single treated | | | |
| Sorafenib | 28.55 ± 11.41$^{dgh}$ | 8.94 ± 1.80$^{dfh}$ | 21.17 ± 6.67$^{ab}$ |
| YMJHT | 70.22 ± 11.67$^{dfh}$ | 19.28 ± 2.67$^{dfh}$ | 56.57 ± 6.18$^{abc}$ |
| Sorafenib and YMJHT co-administered | | | |
| 100 mg/kg | 61.81 ± 10.25$^{dfh}$ | 18.77 ± 1.96$^{dgh}$ | 57.47 ± 10.64$^{abc}$ |
| 200 mg/kg | 70.73 ± 10.87$^{efh}$ | 19.83 ± 2.13$^{dfh}$ | 64.26 ± 7.70$^{abc}$ |
| 400 mg/kg | 79.40 ± 10.32$^{fh}$ | 25.11 ± 5.83$^{dfh}$ | 73.26 ± 12.08$^{bc}$ |

In the tumor-bearing control, compared with the vehicle control, the splenic TNF-α content changed by −53.15%. In the single sorafenib 20 mg/kg- and YMJHT 400 mg/kg administered groups and the YMJHT 100, 200 and 400 mg/kg and sorafenib 20 mg/kg co-administered groups, the splenic TNF-α contents changed by −35.94%, 57.58%, 38.70%, 58.71%, and 78.18%, respectively, compared with the tumor-bearing control.

In the tumor-bearing control, the splenic IL-1β content changed by −68.06%, compared with the vehicle control. In the sorafenib 20 mg/kg- and YMJHT 400 mg/kg single treated groups and the YMJHT 100, 200 and 400 mg/kg and sorafenib 20 mg/kg co-administered groups, the splenic IL-1β contents changed by −33.28%, 43.88%, 40.14%, 48.01%, and 87.40%, respectively, compared with the tumor-bearing control.

In the tumor-bearing control, compared with the vehicle control, the splenic IL-10 content changed by −51.24%. In the sorafenib 20 mg/kg and YMJHT 400 mg/kg single treated groups and the YMJHT 100, 200 and 400 mg/kg and sorafenib 20 mg/kg co-administered groups, the splenic IL-1β contents changed by −48.47%, 37.66%, 39.86%, 56.39%, and 78.30%, respectively, compared with the tumor-bearing control.

Figure 87:
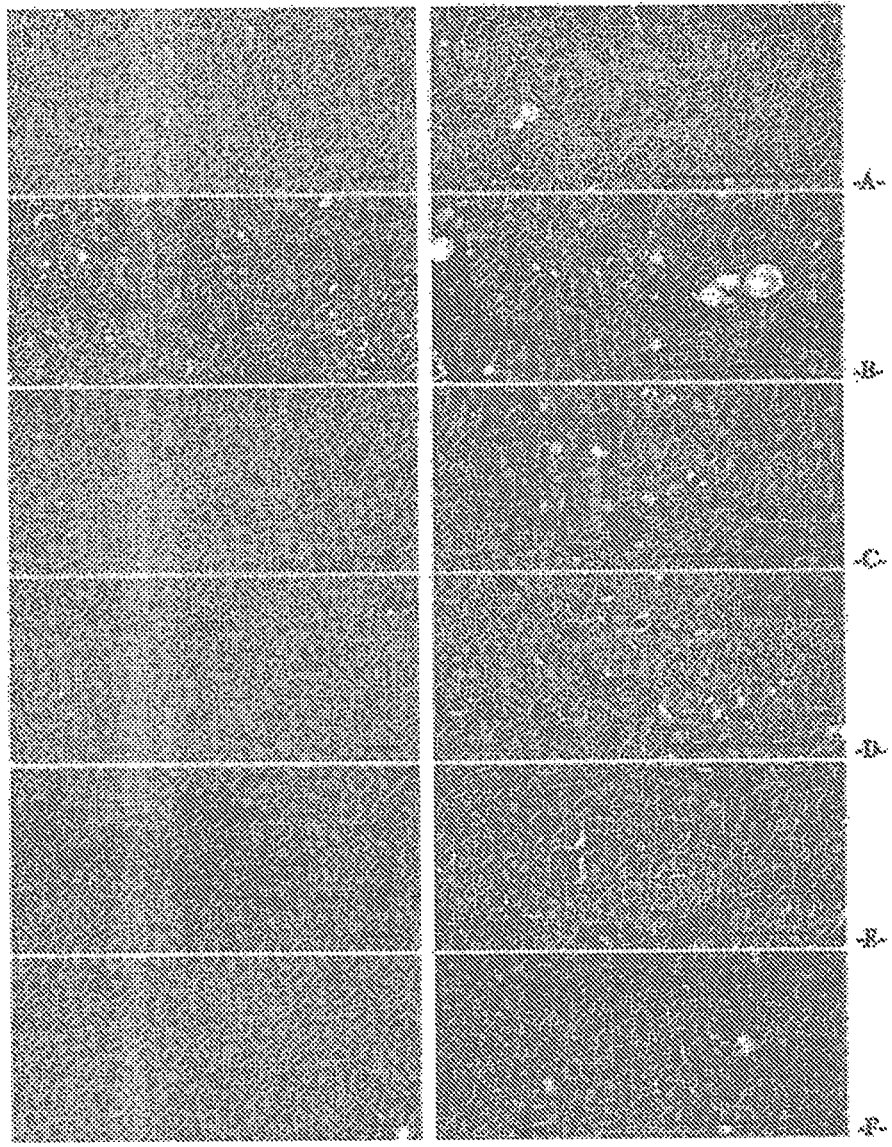
FIG. 87 shows histopathological changes of a tumor mass for each group.
Figure 88:
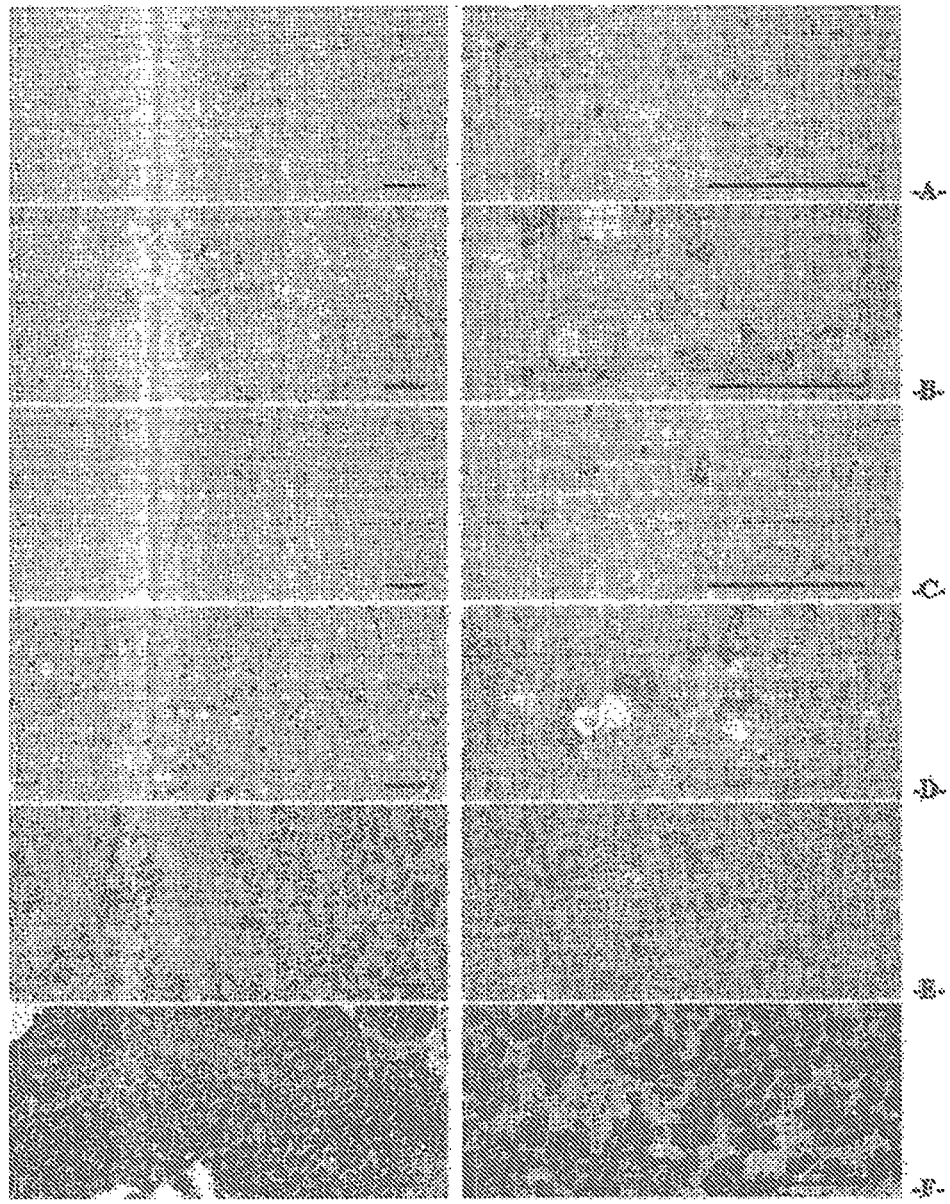
FIG. 88 shows changes in number of caspase-3 immunoreactive cells in tumor mass in groups.
Figure 89:
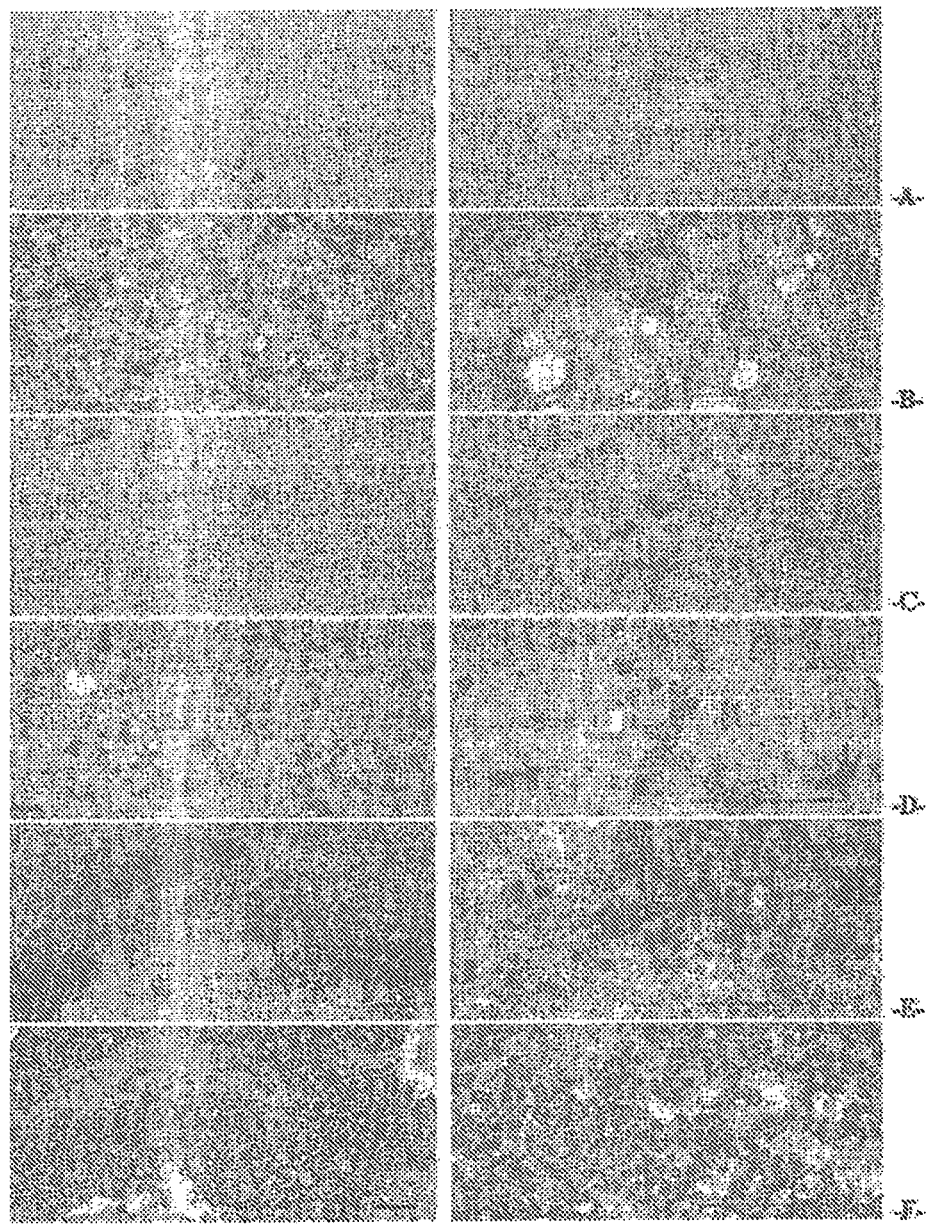
FIG. 89 shows changes in number of PARP immunoreactive cells in tumor mass in groups.
Figure 90:
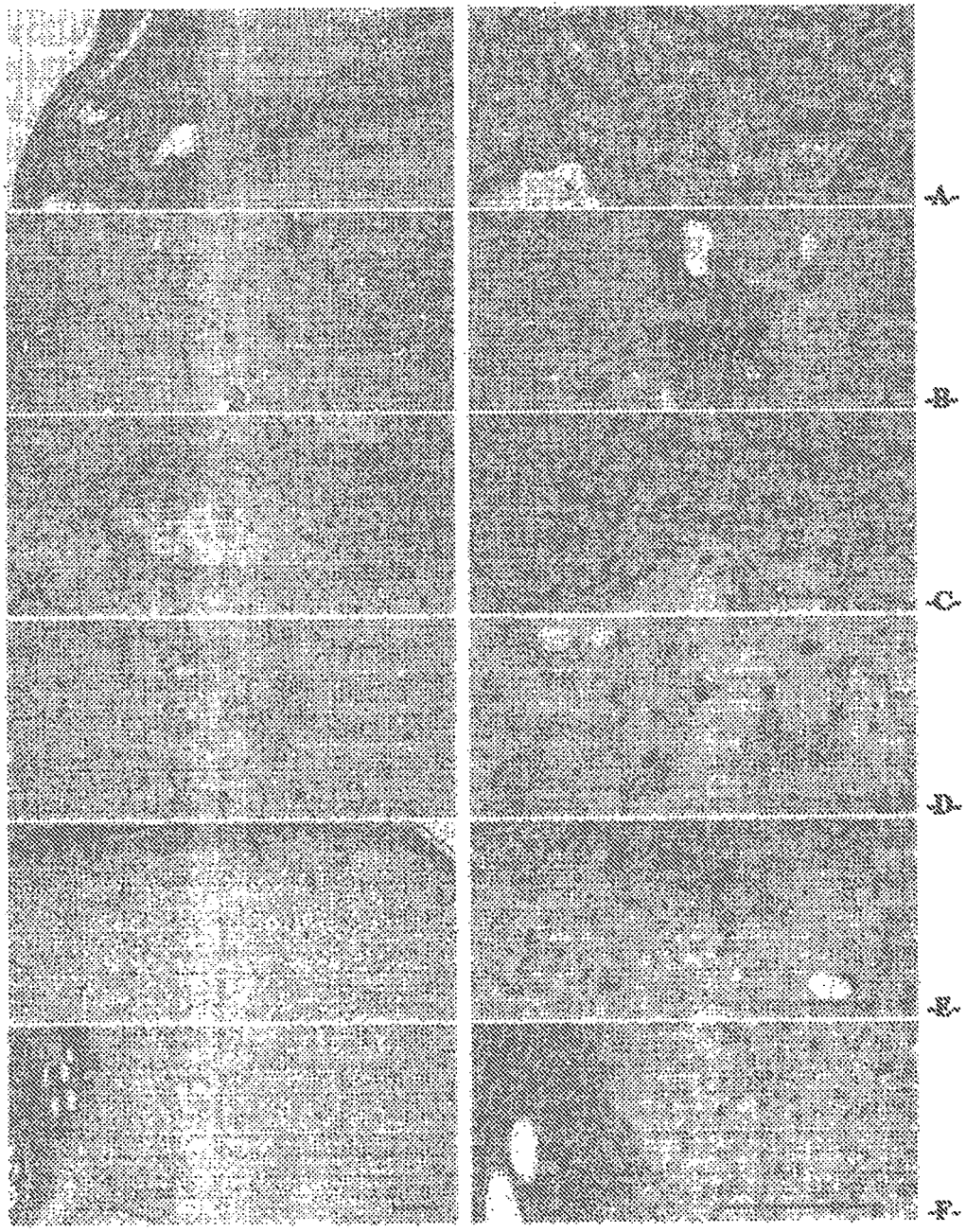
FIG. 90 shows changes in number of COX-2 immunoreactive cells in tumor mass in groups.

11.14. Confirmation of Histological Changes 11.14.1. Confirmation of Histopathological Change in Tumor Mass Undifferentiated polymorphic hepatocellular carcinoma (HepG2) cells were compactly distributed in the tumor-bearing control, and an eosinophilic increase and pyknosis in the cytoplasm by apoptosis were observed in some cells. Also, mitotic divisions were often observed in the cells. Meanwhile, remarkable increases in apoptotic cells were observed in the sorafenib and YMJHT single treated groups and all of the YMJHT 100, 200 and 400 mg/kg and sorafenib co-administered groups, compared with the tumor-bearing control, and therefore the percentage of the HepG2 cells was remarkably reduced. In particular, a significant decrease (p<0.01 or p<0.05) in volume of the tumor cells and a significant increase (p<0.01 or p<0.05) in number of apoptotic cells were observed in the YMJHT 200 and 400 mg/kg and sorafenib 20 mg/kg co-administered groups, compared with the sorafenib single treated group (Table 48, and FIG. 87). Also, a significant decrease (p<0.01 or p<0.05) in number of COX-2 immunoreactive cells in a tumor mass was observed with significant increases (p<0.01 or p<0.05) in numbers of caspase-3 and PARP immunoreactive cells in all of the administered groups including the YMJHT 400 mg/kg single treated group, compared with the tumor-bearing control. In particular, significant increases (p<0.01) in numbers of the caspase-3 and PARP immunoreactive cells were observed with a significant decrease (p<0.01) in number of COX-2 immunoreactive cells in the YMJHT 200 and 400 mg/kg and sorafenib 20 mg/kg co-administered groups, compared with the sorafenib single treated group (Table 48, and FIGS. 88 to 90).

changed by 267.61%, 44.56%, 307.48%, 695.43%, and 1,066.28%, respectively, compared with the tumor-bearing control.

In the sorafenib 20 mg/kg- and YMJHT 400 mg/kg single treated groups and the YMJHT 100, 200 and 400 mg/kg and sorafenib 20 mg/kg co-administered groups, the percentages of the COX-2 immunoreactive cells in the tumor tissues

TABLE 48

| Group | Tumor cell volume (%/mm$^2$) | Apoptotic cell percentage (%) | Immunoreactive cell percentage (%/tumor cells) | | | | |
|---|---|---|---|---|---|---|---|
| | | | Caspase-3 | PARP | COX-2 | iNOS | TNF-α |
| Control | | | | | | | |
| TB | 85.23 ± 10.52 | 6.85 ± 2.20 | 6.88 ± 2.20 | 4.97 ± 1.53 | 57.79 ± 11.12 | 7.64 ± 2.38 | 5.24 ± 2.72 |
| Single treated | | | | | | | |
| Sorafenib | 62.16 ± 10.58$^a$ | 23.32 ± 6.03$^d$ | 17.17 ± 2.25$^d$ | 18.25 ± 5.91$^d$ | 29.17 ± 2.04$^d$ | 11.22 ± 3.24 | 9.94 ± 1.60$^d$ |
| YMJHT | 68.71 ± 10.11$^a$ | 13.03 ± 3.53$^{df}$ | 10.21 ± 1.97$^{ef}$ | 7.18 ± 1.29$^{df}$ | 37.45 ± 6.92$^{dg}$ | 19.60 ± 1.53$^{df}$ | 22.27 ± 4.76$^{df}$ |
| Sorafenib and YMJHT co-administered | | | | | | | |
| 100 mg/kg | 60.56 ± 10.69$^a$ | 27.04 ± 5.47$^d$ | 20.62 ± 6.83$^d$ | 20.23 ± 3.46$^d$ | 26.48 ± 7.55$^d$ | 24.98 ± 7.75$^{df}$ | 26.89 ± 6.34$^d$ |
| 200 mg/kg | 48.01 ± 8.42$^{ac}$ | 38.30 ± 5.63$^{df}$ | 42.57 ± 4.11$^{df}$ | 39.50 ± 10.39$^{df}$ | 16.62 ± 2.90$^{df}$ | 51.04 ± 8.68$^{df}$ | 46.96 ± 8.83$^{df}$ |
| 400 mg/kg | 38.15 ± 8.43$^{ab}$ | 46.26 ± 14.64$^{df}$ | 61.89 ± 13.88$^{df}$ | 57.91 ± 8.16$^{df}$ | 11.38 ± 3.47$^{df}$ | 64.04 ± 12.02$^{df}$ | 62.49 ± 6.78$^{df}$ |

Figure 91:
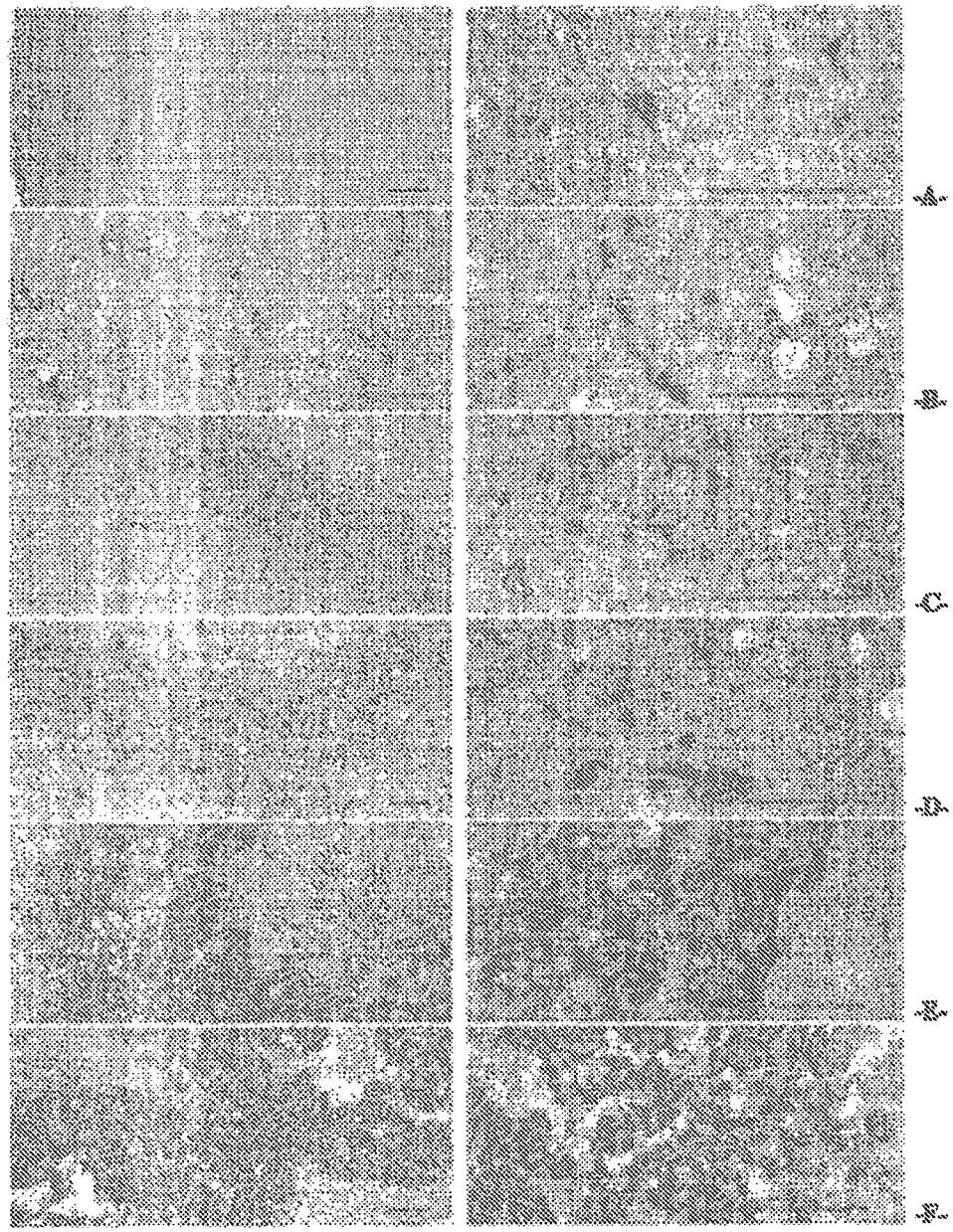
FIG. 91 shows changes in iNOS immunoreactive cells in a tumor mass for each group.
Figure 92:
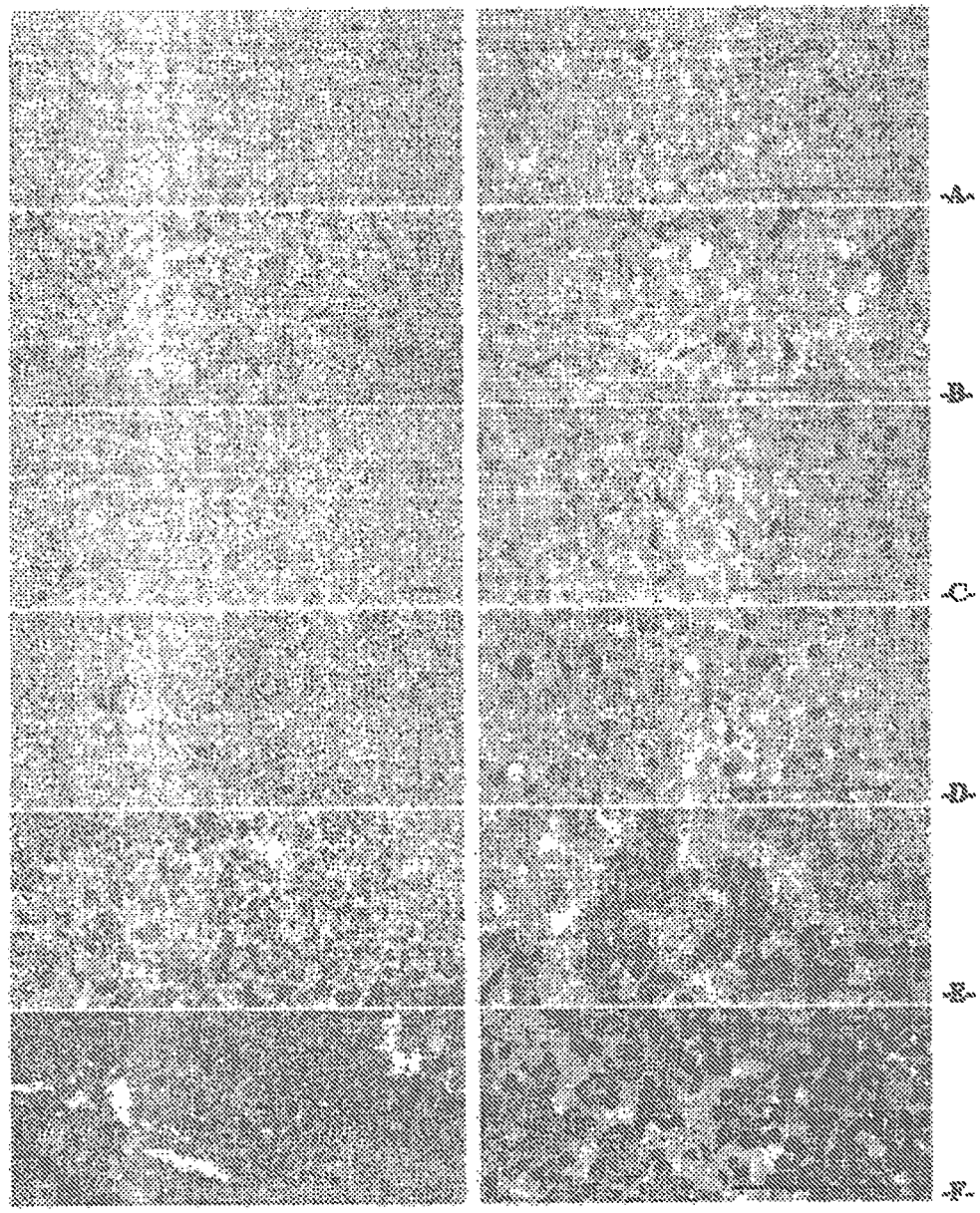
FIG. 92 shows changes in TNF-α immunoreactive cells in a tumor mass for each group.

Also, significant increases (p<0.01) in numbers of the iNOS and TNF-α immunoreactive cells in the tumor mass were observed in all of the YMJHT single treated groups and the co-administered groups, compared with the tumor-bearing control. In particular, significant increases (p<0.01) in numbers of the iNOS and TNF-α immunoreactive cells were also observed in the YMJHT 200 and 400 mg/kg and sorafenib 20 mg/kg co-administered groups, compared with the sorafenib single treated group, and a significant increase (p<0.01) in number of the TNF-α immunoreactive cells and an insignificant increase in number of the iNOS immunoreactive cells were also observed in the sorafenib single treated group, compared with the tumor-bearing control (Table 48, and FIGS. 91 and 92).

In the sorafenib 20 mg/kg and YMJHT 400 mg/kg single treated groups and the YMJHT 100, 200 and 400 mg/kg and sorafenib 20 mg/kg co-administered groups, the percentages of the tumor cells in tumor tissues changed by −27.07%, −19.39%, −28.95%, −43.67%, and −55.24%, respectively, compared with the tumor-bearing control.

In the sorafenib 20 mg/kg and YMJHT 400 mg/kg single treated groups and the YMJHT 100, 200 and 400 mg/kg and sorafenib 20 mg/kg co-administered groups, the percentages of the apoptotic cells in the tumor tissues changed by 240.16%, 90.14%, 294.54%, 458.80%, and 574.93%, respectively, compared with the tumor-bearing control.

In the sorafenib 20 mg/kg and YMJHT 400 mg/kg single treated groups and the YMJHT 100, 200 and 400 mg/kg and sorafenib 20 mg/kg co-administered groups, the percentages of the caspase-3 immunoreactive cells in the tumor tissues changed by 149.44%, 48.32%, 199.58%, 518.56%, and 799.23%, respectively, compared with the tumor-bearing control.

In the sorafenib 20 mg/kg and YMJHT 400 mg/kg single treated groups and the YMJHT 100, 200 and 400 mg/kg and sorafenib 20 mg/kg co-administered groups, the percentages of the PARP immunoreactive cells in the tumor tissues changed by −49.53%, −35.19%, −54.17%, −71.24%, and −80.30%, respectively, compared with the tumor-bearing control.

In the sorafenib 20 mg/kg and YMJHT 400 mg/kg single treated groups and the YMJHT 100, 200 and 400 mg/kg and sorafenib 20 mg/kg co-administered groups, the percentages of the iNOS immunoreactive cells in the tumor tissues changed by 46.88%, 156.64%, 227.05%, 568.26%, and 738.51%, respectively, compared with the tumor-bearing control.

In the sorafenib 20 mg/kg and YMJHT 400 mg/kg single treated groups and the YMJHT 100, 200 and 400 mg/kg and sorafenib 20 mg/kg co-administered groups, the percentages of the TNF-α immunoreactive cells in the tumor tissues changed by 89.59%, 324.71%, 412.67%, 795.53%, and 1091.50%, respectively, compared with the tumor-bearing control.

11.14.2. Confirmation of Histopathological Change in Spleen

Figure 93:
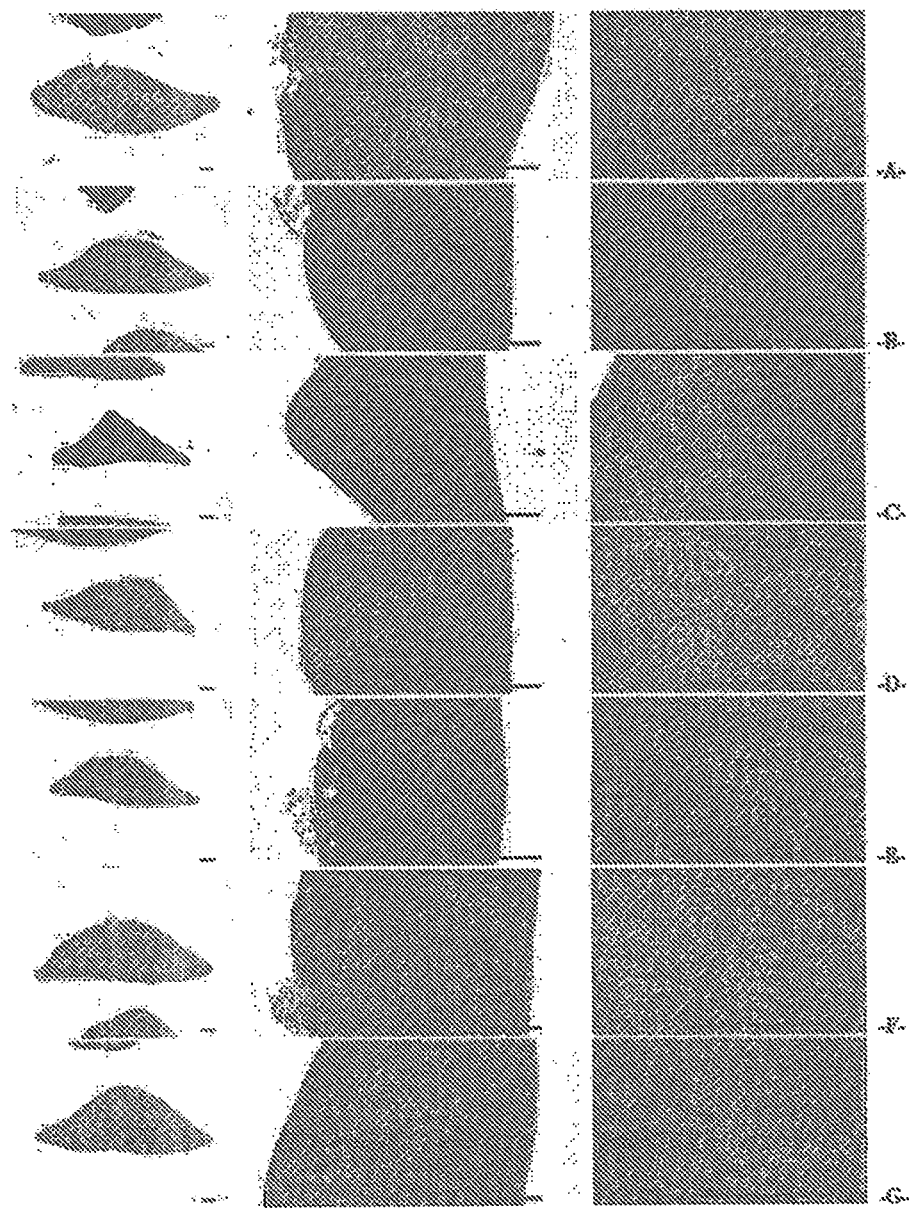
FIG. 93 shows histopathological changes in spleens.

Atrophy characterized by a significant decrease in number of lymphocytes in a splenic white pulp was observed, and therefore significant decreases (p<0.01) in spleen thickness, and diameter and number of white pulps were also observed in the tumor-bearing control, compared with the vehicle control. Meanwhile, remarkable increases in the spleen thickness and diameter and number of the white pulps were observed in a histopathologic aspect in the YMJHT single treated group and all of the YMJHT 100, 200, and 400 mg/kg co-administered groups, compared with the tumor-bearing control. In particular, significant increases (p<0.01) in the spleen thickness and the diameter and number of the white pulps were also observed in all of the YMJHT 100, 200 and 400 mg/kg and sorafenib 20 mg/kg co-administered groups, compared with the sorafenib single treated group. Meanwhile, significant decreases (p<0.01 or p<0.05) in the spleen thickness and the diameter and number of the white pulps were also observed in the sorafenib single treated group, compared with the tumor-bearing control (Table 49, and FIG. 93).

TABLE 49

| Group | Total thickness (mm/central region) | White pulp number (/mm²) | White pulp diameter (μM/white pulps) |
|---|---|---|---|
| Control | | | |
| Intact | 2077.13 ± 254.53 | 17.57 ± 1.99 | 803.34 ± 125.98 |
| TB | 1353.44 ± 155.94$^a$ | 8.00 ± 1.15$^a$ | 462.75 ± 91.93$^e$ |
| Single treated | | | |
| Sorafenib | 1066.54 ± 133.39$^{ab}$ | 5.57 ± 0.79$^{ab}$ | 339.42 ± 37.25$^{eg}$ |
| YMJHT | 1549.92 ± 77.95$^{acd}$ | 10.43 ± 1.81$^{abd}$ | 586.02 ± 64.43$^{egh}$ |
| Sorafenib and YMJHT co-administered | | | |
| 100 mg/kg | 1511.67 ± 130.60$^{ad}$ | 10.57 ± 2.23$^{abd}$ | 519.57 ± 68.25$^{eh}$ |
| 200 mg/kg | 1702.30 ± 148.29$^{abd}$ | 13.43 ± 1.51$^{abd}$ | 709.05 ± 77.59$^{fh}$ |
| 400 mg/kg | 1761.10 ± 137.66$^{abd}$ | 16.57 ± 1.27$^{bd}$ | 746.65 ± 134.69$^{fh}$ |

TABLE 50

| Group | Total thickness (μM/central region) | Number of cortex lymphoid cell follicles (/mm²) | Cortex thickness (μM/lymph node) |
|---|---|---|---|
| Control | | | |
| Intact | 1457.99 ± 257.94 | 21.00 ± 2.16 | 745.98 ± 56.11 |
| TB | 639.99 ± 102.09$^e$ | 8.29 ± 1.11$^a$ | 340.08 ± 47.24$^a$ |
| Single treated | | | |
| Sorafenib | 482.51 ± 86.48$^{ef}$ | 5.29 ± 2.21$^{ab}$ | 268.56 ± 46.42$^{ac}$ |
| YMJHT | 858.39 ± 101.99$^{efh}$ | 12.00 ± 1.15$^{abd}$ | 473.12 ± 54.63$^{abd}$ |
| Sorafenib and YMJHT co-administered | | | |
| 100 mg/kg | 790.06 ± 82.72$^{egh}$ | 11.86 ± 1.35$^{abd}$ | 413.95 ± 43.70$^{acd}$ |
| 200 mg/kg | 1018.55 ± 115.79$^{efh}$ | 15.00 ± 1.41$^{abd}$ | 623.12 ± 64.84$^{abd}$ |
| 400 mg/kg | 1117.47 ± 121.64$^{efh}$ | 19.43 ± 1.72$^{bd}$ | 690.96 ± 75.15$^{bd}$ |

In the tumor-bearing control, compared with the vehicle control, the total thickness of the spleen changed by −34.84%. In the sorafenib 20 mg/kg and YMJHT 400 mg/kg single treated groups and the YMJHT 100, 200 and 400 mg/kg and sorafenib 20 mg/kg co-administered groups, the total thicknesses of the spleens changed by −21.20%, 14.52%, 11.69%, 25.78%, and 30.12%, respectively, compared with the tumor-bearing control.

In the tumor-bearing control, compared with the vehicle control, the number of splenic white pulps changed by −54.47%. In the sorafenib 20 mg/kg and YMJHT 400 mg/kg single treated groups and the YMJHT 100, 200 and 400 mg/kg and sorafenib 20 mg/kg co-administered groups, the numbers of the splenic white pulps changed by −30.36%, 30.36%, 32.14%, 67.86%, and 107.14%, respectively, compared with the tumor-bearing control.

In the tumor-bearing control, compared with the vehicle control, the diameter of the splenic white pulp changed by −42.40%. In the sorafenib 20 mg/kg and YMJHT 400 mg/kg single treated groups and the YMJHT 100, 200 and 400 mg/kg and sorafenib 20 mg/kg co-administered groups, the diameters of the splenic white pulps changed by −26.65%, 26.64%, 12.28%, 53.22%, and 61.35%, respectively, compared with the tumor-bearing control.

11.14.3. Confirmation of Histopathological Change in Submandibular Lymph Node

Figure 94:
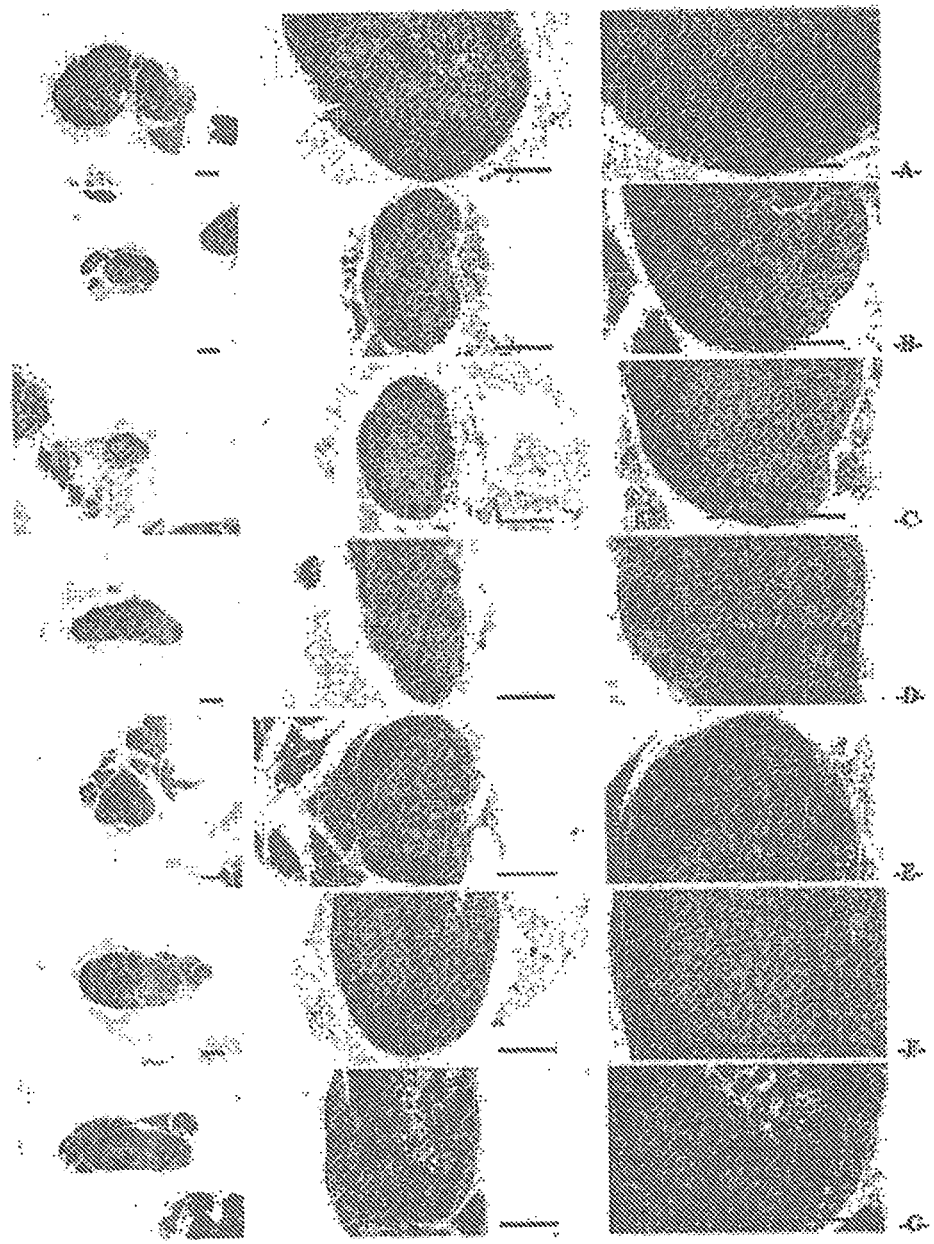
FIG. 94 shows histopathological changes in submandibular lymph nodes.

Atrophy caused by a remarkable decrease in number of lymphocytes in a lymph node cortex was observed in the tumor-bearing control, compared with the vehicle control, and thus significant decreases (p<0.01) in thicknesses of all of the submandibular lymph nodes and the cortex and number of follicles in the cortex were also observed. Meanwhile, significant increases in total thicknesses of the lymph node, cortex thickness and number of follicles in the cortex were observed in a histopathologic aspect in all of the YMJHT single treated groups and the YMJHT 100, 200, and 400 mg/kg co-administered groups, compared with the tumor-bearing control. In particular, significant increases (p<0.01) in total thicknesses of the lymph node, cortex thickness and number of follicles in the cortex were also observed in the YMJHT 100, 200 and 400 mg/kg and sorafenib 20 mg/kg co-administered groups, compared with the sorafenib single treated group. Meanwhile, significant decreases (p<0.01 or p<0.05) in total thicknesses of the lymph node, cortex thickness and number of follicles in the cortex were observed in the sorafenib single treated group, compared with the tumor-bearing control (Table 50, and FIG. 94).

In the tumor-bearing control, compared with the vehicle control, the total thickness of the submandibular lymph node changed by −56.10%. In the sorafenib 20 mg/kg and YMJHT 400 mg/kg single treated groups and the YMJHT 100, 200 and 400 mg/kg and sorafenib 20 mg/kg co-administered groups, the total thicknesses of the submandibular lymph nodes changed by −24.61%, 34.13%, 23.45%, 59.15%, and 74.61%, respectively, compared with the tumor-bearing control.

In the tumor-bearing control, compared with the vehicle control, the number of the follicles in the submandibular lymph node cortex changed by −60.54%. In the sorafenib 20 mg/kg and YMJHT 400 mg/kg single treated groups and the YMJHT 100, 200 and 400 mg/kg and sorafenib 20 mg/kg co-administered groups, the numbers of follicles in the submandibular lymph node cortex changed by −36.21%, 44.83%, 43.10%, 81.03%, and 134.48%, respectively, compared with the tumor-bearing control.

In the tumor-bearing control, the thickness of the submandibular lymph node cortex changed by −54.41%, compared with the vehicle control. In the sorafenib 20 mg/kg and YMJHT 400 mg/kg single treated groups and the YMJHT 100, 200 and 400 mg/kg and sorafenib 20 mg/kg co-administered groups, the thicknesses of submandibular lymph node cortices changed by −21.03%, 39.12%, 21.72%, 83.23%, and 103.18%, respectively, compared with the tumor-bearing control.

11.14.4. Confirmation of Histopathological Change in Periovarian Fat Pad

Figure 95:
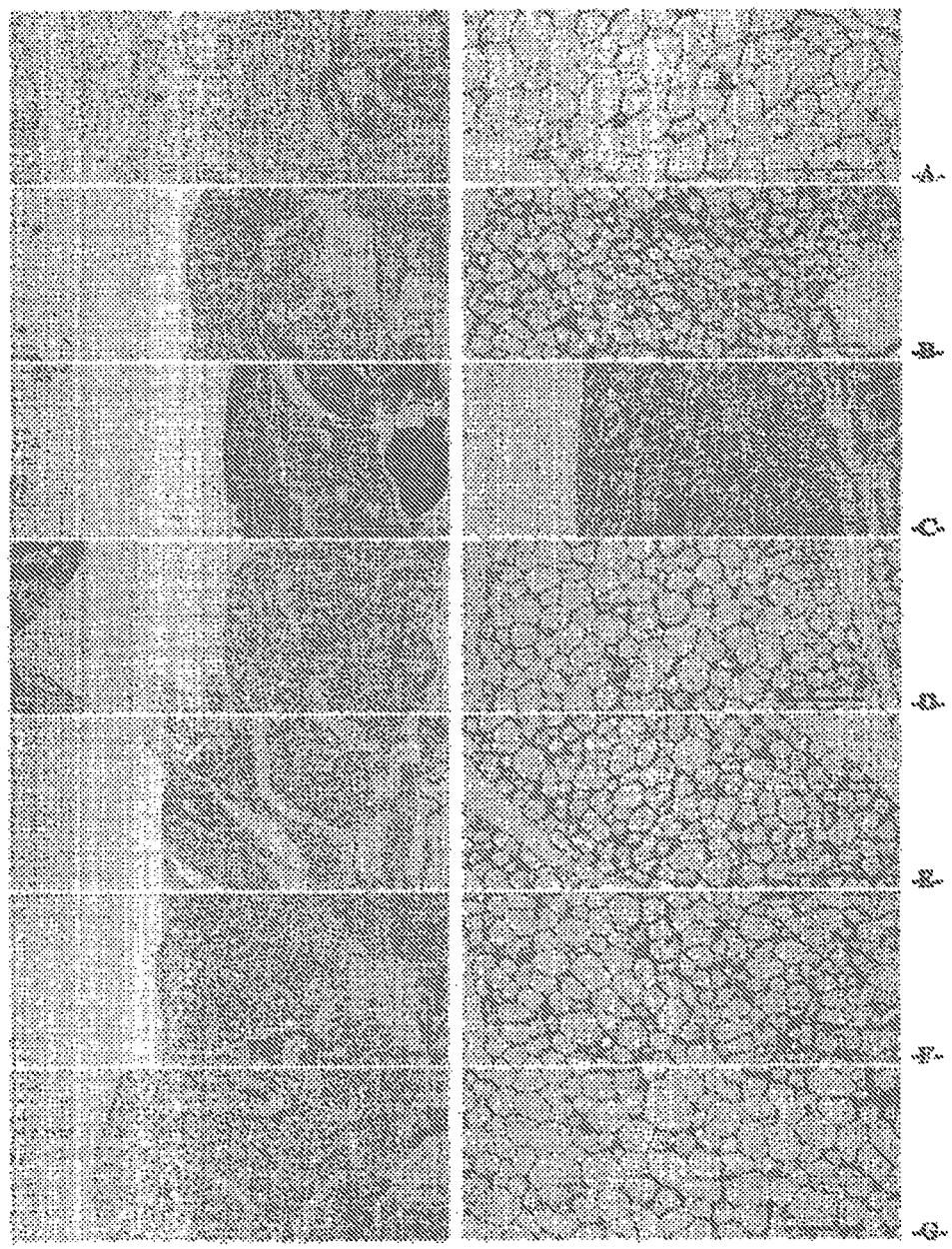
FIG. 95 shows histopathological changes in periovarian fat pads.

Atrophy characterized by a significant decrease in size of white adipocytes was observed, and thus a significant decrease (p<0.01) in thickness of accumulated fats and mean diameter of the white adipocyte were also observed in the tumor-bearing control, compared with the vehicle control. Meanwhile, significant increases (p<0.01) in thickness of the accumulated fats and mean diameter of the white adipocyte were observed in a histopathologic aspect in the YMJHT single treated group and the YMJHT 100, 200 and 400 mg/kg and sorafenib co-administered groups, compared with the tumor-bearing control. In particular, significant increases (p<0.01) in thickness of the accumulated fats and mean diameter of the white adipocyte were also observed in all of the YMJHT 100, 200 and 400 mg/kg and sorafenib co-administered groups, compared with the sorafenib single treated group. Meanwhile, significant decreases (p<0.01) in thicknesses of the accumulated fats and mean diameter of the white adipocyte were also observed in the sorafenib single treated group, compared with the tumor-bearing control (FIG. 95, and Table 51).

TABLE 51

| Group | Total thickness (mm/central region) | White adipocyte diameter (μM) |
|---|---|---|
| Control | | |
| Intact | 1744.13 ± 161.09 | 57.22 ± 5.86 |
| TB | 794.91 ± 113.58[a] | 24.90 ± 4.13[e] |
| Single treated | | |
| Sorafenib | 531.72 ± 117.07[ab] | 17.73 ± 3.42[eg] |
| YMJHT | 1104.78 ± 134.68[abc] | 35.98 ± 4.30[egh] |
| Sorafenib and YMJHT co-administered | | |
| 100 mg/kg | 1133.52 ± 129.27[abc] | 32.17 ± 3.42[egh] |
| 200 mg/kg | 1305.81 ± 186.43[abc] | 43.21 ± 7.65[egh] |
| 400 mg/kg | 1535.30 ± 120.35[abc] | 48.69 ± 5.70[fgh] |

In the tumor-bearing control, compared with the vehicle control, the thickness of the periovarian fat pad changed by −54.42%. In the single sorafenib 20 mg/kg and 400 mg/kg YMJHT-administered groups and the YMJHT 100, 200 and 400 mg/kg and sorafenib 20 mg/kg co-administered groups, the thicknesses of the periovarian fat pad changed by −33.11%, 38.98%, 42.60%, 64.27%, and 93.14%, respectively, compared with the tumor-bearing control.

In the tumor-bearing control, compared with the vehicle control, the mean diameter of the periovarian white adipocyte changed by −56.48%. In the sorafenib 20 mg/kg and YMJHT 400 mg/kg single treated groups and the YMJHT 100, 200 and 400 mg/kg and sorafenib 20 mg/kg co-administered groups, the mean diameters of the periovarian white adipocytes changed by −28.80%, 44.49%, 29.18%, 73.52%, and 95.52%, respectively, compared with the tumor-bearing control.

As seen from the results obtained according to Example 11, it was shown that $IC_{50}$s of YMJHT and sorafenib to HepG2 cells were estimated at 49.07 mg/ml and 2.81 μM (1.31 g/ml), respectively, and the remarkable decreases in the spleen and submandibular lymph node weights, the blood IFN-γ content, the splenic TNF-α, IL-1β and IL-1β contents, and the activities of the splenic peritoneal macrophagocytes, which were caused by grafting of the HepG2 cells, were observed with the histopathological finding of atrophy due to the decreases in number of lymphocytes in the spleen and the submandibular lymph node, and decreases in body weight and body weight gain were observed. Also, an increase in blood IL-6 content, a decrease in weight of a periovarian fat pad, and histopathologic atrophy of the periovarian fat tissues were also observed. Therefore, it is determined that typical tumor-associated immunosuppression and cachexia were caused after tumor grafting. Meanwhile, the decreases in the volume and weight of the tumor mass caused by sorafenib 20 mg/kg single administration were observed with the decrease in the percentages of the tumor cells caused by the increase in the apoptosis cells in the tumor mass in a histopathologic test, and the decreases in number of the COX-2 immunoreactive cells were observed with the increases in caspase-3, PARP, iNOS and TNF-α immunoreactivities in the tumor mass. However, it was observed that the tumor-associated cachexia (the changes in the body weight, the weight of periovarian fat pad, and the blood IL-6 contents) and immunosuppression (the changes in the weights of the spleen and the submandibular lymph nodes, the blood IFN-γ content, the activities of the NK cells, and the TNF-α, IL-1β and IL-1β contents in the spleen) were rather significantly exacerbated, and the remarkable decreases in the immune activities and tumor-associated cachexia were observed in the YMJHT single treated group, compared with the tumor-bearing control. However, it was observed that the anticancer effect on the tumor mass itself was remarkably reduced, compared with the sorafenib-administered groups.

Meanwhile, significant anticancer and immune activities and inhibition of tumor-associated cachexia were observed in three doses of YMJHT and sorafenib co-administered groups, compared with the tumor-bearing control. In particular, a significant increase ($p<0.01$ or $p<0.05$) in the anticancer effect was observed, and a significant increase in the immune activity and the inhibitory effect on cachexia compared with the sorafenib single treated group were also observed in the 400 and 200 mg/kg YMJHT and sorafenib co-administered groups, compared with the sorafenib single treated group. As a result, the previous pharmacokinetic experiments conducted by the researchers showed that the oral YMJHT co-administration within 5 minutes resulted in a remarkable increase in sorafenib absorption, but it was observed that the co-administration of YMJHT at intervals of 3.5 hours does not influence on bioavailability of sorafenib. Thus, it is determined that the co-administration of YMJHT at intervals of 3.5 hours caused remarkable enhancement of the anticancer effect of sorafenib and remarkable inhibition of the tumor-associated cachexia through the immune activities without having an influence on the bioavailability of sorafenib. As a result, the sorafenib and YMJHT co-administration into lung cancer patients is expected to provide a new treating method which is very useful in integrative medicine. Meanwhile, a remarkable inhibitory effect on tumor-associated cachexia due to the immune activity was also observed, but no significant increase in the anticancer activity was observed in the 100 mg/kg YMJHT and sorafenib co-administered group, compared with the sorafenib single treated group. As a result, it is determined that the anticancer effect of sorafenib caused by the immune activity is definitely increased and the tumor-associated cachexia can be regulated by co-administering at least 200 mg/kg or more YMJHT.

Example 12: Experiment for Sorafenib and YMJHT Co-Administration: Confirmation of Effect of YMJHT on Reducing Sorafenib Toxicity 12.1. Preparation of Laboratory Animals In this Example, male ICR mice were used as laboratory animals. A total of 42 mice were divided into six groups [G0M: Vehicle control, G1M: Single 100 mg/kg sorafenib-administered group, G2M: Single 400 mg/kg YMJHT-administered group, G3M: 100 mg/kg sorafenib and 100 mg/kg YMJHT co-administered group, G4M: 100 mg/kg sorafenib and 200 mg/kg YMJHT co-administered group, and G5M: 100 mg/kg sorafenib and 400 mg/kg YMJHT co-administered group] to be used in the experiment.

12.2. Method for Drug Administration

As shown in Table 52, YMJHT was co-administered to sorafenib 100 mg/kg-treated mice at intervals of 3.5 hours daily for 28 days. In the YMJHT or sorafenib single treated group, only the same dose of sterile distilled water was administered. In the vehicle control, only sterile distilled water was administered as a vehicle twice at intervals of 3.5 hours.

TABLE 52

Group | Sex | Dose (mg/kg)
YMJHT: Toxicity tests after repeated oral administration into mice

| Group | Sex | Dose (mg/kg) |
|---|---|---|
| Control | Male | Distilled water (10 ml/kg) |
| Reference | Male | Sorafenib single (100 mg/kg) |
| Reference | Male | YMJHT Single (400 mg/kg) |
| Active | Male | Sorafenib and YMJHT (100 and 100 mg/kg) |
| Active | Male | Sorafenib and YMJHT (100 and 200 mg/kg) |
| Active | Male | Sorafenib and YMJHT (100 and 400 mg/kg) |

12.3. Observation Items

In Example 12, the death rate for 28 days, the clinical symptoms, the change in body weight, the necropsy findings, the organ weight, the hematological (14 items; see Table 53) and hematochemical (20 items; see Table 54) changes, histopathological change and blood biochemical changes, the histopathological changes (23 organs: the brain—the cerebrum, the cerebellum and the myelencephalon, the heart, the thymus, the lung, the testis, the epididymis, the kidney, the suprarenal gland, the spleen, the liver, the pancreas, alimentary tracts—the esophagus, the gastric fundus, the gastric pylorus, the duodenum, the jejunum, the ileum, the appendix, the colon, and the rectum, and the submandibular lymph node), and the activities of splenic and peritoneal NK cells were examined.

TABLE 53

Hematology Items

| Abbreviations | Full name | Units | Methods |
|---|---|---|---|
| 1. RBC | Red blood cell count | M/L | Laser optical (Flow cytometry) |
| 2. HGB | Hemoglobin concentration | g/dl | Cyanmethemoglobin method |
| 3. HCT | Hematocrit | % | Calculated from Items 1 and 4 |
| 4. MCV | Mean corpuscular volume | fL | Laser optical (Flow cytometry) |
| 5. MCH | Mean corpuscular hemoglobin | pg | Calculated from Items 1 and 2 |
| 6. MCHC | Mean corpuscular hemoglobin concentration | g/dL | Calculated from Items 2 and 3 |
| 7. PLT | Platelet count | K/L | Laser optical (Flow cytometry) |
| 8. RET | Reticulocyte count | ea/1000 | Laser optical with cytochemical reaction |
| 9. WBC | White blood cell count | K/L | Laser optical with cytochemical reaction |
| Differential counts of white blood cells | | | |
| 10. NEU % | Percentage of neutrophils | % | Perox optical with chemical reaction |
| 11. LYM % | Percentage of lymphocytes | % | Perox optical with chemical reaction |
| 12. MON % | Percentage of monocytes | % | Perox optical with chemical reaction |
| 13. EOS % | Percentages of eosinophils | % | Perox optical with chemical reaction |
| 14. BAS % | Percentages of basophils | % | Perox optical with chemical reaction |

TABLE 54

Hematology Items

| Abbreviations | Full name | Units | Methods |
|---|---|---|---|
| 1. AST | Aspartate aminotransferase | IU/L | UV-Rate method |
| 2. ALT | Alanine aminotransferase | IU/L | UV-Rate method |
| 3. ALP | Alkaline phosphatase | IU/L | P-NPP method |
| 4. BUN | Blood urea nitrogen | mg/dL | Urease-UV method |
| 5. CRE | Creatinine | mg/dL | Jaffe method |
| 6. GLU | Glucose | mg/dL | Enzyme method |
| 7. CHO | Total cholesterol | mg/dL | Enzyme method |
| 8. PRO | Total protein | g/dL | Biuret method |
| 9. CPK | Creatine phosphokinase | IU/L | UV-Rate method |
| 10. ALB | Albumin | g/dL | BCG method |
| 11. BIL | Total bilirubin | mg/dL | Jendrassik-cleghorn method |
| 12. Globulin | Globulin | g/dL | BCG method |
| 13. A/G | Albumin/globulin ratio | Ratio | Calculated from Items 10 and 12 |
| 14. IP | Inorganic phosphorus | mg/dL | UV method |
| 15. Ca | Calcium | mg/dL | OCPC method |
| 16. TG | Triglyceride | mg/dL | Enzyme method |
| 17. LDH | Lactate dehydrogenase | IU/L | UV-Rate method |
| 18. Na | Sodium | mmol/L | Electrode method |
| 19. K | Potassium | mmol/L | Electrode method |
| 20. Cl | Chloride | mmol/L | Electrode method |

12.4. Confirmation of Death Rate and Clinical Symptoms

As a result of the experiment, death caused by the administration of an experiment material was not observed during the experiment for 28 days, and necropsy was performed on all laboratory animals in all experiment groups (7/7; 100%). Also, as a result of the experiment, no clinical symptoms caused by the administration of the experiment material were observed during the experiment for 28 days (Table 56).

TABLE 55

| Group | Days of treatment period (Day $0^a$ to 27) | Termination date ($28^{th}$ day of administration) | Total* |
|---|---|---|---|
| Vehicle control | | | |
| Distilled water | 0 | 0 | 0/7 (0%) |
| Sorafenib single treated | | | |
| 100 mg/kg | 0 | 0 | 0/7 (0%) |
| YMJHT single | | | |
| 400 mg/kg | 0 | 0 | 0/7 (0%) |

TABLE 55-continued

| Group | Days of treatment period (Day 0$^a$ to 27) | Termination date (28$^{th}$ day of administration) | Total* |
|---|---|---|---|
| sorafenib 100 mg/kg and YMJHT co-treated | | | |
| 100 mg/kg | 0 | 0 | 0/7 (0%) |
| 200 mg/kg | 0 | 0 | 0/7 (0%) |
| 400 mg/kg | 0 | 0 | 0/7 (0%) |

TABLE 56

| Group | Normal appearance | Clinical signs Any abnormal signs |
|---|---|---|
| Vehicle control | | |
| Distilled water | 7/7 (100%) | 0/7 (0%) |
| Single sorafenib treated | | |
| 100 mg/kg | 7/7 (100%) | 0/7 (0%) |
| Singe YMJHT treated | | |
| 400 mg/kg | 7/7 (100%) | 0/7 (0%) |

TABLE 56-continued

| Group | Normal appearance | Clinical signs Any abnormal signs |
|---|---|---|
| 100 mg/kg sorafenib and YMJHT co-treated | | |
| 100 mg/kg | 7/7 (100%) | 0/7 (0%) |
| 200 mg/kg | 7/7 (100%) | 0/7 (0%) |
| 400 mg/kg | 7/7 (100%) | 0/7 (0%) |

12.5. Confirmation of Change in an Organ Weight

Significant decreases ($p<0.01$) in absolute and relative weights of the thymus, the spleen, the testis, the epididymis and the submandibular lymph node were observed in the sorafenib 100 mg/kg single treated group, compared with the vehicle control, but significant increases ($p<0.01$ or $p<0.05$) in the absolute and relative weights of the thymus, the spleen, the testis, the epididymis and the submandibular lymph node were observed in all of the YMJHT 200 and 400 mg/kg and sorafenib co-administered groups, compared with the sorafenib 100 mg/kg single treated group. Also, no significant increases ($p<0.01$ or $p<0.05$) in the weights of the thymus, the spleen and the epididymis were observed, but remarkable increases in the weights of the testis and the submandibular lymph node were also observed in the YMJHT 100 mg/kg and sorafenib co-administered group, compared with the sorafenib 100 mg/kg single treated group. Also, a significant decrease ($p<0.05$) in the absolute weight of the kidney was further observed in the single 100 mg/kg sorafenib-administered group, compared with the vehicle control (Tables 57 and 58).

TABLE 57

| Group | Principal organs | | | | | |
|---|---|---|---|---|---|---|
| | Lung | Heart | Thymus | Kidney L | Adrenal G L | Spleen |
| Vehicle control | 0.173 ± 0.013 | 0.156 ± 0.008 | 0.055 ± 0.010 | 0.301 ± 0.037 | 0.003 ± 0.001 | 0.089 ± 0.005 |
| Sorafenib single | | | | | | |
| 100 mg/kg | 0.165 ± 0.008 | 0.150 ± 0.008 | 0.028 ± 0.006$^a$ | 0.287 ± 0.042$^b$ | 0.003 ± 0.002 | 0.062 ± 0.006$^e$ |
| YMJHT single | | | | | | |
| 400 mg/kg | 0.167 ± 0.015 | 0.156 ± 0.008 | 0.049 ± 0.012$^c$ | 0.255 ± 0.042 | 0.004 ± 0.003 | 0.092 ± 0.022$^f$ |
| Sorafenib 100 mg/kg and YMJHT co-treated | | | | | | |
| 100 mg/kg | 0.172 ± 0.009 | 0.157 ± 0.010 | 0.045 ± 0.009$^{bc}$ | 0.276 ± 0.032 | 0.004 ± 0.004 | 0.094 ± 0.016$^f$ |
| 200 mg/kg | 0.172 ± 0.021 | 0.157 ± 0.007 | 0.045 ± 0.008$^{bc}$ | 0.270 ± 0.045 | 0.004 ± 0.003 | 0.094 ± 0.011$^f$ |
| 400 mg/kg | 0.171 ± 0.015 | 0.158 ± 0.009 | 0.048 ± 0.006$^c$ | 0.294 ± 0.036 | 0.005 ± 0.004 | 0.095 ± 0.011$^f$ |

| Group | Testis L | Liver | Pancreas S | Brain | Epididymis L | LN L |
|---|---|---|---|---|---|---|
| Vehicle control | 0.115 ± 0.009 | 1.277 ± 0.117 | 0.157 ± 0.007 | 0.475 ± 0.018 | 0.045 ± 0.002 | 0.007 ± 0.003 |
| Sorafenib single | | | | | | |
| 100 mg/kg | 0.098 ± 0.007$^e$ | 1.196 ± 0.050 | 0.151 ± 0.014 | 0.470 ± 0.022 | 0.036 ± 0.004$^e$ | 0.002 ± 0.001$^a$ |
| YMJHT single | | | | | | |
| 400 mg/kg | 0.113 ± 0.003$^f$ | 1.184 ± 0.090 | 0.147 ± 0.014 | 0.479 ± 0.020 | 0.044 ± 0.004$^f$ | 0.007 ± 0.004$^c$ |
| Sorafenib 100 mg/kg and YMJHT co-treated | | | | | | |
| 100 mg/kg | 0.109 ± 0.007$^f$ | 1.227 ± 0.064 | 0.165 ± 0.015 | 0.484 ± 0.010 | 0.047 ± 0.003$^f$ | 0.004 ± 0.002 |
| 200 mg/kg | 0.118 ± 0.016$^g$ | 1.177 ± 0.065 | 0.160 ± 0.016 | 0.478 ± 0.016 | 0.047 ± 0.009$^f$ | 0.005 ± 0.002$^d$ |
| 400 mg/kg | 0.121 ± 0.009$^f$ | 1.252 ± 0.143 | 0.168 ± 0.021 | 0.484 ± 0.016 | 0.048 ± 0.005$^f$ | 0.007 ± 0.003$^c$ |

TABLE 58

| Group | Lung | Heart | Thymus | Kidney L | Adrenal G L | Spleen |
|---|---|---|---|---|---|---|
| Vehicle control | 0.529 ± 0.054 | 0.477 ± 0.036 | 0.169 ± 0.028 | 0.922 ± 0.156 | 0.008 ± 0.004 | 0.272 ± 0.013 |
| Sorafenib single | | | | | | |
| 100 mg/kg | 0.505 ± 0.037 | 0.461 ± 0.036 | 0.085 ± 0.018a | 0.877 ± 0.112 | 0.009 ± 0.006 | 0.189 ± 0.022a |
| YMJHT single | | | | | | |
| 400 mg/kg | 0.523 ± 0.069 | 0.487 ± 0.042 | 0.153 ± 0.037c | 0.798 ± 0.144 | 0.012 ± 0.008 | 0.289 ± 0.082c |
| 100 mg/kg sorafenib and YMJHT co-treated | | | | | | |
| 100 mg/kg | 0.519 ± 0.034 | 0.473 ± 0.034 | 0.135 ± 0.028bc | 0.834 ± 0.096 | 0.012 ± 0.011 | 0.284 ± 0.050c |
| 200 mg/kg | 0.542 ± 0.065 | 0.494 ± 0.036 | 0.142 ± 0.027c | 0.849 ± 0.148 | 0.013 ± 0.009 | 0.297 ± 0.044c |
| 400 mg/kg | 0.513 ± 0.053 | 0.474 ± 0.041 | 0.143 ± 0.013c | 0.882 ± 0.121 | 0.015 ± 0.011 | 0.285 ± 0.042c |

| Group | Testis L | Liver | Pancreas S | Brain | Epididymis L | LN L |
|---|---|---|---|---|---|---|
| Vehicle control | 0.346 ± 0.031 | 3.880 ± 0.196 | 0.479 ± 0.036 | 1.451 ± 0.126 | 0.137 ± 0.008 | 0.022 ± 0.010 |
| Sorafenib single | | | | | | |
| 100 mg/kg | 0.300 ± 0.019e | 3.665 ± 0.214 | 0.463 ± 0.051 | 1.443 ± 0.113 | 0.111 ± 0.012a | 0.006 ± 0.002a |
| YMJHT single | | | | | | |
| 400 mg/kg | 0.353 ± 0.017f | 3.697 ± 0.394 | 0.459 ± 0.060 | 1.494 ± 0.096 | 0.138 ± 0.014c | 0.021 ± 0.011c |
| Sorafenib 100 mg/kg and YMJHT co-treated | | | | | | |
| 100 mg/kg | 0.329 ± 0.032 | 3.706 ± 0.283 | 0.500 ± 0.051 | 1.462 ± 0.076 | 0.142 ± 0.011c | 0.013 ± 0.008 |
| 200 mg/kg | 0.370 ± 0.055g | 3.707 ± 0.288 | 0.506 ± 0.068 | 1.505 ± 0.100 | 0.149 ± 0.023c | 0.016 ± 0.006d |
| 400 mg/kg | 0.361 ± 0.037g | 3.754 ± 0.511 | 0.504 ± 0.081 | 1.449 ± 0.108 | 0.144 ± 0.018c | 0.021 ± 0.008c |

12.6. Confirmation of Hematological Change

As a result of 14 hematological tests, it was shown that the decrease in percentage of the lymphocytes and the related increase in percentage of neutrophilic leukocytes were observed with the significant decrease ($p<0.01$) in WBC in the sorafenib single treated group, compared with the vehicle control, but the increase in percentage of the lymphocytes and the related decrease in percentage of the neutrophilic leukocytes were observed with the significant increase ($p<0.01$ or $p<0.05$) in WBC in the YMJHT 100, 200 or 400 mg/kg and sorafenib co-administered groups, compared with the sorafenib 100 mg/kg single treated group. On the other hand, it was shown that the decrease in EOS % was also observed with the significant increase ($p<0.05$) in NEU % in the YMJHT 400 mg/kg single treated group, compared with the vehicle control, and the significant increase ($p<0.05$) in RET was also observed in the YMJHT 100 mg/kg and sorafenib 100 mg/kg co-administered group, compared with the vehicle control. From these results obtained from this experiment, it was shown that no significant changes in RBC, HGB, HCT, MCV, MCH, MCHC, PLT, MON %, EOS % and BAS % were observed in the sorafenib single treated group and all of the YMJHT and sorafenib co-administered groups, compared with the vehicle control (Table 59).

TABLE 59

| | | | | Hematological Items: Red Blood Cells | | | | |
|---|---|---|---|---|---|---|---|---|
| Group | RBC | HGB | HCT | MCV | MCH | MCHC | PLT | RET |
| Vehicle control | 8.84 ± 0.52 | 18.90 ± 1.16 | 40.46 ± 3.23 | 45.73 ± 2.28 | 21.37 ± 0.52 | 44.70 ± 1.11 | 809.14 ± 78.30 | 0.30 ± 0.19 |
| Sorafenib single | | | | | | | | |
| 100 mg/kg | 8.94 ± 0.42 | 18.50 ± 0.64 | 41.74 ± 2.04 | 46.73 ± 2.45 | 20.73 ± 0.87 | 44.37 ± 1.04 | 801.86 ± 98.95 | 0.49 ± 0.32 |
| YMJHT single | | | | | | | | |
| 400 mg/kg | 9.28 ± 0.49 | 18.89 ± 0.78 | 41.76 ± 2.31 | 46.67 ± 2.26 | 20.43 ± 1.08 | 44.49 ± 0.85 | 766.86 ± 89.74 | 0.46 ± 0.25 |
| Sorafenib 100 mg/kg and YMJHT co-treated | | | | | | | | |
| 100 mg/kg | 9.31 ± 0.42 | 18.91 ± 0.69 | 41.37 ± 3.52 | 47.14 ± 1.72 | 20.86 ± 1.06 | 43.79 ± 1.07 | 783.14 ± 91.19 | 0.59 ± 0.31[b] |
| 200 mg/kg | 9.29 ± 0.44 | 18.10 ± 1.05 | 41.76 ± 2.57 | 45.23 ± 2.68 | 20.49 ± 1.39 | 43.86 ± 1.24 | 818.14 ± 151.31 | 0.43 ± 0.18 |
| 400 mg/kg | 9.27 ± 0.50 | 18.64 ± 0.74 | 41.67 ± 2.81 | 47.27 ± 2.47 | 20.81 ± 1.00 | 43.36 ± 2.02 | 758.86 ± 124.35 | 0.56 ± 0.25 |

TABLE 59-continued

Hematological Items: White Blood Cells

| Group | WBC | NEU (%) | LYM (%) | MONO (%) | EOS (%) | BASO (%) |
|---|---|---|---|---|---|---|
| Vehicle control | 4.47 ± 0.33 | 7.97 ± 0.69 | 83.30 ± 1.53 | 3.69 ± 1.39 | 0.84 ± 0.84 | 0.31 ± 0.17 |
| Sorafenib single | | | | | | |
| 100 mg/kg | 1.83 ± 0.52$^a$ | 17.34 ± 5.16$^d$ | 69.91 ± 5.88$^d$ | 5.27 ± 1.52 | 1.84 ± 2.08 | 0.31 ± 0.20 |
| YMJHT Single | | | | | | |
| 400 mg/kg | 4.88 ± 1.37 | 9.07 ± 1.48$^{ef}$ | 82.80 ± 1.52$^f$ | 4.26 ± 1.24 | 0.17 ± 0.16$^e$ | 0.17 ± 0.17 |
| Sorafenib 100 mg/kg and YMJHT co-treated | | | | | | |
| 100 mg/kg | 3.68 ± 0.42$^{bc}$ | 10.80 ± 1.21$^{dg}$ | 77.66 ± 4.86$^{dg}$ | 5.11 ± 1.68 | 1.79 ± 3.31 | 0.21 ± 0.09 |
| 200 mg/kg | 4.16 ± 0.52$^c$ | 10.24 ± 1.35$^{df}$ | 78.40 ± 2.92$^{df}$ | 4.44 ± 1.69 | 1.69 ± 1.68 | 0.26 ± 0.18 |
| 400 mg/kg | 4.25 ± 0.43$^c$ | 9.50 ± 0.85$^{df}$ | 80.16 ± 1.60$^{df}$ | 4.77 ± 1.39 | 1.11 ± 1.41 | 0.33 ± 0.14 |

12.7. Necropsy Findings

Remarkable increases in observation frequencies of atrophy in the thymus, the spleen and the submandibular lymph node were observed in the sorafenib 100 mg/kg single treated group, compared with the vehicle control. However, remarkable decreases in the observation frequencies of the atrophy in the thymus, the spleen and the submandibular lymph node were observed in the YMJHT 100, 200 or 400 mg/kg and sorafenib co-administered groups, compared with the sorafenib single treated group. Meanwhile, increases in observation frequencies of enlargement in the spleen and the submandibular lymph node were observed in the YMJHT 400 mg/kg single treated group, compared with the vehicle control, and the mild [1+] pulmonary congestion were sporadically observed in all of the experiment groups including the vehicle control (Table 60).

TABLE 60

| Group | Vehicle control | Sorafenib single 100 mg/kg | YMJHT single 400 mg/kg | sorafenib 100 mg/kg and YMJHT co-administration 100 mg/kg | 200 mg/kg | 400 mg/kg |
|---|---|---|---|---|---|---|
| Lung | | | | | | |
| Normal | 5/7 | 5/7 | 7/7 | 5/7 | 6/7 | 6/7 |
| Congestion | 2/7 | 2/7 | 0/7 | 2/7 | 1/7 | 1/7 |
| 1+ | 2/7 | 2/7 | 0/7 | 2/7 | 1/7 | 1/7 |
| Thymus | | | | | | |
| Normal | 6/7 | 2/7 | 6/7 | 5/7 | 6/7 | 6/7 |
| Atrophy | 1/7 | 5/7 | 1/7 | 2/7 | 1/7 | 1/7 |
| 1+ | 1/7 | 5/7 | 1/7 | 2/7 | 1/7 | 1/7 |
| Spleen | | | | | | |
| Normal | 5/7 | 0/7 | 3/7 | 3/7 | 5/7 | 5/7 |
| Atrophy | 2/7 | 7/7 | 0/7 | 4/7 | 2/7 | 1/7 |
| 1+ | 2/7 | 7/7 | 0/7 | 4/7 | 2/7 | 1/7 |
| Hypertrophy | 0/7 | 0/7 | 4/7 | 0/7 | 0/7 | 1/7 |
| 1+ | 0/7 | 0/7 | 4/7 | 0/7 | 0/7 | 1/7 |
| Lymph node$^{a)}$ | | | | | | |
| Normal | 7/7 | 1/7 | 5/7 | 6/7 | 4/7 | 4/7 |
| Atrophy | 0/7 | 6/7 | 0/7 | 1/7 | 0/7 | 0/7 |
| 1+ | 0/7 | 6/7 | 0/7 | 1/7 | 0/7 | 0/7 |
| Hypertrophy | 0/7 | 0/7 | 2/7 | 0/7 | 3/7 | 3/7 |
| 1+ | 0/7 | 0/7 | 2/7 | 0/7 | 3/7 | 3/7 |
| Others | | | | | | |
| Normal | 7/7 | 7/7 | 7/7 | 7/7 | 7/7 | 7/7 |

12.8. Change in NK Cell Activity

Figure 96:
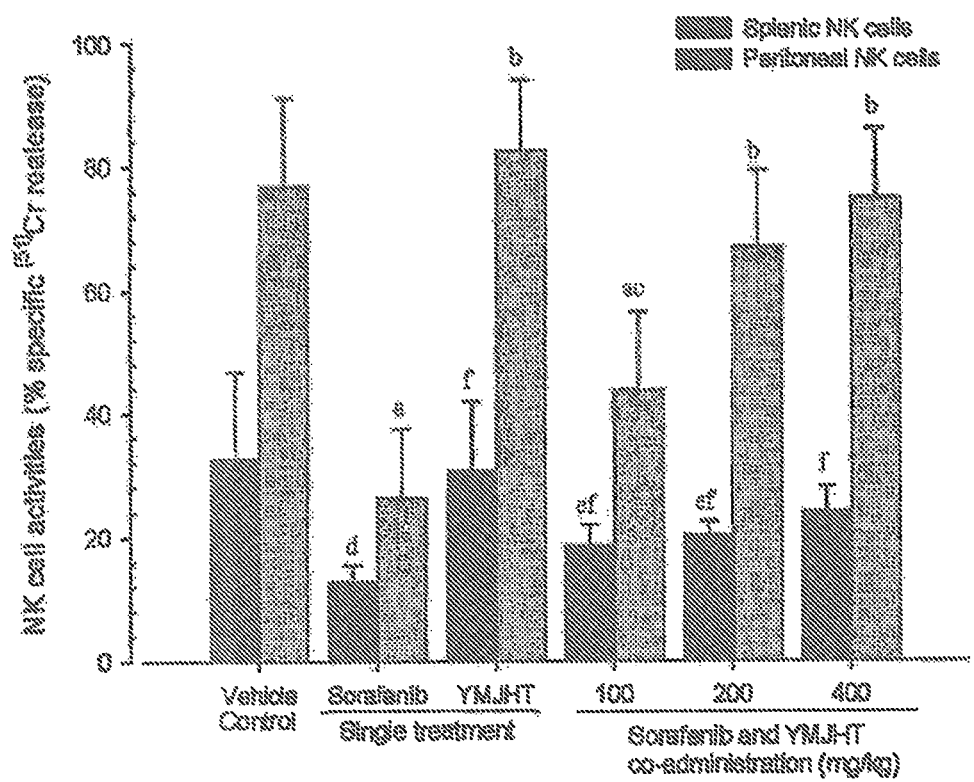
FIG. 96 shows variations in NK cell activities in the male ICR mice for each group according to Example 2.

Significant decreases (p<0.01) in activities of splenic and peritoneal NK cells were observed in the sorafenib 100 mg/kg single treated group, compared with the vehicle control. However, significant increases (p≤0.01 or p<0.05) in the activities of the splenic and peritoneal NK cells were observed in all of the YMJHT co-administered groups, compared with the sorafenib single treated group. Meanwhile, no significant changes in the activities of the splenic and peritoneal NK cells were observed in the YMJHT 400 mg/kg single treated group, compared with the vehicle control (FIG. 96).

In the sorafenib 100 mg/kg single treated group, the activities of the splenic NK cells changed by −60.77%, compared with the vehicle control. In the YMJHT 400 mg/kg single treated group and the YMJHT 100, 200 or 400 mg/kg and sorafenib co-administered groups, the activities of the splenic NK cells changed by 139.23%, 43.93%, 57.97%, and 88.42%, respectively, compared with the sorafenib 100 mg/kg single treated group.

In the sorafenib 100 mg/kg single treated group, the activities of the peritoneal NK cells changed by −65.86%, compared with the vehicle control. In the YMJHT 400 mg/kg single treated group and the YMJHT 100, 200 or 400 mg/kg and sorafenib co-administered groups, the activities of the peritoneal NK cells changed by 214.82%, 66.74%, 155.10%, and 185.38%, respectively, compared with the sorafenib 100 mg/kg single treated group.

12.9. Histopathological Observation

Figure 97:
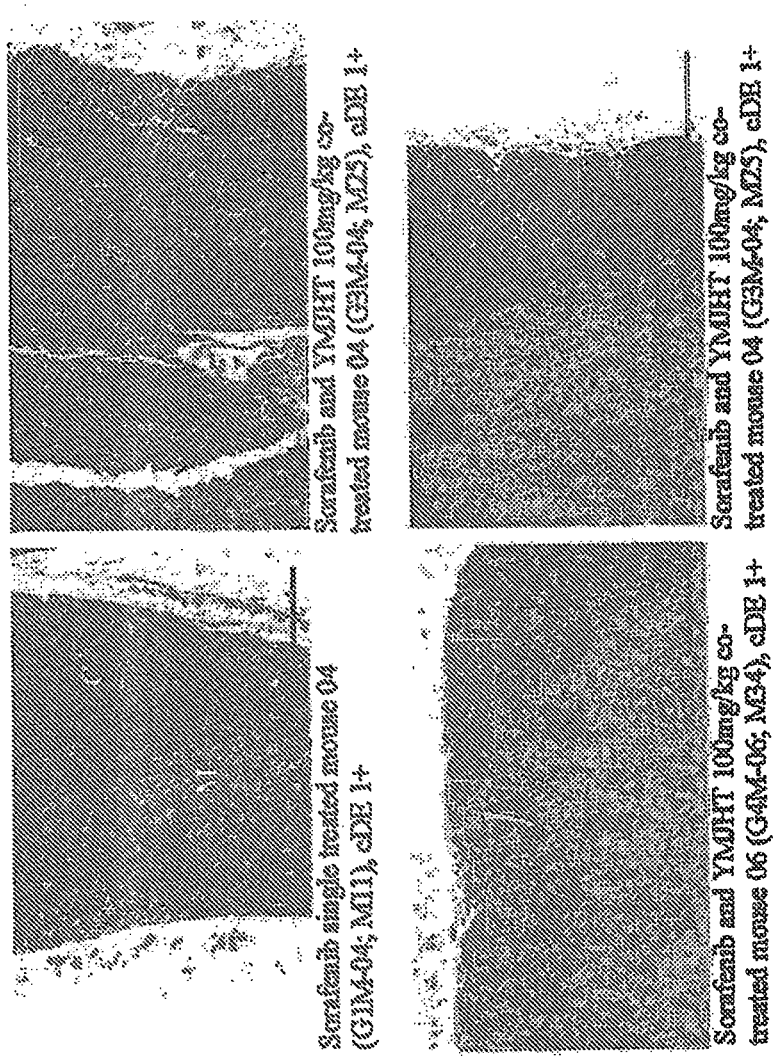
FIG. 97 shows histopathological changes in thymic cortices in a sorafenib single treated group and a sorafenib and yukmijihwang-tang 400 mg/kg co-administered group.
Figure 98:
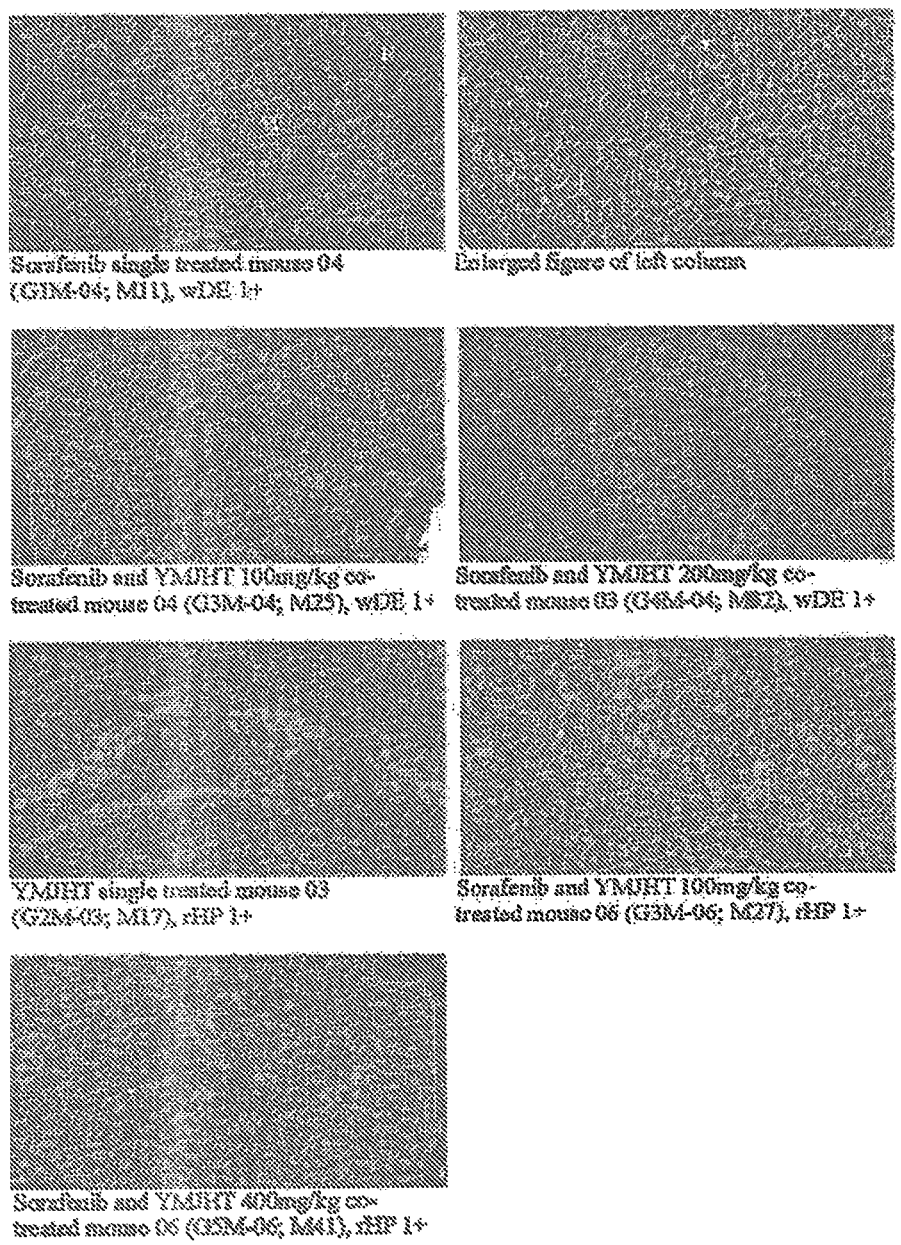
FIG. 98 shows histopathological changes in splenic white pulps for each group.
Figure 99:
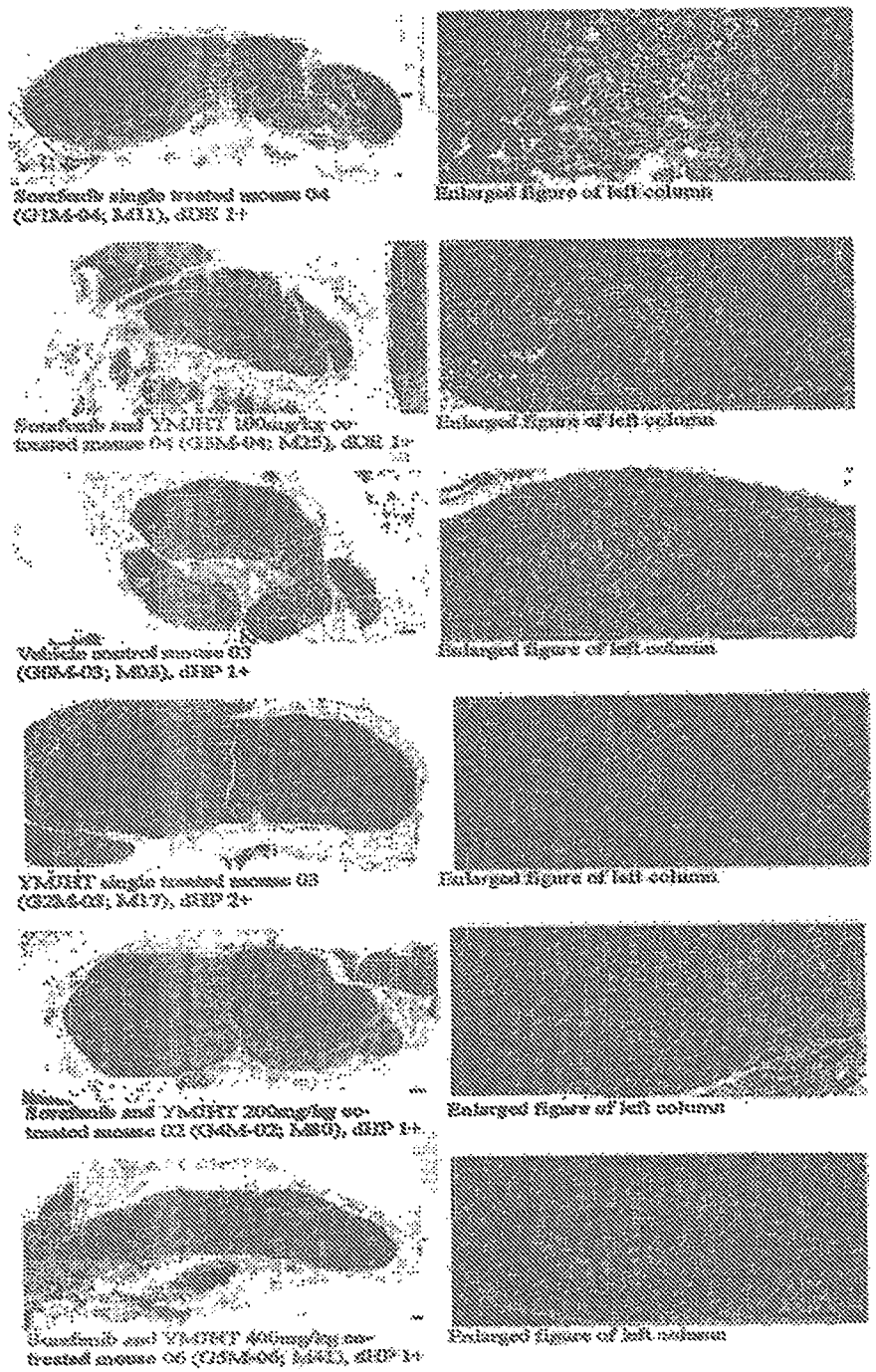
FIG. 99 shows histopathological changes in submandibular lymph nodes in sorafenib and yukmijihwang-tang single treated groups and sorafenib and yukmijihwang-tang 200 mg/kg and 400 mg/kg co-administered groups.
Figure 100:
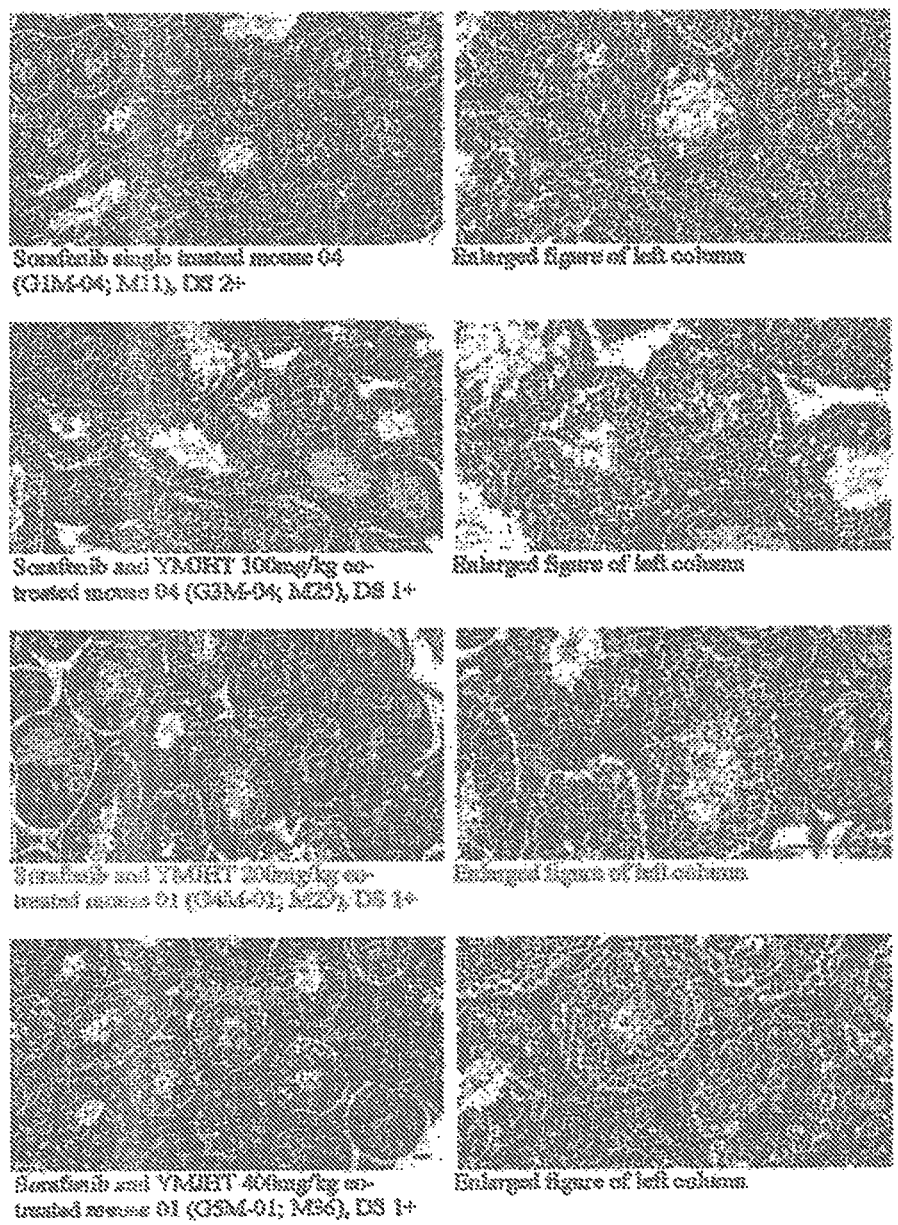
FIG. 100 shows histopathological changes of testicular seminiferous tubules in a sorafenib single treated group and sorafenib and yukmijihwang-tang 100 mg/kg, 200 mg/kg and 400 mg/kg co-administered groups.
Figure 101:
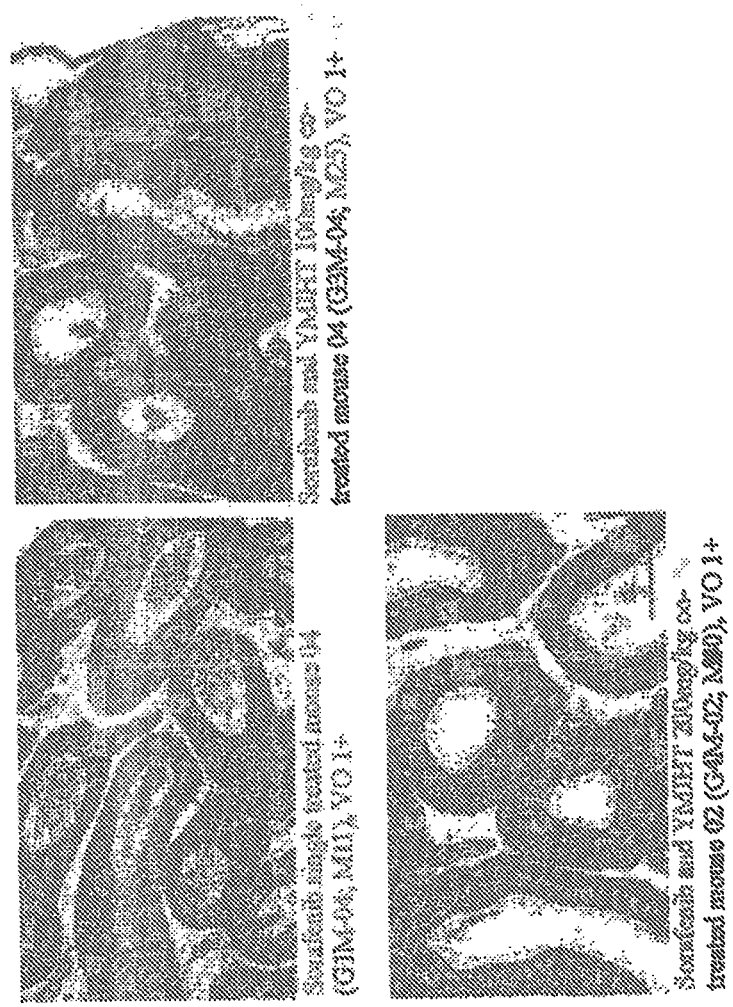
FIG. 101 shows severities of epithelial vacuolation of epididymal tubules and changes in observation frequencies in a sorafenib single treated group and sorafenib and yukmijihwang-tang 100 mg/kg and 200 mg/kg co-administered groups.
Figure 102:
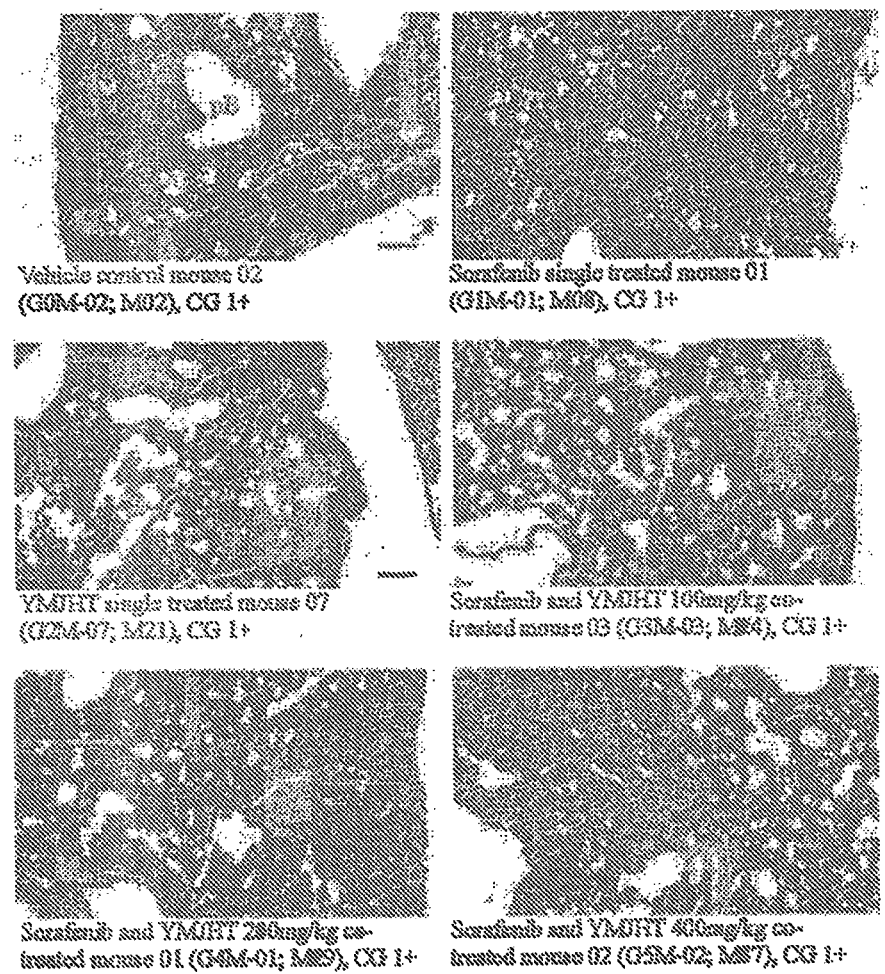
FIG. 102 shows pulmonary congestion observed in a control, a sorafenib single treated group, and sorafenib and yukmijihwang-tang 100 mg/kg, 200 mg/kg and 400 mg/kg co-administered groups.
Figure 103:
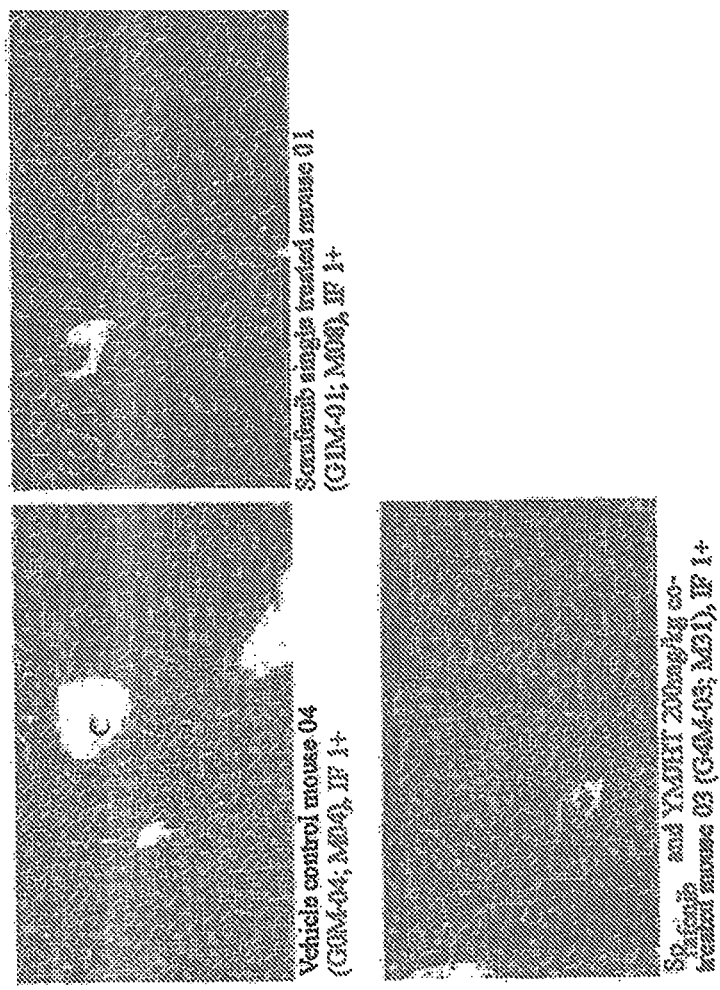
FIG. 103 shows the results obtained by observing local inflammatory cell infiltration in the liver in the control group, the sorafenib single treated group, and yukmijihwang-tang 100 mg/kg, 200 mg/kg and 400 mg/kg co-administered groups.

Mild [1+] and moderate [2+] decreases in numbers of lymphocytes in the thymic cortex (FIG. 97), the splenic white pulp (FIG. 98) and the submandibular lymph node (FIG. 99), decreases in numbers of spermatogenic cells in testicular seminiferous tubules (FIG. 100) and increases in severity and observation frequency of epithelial vacuolation of epididymal tubules (FIG. 101) were observed in the sorafenib 100 mg/kg single treated group, compared with the vehicle control. However, remarkable decreases in number of lymphocytes in such lymphoid organs, histopathological changes of reproductive organs, and occurrence frequency were observed in the YMJHT 400, 200 or 100 mg/kg and sorafenib co-administered group, compared with the sorafenib single treated group. Meanwhile, increases in severities and observation frequencies of diffuse lymphocyte enlargements in the splenic red pulp (FIG. 98) and the submandibular lymph node (FIG. 99) were observed in the YMJHT 400 mg/kg single treated group, compared with the vehicle control, and mild pulmonary congestion (FIG. 102) and local inflammatory cell infiltration (FIG. 103) in the liver were sporadically observed in all of the experiment groups including the vehicle control (Table 61).

TABLE 61

| Group | Vehicle control | Sorafenib single 100 mg/kg | YMJHT single 400 mg/kg | Sorafenib 100 mg/kg and YMJHT co-administration 100 mg/kg | 200 mg/kg | 400 mg/kg |
|---|---|---|---|---|---|---|
| Lung | | | | | | |
| Normal | 4/7 | 5/7 | 6/7 | 6/7 | 6/7 | 6/7 |
| CG 1+ | 3/7 | 2/7 | 1/7 | 1/7 | 1/7 | 1/7 |
| Thymus | | | | | | |
| Normal | 7/7 | 0/7 | 7/7 | 5/7 | 6/7 | 6/7 |
| cDE 1+ | 0/7 | 7/7 | 0/7 | 2/7 | 1/7 | 1/7 |
| Spleen | | | | | | |
| Normal | 7/7 | 0/7 | 4/7 | 2/7 | 5/7 | 6/7 |
| wDE1+ | 0/7 | 7/7 | 0/7 | 4/7 | 2/7 | 0/7 |
| rHP | 0/7 | 0/7 | 3/7 | 1/7 | 0/7 | 1/7 |
| 1+ | 0/7 | 0/7 | 3/7 | 1/7 | 0/7 | 1/7 |
| 2+ | 0/7 | 0/7 | 0/7 | 0/7 | 0/7 | 0/7 |
| Testis | | | | | | |
| Normal | 0/7 | 0/7 | 7/7 | 1/7 | 4/7 | 5/7 |
| DS | 0/7 | 7/7 | 0/7 | 6/7 | 3/7 | 2/7 |
| 1+ | 0/7 | 4/7 | 0/7 | 6/7 | 3/7 | 2/7 |
| 2+ | 0/7 | 3/7 | 0/7 | 0/7 | 0/7 | 0/7 |
| Liver | | | | | | |
| Normal | 5/7 | 5/7 | 7/7 | 7/7 | 6/7 | 7/7 |
| IF1+ | 2/7 | 2/7 | 0/7 | 0/7 | 1/7 | 0/7 |
| Epididymis | | | | | | |
| Normal | 7/7 | 0/7 | 7/7 | 4/7 | 5/7 | 7/7 |
| VO | 0/7 | 7/7 | 0/7 | 3/7 | 2/7 | 0/7 |
| 1+ | 0/7 | 5/7 | 0/7 | 3/7 | 2/7 | 0/7 |
| 2+ | 0/7 | 2/7 | 0/7 | 0/7 | 0/7 | 0/7 |
| Lymph node[a] | | | | | | |
| Normal | 5/7 | 1/7 | 5/7 | 5/7 | 4/7 | 5/7 |
| dHP | 2/7 | 0/7 | 2/7 | 0/7 | 3/7 | 2/7 |
| 1+ | 2/7 | 0/7 | 0/7 | 0/7 | 3/7 | 2/7 |
| 2+ | 0/7 | 0/7 | 2/7 | 0/7 | 0/7 | 0/7 |

TABLE 61-continued

|  | Vehicle control | Sorafenib single 100 mg/kg | YMJHT single 400 mg/kg | Sorafenib 100 mg/kg and YMJHT co-administration | | |
|---|---|---|---|---|---|---|
|  |  |  |  | 100 mg/kg | 200 mg/kg | 400 mg/kg |
| 3+ | 0/7 | 0/7 | 0/7 | 0/7 | 0/7 | 0/7 |
| dDE 1+ | 0/7 | 6/7 | 0/7 | 2/7 | 0/7 | 0/7 |
| Others |  |  |  |  |  |  |
| Normal | 7/7 | 7/7 | 7/7 | 7/7 | 7/7 | 7/7 |

According to Example 12, it was shown that co-administration of YMJHT 400, 200 or 100 mg/kg at intervals of 3.5 hours remarkably inhibited damage to the organs such as testis and epididymis, which was presumed to increase immunosuppression and apoptosis caused by a decrease in number of lymphocytes and inhibition of NK cell activity by sorafenib due to immune activity of YMJHT. Therefore, it was confirmed that the YMJHT 100 mg/kg or more co-administration at intervals of 3.5 hours remarkably reduced immunosuppression and reproductive organ damage, caused by the administration of sorafenib due to the immune activity without an influence on bioavailability of sorafenib. As a result, the co-administration of sorafenib and YMJHT to liver cancer patients is expected to provide a new treating method which is very useful in integrative medicine.

A composition for treating breast cancer of the present invention, which includes jaeumganghwa-tang, enhances an anticancer effect, when co-administered with an anticancer agent.

In addition, the composition of the present invention can be used as a new alternative for solving problems made when an anticancer agent is administered alone to treat cancer in the conventional art, which has side effects such as anemia, liver disorders and cachexia.

A composition for treating lung cancer of the present invention, which includes bojungikgi-tang, enhances an anticancer effect, when co-administered with an anticancer agent.

In addition, the composition of the present invention can be used as a new alternative for treating cancer to solve the conventional technical problems having side effects such as anemia, liver disorders, and cachexia when an anticancer agent is administered alone to treat cancer.

A composition for treating a neoplastic disease of the present invention, which includes a bojungikgi-tang extract as an active ingredient, is co-administered with an anticancer agent to improve efficiency of treating a neoplastic disease and reduce side effects occurring in single administration of the anticancer agent.

A composition for treating a neoplastic disease of the present invention, which includes a yukmijihwang-tang extract as an active ingredient, is co-administered with an anticancer agent to improve efficiency of treating a neoplastic disease and reduce side effects occurring in single administration of the anticancer agent.

While the invention has been shown and described with reference to certain exemplary embodiments thereof, it will be understood by those skilled in the art that various change in form and details may be made therein without departing from the scope of the invention as defined by the appended claims.

What is claimed is:

1. A method of treating an individual having cancer comprising administering effective amounts of an anticancer agent and a medicine to said individual, wherein:
   the cancer is chosen from breast cancer, liver cancer, and renal cancer;
   the only anticancer agent is tamoxifen, gefitinib or sorafenib; and
   the medicine is jaeumganghwa-tang, bojungikgi-tang, a bojungikgi-tang extract, or a yukmijihwang-tang extract.

2. The method of claim 1, wherein the anticancer agent and the medicine are parenterally, orally, locoregionally, or percutaneously administered.

3. The method of claim 1, wherein the medicine is administered within 30 minutes of administration of the anticancer agent.

4. The method of claim 1, wherein the cancer is breast cancer.

5. The method of claim 1, wherein the cancer is lung cancer.

6. The method of claim 1, wherein the cancer is renal cancer.

7. The method of claim 1, wherein the medicine is jaeumganghwa-tang.

8. The method of claim 1, wherein the medicine is bojungikgi-tang.

9. The method of claim 1, wherein the medicine is a bojungikgi-tang extract.

10. The method of claim 1, wherein the medicine is a yukmijihwang-tang extract.

* * * * *